US009303086B2

(12) United States Patent
Nakamura et al.

(10) Patent No.: US 9,303,086 B2
(45) Date of Patent: Apr. 5, 2016

(54) ANTI-HDLK-1 ANTIBODY HAVING AN ANTITUMOR ACTIVITY IN VIVO

(71) Applicant: LivTech, Inc., Kanagawa (JP)

(72) Inventors: Koji Nakamura, Tokyo (JP); Hiroyuki Yanai, Kanagawa (JP); Toru Kanke, Kanagawa (JP); Naoya Tsurushita, Palo Alto, CA (US); Shankar Kumar, Pleasanton, CA (US)

(73) Assignee: LIVTECH, INC., Kanagawa (JP)

( * ) Notice: Subject to any disclaimer, the term of this patent is extended or adjusted under 35 U.S.C. 154(b) by 0 days.

(21) Appl. No.: 14/045,326

(22) Filed: Oct. 3, 2013

(65) Prior Publication Data

US 2014/0193432 A1    Jul. 10, 2014

Related U.S. Application Data

(60) Provisional application No. 61/709,282, filed on Oct. 3, 2012.

(51) Int. Cl.
*C07K 16/28* (2006.01)
*G01N 33/574* (2006.01)
*A61K 39/00* (2006.01)

(52) U.S. Cl.
CPC .......... *C07K 16/28* (2013.01); *G01N 33/57492* (2013.01); *A61K 2039/505* (2013.01); *A61K 2039/545* (2013.01); *C07K 2317/24* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 5,565,332 A | 10/1996 | Hoogenboom et al. | |
| 5,580,738 A | 12/1996 | Laborda | |
| 5,595,756 A * | 1/1997 | Bally et al. ................ | 424/450 |
| 5,644,031 A | 7/1997 | Laborda | |
| 2003/0185815 A1 | 10/2003 | Padigaru et al. | |
| 2004/0241170 A1 | 12/2004 | Jensen et al. | |
| 2005/0221392 A1 | 10/2005 | Harken Jensen et al. | |
| 2008/0112956 A1 | 5/2008 | Nakamura et al. | |
| 2009/0299038 A1 | 12/2009 | Nakamura et al. | |
| 2009/0326205 A1 | 12/2009 | Nakamura et al. | |

FOREIGN PATENT DOCUMENTS

| | | |
|---|---|---|
| EP | 1702982 A1 | 9/2006 |
| JP | 6-510671 A | 12/1994 |
| JP | 2001269174 A | 10/2001 |
| WO | 02081625 A2 | 10/2002 |
| WO | 2004003019 A2 | 1/2004 |
| WO | 2004030615 A2 | 4/2004 |
| WO | 2005052156 A1 | 6/2005 |
| WO | 2008056833 A1 | 5/2008 |
| WO | 2009116670 A1 | 9/2009 |

OTHER PUBLICATIONS

Ricci et al (The Oncologist 2006;11:342-357).*
Ma (Modern Drug Discovery 2004, 7(6)).*
Auerbach et al (Cancer and Metastasis Reviews, 2000, 19: 167-172).*
Gura T (Science, 1997, 278(5340): 1041-1042, encloses 1-5).*
Sporn et al, "Chemoprevention of Cancer," Carcinogenesis, vol. 21 (2000), 525-530.*
Jain RK (Scientific American, Jul. 1994,58-65).*
International Search Report, mailed Dec. 17, 2013, which issued during the prosecution of International Patent Application No. PCT/JP2013/077540, which corresponds to the present application.
J.D. Marks et al., By-passing immunization: Building high affinity human antibodies by chain shuffling, Biotechnology, vol. 10, Jul. 1992. pp. 779-783.
C. F. Barbas III et al., In vitro evolution of a neutralizing human antibody to human immunodeficiency virus type 1 to enhance affinity and broaden strain cross-reactivity, Proc. Natl. Acad. Sci. USA, vol. 91, No. 9, pp. 3809-3813, Apr. 1994.
R. Schier et al., Identification of functional and structural amino-acid residues by parsimonious mutagenesis, Gene, vol. 169, No. 2, 1996, pp. 147-155.
D. E. Yelton et al., Affinity Maturation of the BR96 Anti-Carcinoma Antibody by Codon-Based Mutagenesis, J. Immunol., 1995, vol. 155, No. 4, pp. 1994-2004.
J. R. Jackson et al., In Vitro Antibody Maturation, Improvement of a High Affinity, Neutralizing Antibody Againt IL-1 beta, J. Immunol., 1995, vol. 154, No. 7, pp. 3310-3319.
R.E. Hawkins et al., Selection of Phage Antibodies by Binding Affinity Mimicking Affinity Maturation, J. Mol. Biol., 1992, vol. 226, No. 3, pp. 889-896.
Office Action, mailed May 16, 2011, which issued during the prosecution of U.S. Appl. No. 12/514,230, which is related to the present application.
Office Action, mailed Dec. 6, 2011, which issued during the prosecution of U.S. Appl. No. 12/514,230, which is related to the present application.

(Continued)

*Primary Examiner* — Brian J Gangle
*Assistant Examiner* — Andrea McCollum
(74) *Attorney, Agent, or Firm* — McDermott Will & Emery LLP

(57) ABSTRACT

The present invention provides: antibodies specifically reacting against hDlk-1 and having anti-tumor activity in vivo (anti-hDlk-1 antibodies, and in particular, humanized anti-hDlk-1 antibodies); fragments of the antibodies; hybridomas that produce the antibodies; a complex of the antibody or antibody fragment and an agent; a pharmaceutical composition, a tumor therapeutic agent, a tumor diagnostic agent and an agent for inducing apoptosis in tumor cells, each of which comprises the aforementioned antibody or the like; a method for treating tumor, a method for detecting tumor, a method for inducing apoptosis in tumor cells, a kit for detecting and/or diagnosing tumor and a kit for inducing apoptosis in tumor cells, each of which comprises the use of the aforementioned antibody or the like; etc.

25 Claims, 34 Drawing Sheets

(56) References Cited

OTHER PUBLICATIONS

Notice of Allowance, mailed Mar. 29, 2012, which issued during the prosecution of U.S. Appl. No. 12/514,230, which is related to the present application.
Extended European Search Report, mailed Oct. 13, 2010, which issued during the prosecution of European Application No. 07832065.2, which is related to the present application.
Ceder et al., Delta-Like 1 (Dlk-1), a Novel Marker of Prostate Basal and Candidate Epithelial Stem Cells, Is Downregulated by Notch Signalling in Intermediate/Transit Amplifying Cells of the Human Prostate, European Urology, 54 (2008), 1344-1353.
H. S. Sul, Minireview: Pref-1:Role in Adipogenesis and Mesenchymal Cell Fate, Mol Endocrinol, Nov. 2009, 23 (11): 1717-1725.
Yanai et al., Dlk-1, a cell surface antigen on foetal hepatic stem/progenitor cells, is expressed in hepatocellular, colon, pancreas and breast carcinomas at a high frequency, J. Biochem. 2010; 148(1): 85-92.
Wang et al., Pref-1 Interacts with Fibronectin To Inhibit Adipocyte Differentiation, Mol. Cell. Biol. Jul. 2010, 30(14): 3480-3492.
Casset et al., "A peptide mimetic of an anti-CD4 monoclonal antibody by rational design," Biochemical and Biophysical Research Communications, vol. 307, pp. 198-205 (2003).
Chen et al., "Selection and Analysis of an Optimized Anti-VEGF Antibody: Crystal Structure of an Affinity-matured Fab in Complex with Antigen," J. Mol. Biol., vol. 293, pp. 865-881 (1999).
De Pascalis et al, "Grafting of "Abbreviated" Complementarity-Determining Regions Containing Specificity-Determining Residues Essential for Ligand Contract to Engineer a Less Immunogenic Humanized Monoclonal Antibody," The Journal of Immunology, vol. 169, pp. 3076-3084 (2002).
Holm et al., "Functional mapping and single chain construction of the anti-cytokeratin 8 monoclonal antibody TS1," Molecular Immunology, vol. 44, pp. 1075-1084 (2007).
Luo et al., "Transcriptomic and Genomic Analysis of Human Hepatocellular Carcinomas and Hepatoblastomas," Hepatology, vol. 44, No. 4, pp. 1012-1024 (2006).
MacCallum et al., "Antibody-antigen Interactions: Contact Analysis and Binding Site Topography," J. Mol. Biol., vol. 262, pp. 732-745 (1996).
Vajdos et al, "Comprehensive Functional Maps of the Antigen-binding Site of an Anti-ErbB2 Antibody Obtained with Shotgun Scanning Mutagenesis," J. Mol. Biol., vol. 320, pp. 415-428 (2002).
Wu et al., "Humanization of a Murine Monoclonal Antibody by Simultaneous Optimization of Framework and CDR Residues," J. Mol. Biol., vol. 294, pp. 151-162 (1999).
"dlk, a Putative Mammalian Homeotic Gene Differentially Expressed in Small Cell Lung Carcinoma and Neuroendocrine Tumor Cell Line*", by Laborda et al., J. Biol.Chem., vol. 268 (6), p. 3817-3820 (1993).
"Pref-1, a Protein Containing EGF-like Repeats, Inhibits Adipocyte Differentiation", by SMAS et al., Cell, vol. 73 (4), p. 725-734 (1993).
"Molecular markers of neuroendocrine development and evidence of environmental regulation", by HELMANet al., Proc. Natl. Acad. Sci. USA, vol. 84, p. 2336-2339 (1987).
"Mus musculus SCP-1 mRNA for stromal cell derived protein-1, complete cds", by Maruyama et al., Unpublished, Genebank accession No. D16847 (1993).
"Cloning of a Membrane-Spanning Protein with Epidermal rowth Factor-Like Repeat Motifs from Adrenal Glomerulosa Cells*", by HALDERet al., Endocrinology, vol. 139, p. 3316-3328 (1998).
"Two fetal antigens (FA-1 and FA-2) and endometrial proteins (PP12 and PP14) isolated from amniotic fluid; preliminary observations in fetal and maternal tissues", by Fay et al., Eur. J. Obstet. Gynecol. Reprod. Biol., vol. 29, p. 73-85 (1988).
"Expression of Dlk/Pref-1 defines a subpopulation in the oval cell compartment of rat liver", by Tanimizu et al., Gene Expression Patterns, vol. 5, p. 209-218 (2004).

"Transit-Amplifying Ductular (Oval) Cells and Their Hepatocytic Progeny Are Characterized by a Novel and Distinctive Expression of Delta-Like Protein/Preadipocyte Factor 1/Fetal Antigen 1", by Jensen et al., Am. J. Pathol., vol. 164 (4), p. 1347-1359 (2004).
"Regulation of Human Skeletal Stem Cells Differentiation by Dlk 1/Pref-1" by Abdallah et al., J. Bone Miner. Res., vol. 19 (5), p. 841-852 (2004).
"Fetal antigen 1, a member of the epidermal growth factor superfamily in neurofibromas and serum from patients with neurofibromatosis type 1", by Jensen et al., Br. J. Dermatol., vol. 140 (6), p. 1054-1059 (1999).
"Elevated Serum Levels of Fetal Antigen 1, a Member of the Epidermal Growth Factor Superfamily, in Patients with Small Cell Lung Cancer", by Jensen et al., Tumour Biol., vol. 20 (5), p. 256-262 (1999).
"Imprinting status of DLK1 gene in brain tumors and lymphomas" by Yin et al., Int. J. Oncol., vol. 24 (4), p. 1011-1015 (2004).
"DLK1: increased expression in gliomas and associated with oncogenic activities", by Yin et al., Oncogene, vol. 25 (13), p. 1852-1861 (2006).
"Imprinting, expression and localisation of DLK1 in Wilms tumours", by Fukuzawa et al., J. Clin. Pathol., vol. 58, p. 145-150 (2005).
"Identification of myelodysplastic syndrome-specific genes by DNA microarray analysis with purified hematopoietic stem cell fraction", by Miyazato et al., Blood, vol. 98, p. 422-427 (2001).
"Dlk 1 in normal and abnormal hematopoiesis", by Sakajiri et al., Leukemia, vol. 19 (8), p. 1404-1410 (2005).
"Antibody engineering, A Practical Approach", by Djavardi-Ohaniance et al. (1996), In Antibody Engineering, Chapter 4, pp. 77-97. IRL Press, Oxford.
"Protein structure of fetal antigen 1 (FA1), A novel circulating human epidermal-growth-factor-like protein expressed in neuroendocrine tumors and its relation to the gene products of dlk and pG2", by Jensen et al., European Journal of Biochemistry, vol. 225, p. 83-92 (1994).
"A Role for Pref-1 and HES-1 in Thymocyte Development", by Kaneta et al., Journal of Immunology, vol. 164, p. 256-264 (2000).
"Isolation of hepatoblasts based on the expression of Dlk/Pref-1", by Tanimizu et al., Journal of Cell Science, vol. 116, p. 1775-1786 (2003).
"Membrane protein of hepatic stem cell as molecular target for liver cencer", by Miyajima et al., Abstracts of the 45th General Meeting of Japan Society of Clinical Oncology (Sep. 20, 2007), vol. 42 (2), p. 212 with its English translation.
P. Dufner, et al., Harnessing phage and ribosome display for antibody optimisation, Trends in Biotechnology, vol. 24, No. 11, pp. 523-529, 2006.
Ward et al. (Nature 341:544-546 (1989)).
Smith-Gill et al. (J. Immunol. 139:4135-4144 (1987)).
Kumar et al. (J. Bioi. Chem. 275:35129-35136 (2000)).
Song et al. (Biochem Biophys Res Comm 268:390-394 (2000)).
Voskoglou-Nomikos (Clin. Can. Res. 9:4227-4239 (2003)).
Dennis (Nature 442:739-741 (2006)).
Cespedes et al. (Clin. Transl. Oncol. 8(5):318-329 (2006)).
Talmadge et al. (Am. J. Pathol 170(3):793-804 (2007)).
Fujimori et al. (J. Nuc. Med. 31:1191-1198 (1990)).
Beckman et al. (Can. 109:170-179 (2007)).
Thurber et al. (Adv. Drug Deliv. Rev. 60:1421-1434 (2008)).
Rudnick et al. (Can. Biotherp. & Radiopharm. 24: 155-162 (2009)).
Office Action, mailed Aug. 3, 2010, which issued during the prosecution of U.S. Appl. No. 12/404,419, which is related to the present application.
Notice of Allowance, mailed ailed Apr. 11, 2011, which issued during the prosecution of U.S. Appl. No. 12/404,419, which is related to the present application.
Office Action, mailed Sep. 17, 2010, which issued during the prosecution of U.S. Appl. No. 12/514,230, which is related to the present application.

\* cited by examiner

Fig. 1

```
ATGGGTTGGAGCTGTATCATCTTCTTTCTGGTAGCAACAGCTACAGGTGTGCACTCCCAG
 M  G  W  S  C  I  I  F  F  L  V  A  T  A  T  G  V  H  S  Q

GTCCAGCTGCAGCAGTCTGGGCCTGAGCTGGTGAGGCCTGGGGTCTCAGTGAAGATTTCC
 V  Q  L  Q  Q  S  G  P  E  L  V  R  P  G  V  S  V  K  I  S

TGCAAGGGTTCCGGCTACACATTCACTGATTATGCTATGCACTGGGTGAAGCAGAGTCAT
 C  K  G  S  G  Y  T  F  T  D  Y  A  M  H  W  V  K  Q  S  H

GCAAAGAGTCTAGAGTGGATTGGAGTTATTAGTACTTACTATGGTAATACAAACTACAAC
 A  K  S  L  E  W  I  G  V  I  S  T  Y  Y  G  N  T  N  Y  N

CAGAAGTTTAAGGGCAAGGCCACAATGACTGTAGACAAATCCTCCAGCACAGCCTATATG
 Q  K  F  K  G  K  A  T  M  T  V  D  K  S  S  S  T  A  Y  M

GAACTTGCCAGATTGACATCTGAGGATTCTGCCATCTATTACTGTGCAAGAGGAGGATTA
 E  L  A  R  L  T  S  E  D  S  A  I  Y  Y  C  A  R  G  G  L

CGAGAGTATTACTATGCTATGGACTACTGGGGTCAAGGAACCTCAGTCACCGTCTCCTCA
 R  E  Y  Y  Y  A  M  D  Y  W  G  Q  G  T  S  V  T  V  S  S
```

Fig. 2

ATGGAATCACAGACCCAGGTCCTCATGTTTCTTCTGCTCTGGGTATCTGGTGCCTGTGCA
 M   E   S   Q   T   Q   V   L   M   F   L   L   L   W   V   S   G   A   C   A

GACATTGTGATGACACAGTCTCCATCCTCCCTGGCTATGTCAGTAGGACAGAAGGTCACT
 <u>D</u>   I   V   M   T   Q   S   P   S   S   L   A   M   S   V   G   Q   K   V   T

ATGAGCTGCAAGTCCAGTCAGAGCCTTTTAAATAGTAGCAATCAAAAGAACTATTTGGCC
 M   S   C   <u>K   S   S   Q   S   L   L   N   S   S   N   Q   K   N   Y   L   A</u>

TGGTACCAGCAGAAACCAGGACAGTCTCCTAAACTTCTGGTATACTTTGCATCCACTAGG
 W   Y   Q   Q   K   P   G   Q   S   P   K   L   L   V   Y   <u>F   A   S   T   R</u>

GAATCTGGGGTCCCTGATCGCTTCATAGGCAGTGGATCTGGGACAGATTTCACTCTTACC
 <u>E   S</u>   G   V   P   D   R   F   I   G   S   G   S   G   T   D   F   T   L   T

ATCAGCAGTGTGCAGGCTGAAGACCTGGCAGATTACTTCTGTCAGCAACATTATAGCACT
 I   S   S   V   Q   A   E   D   L   A   D   Y   F   C   <u>Q   Q   H   Y   S   T</u>

CCTCCCACGTTCGGTGCTGGGACCAAGCTGGAGCTGAAA
 <u>P   P   T</u>   F   G   A   G   T   K   L   E   L   K

Fig. 3

```
SpeI
ACTAGTACCACCATGGGTTGGAGCTGTATCATCTTCTTTCTGGTAGCAACAGCTACAGGT
            M  G  W  S  C  I  I  F  F  L  V  A  T  A  T  G

GTGCACTCCCAGGTCCAGCTGCAGCAGTCTGGGCCTGAGCTGGTGAGGCCTGGGGTCTCA
 V  H  S  Q  V  Q  L  Q  Q  S  G  P  E  L  V  R  P  G  V  S
       =

GTGAAGATTTCCTGCAAGGGTTCCGGCTACACATTCACTGATTATGCTATGCACTGGGTG
 V  K  I  S  C  K  G  S  G  Y  T  F  T  D  Y  A  M  H  W  V

AAGCAGAGTCATGCAAAGAGTCTAGAGTGGATTGGAGTTATTAGTACTTACTATGGTAAT
 K  Q  S  H  A  K  S  L  E  W  I  G  V  I  S  T  Y  Y  G  N

ACAAACTACAACCAGAAGTTTAAGGGCAAGGCCACAATGACTGTAGACAAATCCTCCAGC
 T  N  Y  N  Q  K  F  K  G  K  A  T  M  T  V  D  K  S  S  S

ACAGCCTATATGGAACTTGCCAGATTGACATCTGAGGATTCTGCCATCTATTACTGTGCA
 T  A  Y  M  E  L  A  R  L  T  S  E  D  S  A  I  Y  Y  C  A

AGAGGAGGATTACGAGAGTATTACTATGCTATGGACTACTGGGGTCAAGGAACCTCAGTC
 R  G  G  L  R  E  Y  Y  Y  A  M  D  Y  W  G  Q  G  T  S  V

HindIII
ACCGTCTCCTCAGGTAAGAATGGCCTCTCAAGCTT
 T  V  S  S
```

Fig. 4

NheI
GCTAGCACCACCATGGAATCACAGACCCAGGTCCTCATGTTTCTTCTGCTCTGGGTATCT
         M  E  S  Q  T  Q  V  L  M  F  L  L  L  W  V  S

GGTGCCTGTGCAGACATTGTGATGACACAGTCTCCATCCTCCCTGGCTATGTCAGTAGGA
 G  A  C  A  D  I  V  M  T  Q  S  P  S  S  L  A  M  S  V  G

CAGAAGGTCACTATGAGCTGCAAGTCCAGTCAGAGCCTTTTAAATAGTAGCAATCAAAAG
 Q  K  V  T  M  S  C  K  S  S  Q  S  L  L  N  S  S  N  Q  K

AACTATTTGGCCTGGTACCAGCAGAAACCAGGACAGTCTCCTAAACTTCTGGTATACTTT
 N  Y  L  A  W  Y  Q  Q  K  P  G  Q  S  P  K  L  L  V  Y  F

GCATCCACTAGGGAATCTGGGGTCCCTGATCGCTTCATAGGCAGTGGATCTGGGACAGAT
 A  S  T  R  E  S  G  V  P  D  R  F  I  G  S  G  S  G  T  D

TTCACTCTTACCATCAGCAGTGTGCAGGCTGAAGACCTGGCAGATTACTTCTGTCAGCAA
 F  T  L  T  I  S  S  V  Q  A  E  D  L  A  D  Y  F  C  Q  Q

CATTATAGCACTCCTCCCACGTTCGGTGCTGGGACCAAGCTGGAGCTGAAACGTAAGTAC
 H  Y  S  T  P  P  T  F  G  A  G  T  K  L  E  L  K

EcoRI
ACTTTTCTGAATTC

Fig. 6

```
                         1          2          3
             123456789  0123456789 0123456789 0123456789
BA-1-3D VH   QVQLQQSGP  ELVRPGVSVK ISCKGSGYTF TDYAMHWVKQ
HuBA-1-3D VH1 QVQLVQSGA EVKKPGASVK VSCKASGYTF TDYAMHWVRQ
HuBA-1-3D VH2 QVQLVQSGA EVKKPGASVK VSCKASGYTF TDYAMHWVRQ
U00503 VH    QVQLVQSGA  EVKKPGASVK VSCKASGYTF T-----WVRQ 4          5           6          7
             0123456789 01223456789 0123456789 0123456789
                            a
BA-1-3D VH   SHAKSLEWIG VISTYYGNTNY NQKFKGKATM TVDKSSSTAY
HuBA-1-3D VH1 APGQGLEWIG VISTYYGNTNY NQKFKGKATM TVDTSTSTAY
HuBA-1-3D VH2 APGQGLEWIG VISTYYGNTNY NQKFKGRATM TVDTSTSTAY
U00503 VH    APGQGLEWMG ----------- ------RVTM TTDTSTSTAY 1            1
             8            9            0            1
             0122223456789 0123456789 00000123456789 0123
                abc                      abcd
BA-1-3D VH   MELARLTSEDSAI YYCARGGLRE YYYAMDYWGQGTSV TVSS
HuBA-1-3D VH1 MELRSLRSDDTAV YYCARGGLRE YYYAMDYWGQGTMV TVSS
HuBA-1-3D VH2 MELRSLRSDDTAV YYCARGGLRE YYYAMDYWGQGTMV TVSS
U00503 VH    MELRSLRSDDTAV YYCAR----- -------WGQGTMV TVSS
```

Fig. 7

```
                             1          2                    3
                    123456789 0123456789 0123456777777789 0123456789
                                                  abcdef
BA-1-3D VL          DIVMTQSPS SLAMSVGQKV TMSCKSSQSLLNSSNQ KNYLAWYQQK
HuBA-1-3D VL        DIVMTQSPD SLAVSLGERA TINCKSSQSLLNSSNQ KNYLAWYQQK
Z46622 VL           DIVMTQSPD SLAVSLGERA TINC------------ -----WYQQK 4          5          6          7
                    0123456789 0123456789 0123456789 0123456789
BA-1-3D VL          PGQSPKLLVY FASTRESGVP DRFIGSGSGT DFTLTISSVQ
HuBA-1-3D VL        PGQPPKLLVY FASTRESGVP DRFSGSGSGT DFTLTISSLQ
Z46622 VL           PGQPPKLLIY -------GVP DRFSGSGSGT DFTLTISSLQ 1
                        8          9          0
                    0123456789 0123456789 01234567
BA-1-3D VL          AEDLADYFCQ QHYSTPPTFG AGTKLELK
HuBA-1-3D VL        AEDVAVYYCQ QHYSTPPTFG QGTKLEIK
Z46622 VL           AEDVAVYYC- --------FG QGTKLEIKR
```

Fig. 8

SpeI
ACTAGTACCACCATGGGTTGGAGCTGTATCATCTTCTTTCTGGTAGCAACAGCTACAGGC
           M  G  W  S  C  I  I  F  F  L  V  A  T  A  T  G

GTGCACTCCCAAGTCCAGCTGGTGCAGTCTGGGGCTGAAGTGAAGAAGCCTGGGGCCTCA
 V  H  S  Q  V  Q  L  V  Q  S  G  A  E  V  K  K  P  G  A  S

GTGAAAGTCTCCTGCAAGGCTTCCGGCTACACATTCACTGATTATGCTATGCACTGGGTG
 V  K  V  S  C  K  A  S  G  Y  T  F  T  D  Y  A  M  H  W  V

CGACAGGCCCCTGGACAAGGCCTGGAGTGGATTGGAGTTATTAGTACTTACTATGGTAAT
 R  Q  A  P  G  Q  G  L  E  W  I  G  V  I  S  T  Y  Y  G  N

ACAAACTACAACCAGAAGTTTAAGGGCAAGGCCACAATGACTGTCGACACATCCACCAGC
 T  N  Y  N  Q  K  F  K  G  K  A  T  M  T  V  D  T  S  T  S

ACAGCCTATATGGAACTTAGGAGCTTGAGATCTGACGATACTGCCGTGTATTACTGTGCA
 T  A  Y  M  E  L  R  S  L  R  S  D  D  T  A  V  Y  Y  C  A

AGAGGAGGATTGCGAGAGTATTACTATGCTATGGACTACTGGGGTCAAGGAACCATGGTC
 R  G  G  L  R  E  Y  Y  Y  A  M  D  Y  W  G  Q  G  T  M  V

HindIII
ACCGTCTCCTCAGGTAAGATGGGCTTTCCTAAGCTT
 T  V  S  S

Fig. 9

```
SpeI
ACTAGTACCACCATGGGTTGGAGCTGTATCATCTTCTTTCTGGTAGCAACAGCTACAGGC
          M  G  W  S  C  I  I  F  F  L  V  A  T  A  T  G

GTGCACTCCCAAGTCCAGCTGGTGCAGTCTGGGGCTGAAGTGAAGAAGCCTGGGGCCTCA
 V  H  S  Q  V  Q  L  V  Q  S  G  A  E  V  K  K  P  G  A  S

GTGAAAGTCTCCTGCAAGGCTTCCGGCTACACATTCACTGATTATGCTATGCACTGGGTG
 V  K  V  S  C  K  A  S  G  Y  T  F  T  D  Y  A  M  H  W  V

CGACAGGCCCCTGGACAAGGCCTGGAGTGGATTGGAGTTATTAGTACTTACTATGGTAAT
 R  Q  A  P  G  Q  G  L  E  W  I  G  V  I  S  T  Y  Y  G  N

ACAAACTACAACCAGAAGTTTAAGGGCCGAGCCACAATGACTGTCGACACATCCACCAGC
 T  N  Y  N  Q  K  F  K  G  R  A  T  M  T  V  D  T  S  T  S

ACAGCCTATATGGAACTTAGGAGCTTGAGATCTGACGATACTGCCGTGTATTACTGTGCA
 T  A  Y  M  E  L  R  S  L  R  S  D  D  T  A  V  Y  Y  C  A

AGAGGAGGATTGCGAGAGTATTACTATGCTATGGACTACTGGGGTCAAGGAACCATGGTC
 R  G  G  L  R  E  Y  Y  Y  A  M  D  Y  W  G  Q  G  T  M  V

HindIII
ACCGTCTCCTCAGGTAAGATGGGCTTTCCTAAGCTT
 T  V  S  S
```

Fig. 10

```
NheI
GCTAGCACCACCATGGAATCACAGACCCAGGTCCTCATGTTTCTTCTGCTCTGGGTATCT
         M  E  S  Q  T  Q  V  L  M  F  L  L  L  W  V  S

GGTGCCTGTGCAGACATTGTCATGACACAGTCTCCAGACTCCCTGGCTGTGTCACTGGGA
 G  A  C  A  D  I  V  M  T  Q  S  P  D  S  L  A  V  S  L  G

GAGAGGGCCACTATCAACTGCAAGTCCAGTCAGAGCCTTCTGAATAGTAGCAATCAAAAG
 E  R  A  T  I  N  C  K  S  S  Q  S  L  L  N  S  S  N  Q  K

AACTATTTGGCCTGGTACCAGCAGAAACCAGGACAGCCTCCTAAACTTCTGGTCTACTTT
  N  Y  L  A  W  Y  Q  Q  K  P  G  Q  P  P  K  L  L  V  Y  F

GCATCCACTAGGGAATCTGGGGTCCCTGATCGCTTCAGTGGCAGTGGATCTGGGACAGAT
  A  S  T  R  E  S  G  V  P  D  R  F  S  G  S  G  S  G  T  D

TTCACTCTTACCATCAGCAGTCTGCAGGCTGAAGATGTGGCAGTTTACTACTGTCAGCAA
 F  T  L  T  I  S  S  L  Q  A  E  D  V  A  V  Y  Y  C  Q  Q

CATTATAGCACTCCTCCCACATTCGGTCAGGGGACCAAGCTGGAGATCAAACGTAAGTAC
  H  Y  S  T  P  P  T  F  G  Q  G  T  K  L  E  I  K

EcoRI
TTTTTTTTCGAATTC
```

Fig. 11

| | |
|---|---|
| CMV2 | GAACCGTCAGATCGCCTGGAGACG |
| JNT026 | TGAAAGATGAGCTGGAGGAC |
| JNT082 | CTTTCTTGTCCACCTTGGTG |
| JNT097 | GCTGTCCTACAGTCCTCAG |
| JNT098 | ACGTGCCAAGCATCCTCG |

Fig. 12

```
   1 ATGGGTTGGAGCTGTATCATCTTCTTTCTGGTAGCAACAGCTACAGGTGTGCACTCCCAG
     M  G  W  S  C  I  I  F  F  L  V  A  T  A  T  G  V  H  S  Q
  61 GTCCAGCTGCAGCAGTCTGGGCCTGAGCTGGTGAGGCCTGGGGTCTCAGTGAAGATTTCC
     V  Q  L  Q  Q  S  G  P  E  L  V  R  P  G  V  S  V  K  I  S
 121 TGCAAGGGTTCCGGCTACACATTCACTGATTATGCTATGCACTGGGTGAAGCAGAGTCAT
     C  K  G  S  G  Y  T  F  T  D  Y  A  M  H  W  V  K  Q  S  H
 181 GCAAAGAGTCTAGAGTGGATTGGAGTTATTAGTACTTACTATGGTAATACAAACTACAAC
     A  K  S  L  E  W  I  G  V  I  S  T  Y  Y  G  N  T  N  Y  N
 241 CAGAAGTTTAAGGGCAAGGCCACAATGACTGTAGACAAATCCTCCAGCACAGCCTATATG
     Q  K  F  K  G  K  A  T  M  T  V  D  K  S  S  S  T  A  Y  M
 301 GAACTTGCCAGATTGACATCTGAGGATTCTGCCATCTATTACTGTGCAAGAGGAGGATTA
     E  L  A  R  L  T  S  E  D  S  A  I  Y  Y  C  A  R  G  G  L
 361 CGAGAGTATTACTATGCTATGGACTACTGGGGTCAAGGAACCTCAGTCACCGTCTCCTCA
     R  E  Y  Y  Y  A  M  D  Y  W  G  Q  G  T  S  V  T  V  S  S
 421 GCCTCCACCAAGGGCCCATCGGTCTTCCCCCTGGCACCCTCCTCCAAGAGCACCTCTGGG
     A  S  T  K  G  P  S  V  F  P  L  A  P  S  S  K  S  T  S  G
 481 GGCACAGCGGCCCTGGGCTGCCTGGTCAAGGACTACTTCCCCGAACCGGTGACGGTGTCG
     G  T  A  A  L  G  C  L  V  K  D  Y  F  P  E  P  V  T  V  S
 541 TGGAACTCAGGCGCCCTGACCAGCGGCGTGCACACCTTCCCGGCTGTCCTACAGTCCTCA
     W  N  S  G  A  L  T  S  G  V  H  T  F  P  A  V  L  Q  S  S
 601 GGACTCTACTCCCTCAGCAGCGTGGTGACCGTGCCCTCCAGCAGCTTGGGCACCCAGACC
     G  L  Y  S  L  S  S  V  V  T  V  P  S  S  S  L  G  T  Q  T
 661 TACATCTGCAACGTGAATCACAAGCCCAGCAACACCAAGGTGGACAAGAAAGTTGAGCCC
     Y  I  C  N  V  N  H  K  P  S  N  T  K  V  D  K  K  V  E  P
 721 AAATCTTGTGACAAAACTCACACATGCCCACCGTGCCCAGCACCTGAACTCCTGGGGGGA
     K  S  C  D  K  T  H  T  C  P  P  C  P  A  P  E  L  L  G  G
 781 CCGTCAGTCTTCCTCTTCCCCCCAAAACCCAAGGACACCCTCATGATCTCCCGGACCCCT
     P  S  V  F  L  F  P  P  K  P  K  D  T  L  M  I  S  R  T  P
 841 GAGGTCACATGCGTGGTGGTGGACGTGAGCCACGAAGACCCTGAGGTCAAGTTCAACTGG
     E  V  T  C  V  V  V  D  V  S  H  E  D  P  E  V  K  F  N  W
 901 TACGTGGACGGCGTGGAGGTGCATAATGCCAAGACAAAGCCGCGGGAGGAGCAGTACAAC
     Y  V  D  G  V  E  V  H  N  A  K  T  K  P  R  E  E  Q  Y  N
 961 AGCACGTACCGTGTGGTCAGCGTCCTCACCGTCCTGCACCAGGACTGGCTGAATGGCAAG
     S  T  Y  R  V  V  S  V  L  T  V  L  H  Q  D  W  L  N  G  K
1021 GAGTACAAGTGCAAGGTCTCCAACAAAGCCCTCCCAGCCCCCATCGAGAAAACCATCTCC
     E  Y  K  C  K  V  S  N  K  A  L  P  A  P  I  E  K  T  I  S
1081 AAAGCCAAAGGGCAGCCCCGAGAACCACAGGTGTACACCCTGCCCCCATCCCGGGATGAG
     K  A  K  G  Q  P  R  E  P  Q  V  Y  T  L  P  P  S  R  D  E
1141 CTGACCAAGAACCAGGTCAGCCTGACCTGCCTGGTCAAAGGCTTCTATCCCAGCGACATC
     L  T  K  N  Q  V  S  L  T  C  L  V  K  G  F  Y  P  S  D  I
1201 GCCGTGGAGTGGGAGAGCAATGGGCAGCCGGAGAACAACTACAAGACCACGCCTCCCGTG
     A  V  E  W  E  S  N  G  Q  P  E  N  N  Y  K  T  T  P  P  V
1261 CTGGACTCCGACGGCTCCTTCTTCCTCTACAGCAAGCTCACCGTGGACAAGAGCAGGTGG
     L  D  S  D  G  S  F  F  L  Y  S  K  L  T  V  D  K  S  R  W
1321 CAGCAGGGGAACGTCTTCTCATGCTCCGTGATGCATGAGGCTCTGCACAACCACTACACG
     Q  Q  G  N  V  F  S  C  S  V  M  H  E  A  L  H  N  H  Y  T
1381 CAGAAGAGCCTCTCCCTGTCTCCGGGTAAATGA
     Q  K  S  L  S  L  S  P  G  K  *
```

Fig. 13

```
  1 ATGGAATCACAGACCCAGGTCCTCATGTTTCTTCTGCTCTGGGTATCTGGTGCCTGTGCA
    M  E  S  Q  T  Q  V  L  M  F  L  L  L  W  V  S  G  A  C  A
 61 GACATTGTGATGACACAGTCTCCATCCTCCCTGGCTATGTCAGTAGGACAGAAGGTCACT
    D  I  V  M  T  Q  S  P  S  S  L  A  M  S  V  G  Q  K  V  T
121 ATGAGCTGCAAGTCCAGTCAGAGCCTTTTAAATAGTAGCAATCAAAAGAACTATTTGGCC
    M  S  C  K  S  S  Q  S  L  L  N  S  S  N  Q  K  N  Y  L  A
181 TGGTACCAGCAGAAACCAGGACAGTCTCCTAAACTTCTGGTATACTTTGCATCCACTAGG
    W  Y  Q  Q  K  P  G  Q  S  P  K  L  L  V  Y  F  A  S  T  R
241 GAATCTGGGGTCCCTGATCGCTTCATAGGCAGTGGATCTGGGACAGATTTCACTCTTACC
    E  S  G  V  P  D  R  F  I  G  S  G  S  G  T  D  F  T  L  T
301 ATCAGCAGTGTGCAGGCTGAAGACCTGGCAGATTACTTCTGTCAGCAACATTATAGCACT
    I  S  S  V  Q  A  E  D  L  A  D  Y  F  C  Q  Q  H  Y  S  T
361 CCTCCCACGTTCGGTGCTGGGACCAAGCTGGAGCTGAAACGAACTGTGGCTGCACCATCT
    P  P  T  F  G  A  G  T  K  L  E  L  K  R  T  V  A  A  P  S
421 GTCTTCATCTTCCCGCCATCTGATGAGCAGTTGAAATCTGGAACTGCCTCTGTTGTGTGC
    V  F  I  F  P  P  S  D  E  Q  L  K  S  G  T  A  S  V  V  C
481 CTGCTGAATAACTTCTATCCCAGAGAGGCCAAAGTACAGTGGAAGGTGGATAACGCCCTC
    L  L  N  N  F  Y  P  R  E  A  K  V  Q  W  K  V  D  N  A  L
541 CAATCGGGTAACTCCCAGGAGAGTGTCACAGAGCAGGACAGCAAGGACAGCACCTACAGC
    Q  S  G  N  S  Q  E  S  V  T  E  Q  D  S  K  D  S  T  Y  S
601 CTCAGCAGCACCCTGACGCTGAGCAAAGCAGACTACGAGAAACACAAAGTCTACGCCTGC
    L  S  S  T  L  T  L  S  K  A  D  Y  E  K  H  K  V  Y  A  C
661 GAAGTCACCCATCAGGGCCTGAGCTCGCCCGTCACAAAGAGCTTCAACAGGGGAGAGTGT
    E  V  T  H  Q  G  L  S  S  P  V  T  K  S  F  N  R  G  E  C
721 TAG
    •
```

Fig. 14

```
   1 ATGGGTTGGAGCTGTATCATCTTCTTTCTGGTAGCAACAGCTACAGGCGTGCACTCCCAA
     M  G  W  S  C  I  I  F  L  V  A  T  A  T  G  V  H  S  Q
  61 GTCCAGCTGGTGCAGTCTGGGGCTGAAGTGAAGAAGCCTGGGGCCTCAGTGAAAGTCTCC
     V  Q  L  V  Q  S  G  A  E  V  K  K  P  G  A  S  V  K  V  S
 121 TGCAAGGCTTCCGGCTACACATTCACTGATTATGCTATGCACTGGGTGCGACAGGCCCCT
     C  K  A  S  G  Y  T  F  T  D  Y  A  M  H  W  V  R  Q  A  P
 181 GGACAAGGCCTGGAGTGGATTGGAGTTATTAGTACTTACTATGGTAATACAAACTACAAC
     G  Q  G  L  E  W  I  G  V  I  S  T  Y  Y  G  N  T  N  Y  N
 241 CAGAAGTTTAAGGGCAAGGCCACAATGACTGTCGACACATCCACCAGCACAGCCTATATG
     Q  K  F  K  G  K  A  T  M  T  V  D  T  S  T  S  T  A  Y  M
 301 GAACTTAGGAGCTTGAGATCTGACGATACTGCCGTGTATTACTGTGCAAGAGGAGGATTG
     E  L  R  S  L  R  S  D  D  T  A  V  Y  Y  C  A  R  G  G  L
 361 CGAGAGTATTACTATGCTATGGACTACTGGGGTCAAGGAACCATGGTCACCGTCTCCTCA
     R  E  Y  Y  Y  A  M  D  Y  W  G  Q  G  T  M  V  T  V  S  S
 421 GCCTCCACCAAGGGCCCATCGGTCTTCCCCCTGGCACCCTCCTCCAAGAGCACCTCTGGG
     A  S  T  K  G  P  S  V  F  P  L  A  P  S  S  K  S  T  S  G
 481 GGCACAGCGGCCCTGGGCTGCCTGGTCAAGGACTACTTCCCCGAACCGGTGACGGTGTCG
     G  T  A  A  L  G  C  L  V  K  D  Y  F  P  E  P  V  T  V  S
 541 TGGAACTCAGGCGCCCTGACCAGCGGCGTGCACACCTTCCCGGCTGTCCTACAGTCCTCA
     W  N  S  G  A  L  T  S  G  V  H  T  F  P  A  V  L  Q  S  S
 601 GGACTCTACTCCCTCAGCAGCGTGGTGACCGTGCCCTCCAGCAGCTTGGGCACCCAGACC
     G  L  Y  S  L  S  S  V  V  T  V  P  S  S  S  L  G  T  Q  T
 661 TACATCTGCAACGTGAATCACAAGCCCAGCAACACCAAGGTGGACAAGAAAGTTGAGCCC
     Y  I  C  N  V  N  H  K  P  S  N  T  K  V  D  K  K  V  E  P
 721 AAATCTTGTGACAAAACTCACACATGCCCACCGTGCCCAGCACCTGAACTCCTGGGGGGA
     K  S  C  D  K  T  H  T  C  P  P  C  P  A  P  E  L  L  G  G
 781 CCGTCAGTCTTCCTCTTCCCCCCAAAACCCAAGGACACCCTCATGATCTCCCGGACCCCT
     P  S  V  F  L  F  P  P  K  P  K  D  T  L  M  I  S  R  T  P
 841 GAGGTCACATGCGTGGTGGTGGACGTGAGCCACGAAGACCCTGAGGTCAAGTTCAACTGG
     E  V  T  C  V  V  V  D  V  S  H  E  D  P  E  V  K  F  N  W
 901 TACGTGGACGGCGTGGAGGTGCATAATGCCAAGACAAAGCCGCGGGAGGAGCAGTACAAC
     Y  V  D  G  V  E  V  H  N  A  K  T  K  P  R  E  E  Q  Y  N
 961 AGCACGTACCGTGTGGTCAGCGTCCTCACCGTCCTGCACCAGGACTGGCTGAATGGCAAG
     S  T  Y  R  V  V  S  V  L  T  V  L  H  Q  D  W  L  N  G  K
1021 GAGTACAAGTGCAAGGTCTCCAACAAAGCCCTCCCAGCCCCCATCGAGAAAACCATCTCC
     E  Y  K  C  K  V  S  N  K  A  L  P  A  P  I  E  K  T  I  S
1081 AAAGCCAAAGGGCAGCCCCGAGAACCACAGGTGTACACCCTGCCCCCATCCCGGGATGAG
     K  A  K  G  Q  P  R  E  P  Q  V  Y  T  L  P  P  S  R  D  E
1141 CTGACCAAGAACCAGGTCAGCCTGACCTGCCTGGTCAAAGGCTTCTATCCCAGCGACATC
     L  T  K  N  Q  V  S  L  T  C  L  V  K  G  F  Y  P  S  D  I
1201 GCCGTGGAGTGGGAGAGCAATGGGCAGCCGGAGAACAACTACAAGACCACGCCTCCCGTG
     A  V  E  W  E  S  N  G  Q  P  E  N  N  Y  K  T  T  P  P  V
1261 CTGGACTCCGACGGCTCCTTCTTCCTCTACAGCAAGCTCACCGTGGACAAGAGCAGGTGG
     L  D  S  D  G  S  F  F  L  Y  S  K  L  T  V  D  K  S  R  W
1321 CAGCAGGGGAACGTCTTCTCATGCTCCGTGATGCATGAGGCTCTGCACAACCACTACACG
     Q  Q  G  N  V  F  S  C  S  V  M  H  E  A  L  H  N  H  Y  T
1381 CAGAAGAGCCTCTCCCTGTCTCCGGGTAAATGA
     Q  K  S  L  S  L  S  P  G  K  *
```

Fig. 15

```
   1 ATGGGTTGGAGCTGTATCATCTTCTTTCTGGTAGCAACAGCTACAGGCGTGCACTCCCAA
     M  G  W  S  C  I  I  F  F  L  V  A  T  A  T  G  V  H  S  Q
  61 GTCCAGCTGGTGCAGTCTGGGGCTGAAGTGAAGAAGCCTGGGGCCTCAGTGAAAGTCTCC
     V  Q  L  V  Q  S  G  A  E  V  K  K  P  G  A  S  V  K  V  S
 121 TGCAAGGCTTCCGGCTACACATTCACTGATTATGCTATGCACTGGGTGCGACAGGCCCCT
     C  K  A  S  G  Y  T  F  T  D  Y  A  M  H  W  V  R  Q  A  P
 181 GGACAAGGCCTGGAGTGGATTGGAGTTATTAGTACTTACTATGGTAATACAAACTACAAC
     G  Q  G  L  E  W  I  G  V  I  S  T  Y  Y  G  N  T  N  Y  N
 241 CAGAAGTTTAAGGGCCGAGCCACAATGACTGTCGACACATCCACCAGCACAGCCTATATG
     Q  K  F  K  G  R  A  T  M  T  V  D  T  S  T  S  T  A  Y  M
 301 GAACTTAGGAGCTTGAGATCTGACGATACTGCCGTGTATTACTGTGCAAGAGGAGGATTG
     E  L  R  S  L  R  S  D  D  T  A  V  Y  Y  C  A  R  G  G  L
 361 CGAGAGTATTACTATGCTATGGACTACTGGGGTCAAGGAACCATGGTCACCGTCTCCTCA
     R  E  Y  Y  Y  A  M  D  Y  W  G  Q  G  T  M  V  T  V  S  S
 421 GCCTCCACCAAGGGCCCATCGGTCTTCCCCCTGGCACCCTCCTCCAAGAGCACCTCTGGG
     A  S  T  K  G  P  S  V  F  P  L  A  P  S  S  K  S  T  S  G
 481 GGCACAGCGGCCCTGGGCTGCCTGGTCAAGGACTACTTCCCCGAACCGGTGACGGTGTCG
     G  T  A  A  L  G  C  L  V  K  D  Y  F  P  E  P  V  T  V  S
 541 TGGAACTCAGGCGCCCTGACCAGCGGCGTGCACACCTTCCCGGCTGTCCTACAGTCCTCA
     W  N  S  G  A  L  T  S  G  V  H  T  F  P  A  V  L  Q  S  S
 601 GGACTCTACTCCCTCAGCAGCGTGGTGACCGTGCCCTCCAGCAGCTTGGGCACCCAGACC
     G  L  Y  S  L  S  S  V  V  T  V  P  S  S  S  L  G  T  Q  T
 661 TACATCTGCAACGTGAATCACAAGCCCAGCAACACCAAGGTGGACAAGAAAGTTGAGCCC
     Y  I  C  N  V  N  H  K  P  S  N  T  K  V  D  K  K  V  E  P
 721 AAATCTTGTGACAAAACTCACACATGCCCACCGTGCCCAGCACCTGAACTCCTGGGGGGA
     K  S  C  D  K  T  H  T  C  P  P  C  P  A  P  E  L  L  G  G
 781 CCGTCAGTCTTCCTCTTCCCCCCAAAACCCAAGGACACCCTCATGATCTCCCGGACCCCT
     P  S  V  F  L  F  P  P  K  P  K  D  T  L  M  I  S  R  T  P
 841 GAGGTCACATGCGTGGTGGTGGACGTGAGCCACGAAGACCCTGAGGTCAAGTTCAACTGG
     E  V  T  C  V  V  V  D  V  S  H  E  D  P  E  V  K  F  N  W
 901 TACGTGGACGGCGTGGAGGTGCATAATGCCAAGACAAAGCCGCGGGAGGAGCAGTACAAC
     Y  V  D  G  V  E  V  H  N  A  K  T  K  P  R  E  E  Q  Y  N
 961 AGCACGTACCGTGTGGTCAGCGTCCTCACCGTCCTGCACCAGGACTGGCTGAATGGCAAG
     S  T  Y  R  V  V  S  V  L  T  V  L  H  Q  D  W  L  N  G  K
1021 GAGTACAAGTGCAAGGTCTCCAACAAAGCCCTCCCAGCCCCCATCGAGAAAACCATCTCC
     E  Y  K  C  K  V  S  N  K  A  L  P  A  P  I  E  K  T  I  S
1081 AAAGCCAAAGGGCAGCCCCGAGAACCACAGGTGTACACCCTGCCCCCATCCCGGGATGAG
     K  A  K  G  Q  P  R  E  P  Q  V  Y  T  L  P  P  S  R  D  E
1141 CTGACCAAGAACCAGGTCAGCCTGACCTGCCTGGTCAAAGGCTTCTATCCCAGCGACATC
     L  T  K  N  Q  V  S  L  T  C  L  V  K  G  F  Y  P  S  D  I
1201 GCCGTGGAGTGGGAGAGCAATGGGCAGCCGGAGAACAACTACAAGACCACGCCTCCCGTG
     A  V  E  W  E  S  N  G  Q  P  E  N  N  Y  K  T  T  P  P  V
1261 CTGGACTCCGACGGCTCCTTCTTCCTCTACAGCAAGCTCACCGTGGACAAGAGCAGGTGG
     L  D  S  D  G  S  F  F  L  Y  S  K  L  T  V  D  K  S  R  W
1321 CAGCAGGGGAACGTCTTCTCATGCTCCGTGATGCATGAGGCTCTGCACAACCACTACACG
     Q  Q  G  N  V  F  S  C  S  V  M  H  E  A  L  H  N  H  Y  T
1381 CAGAAGAGCCTCTCCCTGTCTCCGGGTAAATGA
     Q  K  S  L  S  L  S  P  G  K  •
```

Fig. 16

```
  1 ATGGAATCACAGACCCAGGTCCTCATGTTTCTTCTGCTCTGGGTATCTGGTGCCTGTGCA
    M  E  S  Q  T  Q  V  L  M  F  L  L  L  W  V  S  G  A  C  A
 61 GACATTGTCATGACACAGTCTCCAGACTCCCTGGCTGTGTCACTGGGAGAGAGGGCCACT
    D  I  V  M  T  Q  S  P  D  S  L  A  V  S  L  G  E  R  A  T
121 ATCAACTGCAAGTCCAGTCAGAGCCTTCTGAATAGTAGCAATCAAAAGAACTATTTGGCC
    I  N  C  K  S  S  Q  S  L  L  N  S  S  N  Q  K  N  Y  L  A
181 TGGTACCAGCAGAAACCAGGACAGCCTCCTAAACTTCTGGTCTACTTTGCATCCACTAGG
    W  Y  Q  Q  K  P  G  Q  P  P  K  L  L  V  Y  F  A  S  T  R
241 GAATCTGGGGTCCCTGATCGCTTCAGTGGCAGTGGATCTGGGACAGATTTCACTCTTACC
    E  S  G  V  P  D  R  F  S  G  S  G  S  G  T  D  F  T  L  T
301 ATCAGCAGTCTGCAGGCTGAAGATGTGGCAGTTTACTACTGTCAGCAACATTATAGCACT
    I  S  S  L  Q  A  E  D  V  A  V  Y  Y  C  Q  Q  H  Y  S  T
361 CCTCCCACATTCGGTCAGGGGACCAAGCTGGAGATCAAACGAACTGTGGCTGCACCATCT
    P  P  T  F  G  Q  G  T  K  L  E  I  K  R  T  V  A  A  P  S
421 GTCTTCATCTTCCCGCCATCTGATGAGCAGTTGAAATCTGGAACTGCCTCTGTTGTGTGC
    V  F  I  F  P  P  S  D  E  Q  L  K  S  G  T  A  S  V  V  C
481 CTGCTGAATAACTTCTATCCCAGAGAGGCCAAAGTACAGTGGAAGGTGGATAACGCCCTC
    L  L  N  N  F  Y  P  R  E  A  K  V  Q  W  K  V  D  N  A  L
541 CAATCGGGTAACTCCCAGGAGAGTGTCACAGAGCAGGACAGCAAGGACAGCACCTACAGC
    Q  S  G  N  S  Q  E  S  V  T  E  Q  D  S  K  D  S  T  Y  S
601 CTCAGCAGCACCCTGACGCTGAGCAAAGCAGACTACGAGAAACACAAAGTCTACGCCTGC
    L  S  S  T  L  T  L  S  K  A  D  Y  E  K  H  K  V  Y  A  C
661 GAAGTCACCCATCAGGGCCTGAGCTCGCCCGTCACAAAGAGCTTCAACAGGGGAGAGTGT
    E  V  T  H  Q  G  L  S  S  P  V  T  K  S  F  N  R  G  E  C
721 TAG
     *
```

Fig. 22

```
                        1          2          3          4          5
             123456789  0123456789 0123456789 0123456789 0123456789 01223456789
                                                                              a
HuBA1-3D VH1 QVQLVQSGA  EVKKPGASVK VSCKASGYTF TDYAMHWVRQ APGQGLEWIG VISTYYGNTNY
V5Q          ----Q----  ---------- ---------- ---------- ---------- -----------
A9P          ---------  -------P-- ---------- ---------- ---------- -----------
V11L         ---------  -L-------- ---------- ---------- ---------- -----------
K12V         ---------  --V------- ---------- ---------- ---------- -----------
K13R         ---------  ---R------ ---------- ---------- ---------- -----------
A16V         ---------  ------V--- ---------- ---------- ---------- -----------
V20I         ---------  ---------- I--------- ---------- ---------- -----------
A24G         ---------  ---------- ----G----- ---------- ---------- -----------
R38K         ---------  ---------- ---------- --------K- ---------- -----------
A40S         ---------  ---------- ---------- ---------- S--------- -----------
P41H         ---------  ---------- ---------- ---------- -H-------- -----------
G42A         ---------  ---------- ---------- ---------- --A------- -----------
Q43K         ---------  ---------- ---------- ---------- ---K------ -----------
G44S         ---------  ---------- ---------- ---------- ----S----- -----------
T73K         ---------  ---------- ---------- ---------- ---------- -----------
T75S         ---------  ---------- ---------- ---------- ---------- -----------
R82aA        ---------  ---------- ---------- ---------- ---------- -----------
S82bR        ---------  ---------- ---------- ---------- ---------- -----------
R83T         ---------  ---------- ---------- ---------- ---------- -----------
D85E         ---------  ---------- ---------- ---------- ---------- -----------
T87S         ---------  ---------- ---------- ---------- ---------- -----------
V89I         ---------  ---------- ---------- ---------- ---------- -----------
M108S        ---------  ---------- ---------- ---------- ---------- -----------
V5Q/T73K     ----Q----  ---------- ---------- ---------- ---------- -----------
V11L/T73K    ---------  -L-------- ---------- ---------- ---------- -----------
A24G/T73K    ---------  ---------- ----G----- ---------- ---------- -----------
T73K/T75S    ---------  ---------- ---------- ---------- ---------- -----------

1          1
             6          7          8          9          0          1
             0123456789 0123456789 0122223456789 0123456789 00000123456789 0123
                                   abc                      abcd
HuBA1-3D VH1 NQKFKGKATM TVDTSTSTAY MELRSLRSDDTAV YYCARGGLRE YYYAMDYWGQGTMV TVSS
V5Q          ---------- ---------- ------------- ---------- -------------- ----
A9P          ---------- ---------- ------------- ---------- -------------- ----
V11L         ---------- ---------- ------------- ---------- -------------- ----
K12V         ---------- ---------- ------------- ---------- -------------- ----
K13R         ---------- ---------- ------------- ---------- -------------- ----
A16V         ---------- ---------- ------------- ---------- -------------- ----
V20I         ---------- ---------- ------------- ---------- -------------- ----
A24G         ---------- ---------- ------------- ---------- -------------- ----
R38K         ---------- ---------- ------------- ---------- -------------- ----
A40S         ---------- ---------- ------------- ---------- -------------- ----
P41H         ---------- ---------- ------------- ---------- -------------- ----
G42A         ---------- ---------- ------------- ---------- -------------- ----
Q43K         ---------- ---------- ------------- ---------- -------------- ----
G44S         ---------- ---------- ------------- ---------- -------------- ----
T73K         ---------- ---K------ ------------- ---------- -------------- ----
T75S         ---------- -----S---- ------------- ---------- -------------- ----
R82aA        ---------- ---------- ---A--------- ---------- -------------- ----
S82bR        ---------- ---------- ----R-------- ---------- -------------- ----
R83T         ---------- ---------- -----T------- ---------- -------------- ----
D85E         ---------- ---------- -------E----- ---------- -------------- ----
T87S         ---------- ---------- ---------S--- ---------- -------------- ----
V89I         ---------- ---------- -----------I- ---------- -------------- ----
M108S        ---------- ---------- ------------- ---------- ------------S- ----
V5Q/T73K     ---------- ---K------ ------------- ---------- -------------- ----
V11L/T73K    ---------- ---K------ ------------- ---------- -------------- ----
A24G/T73K    ---------- ---K------ ------------- ---------- -------------- ----
T73K/T75S    ---------- ---K-S---- ------------- ---------- -------------- ----
```

Fig. 24

```
   1 ATGGGTTGGAGCTGTATCATCTTCTTTCTGGTAGCAACAGCTACAGGCGTGCACTCCCAA
     M  G  W  S  C  I  I  F  F  L  V  A  T  A  T  G  V  H  S  Q
  61 GTCCAGCTGGTGCAGTCTGGGGCTGAAGTGAAGAAGCCTGGGGCCTCAGTGAAAGTCTCC
     V  Q  L  V  Q  S  G  A  E  V  K  K  P  G  A  S  V  K  V  S
 121 TGCAAGGCTTCCGGCTACACATTCACTGATTATGCTATGCACTGGGTGCGACAGGCCCCT
     C  K  A  S  G  Y  T  F  T  D  Y  A  M  H  W  V  R  Q  A  P
 181 GGACAAGGCCTGGAGTGGATTGGAGTTATTAGTACTTACTATGGTAATACAAACTACAAC
     G  Q  G  L  E  W  I  G  V  I  S  T  Y  Y  G  N  T  N  Y  N
 241 CAGAAGTTTAAGGGCAAGGCCACAATGACTGTCGACAAATCCACCAGCACAGCCTATATG
     Q  K  F  K  G  K  A  T  M  T  V  D  K  S  T  S  T  A  Y  M
 301 GAACTTAGGAGCTTGAGATCTGACGATACTGCCGTGTATTACTGTGCAAGAGGAGGATTG
     E  L  R  S  L  R  S  D  D  T  A  V  Y  Y  C  A  R  G  G  L
 361 CGAGAGTATTACTATGCTATGGACTACTGGGGTCAAGGAACCATGGTCACCGTCTCCTCA
     R  E  Y  Y  Y  A  M  D  Y  W  G  Q  G  T  M  V  T  V  S  S
 421 GCCTCCACCAAGGGCCCATCGGTCTTCCCCCTGGCACCCTCCTCCAAGAGCACCTCTGGG
     A  S  T  K  G  P  S  V  F  P  L  A  P  S  S  K  S  T  S  G
 481 GGCACAGCGGCCCTGGGCTGCCTGGTCAAGGACTACTTCCCCGAACCGGTGACGGTGTCG
     G  T  A  A  L  G  C  L  V  K  D  Y  F  P  E  P  V  T  V  S
 541 TGGAACTCAGGCGCCCTGACCAGCGGCGTGCACACCTTCCCGGCTGTCCTACAGTCCTCA
     W  N  S  G  A  L  T  S  G  V  H  T  F  P  A  V  L  Q  S  S
 601 GGACTCTACTCCCTCAGCAGCGTGGTGACCGTGCCCTCCAGCAGCTTGGGCACCCAGACC
     G  L  Y  S  L  S  S  V  V  T  V  P  S  S  S  L  G  T  Q  T
 661 TACATCTGCAACGTGAATCACAAGCCCAGCAACACCAAGGTGGACAAGAAAGTTGAGCCC
     Y  I  C  N  V  N  H  K  P  S  N  T  K  V  D  K  K  V  E  P
 721 AAATCTTGTGACAAAACTCACACATGCCCACCGTGCCCAGCACCTGAACTCCTGGGGGGA
     K  S  C  D  K  T  H  T  C  P  P  C  P  A  P  E  L  L  G  G
 781 CCGTCAGTCTTCCTCTTCCCCCCAAAACCCAAGGACACCCTCATGATCTCCCGGACCCCT
     P  S  V  F  L  F  P  P  K  P  K  D  T  L  M  I  S  R  T  P
 841 GAGGTCACATGCGTGGTGGTGGACGTGAGCCACGAAGACCCTGAGGTCAAGTTCAACTGG
     E  V  T  C  V  V  V  D  V  S  H  E  D  P  E  V  K  F  N  W
 901 TACGTGGACGGCGTGGAGGTGCATAATGCCAAGACAAAGCCGCGGGAGGAGCAGTACAAC
     Y  V  D  G  V  E  V  H  N  A  K  T  K  P  R  E  E  Q  Y  N
 961 AGCACGTACCGTGTGGTCAGCGTCCTCACCGTCCTGCACCAGGACTGGCTGAATGGCAAG
     S  T  Y  R  V  V  S  V  L  T  V  L  H  Q  D  W  L  N  G  K
1021 GAGTACAAGTGCAAGGTCTCCAACAAAGCCCTCCCAGCCCCCATCGAGAAAACCATCTCC
     E  Y  K  C  K  V  S  N  K  A  L  P  A  P  I  E  K  T  I  S
1081 AAAGCCAAAGGGCAGCCCCGAGAACCACAGGTGTACACCCTGCCCCCATCCCGGGATGAG
     K  A  K  G  Q  P  R  E  P  Q  V  Y  T  L  P  P  S  R  D  E
1141 CTGACCAAGAACCAGGTCAGCCTGACCTGCCTGGTCAAAGGCTTCTATCCCAGCGACATC
     L  T  K  N  Q  V  S  L  T  C  L  V  K  G  F  Y  P  S  D  I
1201 GCCGTGGAGTGGGAGAGCAATGGGCAGCCGGAGAACAACTACAAGACCACGCCTCCCGTG
     A  V  E  W  E  S  N  G  Q  P  E  N  N  Y  K  T  T  P  P  V
1261 CTGGACTCCGACGGCTCCTTCTTCCTCTACAGCAAGCTCACCGTGGACAAGAGCAGGTGG
     L  D  S  D  G  S  F  F  L  Y  S  K  L  T  V  D  K  S  R  W
1321 CAGCAGGGGAACGTCTTCTCATGCTCCGTGATGCATGAGGCTCTGCACAACCACTACACG
     Q  Q  G  N  V  F  S  C  S  V  M  H  E  A  L  H  N  H  Y  T
1381 CAGAAGAGCCTCTCCCTGTCTCCGGGTAAATGA
     Q  K  S  L  S  L  S  P  G  K  *
```

Fig. 25

```
   1 ATGGGTTGGAGCTGTATCATCTTCTTTCTGGTAGCAACAGCTACAGGCGTGCACTCCCAA
     M  G  W  S  C  I  I  F  F  L  V  A  T  A  T  G  V  H  S  Q
  61 GTCCAGCTGGTGCAGTCTGGGGCTGAAGTGAAGAAGCCTGGGGCCTCAGTGAAAGTCTCC
     V  Q  L  V  Q  S  G  A  E  V  K  K  P  G  A  S  V  K  V  S
 121 TGCAAGGGTTCCGGCTACACATTCACTGATTATGCTATGCACTGGGTGCGACAGGCCCCT
     C  K  G  S  G  Y  T  F  T  D  Y  A  M  H  W  V  R  Q  A  P
 181 GGACAAGGCCTGGAGTGGATTGGAGTTATTAGTACTTACTATGGTAATACAAACTACAAC
     G  Q  G  L  E  W  I  G  V  I  S  T  Y  Y  G  N  T  N  Y  N
 241 CAGAAGTTTAAGGGCAAGGCCACAATGACTGTCGACAAATCCACCAGCACAGCCTATATG
     Q  K  F  K  G  K  A  T  M  T  V  D  K  S  T  S  T  A  Y  M
 301 GAACTTAGGAGCTTGAGATCTGACGATACTGCCGTGTATTACTGTGCAAGAGGAGGATTG
     E  L  R  S  L  R  S  D  D  T  A  V  Y  Y  C  A  R  G  G  L
 361 CGAGAGTATTACTATGCTATGGACTACTGGGGTCAAGGAACCATGGTCACCGTCTCCTCA
     R  E  Y  Y  Y  A  M  D  Y  W  G  Q  G  T  M  V  T  V  S  S
 421 GCCTCCACCAAGGGCCCATCGGTCTTCCCCCTGGCACCCTCCTCCAAGAGCACCTCTGGG
     A  S  T  K  G  P  S  V  F  P  L  A  P  S  S  K  S  T  S  G
 481 GGCACAGCGGCCCTGGGCTGCCTGGTCAAGGACTACTTCCCCGAACCGGTGACGGTGTCG
     G  T  A  A  L  G  C  L  V  K  D  Y  F  P  E  P  V  T  V  S
 541 TGGAACTCAGGCGCCCTGACCAGCGGCGTGCACACCTTCCCGGCTGTCCTACAGTCCTCA
     W  N  S  G  A  L  T  S  G  V  H  T  F  P  A  V  L  Q  S  S
 601 GGACTCTACTCCCTCAGCAGCGTGGTGACCGTGCCCTCCAGCAGCTTGGGCACCCAGACC
     G  L  Y  S  L  S  S  V  V  T  V  P  S  S  S  L  G  T  Q  T
 661 TACATCTGCAACGTGAATCACAAGCCCAGCAACACCAAGGTGGACAAGAAAGTTGAGCCC
     Y  I  C  N  V  N  H  K  P  S  N  T  K  V  D  K  K  V  E  P
 721 AAATCTTGTGACAAAACTCACACATGCCCACCGTGCCCAGCACCTGAACTCCTGGGGGGA
     K  S  C  D  K  T  H  T  C  P  P  C  P  A  P  E  L  L  G  G
 781 CCGTCAGTCTTCCTCTTCCCCCCAAAACCCAAGGACACCCTCATGATCTCCCGGACCCCT
     P  S  V  F  L  F  P  P  K  P  K  D  T  L  M  I  S  R  T  P
 841 GAGGTCACATGCGTGGTGGTGGACGTGAGCCACGAAGACCCTGAGGTCAAGTTCAACTGG
     E  V  T  C  V  V  V  D  V  S  H  E  D  P  E  V  K  F  N  W
 901 TACGTGGACGGCGTGGAGGTGCATAATGCCAAGACAAAGCCGCGGGAGGAGCAGTACAAC
     Y  V  D  G  V  E  V  H  N  A  K  T  K  P  R  E  E  Q  Y  N
 961 AGCACGTACCGTGTGGTCAGCGTCCTCACCGTCCTGCACCAGGACTGGCTGAATGGCAAG
     S  T  Y  R  V  V  S  V  L  T  V  L  H  Q  D  W  L  N  G  K
1021 GAGTACAAGTGCAAGGTCTCCAACAAAGCCCTCCCAGCCCCCATCGAGAAAACCATCTCC
     E  Y  K  C  K  V  S  N  K  A  L  P  A  P  I  E  K  T  I  S
1081 AAAGCCAAAGGGCAGCCCCGAGAACCACAGGTGTACACCCTGCCCCCATCCCGGGATGAG
     K  A  K  G  Q  P  R  E  P  Q  V  Y  T  L  P  P  S  R  D  E
1141 CTGACCAAGAACCAGGTCAGCCTGACCTGCCTGGTCAAAGGCTTCTATCCCAGCGACATC
     L  T  K  N  Q  V  S  L  T  C  L  V  K  G  F  Y  P  S  D  I
1201 GCCGTGGAGTGGGAGAGCAATGGGCAGCCGGAGAACAACTACAAGACCACGCCTCCCGTG
     A  V  E  W  E  S  N  G  Q  P  E  N  N  Y  K  T  T  P  P  V
1261 CTGGACTCCGACGGCTCCTTCTTCCTCTACAGCAAGCTCACCGTGGACAAGAGCAGGTGG
     L  D  S  D  G  S  F  F  L  Y  S  K  L  T  V  D  K  S  R  W
1321 CAGCAGGGGAACGTCTTCTCATGCTCCGTGATGCATGAGGCTCTGCACAACCACTACACG
     Q  Q  G  N  V  F  S  C  S  V  M  H  E  A  L  H  N  H  Y  T
1381 CAGAAGAGCCTCTCCCTGTCTCCGGGTAAATGA
     Q  K  S  L  S  L  S  P  G  K  •
```

Fig. 27
(A)
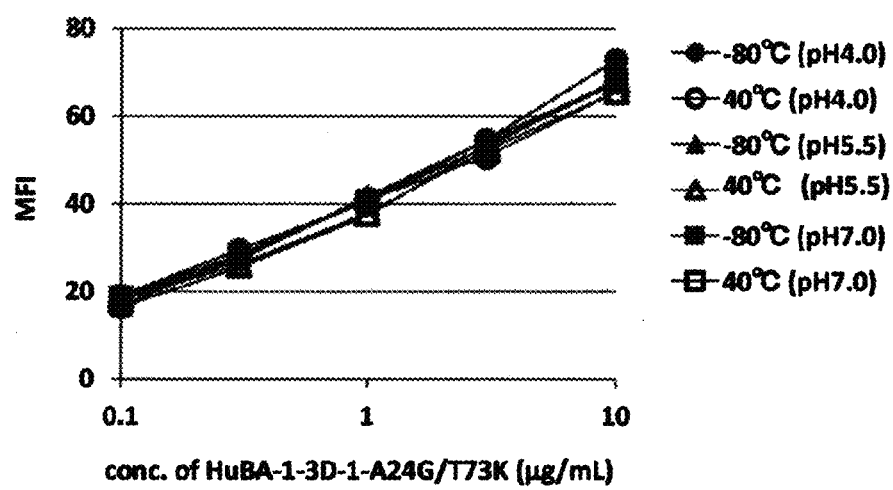
(B)
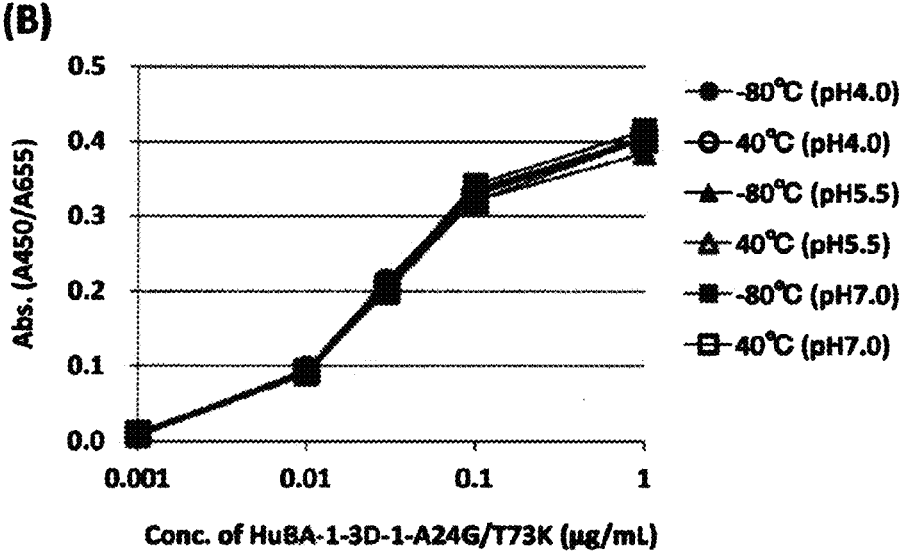

Fig. 29
A
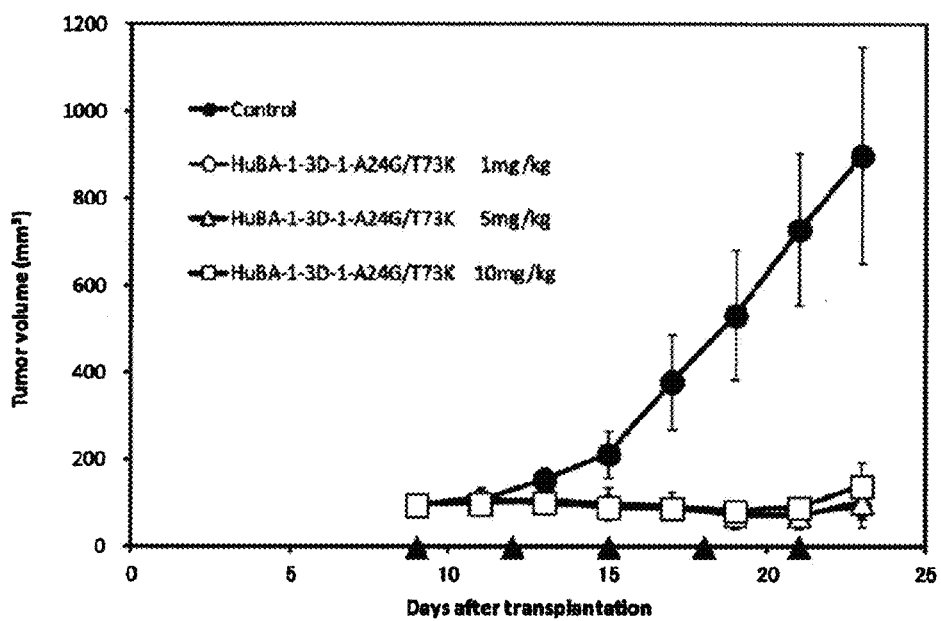
B
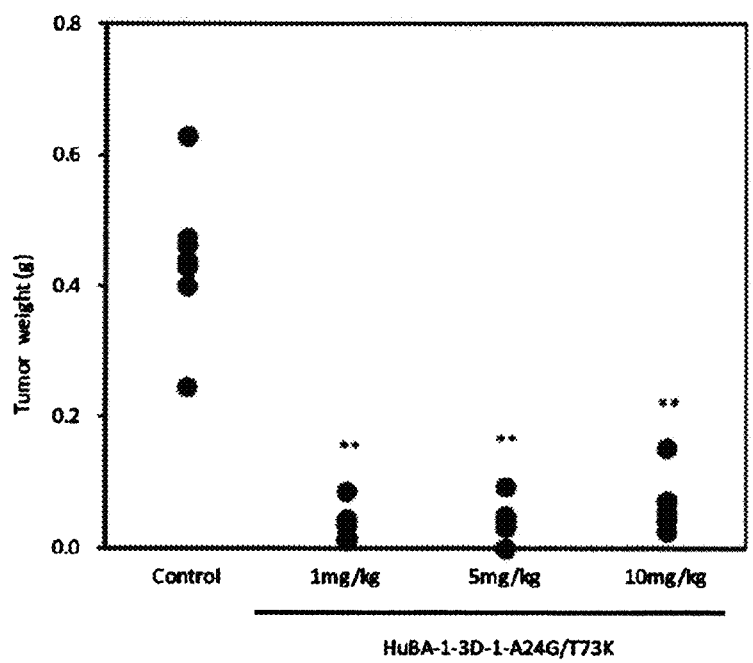

Fig. 30
A
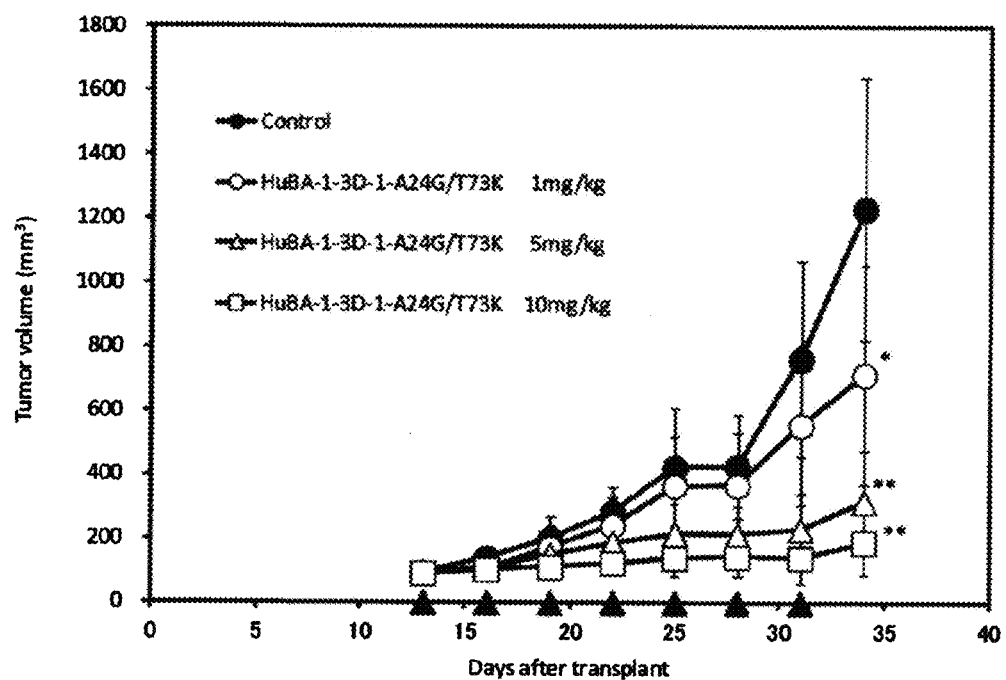
B
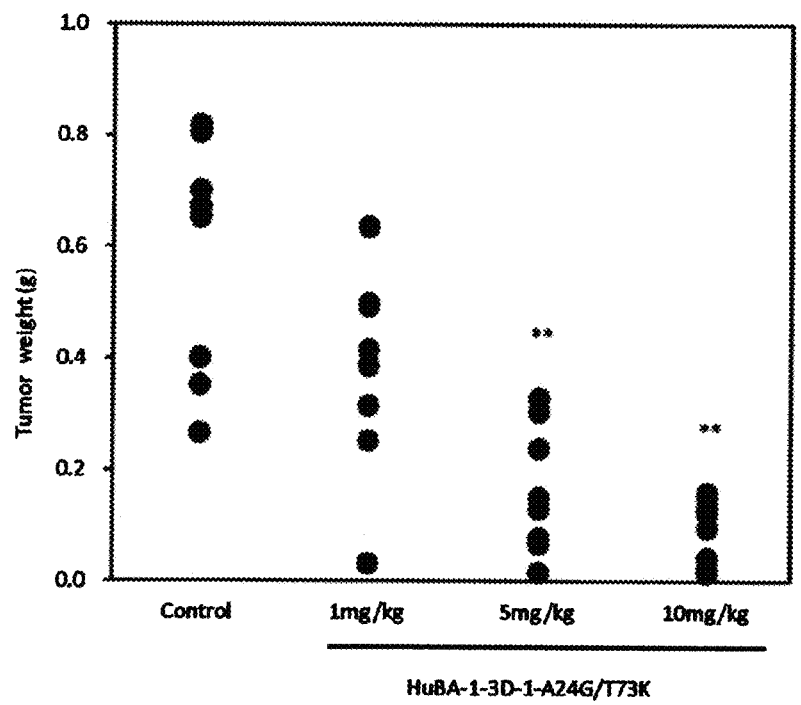

Fig. 32
A
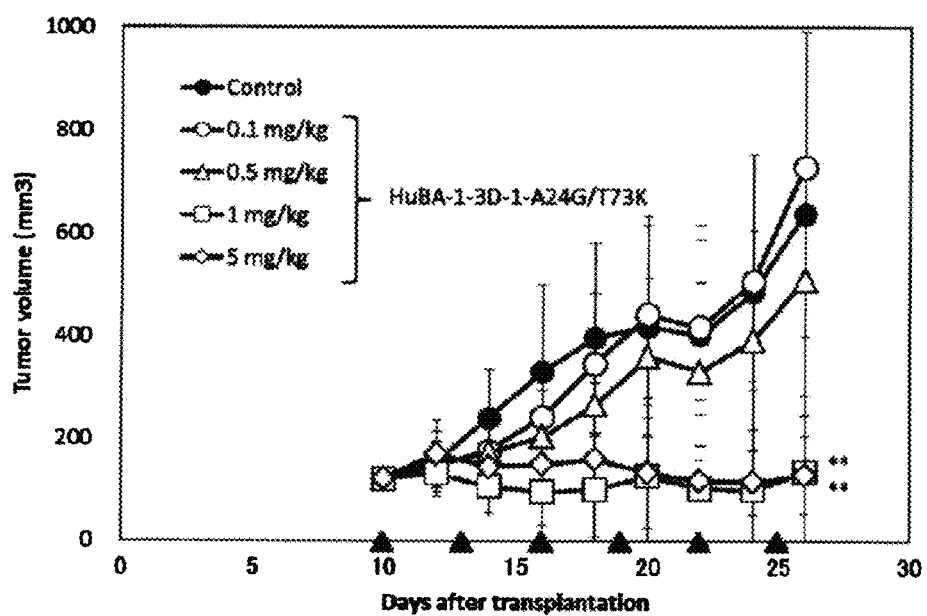
B
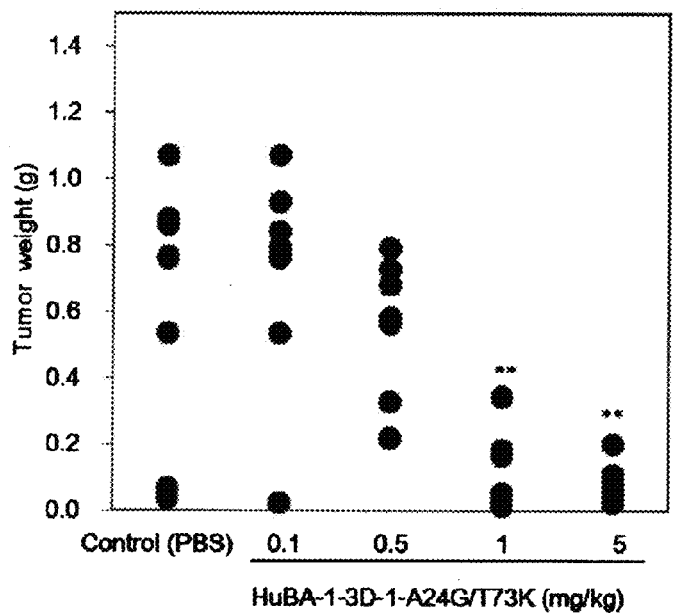

Fig. 33
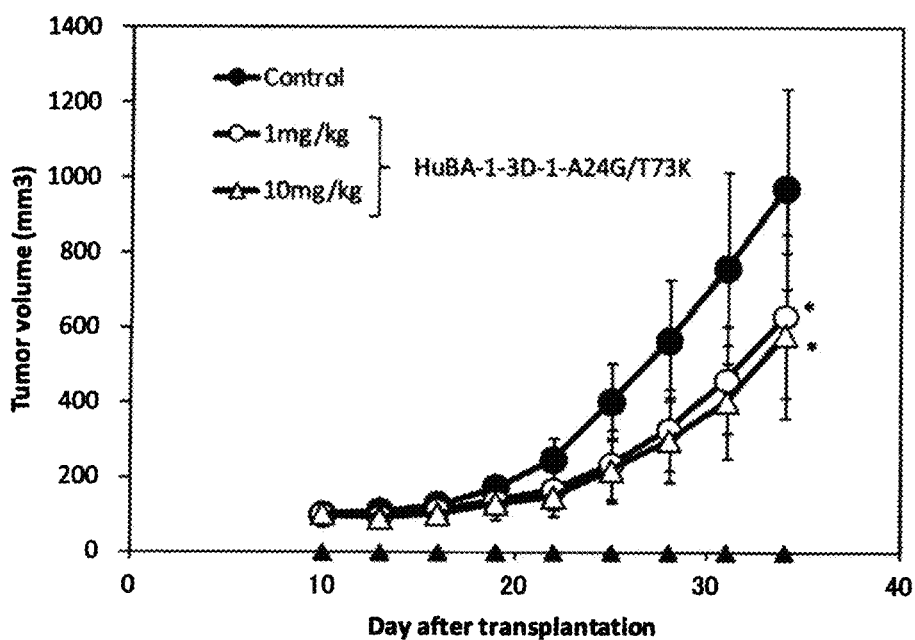
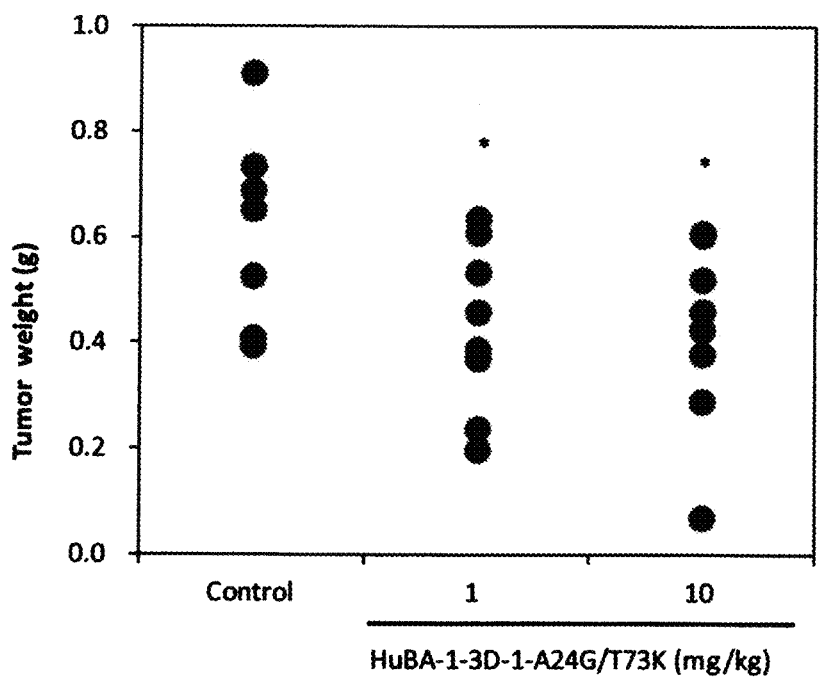

SEQUENCE LISTING

```
<160> NUMBER OF SEQ ID NOS: 89

<210> SEQ ID NO 1
<211> LENGTH: 1532
<212> TYPE: DNA
<213> ORGANISM: Homo sapiens
<220> FEATURE:
<221> NAME/KEY: CDS
<222> LOCATION: (154)..(1305)

<400> SEQUENCE: 1
gagagcgcag cgcgcagccc ggtgcagccc tggctttccc ctcgctgcgc gcccgcgccc      60
cctttcgcgt ccgcaaccag aagcccagtg cggcgccagg agccggaccc cgcgcccgca     120
cgctcccggg accgcgaccc cggccgccca gag atg acc gcg acc gaa gcc ctc      174
                                    Met Thr Ala Thr Glu Ala Leu
                                    1               5 ctg cgc gtc ctc ttg ctc ctg gct ttc ggc cac agc acc tat ggg           222
Leu Arg Val Leu Leu Leu Leu Ala Phe Gly His Ser Thr Tyr Gly
        10                  15                  20 gct gaa tgc ttc ccg gcc tgc aac ccc caa aat gga ttc tgc gag gat       270
Ala Glu Cys Phe Pro Ala Cys Asn Pro Gln Asn Gly Phe Cys Glu Asp
 25                  30                  35 gac aat gtt tgc agg tgc cag cct ggc tgg cag ggt ccc ctt tgt gac       318
Asp Asn Val Cys Arg Cys Gln Pro Gly Trp Gln Gly Pro Leu Cys Asp
40                  45                  50                  55 cag tgc gtg acc tct ccc ggc tgc ctt cac gga ctc tgt gga gaa ccc       366
Gln Cys Val Thr Ser Pro Gly Cys Leu His Gly Leu Cys Gly Glu Pro
                60                  65                  70 ggg cag tgc att tgc acc gac ggc tgg gac ggg gag ctc tgt gat aga       414
Gly Gln Cys Ile Cys Thr Asp Gly Trp Asp Gly Glu Leu Cys Asp Arg
            75                  80                  85 gat gtt cgg gcc tgc tcc tcg gcc ccc tgt gcc aac aac ggg acc tgc       462
Asp Val Arg Ala Cys Ser Ser Ala Pro Cys Ala Asn Asn Gly Thr Cys
        90                  95                 100 gtg agc ctg gac gat ggc ctc tat gaa tgc tcc tgt gcc ccc ggg tac       510
Val Ser Leu Asp Asp Gly Leu Tyr Glu Cys Ser Cys Ala Pro Gly Tyr
105                 110                 115 tcg gga aag gac tgc cag aaa aag gac ggg ccc tgt gtg atc aac ggc       558
Ser Gly Lys Asp Cys Gln Lys Lys Asp Gly Pro Cys Val Ile Asn Gly
120                 125                 130                 135 tcc ccc tgc cag cac gga ggc acc tgc gtg gat gat gag ggc cgg gcc       606
Ser Pro Cys Gln His Gly Gly Thr Cys Val Asp Asp Glu Gly Arg Ala
                140                 145                 150 tcc cat gcc tcc tgc ctg tgc cct ggc ttc tca ggc aat ttc tgc           654
Ser His Ala Ser Cys Leu Cys Pro Gly Phe Ser Gly Asn Phe Cys
            155                 160                 165 gag atc gtg gcc aac agc tgc acc ccc aac cca tgc gag aac gac ggc       702
```

```
                    Glu Ile Val Ala Asn Ser Cys Thr Pro Asn Pro Cys Glu Asn Asp Gly
                                    170                 175                 180 gtc tgc act gac att ggg ggc gac ttc cgc tgc cgg tgc cca gcc ggc                750
Val Cys Thr Asp Ile Gly Gly Asp Phe Arg Cys Arg Cys Pro Ala Gly
        185                 190                 195 ttc atc gac aag acc tgc agc cgc ccg gtg acc aac tgc gcc agc agc                798
Phe Ile Asp Lys Thr Cys Ser Arg Pro Val Thr Asn Cys Ala Ser Ser
200                 205                 210                 215 ccg tgc cag aac ggg ggc acc tgc ctg cag cac acc cag gtg agc tac                846
Pro Cys Gln Asn Gly Gly Thr Cys Leu Gln His Thr Gln Val Ser Tyr
                220                 225                 230 gag tgt ctg tgc aag ccc gag ttc aca ggt ctc acc tgt gtc aag aag                894
Glu Cys Leu Cys Lys Pro Glu Phe Thr Gly Leu Thr Cys Val Lys Lys
            235                 240                 245 cgc gcg ctg agc ccc cag cag gtc acc cgt ctg ccc agc ggc tat ggg                942
Arg Ala Leu Ser Pro Gln Gln Val Thr Arg Leu Pro Ser Gly Tyr Gly
        250                 255                 260 ctg gcc tac cgc ctg acc cct ggg gtg cac gag ctg ccg gtg cag cag                990
Leu Ala Tyr Arg Leu Thr Pro Gly Val His Glu Leu Pro Val Gln Gln
    265                 270                 275 ccg gag cac cgc atc ctg aag gtg tcc atg aaa gag ctc aac aag aaa               1038
Pro Glu His Arg Ile Leu Lys Val Ser Met Lys Glu Leu Asn Lys Lys
280                 285                 290                 295 acc cct ctc ctc acc gag ggc cag gcc atc tgc ttc acc atc ctg ggc               1086
Thr Pro Leu Leu Thr Glu Gly Gln Ala Ile Cys Phe Thr Ile Leu Gly
                300                 305                 310 gtg ctc acc agc ctg gtg gtg ctg ggc act gtg ggt atc gtc ttc ctc               1134
Val Leu Thr Ser Leu Val Val Leu Gly Thr Val Gly Ile Val Phe Leu
            315                 320                 325 aac aag tgc gag acc tgg gtg tcc aac ctg cgc tac aac cac atg ctg               1182
Asn Lys Cys Glu Thr Trp Val Ser Asn Leu Arg Tyr Asn His Met Leu
        330                 335                 340 cgg aag aag aag aac ctg ctg ctt cag tac aac agc ggg gag gac ctg               1230
Arg Lys Lys Lys Asn Leu Leu Leu Gln Tyr Asn Ser Gly Glu Asp Leu
    345                 350                 355 gcc gtc aac atc atc ttc ccc gag aag atc gac atg acc acc ttc agc               1278
Ala Val Asn Ile Ile Phe Pro Glu Lys Ile Asp Met Thr Thr Phe Ser
360                 365                 370                 375 aag gag gcc ggc gac gag gag atc taa gcagcgttcc cacagccccc                     1325
Lys Glu Ala Gly Asp Glu Glu Ile
                380 tctagattct tggagttccg cagagcttac tatacgcggt ctgtcctaat ctttgtggtg             1385 ttcgctatct cttgtgtcaa atctggtgaa cgctacgctt acatatattg tctttgtgct             1445 gctgtgtgac aaacgcaatg caaaaacaat cctctttctc tctcttaatg catgatacag             1505 aataataata agaatttcat ctttaaa                                                 1532

<210> SEQ ID NO 2
<211> LENGTH: 383
<212> TYPE: PRT
<213> ORGANISM: Homo sapiens

<400> SEQUENCE: 2

Met Thr Ala Thr Glu Ala Leu Leu Arg Val Leu Leu Leu Leu Leu Ala
1               5                   10                  15

Phe Gly His Ser Thr Tyr Gly Ala Glu Cys Phe Pro Ala Cys Asn Pro
            20                  25                  30

Gln Asn Gly Phe Cys Glu Asp Asp Asn Val Cys Arg Cys Gln Pro Gly
        35                  40                  45
```

```
Trp Gln Gly Pro Leu Cys Asp Gln Cys Val Thr Ser Pro Gly Cys Leu
 50                  55                  60
His Gly Leu Cys Gly Glu Pro Gly Gln Cys Ile Cys Thr Asp Gly Trp
 65                  70                  75                  80
Asp Gly Glu Leu Cys Asp Arg Asp Val Arg Ala Cys Ser Ser Ala Pro
                 85                  90                  95
Cys Ala Asn Asn Gly Thr Cys Val Ser Leu Asp Asp Gly Leu Tyr Glu
            100                 105                 110
Cys Ser Cys Ala Pro Gly Tyr Ser Gly Lys Asp Cys Gln Lys Lys Asp
        115                 120                 125
Gly Pro Cys Val Ile Asn Gly Ser Pro Cys Gln His Gly Gly Thr Cys
    130                 135                 140
Val Asp Asp Glu Gly Arg Ala Ser His Ala Ser Cys Leu Cys Pro Pro
145                 150                 155                 160
Gly Phe Ser Gly Asn Phe Cys Glu Ile Val Ala Asn Ser Cys Thr Pro
                165                 170                 175
Asn Pro Cys Glu Asn Asp Gly Val Cys Thr Asp Ile Gly Gly Asp Phe
            180                 185                 190
Arg Cys Arg Cys Pro Ala Gly Phe Ile Asp Lys Thr Cys Ser Arg Pro
        195                 200                 205
Val Thr Asn Cys Ala Ser Ser Pro Cys Gln Asn Gly Gly Thr Cys Leu
    210                 215                 220
Gln His Thr Gln Val Ser Tyr Glu Cys Leu Cys Lys Pro Glu Phe Thr
225                 230                 235                 240
Gly Leu Thr Cys Val Lys Lys Arg Ala Leu Ser Pro Gln Gln Val Thr
                245                 250                 255
Arg Leu Pro Ser Gly Tyr Gly Leu Ala Tyr Arg Leu Thr Pro Gly Val
            260                 265                 270
His Glu Leu Pro Val Gln Gln Pro Glu His Arg Ile Leu Lys Val Ser
        275                 280                 285
Met Lys Glu Leu Asn Lys Lys Thr Pro Leu Leu Thr Glu Gly Gln Ala
    290                 295                 300
Ile Cys Phe Thr Ile Leu Gly Val Leu Thr Ser Leu Val Val Leu Gly
305                 310                 315                 320
Thr Val Gly Ile Val Phe Leu Asn Lys Cys Glu Thr Trp Val Ser Asn
                325                 330                 335
Leu Arg Tyr Asn His Met Leu Arg Lys Lys Asn Leu Leu Leu Gln
            340                 345                 350
Tyr Asn Ser Gly Glu Asp Leu Ala Val Asn Ile Ile Phe Pro Glu Lys
        355                 360                 365
Ile Asp Met Thr Thr Phe Ser Lys Glu Ala Gly Asp Glu Glu Ile
    370                 375                 380

<210> SEQ ID NO 3
<211> LENGTH: 45
<212> TYPE: DNA
<213> ORGANISM: Artificial
<220> FEATURE:
<223> OTHER INFORMATION: Synthetic DNA

<400> SEQUENCE: 3
ctaatacgac tcactatagg gcaagcagtg gtatcaacgc agagt                45

<210> SEQ ID NO 4
<211> LENGTH: 22
```

```
<212> TYPE: DNA
<213> ORGANISM: Artificial
<220> FEATURE:
<223> OTHER INFORMATION: Synthetic DNA

<400> SEQUENCE: 4
ctaatacgac tcactatagg gc                                              22

<210> SEQ ID NO 5
<211> LENGTH: 23
<212> TYPE: DNA
<213> ORGANISM: Artificial
<220> FEATURE:
<223> OTHER INFORMATION: Synthetic DNA

<400> SEQUENCE: 5
aagcagtggt atcaacgcag agt                                             23

<210> SEQ ID NO 6
<211> LENGTH: 20
<212> TYPE: DNA
<213> ORGANISM: Artificial
<220> FEATURE:
<223> OTHER INFORMATION: Synthetic DNA

<400> SEQUENCE: 6
gccagtggat agaccgatgg                                                 20

<210> SEQ ID NO 7
<211> LENGTH: 21
<212> TYPE: DNA
<213> ORGANISM: Artificial
<220> FEATURE:
<223> OTHER INFORMATION: Synthetic DNA

<400> SEQUENCE: 7
gatggataca gttggtgcag c                                               21

<210> SEQ ID NO 8
<211> LENGTH: 33
<212> TYPE: DNA
<213> ORGANISM: Artificial
<220> FEATURE:
<223> OTHER INFORMATION: Synthetic DNA

<400> SEQUENCE: 8
gcaactagta ccaccatggg ttggagctgt atc                                  33

<210> SEQ ID NO 9
<211> LENGTH: 47
<212> TYPE: DNA
<213> ORGANISM: Artificial
<220> FEATURE:
<223> OTHER INFORMATION: Synthetic DNA

<400> SEQUENCE: 9
gggaagcttg agaggccatt cttacctgag gagacggtga ctgaggt                   47

<210> SEQ ID NO 10
<211> LENGTH: 33
<212> TYPE: DNA
<213> ORGANISM: Artificial
<220> FEATURE:
<223> OTHER INFORMATION: Synthetic DNA

<400> SEQUENCE: 10
```

```
gctgctagca ccaccatgga atcacagacc cag                                     33
```

<210> SEQ ID NO 11
<211> LENGTH: 46
<212> TYPE: DNA
<213> ORGANISM: Artificial
<220> FEATURE:
<223> OTHER INFORMATION: Synthetic DNA

<400> SEQUENCE: 11

```
gcagaattca gaaaagtgta cttacgtttc agctccagct tggtcc                       46
```

<210> SEQ ID NO 12
<211> LENGTH: 420
<212> TYPE: DNA
<213> ORGANISM: Mus musculus
<220> FEATURE:
<221> NAME/KEY: CDS
<222> LOCATION: (1)..(420)

<400> SEQUENCE: 12

```
atg ggt tgg agc tgt atc atc ttc ttt ctg gta gca aca gct aca ggt          48
Met Gly Trp Ser Cys Ile Ile Phe Phe Leu Val Ala Thr Ala Thr Gly
1               5                   10                  15 gtg cac tcc cag gtc cag ctg cag cag tct ggg cct gag ctg gtg agg          96
Val His Ser Gln Val Gln Leu Gln Gln Ser Gly Pro Glu Leu Val Arg
            20                  25                  30 cct ggg gtc tca gtg aag att tcc tgc aag ggt tcc ggc tac aca ttc          144
Pro Gly Val Ser Val Lys Ile Ser Cys Lys Gly Ser Gly Tyr Thr Phe
        35                  40                  45 act gat tat gct atg cac tgg gtg aag cag agt cat gca aag agt cta          192
Thr Asp Tyr Ala Met His Trp Val Lys Gln Ser His Ala Lys Ser Leu
    50                  55                  60 gag tgg att gga gtt att agt act tac tat ggt aat aca aac tac aac          240
Glu Trp Ile Gly Val Ile Ser Thr Tyr Tyr Gly Asn Thr Asn Tyr Asn
65                  70                  75                  80 cag aag ttt aag ggc aag gcc aca atg act gta gac aaa tcc tcc agc          288
Gln Lys Phe Lys Gly Lys Ala Thr Met Thr Val Asp Lys Ser Ser Ser
                85                  90                  95 aca gcc tat atg gaa ctt gcc aga ttg aca tct gag gat tct gcc atc          336
Thr Ala Tyr Met Glu Leu Ala Arg Leu Thr Ser Glu Asp Ser Ala Ile
            100                 105                 110 tat tac tgt gca aga gga gga tta cga gag tat tac tat gct atg gac          384
Tyr Tyr Cys Ala Arg Gly Gly Leu Arg Glu Tyr Tyr Tyr Ala Met Asp
        115                 120                 125 tac tgg ggt caa gga acc tca gtc acc gtc tcc tca                          420
Tyr Trp Gly Gln Gly Thr Ser Val Thr Val Ser Ser
    130                 135                 140
```

<210> SEQ ID NO 13
<211> LENGTH: 140
<212> TYPE: PRT
<213> ORGANISM: Mus musculus

<400> SEQUENCE: 13

```
Met Gly Trp Ser Cys Ile Ile Phe Phe Leu Val Ala Thr Ala Thr Gly
1               5                   10                  15

Val His Ser Gln Val Gln Leu Gln Gln Ser Gly Pro Glu Leu Val Arg
            20                  25                  30

Pro Gly Val Ser Val Lys Ile Ser Cys Lys Gly Ser Gly Tyr Thr Phe
        35                  40                  45

Thr Asp Tyr Ala Met His Trp Val Lys Gln Ser His Ala Lys Ser Leu
```

```
                    50                  55                  60
Glu Trp Ile Gly Val Ile Ser Thr Tyr Tyr Gly Asn Thr Asn Tyr Asn
 65                  70                  75                  80

Gln Lys Phe Lys Gly Lys Ala Thr Met Thr Val Asp Lys Ser Ser Ser
                 85                  90                  95

Thr Ala Tyr Met Glu Leu Ala Arg Leu Thr Ser Glu Asp Ser Ala Ile
            100                 105                 110

Tyr Tyr Cys Ala Arg Gly Gly Leu Arg Glu Tyr Tyr Tyr Ala Met Asp
        115                 120                 125

Tyr Trp Gly Gln Gly Thr Ser Val Thr Val Ser Ser
    130                 135                 140

<210> SEQ ID NO 14
<211> LENGTH: 363
<212> TYPE: DNA
<213> ORGANISM: Mus musculus
<220> FEATURE:
<221> NAME/KEY: CDS
<222> LOCATION: (1)..(363)

<400> SEQUENCE: 14 cag gtc cag ctg cag cag tct ggg cct gag ctg gtg agg cct ggg gtc      48
Gln Val Gln Leu Gln Gln Ser Gly Pro Glu Leu Val Arg Pro Gly Val
  1               5                  10                  15 tca gtg aag att tcc tgc aag ggt tcc ggc tac aca ttc act gat tat      96
Ser Val Lys Ile Ser Cys Lys Gly Ser Gly Tyr Thr Phe Thr Asp Tyr
             20                  25                  30 gct atg cac tgg gtg aag cag agt cat gca aag agt cta gag tgg att     144
Ala Met His Trp Val Lys Gln Ser His Ala Lys Ser Leu Glu Trp Ile
         35                  40                  45 gga gtt att agt act tac tat ggt aat aca aac tac aac cag aag ttt     192
Gly Val Ile Ser Thr Tyr Tyr Gly Asn Thr Asn Tyr Asn Gln Lys Phe
     50                  55                  60 aag ggc aag gcc aca atg act gta gac aaa tcc tcc agc aca gcc tat     240
Lys Gly Lys Ala Thr Met Thr Val Asp Lys Ser Ser Ser Thr Ala Tyr
 65                  70                  75                  80 atg gaa ctt gcc aga ttg aca tct gag gat tct gcc atc tat tac tgt     288
Met Glu Leu Ala Arg Leu Thr Ser Glu Asp Ser Ala Ile Tyr Tyr Cys
                 85                  90                  95 gca aga gga gga tta cga gag tat tac tat gct atg gac tac tgg ggt     336
Ala Arg Gly Gly Leu Arg Glu Tyr Tyr Tyr Ala Met Asp Tyr Trp Gly
            100                 105                 110 caa gga acc tca gtc acc gtc tcc tca                                 363
Gln Gly Thr Ser Val Thr Val Ser Ser
        115                 120

<210> SEQ ID NO 15
<211> LENGTH: 121
<212> TYPE: PRT
<213> ORGANISM: Mus musculus

<400> SEQUENCE: 15

Gln Val Gln Leu Gln Gln Ser Gly Pro Glu Leu Val Arg Pro Gly Val
  1               5                  10                  15

Ser Val Lys Ile Ser Cys Lys Gly Ser Gly Tyr Thr Phe Thr Asp Tyr
             20                  25                  30

Ala Met His Trp Val Lys Gln Ser His Ala Lys Ser Leu Glu Trp Ile
         35                  40                  45

Gly Val Ile Ser Thr Tyr Tyr Gly Asn Thr Asn Tyr Asn Gln Lys Phe
     50                  55                  60
```

```
Lys Gly Lys Ala Thr Met Thr Val Asp Lys Ser Ser Thr Ala Tyr
 65                  70                  75                  80

Met Glu Leu Ala Arg Leu Thr Ser Glu Asp Ser Ala Ile Tyr Tyr Cys
                 85                  90                  95

Ala Arg Gly Gly Leu Arg Glu Tyr Tyr Tyr Ala Met Asp Tyr Trp Gly
            100                 105                 110

Gln Gly Thr Ser Val Thr Val Ser Ser
            115                 120

<210> SEQ ID NO 16
<211> LENGTH: 5
<212> TYPE: PRT
<213> ORGANISM: Mus musculus

<400> SEQUENCE: 16

Asp Tyr Ala Met His
1               5

<210> SEQ ID NO 17
<211> LENGTH: 17
<212> TYPE: PRT
<213> ORGANISM: Mus musculus

<400> SEQUENCE: 17

Val Ile Ser Thr Tyr Tyr Gly Asn Thr Asn Tyr Asn Gln Lys Phe Lys
1               5                   10                  15

Gly

<210> SEQ ID NO 18
<211> LENGTH: 12
<212> TYPE: PRT
<213> ORGANISM: Mus musculus

<400> SEQUENCE: 18

Gly Gly Leu Arg Glu Tyr Tyr Tyr Ala Met Asp Tyr
1               5                   10

<210> SEQ ID NO 19
<211> LENGTH: 399
<212> TYPE: DNA
<213> ORGANISM: Mus musculus
<220> FEATURE:
<221> NAME/KEY: CDS
<222> LOCATION: (1)..(399)

<400> SEQUENCE: 19 atg gaa tca cag acc cag gtc ctc atg ttt ctt ctg ctc tgg gta tct      48
Met Glu Ser Gln Thr Gln Val Leu Met Phe Leu Leu Leu Trp Val Ser
1               5                   10                  15 ggt gcc tgt gca gac att gtg atg aca cag tct cca tcc tcc ctg gct      96
Gly Ala Cys Ala Asp Ile Val Met Thr Gln Ser Pro Ser Ser Leu Ala
                20                  25                  30 atg tca gta gga cag aag gtc act atg agc tgc aag tcc agt cag agc     144
Met Ser Val Gly Gln Lys Val Thr Met Ser Cys Lys Ser Ser Gln Ser
            35                  40                  45 ctt tta aat agt agc aat caa aag aac tat ttg gcc tgg tac cag cag     192
Leu Leu Asn Ser Ser Asn Gln Lys Asn Tyr Leu Ala Trp Tyr Gln Gln
        50                  55                  60 aaa cca gga cag tct cct aaa ctt ctg gta tac ttt gca tcc act agg     240
Lys Pro Gly Gln Ser Pro Lys Leu Leu Val Tyr Phe Ala Ser Thr Arg
65                  70                  75                  80
```

```
gaa tct ggg gtc cct gat cgc ttc ata ggc agt gga tct ggg aca gat        288
Glu Ser Gly Val Pro Asp Arg Phe Ile Gly Ser Gly Ser Gly Thr Asp
                85                  90                  95 ttc act ctt acc atc agc agt gtg cag gct gaa gac ctg gca gat tac        336
Phe Thr Leu Thr Ile Ser Ser Val Gln Ala Glu Asp Leu Ala Asp Tyr
            100                 105                 110 ttc tgt cag caa cat tat agc act cct ccc acg ttc ggt gct ggg acc        384
Phe Cys Gln Gln His Tyr Ser Thr Pro Pro Thr Phe Gly Ala Gly Thr
        115                 120                 125 aag ctg gag ctg aaa                                                    399
Lys Leu Glu Leu Lys
130

<210> SEQ ID NO 20
<211> LENGTH: 133
<212> TYPE: PRT
<213> ORGANISM: Mus musculus

<400> SEQUENCE: 20

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Met Ser Cys Lys Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Ser Pro Lys Leu Leu Val Tyr Phe Ala Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln His Tyr Ser Thr Pro Pro Thr Phe Gly Ala Gly Thr
        115                 120                 125

Lys Leu Glu Leu Lys
    130

<210> SEQ ID NO 21
<211> LENGTH: 339
<212> TYPE: DNA
<213> ORGANISM: Mus musculus
<220> FEATURE:
<221> NAME/KEY: CDS
<222> LOCATION: (1)..(339)

<400> SEQUENCE: 21 gac att gtg atg aca cag tct cca tcc tcc ctg gct atg tca gta gga         48
Asp Ile Val Met Thr Gln Ser Pro Ser Ser Leu Ala Met Ser Val Gly
1               5                   10                  15 cag aag gtc act atg agc tgc aag tcc agt cag agc ctt tta aat agt         96
Gln Lys Val Thr Met Ser Cys Lys Ser Ser Gln Ser Leu Leu Asn Ser
            20                  25                  30 agc aat caa aag aac tat ttg gcc tgg tac cag cag aaa cca gga cag        144
Ser Asn Gln Lys Asn Tyr Leu Ala Trp Tyr Gln Gln Lys Pro Gly Gln
        35                  40                  45 tct cct aaa ctt ctg gta tac ttt gca tcc act agg gaa tct ggg gtc        192
Ser Pro Lys Leu Leu Val Tyr Phe Ala Ser Thr Arg Glu Ser Gly Val
    50                  55                  60 cct gat cgc ttc ata ggc agt gga tct ggg aca gat ttc act ctt acc        240
Pro Asp Arg Phe Ile Gly Ser Gly Ser Gly Thr Asp Phe Thr Leu Thr
```

```
Pro Asp Arg Phe Ile Gly Ser Gly Ser Gly Thr Asp Phe Thr Leu Thr
 65                  70                  75                  80 atc agc agt gtg cag gct gaa gac ctg gca gat tac ttc tgt cag caa     288
Ile Ser Ser Val Gln Ala Glu Asp Leu Ala Asp Tyr Phe Cys Gln Gln
                 85                  90                  95 cat tat agc act cct ccc acg ttc ggt gct ggg acc aag ctg gag ctg     336
His Tyr Ser Thr Pro Pro Thr Phe Gly Ala Gly Thr Lys Leu Glu Leu
            100                 105                 110 aaa                                                                 339
Lys

<210> SEQ ID NO 22
<211> LENGTH: 113
<212> TYPE: PRT
<213> ORGANISM: Mus musculus

<400> SEQUENCE: 22

Asp Ile Val Met Thr Gln Ser Pro Ser Ser Leu Ala Met Ser Val Gly
 1               5                  10                  15

Gln Lys Val Thr Met Ser Cys Lys Ser Ser Gln Ser Leu Leu Asn Ser
                20                  25                  30

Ser Asn Gln Lys Asn Tyr Leu Ala Trp Tyr Gln Lys Pro Gly Gln
            35                  40                  45

Ser Pro Lys Leu Leu Val Tyr Phe Ala Ser Thr Arg Glu Ser Gly Val
     50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                 85                  90                  95

His Tyr Ser Thr Pro Pro Thr Phe Gly Ala Gly Thr Lys Leu Glu Leu
            100                 105                 110

Lys

<210> SEQ ID NO 23
<211> LENGTH: 17
<212> TYPE: PRT
<213> ORGANISM: Mus musculus

<400> SEQUENCE: 23

Lys Ser Ser Gln Ser Leu Leu Asn Ser Ser Asn Gln Lys Asn Tyr Leu
 1               5                  10                  15

Ala

<210> SEQ ID NO 24
<211> LENGTH: 7
<212> TYPE: PRT
<213> ORGANISM: Mus musculus

<400> SEQUENCE: 24

Phe Ala Ser Thr Arg Glu Ser
 1               5

<210> SEQ ID NO 25
<211> LENGTH: 9
<212> TYPE: PRT
<213> ORGANISM: Mus musculus

<400> SEQUENCE: 25

Gln Gln His Tyr Ser Thr Pro Pro Thr
 1               5
```

<210> SEQ ID NO 26
<211> LENGTH: 455
<212> TYPE: DNA
<213> ORGANISM: Artificial
<220> FEATURE:
<223> OTHER INFORMATION: Recombinant DNA

<400> SEQUENCE: 26

```
actagtacca ccatgggttg gagctgtatc atcttctttc tggtagcaac agctacaggt      60
gtgcactccc aggtccagct gcagcagtct gggcctgagc tggtgaggcc tggggtctca     120
gtgaagattt cctgcaaggg ttccggctac acattcactg attatgctat gcactgggtg     180
aagcagagtc atgcaaagag tctagagtgg attggagtta ttagtactta ctatggtaat     240
acaaactaca accagaagtt aagggcaagg ccacaatga ctgtagacaa atcctccagc      300
acagcctata tggaacttgc cagattgaca tctgaggatt ctgccatcta ttactgtgca     360
agaggaggat tacgagagta ttactatgct atggactact ggggtcaagg aacctcagtc     420
accgtctcct caggtaagaa tggcctctca agctt                                455
```

<210> SEQ ID NO 27
<211> LENGTH: 434
<212> TYPE: DNA
<213> ORGANISM: Artificial
<220> FEATURE:
<223> OTHER INFORMATION: Recombinant DNA

<400> SEQUENCE: 27

```
gctagcacca ccatggaatc acagacccag gtcctcatgt tcttctgct ctgggtatct       60
ggtgcctgtg cagacattgt gatgacacag tctccatcct ccctggctat gtcagtagga    120
cagaaggtca ctatgagctg caagtccagt cagagccttt aaatagtag caatcaaaag     180
aactatttgg cctggtacca gcagaaacca ggacagtctc ctaaacttct ggtatacttt     240
gcatccacta gggaatctgg ggtccctgat cgcttcatag gcagtggatc tgggacagat     300
ttcactctta ccatcagcag tgtgcaggct gaagacctgg cagattactt ctgtcagcaa    360
cattatagca ctcctcccac gttcggtgct gggaccaagc tggagctgaa acgtaagtac     420
acttttctga attc                                                       434
```

<210> SEQ ID NO 28
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 28

```
cag gtt cag ctg gtg cag tct gga gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc agc tat       96
Ser Val Lys Val Ser Cys Lys Ala Ser Gly Tyr Thr Phe Thr Ser Tyr
                20                  25                  30 ggt atc agc tgg gtg cga cag gcc cct gga caa ggg ctt gag tgg atg      144
Gly Ile Ser Trp Val Arg Gln Ala Pro Gly Gln Gly Leu Glu Trp Met
            35                  40                  45 gga tgg atc agc gct tac aat ggt aac aca aac tat gca cag aag ctc      192
Gly Trp Ile Ser Ala Tyr Asn Gly Asn Thr Asn Tyr Ala Gln Lys Leu
        50                  55                  60
```

```
cag ggc aga gtc acc atg acc aca gac aca tcc acg agc aca gcc tac      240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt      288
Met Glu Leu Arg Ser Leu Arg Ser Asp Asp Thr Ala Val Tyr Tyr Cys
                85                  90                  95 gcg aga tat att gcc tat gat gct ttt gat atc tgg ggc caa ggg aca      336
Ala Arg Tyr Ile Ala Tyr Asp Ala Phe Asp Ile Trp Gly Gln Gly Thr
            100                 105                 110 atg gtc acc gtc tct tca                                              354
Met Val Thr Val Ser Ser
        115
```

<210> SEQ ID NO 29
<211> LENGTH: 118
<212> TYPE: PRT
<213> ORGANISM: Homo sapiens

<400> SEQUENCE: 29

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Ile Ala Tyr Asp Ala Phe Asp Ile Trp Gly Gln Gly Thr
            100                 105                 110

Met Val Thr Val Ser Ser
        115
```

<210> SEQ ID NO 30
<211> LENGTH: 345
<212> TYPE: DNA
<213> ORGANISM: Homo sapiens
<220> FEATURE:
<221> NAME/KEY: CDS
<222> LOCATION: (1)..(345)

<400> SEQUENCE: 30

```
gac atc gtg atg acc cag tct cca gac tcc ctg gct gtg tct ctg ggc       48
Asp Ile Val Met Thr Gln Ser Pro Asp Ser Leu Ala Val Ser Leu Gly
1               5                   10                  15 gag agg gcc acc atc aac tgc aag tcc agc cag agt gtt tta tac agc       96
Glu Arg Ala Thr Ile Asn Cys Lys Ser Ser Gln Ser Val Leu Tyr Ser
            20                  25                  30 tcc aac aat aag aac tac tta gct tgg tac cag cag aaa cca gga cag      144
Ser Asn Asn Lys Asn Tyr Leu Ala Trp Tyr Gln Gln Lys Pro Gly Gln
        35                  40                  45 cct cct aag ctg ctc att tac tgg gca tct acc cgg gaa tcc ggg gtc      192
Pro Pro Lys Leu Leu Ile Tyr Trp Ala Ser Thr Arg Glu Ser Gly Val
    50                  55                  60 cct gac cga ttc agt ggc agc ggg tct ggg aca gat ttc act ctc acc      240
Pro Asp Arg Phe Ser Gly Ser Gly Ser Gly Thr Asp Phe Thr Leu Thr
65                  70                  75                  80
```

-continued

```
atc agc agc ctg cag gct gaa gat gtg gca gtt tat tac tgt cag caa        288
Ile Ser Ser Leu Gln Ala Glu Asp Val Ala Val Tyr Tyr Cys Gln Gln
                85                  90                  95 tat tat agt act cct tcg tac act ttt ggc cag ggg acc aag ctg gag        336
Tyr Tyr Ser Thr Pro Ser Tyr Thr Phe Gly Gln Gly Thr Lys Leu Glu
            100                 105                 110 atc aaa cga                                                            345
Ile Lys Arg
        115
```

<210> SEQ ID NO 31
<211> LENGTH: 115
<212> TYPE: PRT
<213> ORGANISM: Homo sapiens

<400> SEQUENCE: 31

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ser Tyr Thr Phe Gly Gln Gly Thr Lys Leu Glu
            100                 105                 110

Ile Lys Arg
        115
```

<210> SEQ ID NO 32
<211> LENGTH: 420
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(420)

<400> SEQUENCE: 32

```
atg ggt tgg agc tgt atc atc ttc ttt ctg gta gca aca gct aca ggc         48
Met Gly Trp Ser Cys Ile Ile Phe Phe Leu Val Ala Thr Ala Thr Gly
1               5                   10                  15 gtg cac tcc caa gtc cag ctg gtg cag tct ggg gct gaa gtg aag aag         96
Val His Ser Gln Val Gln Leu Val Gln Ser Gly Ala Glu Val Lys Lys
            20                  25                  30 cct ggg gcc tca gtg aaa gtc tcc tgc aag gct tcc ggc tac aca ttc        144
Pro Gly Ala Ser Val Lys Val Ser Cys Lys Ala Ser Gly Tyr Thr Phe
        35                  40                  45 act gat tat gct atg cac tgg gtg cga cag gcc cct gga caa ggc ctg        192
Thr Asp Tyr Ala Met His Trp Val Arg Gln Ala Pro Gly Gln Gly Leu
    50                  55                  60 gag tgg att gga gtt att agt act tac tat ggt aat aca aac tac aac        240
Glu Trp Ile Gly Val Ile Ser Thr Tyr Tyr Gly Asn Thr Asn Tyr Asn
65                  70                  75                  80 cag aag ttt aag ggc aag gcc aca atg act gtc gac aca tcc acc agc        288
```

```
                                                       Gln Lys Phe Lys Gly Lys Ala Thr Met Thr Val Asp Thr Ser Thr Ser
                                                                       85                  90                  95 aca gcc tat atg gaa ctt agg agc ttg aga tct gac gat act gcc gtg        336
Thr Ala Tyr Met Glu Leu Arg Ser Leu Arg Ser Asp Asp Thr Ala Val
            100                 105                 110 tat tac tgt gca aga gga gga ttg cga gag tat tac tat gct atg gac        384
Tyr Tyr Cys Ala Arg Gly Gly Leu Arg Glu Tyr Tyr Tyr Ala Met Asp
            115                 120                 125 tac tgg ggt caa gga acc atg gtc acc gtc tcc tca                        420
Tyr Trp Gly Gln Gly Thr Met Val Thr Val Ser Ser
130                 135                 140

<210> SEQ ID NO 33
<211> LENGTH: 140
<212> TYPE: PRT
<213> ORGANISM: Artificial
<220> FEATURE:
<223> OTHER INFORMATION: Synthetic Construct (Recombinant Protein)

<400> SEQUENCE: 33

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ala Met His Trp Val Arg Gln Ala Pro Gly Gln Gly Leu
    50                  55                  60

Glu Trp Ile Gly Val Ile Ser Thr Tyr Tyr Gly Asn Thr Asn Tyr Asn
65                  70                  75                  80

Gln Lys Phe Lys Gly Lys Ala Thr Met Thr Val Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Gly Gly Leu Arg Glu Tyr Tyr Tyr Ala Met Asp
            115                 120                 125

Tyr Trp Gly Gln Gly Thr Met Val Thr Val Ser Ser
130                 135                 140

<210> SEQ ID NO 34
<211> LENGTH: 363
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(363)

<400> SEQUENCE: 34 caa gtc cag ctg gtg cag tct ggg gct gaa gtg aag aag cct ggg gcc        48
Gln Val Gln Leu Val Gln Ser Gly Ala Glu Val Lys Lys Pro Gly Ala
1               5                   10                  15 tca gtg aaa gtc tcc tgc aag gct tcc ggc tac aca ttc act gat tat        96
Ser Val Lys Val Ser Cys Lys Ala Ser Gly Tyr Thr Phe Thr Asp Tyr
            20                  25                  30 gct atg cac tgg gtg cga cag gcc cct gga caa ggc ctg gag tgg att        144
Ala Met His Trp Val Arg Gln Ala Pro Gly Gln Gly Leu Glu Trp Ile
        35                  40                  45 gga gtt att agt act tac tat ggt aat aca aac tac aac cag aag ttt        192
Gly Val Ile Ser Thr Tyr Tyr Gly Asn Thr Asn Tyr Asn Gln Lys Phe
```

```
aag ggc aag gcc aca atg act gtc gac aca tcc acc agc aca gcc tat       240
Lys Gly Lys Ala Thr Met Thr Val Asp Thr Ser Thr Ser Thr Ala Tyr
 65                  70                  75                  80 atg gaa ctt agg agc ttg aga tct gac gat act gcc gtg tat tac tgt       288
Met Glu Leu Arg Ser Leu Arg Ser Asp Asp Thr Ala Val Tyr Tyr Cys
                 85                  90                  95 gca aga gga gga ttg cga gag tat tac tat gct atg gac tac tgg ggt       336
Ala Arg Gly Gly Leu Arg Glu Tyr Tyr Tyr Ala Met Asp Tyr Trp Gly
            100                 105                 110 caa gga acc atg gtc acc gtc tcc tca                                   363
Gln Gly Thr Met Val Thr Val Ser Ser
        115                 120
```

<210> SEQ ID NO 35
<211> LENGTH: 121
<212> TYPE: PRT
<213> ORGANISM: Artificial
<220> FEATURE:
<223> OTHER INFORMATION: Synthetic Construct (Recombinant Protein)

<400> SEQUENCE: 35

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
                 20                  25                  30

Ala Met His Trp Val Arg Gln Ala Pro Gly Gln Gly Leu Glu Trp Ile
             35                  40                  45

Gly Val Ile Ser Thr Tyr Tyr Gly Asn Thr Asn Tyr Asn Gln Lys Phe
 50                  55                  60

Lys Gly Lys Ala Thr Met Thr Val Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Gly Leu Arg Glu Tyr Tyr Tyr Ala Met Asp Tyr Trp Gly
            100                 105                 110

Gln Gly Thr Met Val Thr Val Ser Ser
        115                 120
```

<210> SEQ ID NO 36
<211> LENGTH: 456
<212> TYPE: DNA
<213> ORGANISM: Artificial
<220> FEATURE:
<223> OTHER INFORMATION: Recombinant DNA

<400> SEQUENCE: 36

```
actagtacca ccatgggttg agctgtatc atcttctttc tggtagcaac agctacaggc      60
gtgcactccc aagtccagct ggtgcagtct ggggctgaag tgaagaagcc tggggcctca    120
gtgaaagtct cctgcaaggc ttccggctac acattcactg attatgctat gcactgggtg    180
cgacaggccc ctggacaagg cctggagtgg attggagtta ttagtactta ctatggtaat    240
acaaactaca accagaagtt taagggcaag gccacaatga ctgtcgacac atccaccagc    300
acagcctata tggaacttag gagcttgaga tctgacgata ctgccgtgta ttactgtgca    360
agaggaggat tgcgagagta ttactatgct atggactact ggggtcaagg aaccatggtc    420
accgtctcct caggtaagat gggctttcct aagctt                              456
```

-continued

```
<210> SEQ ID NO 37
<211> LENGTH: 420
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(420)

<400> SEQUENCE: 37 atg ggt tgg agc tgt atc atc ttc ttt ctg gta gca aca gct aca ggc     48
Met Gly Trp Ser Cys Ile Ile Phe Phe Leu Val Ala Thr Ala Thr Gly
1               5                   10                  15 gtg cac tcc caa gtc cag ctg gtg cag tct ggg gct gaa gtg aag aag     96
Val His Ser Gln Val Gln Leu Val Gln Ser Gly Ala Glu Val Lys Lys
                20                  25                  30 cct ggg gcc tca gtg aaa gtc tcc tgc aag gct tcc ggc tac aca ttc    144
Pro Gly Ala Ser Val Lys Val Ser Cys Lys Ala Ser Gly Tyr Thr Phe
            35                  40                  45 act gat tat gct atg cac tgg gtg cga cag gcc cct gga caa ggc ctg    192
Thr Asp Tyr Ala Met His Trp Val Arg Gln Ala Pro Gly Gln Gly Leu
        50                  55                  60 gag tgg att gga gtt att agt act tac tat ggt aat aca aac tac aac    240
Glu Trp Ile Gly Val Ile Ser Thr Tyr Tyr Gly Asn Thr Asn Tyr Asn
65                  70                  75                  80 cag aag ttt aag ggc cga gcc aca atg act gtc gac aca tcc acc agc    288
Gln Lys Phe Lys Gly Arg Ala Thr Met Thr Val Asp Thr Ser Thr Ser
                85                  90                  95 aca gcc tat atg gaa ctt agg agc ttg aga tct gac gat act gcc gtg    336
Thr Ala Tyr Met Glu Leu Arg Ser Leu Arg Ser Asp Asp Thr Ala Val
                100                 105                 110 tat tac tgt gca aga gga gga ttg cga gag tat tac tat gct atg gac    384
Tyr Tyr Cys Ala Arg Gly Gly Leu Arg Glu Tyr Tyr Tyr Ala Met Asp
            115                 120                 125 tac tgg ggt caa gga acc atg gtc acc gtc tcc tca                    420
Tyr Trp Gly Gln Gly Thr Met Val Thr Val Ser Ser
        130                 135                 140

<210> SEQ ID NO 38
<211> LENGTH: 140
<212> TYPE: PRT
<213> ORGANISM: Artificial
<220> FEATURE:
<223> OTHER INFORMATION: Synthetic Construct (Recombinant Protein)

<400> SEQUENCE: 38

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asp Tyr Ala Met His Trp Val Arg Gln Ala Pro Gly Gln Gly Leu
        50                  55                  60

Glu Trp Ile Gly Val Ile Ser Thr Tyr Tyr Gly Asn Thr Asn Tyr Asn
65                  70                  75                  80

Gln Lys Phe Lys Gly Arg Ala Thr Met Thr Val Asp Thr Ser Thr Ser
                85                  90                  95

Thr Ala Tyr Met Glu Leu Arg Ser Leu Arg Ser Asp Asp Thr Ala Val
                100                 105                 110
```

```
                Tyr Tyr Cys Ala Arg Gly Gly Leu Arg Glu Tyr Tyr Ala Met Asp
                        115                 120                 125

Tyr Trp Gly Gln Gly Thr Met Val Thr Val Ser Ser
                130                 135                 140

<210> SEQ ID NO 39
<211> LENGTH: 363
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(363)

<400> SEQUENCE: 39 caa gtc cag ctg gtg cag tct ggg gct gaa gtg aag aag cct ggg gcc      48
Gln Val Gln Leu Val Gln Ser Gly Ala Glu Val Lys Lys Pro Gly Ala
1               5                   10                  15 tca gtg aaa gtc tcc tgc aag gct tcc ggc tac aca ttc act gat tat      96
Ser Val Lys Val Ser Cys Lys Ala Ser Gly Tyr Thr Phe Thr Asp Tyr
                20                  25                  30 gct atg cac tgg gtg cga cag gcc cct gga caa ggc ctg gag tgg att     144
Ala Met His Trp Val Arg Gln Ala Pro Gly Gln Gly Leu Glu Trp Ile
            35                  40                  45 gga gtt att agt act tac tat ggt aat aca aac tac aac cag aag ttt     192
Gly Val Ile Ser Thr Tyr Tyr Gly Asn Thr Asn Tyr Asn Gln Lys Phe
        50                  55                  60 aag ggc cga gcc aca atg act gtc gac aca tcc acc agc aca gcc tat     240
Lys Gly Arg Ala Thr Met Thr Val Asp Thr Ser Thr Ser Thr Ala Tyr
65                  70                  75                  80 atg gaa ctt agg agc ttg aga tct gac gat act gcc gtg tat tac tgt     288
Met Glu Leu Arg Ser Leu Arg Ser Asp Asp Thr Ala Val Tyr Tyr Cys
                85                  90                  95 gca aga gga gga ttg cga gag tat tac tat gct atg gac tac tgg ggt     336
Ala Arg Gly Gly Leu Arg Glu Tyr Tyr Tyr Ala Met Asp Tyr Trp Gly
            100                 105                 110 caa gga acc atg gtc acc gtc tcc tca                                 363
Gln Gly Thr Met Val Thr Val Ser Ser
        115                 120

<210> SEQ ID NO 40
<211> LENGTH: 121
<212> TYPE: PRT
<213> ORGANISM: Artificial
<220> FEATURE:
<223> OTHER INFORMATION: Synthetic Construct (Recombinant Protein)

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ala Met His Trp Val Arg Gln Ala Pro Gly Gln Gly Leu Glu Trp Ile
            35                  40                  45

Gly Val Ile Ser Thr Tyr Tyr Gly Asn Thr Asn Tyr Asn Gln Lys Phe
        50                  55                  60

Lys Gly Arg Ala Thr Met Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

Ala Arg Gly Gly Leu Arg Glu Tyr Tyr Tyr Ala Met Asp Tyr Trp Gly
            100                 105                 110

Gln Gly Thr Met Val Thr Val Ser Ser
        115                 120

<210> SEQ ID NO 41
<211> LENGTH: 456
<212> TYPE: DNA
<213> ORGANISM: Artificial
<220> FEATURE:
<223> OTHER INFORMATION: Recombinant DNA

<400> SEQUENCE: 41
actagtacca ccatgggttg gagctgtatc atcttctttc tggtagcaac agctacaggc      60
gtgcactccc aagtccagct ggtgcagtct ggggctgaag tgaagaagcc tggggcctca     120
gtgaaagtct cctgcaaggc ttccggctac acattcactg attatgctat gcactgggtg     180
cgacaggccc ctggacaagg cctggagtgg attggagtta ttagtactta ctatggtaat     240
acaaactaca accagaagtt taagggccga gccacaatga ctgtcgacac atccaccagc     300
acagcctata tggaacttag gagcttgaga tctgacgata ctgccgtgta ttactgtgca     360
agaggaggat tgcgagagta ttactatgct atggactact ggggtcaagg aaccatggtc     420
accgtctcct caggtaagat gggctttcct aagctt                               456

<210> SEQ ID NO 42
<211> LENGTH: 399
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(399)

<400> SEQUENCE: 42 atg gaa tca cag acc cag gtc ctc atg ttt ctt ctg ctc tgg gta tct       48
Met Glu Ser Gln Thr Gln Val Leu Met Phe Leu Leu Leu Trp Val Ser
1               5                   10                  15 ggt gcc tgt gca gac att gtc atg aca cag tct cca gac tcc ctg gct       96
Gly Ala Cys Ala Asp Ile Val Met Thr Gln Ser Pro Asp Ser Leu Ala
            20                  25                  30 gtg tca ctg gga gag agg gcc act atc aac tgc aag tcc agt cag agc      144
Val Ser Leu Gly Glu Arg Ala Thr Ile Asn Cys Lys Ser Ser Gln Ser
        35                  40                  45 ctt ctg aat agt agc aat caa aag aac tat ttg gcc tgg tac cag cag      192
Leu Leu Asn Ser Ser Asn Gln Lys Asn Tyr Leu Ala Trp Tyr Gln Gln
    50                  55                  60 aaa cca gga cag cct cct aaa ctt ctg gtc tac ttt gca tcc act agg      240
Lys Pro Gly Gln Pro Pro Lys Leu Leu Val Tyr Phe Ala Ser Thr Arg
65                  70                  75                  80 gaa tct ggg gtc cct gat cgc ttc agt ggc agt gga tct ggg aca gat      288
Glu Ser Gly Val Pro Asp Arg Phe Ser Gly Ser Gly Ser Gly Thr Asp
                85                  90                  95 ttc act ctt acc atc agc agt ctg cag gct gaa gat gtg gca gtt tac      336
Phe Thr Leu Thr Ile Ser Ser Leu Gln Ala Glu Asp Val Ala Val Tyr
            100                 105                 110 tac tgt cag caa cat tat agc act cct ccc aca ttc ggt cag ggg acc      384
Tyr Cys Gln Gln His Tyr Ser Thr Pro Pro Thr Phe Gly Gln Gly Thr
        115                 120                 125 aag ctg gag atc aaa                                                   399
Lys Leu Glu Ile Lys <210> SEQ ID NO 43
<211> LENGTH: 133
<212> TYPE: PRT
<213> ORGANISM: Artificial
<220> FEATURE:
<223> OTHER INFORMATION: Synthetic Construct (Recombinant Protein)

<400> SEQUENCE: 43

```
Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Pro Pro Lys Leu Leu Val Tyr Phe Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln His Tyr Ser Thr Pro Pro Thr Phe Gly Gln Gly Thr
        115                 120                 125

Lys Leu Glu Ile Lys
    130
```

<210> SEQ ID NO 44
<211> LENGTH: 339
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(339)

<400> SEQUENCE: 44

```
gac att gtc atg aca cag tct cca gac tcc ctg gct gtg tca ctg gga      48
Asp Ile Val Met Thr Gln Ser Pro Asp Ser Leu Ala Val Ser Leu Gly
1               5                   10                  15 gag agg gcc act atc aac tgc aag tcc agt cag agc ctt ctg aat agt      96
Glu Arg Ala Thr Ile Asn Cys Lys Ser Ser Gln Ser Leu Leu Asn Ser
            20                  25                  30 agc aat caa aag aac tat ttg gcc tgg tac cag cag aaa cca gga cag     144
Ser Asn Gln Lys Asn Tyr Leu Ala Trp Tyr Gln Gln Lys Pro Gly Gln
        35                  40                  45 cct cct aaa ctt ctg gtc tac ttt gca tcc act agg gaa tct ggg gtc     192
Pro Pro Lys Leu Leu Val Tyr Phe Ala Ser Thr Arg Glu Ser Gly Val
    50                  55                  60 cct gat cgc ttc agt ggc agt gga tct ggg aca gat ttc act ctt acc     240
Pro Asp Arg Phe Ser Gly Ser Gly Ser Gly Thr Asp Phe Thr Leu Thr
65                  70                  75                  80 atc agc agt ctg cag gct gaa gat gtg gca gtt tac tac tgt cag caa     288
Ile Ser Ser Leu Gln Ala Glu Asp Val Ala Val Tyr Tyr Cys Gln Gln
                85                  90                  95 cat tat agc act cct ccc aca ttc ggt cag ggg acc aag ctg gag atc     336
His Tyr Ser Thr Pro Pro Thr Phe Gly Gln Gly Thr Lys Leu Glu Ile
            100                 105                 110
``` aaa                                                                    339
Lys

<210> SEQ ID NO 45
<211> LENGTH: 113
<212> TYPE: PRT
<213> ORGANISM: Artificial
<220> FEATURE:
<223> OTHER INFORMATION: Synthetic Construct (Recombinant Protein)

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Asn Tyr Leu Ala Trp Tyr Gln Lys Pro Gly Gln
        35                  40                  45

Pro Pro Lys Leu Leu Val Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Thr Pro Pro Thr Phe Gly Gln Gly Thr Lys Leu Glu Ile
            100                 105                 110

Lys

<210> SEQ ID NO 46
<211> LENGTH: 435
<212> TYPE: DNA
<213> ORGANISM: Artificial
<220> FEATURE:
<223> OTHER INFORMATION: Recombinant DNA

<400> SEQUENCE: 46
gctagcacca ccatggaatc acagacccag gtcctcatgt tcttctgct ctgggtatct      60 ggtgcctgtg cagacattgt catgacacag tctccagact ccctggctgt gtcactggga     120
gagagggcca ctatcaactg caagtccagt cagagccttc tgaatagtag caatcaaaag    180
aactatttgg cctggtacca gcagaaacca ggacagcctc ctaaacttct ggtctacttt    240
gcatccacta gggaatctgg ggtccctgat cgcttcagtg gcagtggatc tgggacagat    300
ttcactctta ccatcagcag tctgcaggct gaagatgtgg cagtttacta ctgtcagcaa    360
cattatagca ctcctcccac attcggtcag gggaccaagc tggagatcaa cgtaagtac    420 tttttttcg aattc                                                     435

<210> SEQ ID NO 47
<211> LENGTH: 24
<212> TYPE: DNA
<213> ORGANISM: Artificial
<220> FEATURE:
<223> OTHER INFORMATION: Synthetic DNA

<400> SEQUENCE: 47
gaaccgtcag atcgcctgga gacg                                           24

<210> SEQ ID NO 48
<211> LENGTH: 20
<212> TYPE: DNA

<213> ORGANISM: Artificial
<220> FEATURE:
<223> OTHER INFORMATION: Synthetic DNA

<400> SEQUENCE: 48
tgaaagatga gctggaggac          20

<210> SEQ ID NO 49
<211> LENGTH: 20
<212> TYPE: DNA
<213> ORGANISM: Artificial
<220> FEATURE:
<223> OTHER INFORMATION: Synthetic DNA

<400> SEQUENCE: 49
ctttcttgtc caccttggtg          20

<210> SEQ ID NO 50
<211> LENGTH: 19
<212> TYPE: DNA
<213> ORGANISM: Artificial
<220> FEATURE:
<223> OTHER INFORMATION: Synthetic DNA

<400> SEQUENCE: 50
gctgtcctac agtcctcag           19

<210> SEQ ID NO 51
<211> LENGTH: 18
<212> TYPE: DNA
<213> ORGANISM: Artificial
<220> FEATURE:
<223> OTHER INFORMATION: Synthetic DNA

<400> SEQUENCE: 51
acgtgccaag catcctcg            18

<210> SEQ ID NO 52
<211> LENGTH: 1413
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(1413)

<400> SEQUENCE: 52

```
atg ggt tgg agc tgt atc atc ttc ttt ctg gta gca aca gct aca ggt      48
Met Gly Trp Ser Cys Ile Ile Phe Phe Leu Val Ala Thr Ala Thr Gly
1               5                   10                  15 gtg cac tcc cag gtc cag ctg cag cag tct ggg cct gag ctg gtg agg      96
Val His Ser Gln Val Gln Leu Gln Gln Ser Gly Pro Glu Leu Val Arg
                20                  25                  30 cct ggg gtc tca gtg aag att tcc tgc aag ggt tcc ggc tac aca ttc     144
Pro Gly Val Ser Val Lys Ile Ser Cys Lys Gly Ser Gly Tyr Thr Phe
            35                  40                  45 act gat tat gct atg cac tgg gtg aag cag agt cat gca aag agt cta     192
Thr Asp Tyr Ala Met His Trp Val Lys Gln Ser His Ala Lys Ser Leu
        50                  55                  60 gag tgg att gga gtt att agt act tac tat ggt aat aca aac tac aac     240
Glu Trp Ile Gly Val Ile Ser Thr Tyr Tyr Gly Asn Thr Asn Tyr Asn
65                  70                  75                  80 cag aag ttt aag ggc aag gcc aca atg act gta gac aaa tcc tcc agc     288
Gln Lys Phe Lys Gly Lys Ala Thr Met Thr Val Asp Lys Ser Ser Ser
```

|  |  |  |  |  |  |  |  |  |  |  |  |  |  |  |  |
|---|---|---|---|---|---|---|---|---|---|---|---|---|---|---|---|
|  |  |  |  | 85 |  |  |  | 90 |  |  |  | 95 |  |  |  |
| aca | gcc | tat | atg | gaa | ctt | gcc | aga | ttg | aca | tct | gag | gat | tct | gcc | atc | 336 |
| Thr | Ala | Tyr | Met | Glu | Leu | Ala | Arg | Leu | Thr | Ser | Glu | Asp | Ser | Ala | Ile |  |
|  |  |  | 100 |  |  |  |  | 105 |  |  |  |  | 110 |  |  |  |
| tat | tac | tgt | gca | aga | gga | gga | tta | cga | gag | tat | tac | tat | gct | atg | gac | 384 |
| Tyr | Tyr | Cys | Ala | Arg | Gly | Gly | Leu | Arg | Glu | Tyr | Tyr | Tyr | Ala | Met | Asp |  |
|  |  | 115 |  |  |  |  | 120 |  |  |  |  | 125 |  |  |  |  |
| tac | tgg | ggt | caa | gga | acc | tca | gtc | acc | gtc | tcc | tca | gcc | tcc | acc | aag | 432 |
| Tyr | Trp | Gly | Gln | Gly | Thr | Ser | Val | Thr | Val | Ser | Ser | Ala | Ser | Thr | Lys |  |
| 130 |  |  |  |  | 135 |  |  |  |  | 140 |  |  |  |  |  |  |
| ggc | cca | tcg | gtc | ttc | ccc | ctg | gca | ccc | tcc | tcc | aag | agc | acc | tct | ggg | 480 |
| Gly | Pro | Ser | Val | Phe | Pro | Leu | Ala | Pro | Ser | Ser | Lys | Ser | Thr | Ser | Gly |  |
| 145 |  |  |  |  | 150 |  |  |  |  | 155 |  |  |  |  | 160 |  |
| ggc | aca | gcg | gcc | ctg | ggc | tgc | ctg | gtc | aag | gac | tac | ttc | ccc | gaa | ccg | 528 |
| Gly | Thr | Ala | Ala | Leu | Gly | Cys | Leu | Val | Lys | Asp | Tyr | Phe | Pro | Glu | Pro |  |
|  |  |  |  | 165 |  |  |  |  | 170 |  |  |  |  | 175 |  |  |
| gtg | acg | gtg | tcg | tgg | aac | tca | ggc | gcc | ctg | acc | agc | ggc | gtg | cac | acc | 576 |
| Val | Thr | Val | Ser | Trp | Asn | Ser | Gly | Ala | Leu | Thr | Ser | Gly | Val | His | Thr |  |
|  |  |  | 180 |  |  |  |  | 185 |  |  |  |  | 190 |  |  |  |
| ttc | ccg | gct | gtc | cta | cag | tcc | tca | gga | ctc | tac | tcc | ctc | agc | agc | gtg | 624 |
| Phe | Pro | Ala | Val | Leu | Gln | Ser | Ser | Gly | Leu | Tyr | Ser | Leu | Ser | Ser | Val |  |
|  |  | 195 |  |  |  |  | 200 |  |  |  |  | 205 |  |  |  |  |
| gtg | acc | gtg | ccc | tcc | agc | agc | ttg | ggc | acc | cag | acc | tac | atc | tgc | aac | 672 |
| Val | Thr | Val | Pro | Ser | Ser | Ser | Leu | Gly | Thr | Gln | Thr | Tyr | Ile | Cys | Asn |  |
| 210 |  |  |  |  | 215 |  |  |  |  | 220 |  |  |  |  |  |  |
| gtg | aat | cac | aag | ccc | agc | aac | acc | aag | gtg | gac | aag | aaa | gtt | gag | ccc | 720 |
| Val | Asn | His | Lys | Pro | Ser | Asn | Thr | Lys | Val | Asp | Lys | Lys | Val | Glu | Pro |  |
| 225 |  |  |  |  | 230 |  |  |  |  | 235 |  |  |  |  | 240 |  |
| aaa | tct | tgt | gac | aaa | act | cac | aca | tgc | cca | ccg | tgc | cca | gca | cct | gaa | 768 |
| Lys | Ser | Cys | Asp | Lys | Thr | His | Thr | Cys | Pro | Pro | Cys | Pro | Ala | Pro | Glu |  |
|  |  |  |  | 245 |  |  |  |  | 250 |  |  |  |  | 255 |  |  |
| ctc | ctg | ggg | gga | ccg | tca | gtc | ttc | ctc | ttc | ccc | cca | aaa | ccc | aag | gac | 816 |
| Leu | Leu | Gly | Gly | Pro | Ser | Val | Phe | Leu | Phe | Pro | Pro | Lys | Pro | Lys | Asp |  |
|  |  |  | 260 |  |  |  |  | 265 |  |  |  |  | 270 |  |  |  |
| acc | ctc | atg | atc | tcc | cgg | acc | cct | gag | gtc | aca | tgc | gtg | gtg | gtg | gac | 864 |
| Thr | Leu | Met | Ile | Ser | Arg | Thr | Pro | Glu | Val | Thr | Cys | Val | Val | Val | Asp |  |
|  |  | 275 |  |  |  |  | 280 |  |  |  |  | 285 |  |  |  |  |
| gtg | agc | cac | gaa | gac | cct | gag | gtc | aag | ttc | aac | tgg | tac | gtg | gac | ggc | 912 |
| Val | Ser | His | Glu | Asp | Pro | Glu | Val | Lys | Phe | Asn | Trp | Tyr | Val | Asp | Gly |  |
| 290 |  |  |  |  | 295 |  |  |  |  | 300 |  |  |  |  |  |  |
| gtg | gag | gtg | cat | aat | gcc | aag | aca | aag | ccg | cgg | gag | gag | cag | tac | aac | 960 |
| Val | Glu | Val | His | Asn | Ala | Lys | Thr | Lys | Pro | Arg | Glu | Glu | Gln | Tyr | Asn |  |
| 305 |  |  |  |  | 310 |  |  |  |  | 315 |  |  |  |  | 320 |  |
| agc | acg | tac | cgt | gtg | gtc | agc | gtc | ctc | acc | gtc | ctg | cac | cag | gac | tgg | 1008 |
| Ser | Thr | Tyr | Arg | Val | Val | Ser | Val | Leu | Thr | Val | Leu | His | Gln | Asp | Trp |  |
|  |  |  |  | 325 |  |  |  |  | 330 |  |  |  |  | 335 |  |  |
| ctg | aat | ggc | aag | gag | tac | aag | tgc | aag | gtc | tcc | aac | aaa | gcc | ctc | cca | 1056 |
| Leu | Asn | Gly | Lys | Glu | Tyr | Lys | Cys | Lys | Val | Ser | Asn | Lys | Ala | Leu | Pro |  |
|  |  |  | 340 |  |  |  |  | 345 |  |  |  |  | 350 |  |  |  |
| gcc | ccc | atc | gag | aaa | acc | atc | tcc | aaa | gcc | aaa | ggg | cag | ccc | cga | gaa | 1104 |
| Ala | Pro | Ile | Glu | Lys | Thr | Ile | Ser | Lys | Ala | Lys | Gly | Gln | Pro | Arg | Glu |  |
|  |  | 355 |  |  |  |  | 360 |  |  |  |  | 365 |  |  |  |  |
| cca | cag | gtg | tac | acc | ctg | ccc | cca | tcc | cgg | gat | gag | ctg | acc | aag | aac | 1152 |
| Pro | Gln | Val | Tyr | Thr | Leu | Pro | Pro | Ser | Arg | Asp | Glu | Leu | Thr | Lys | Asn |  |
| 370 |  |  |  |  | 375 |  |  |  |  | 380 |  |  |  |  |  |  |
| cag | gtc | agc | ctg | acc | tgc | ctg | gtc | aaa | ggc | ttc | tat | ccc | agc | gac | atc | 1200 |
| Gln | Val | Ser | Leu | Thr | Cys | Leu | Val | Lys | Gly | Phe | Tyr | Pro | Ser | Asp | Ile |  |
| 385 |  |  |  |  | 390 |  |  |  |  | 395 |  |  |  |  | 400 |  |
| gcc | gtg | gag | tgg | gag | agc | aat | ggg | cag | ccg | gag | aac | aac | tac | aag | acc | 1248 |

```
Ala Val Glu Trp Glu Ser Asn Gly Gln Pro Glu Asn Asn Tyr Lys Thr
                405                 410                 415 acg cct ccc gtg ctg gac tcc gac ggc tcc ttc ttc ctc tac agc aag      1296
Thr Pro Pro Val Leu Asp Ser Asp Gly Ser Phe Phe Leu Tyr Ser Lys
            420                 425                 430 ctc acc gtg gac aag agc agg tgg cag cag ggg aac gtc ttc tca tgc      1344
Leu Thr Val Asp Lys Ser Arg Trp Gln Gln Gly Asn Val Phe Ser Cys
        435                 440                 445 tcc gtg atg cat gag gct ctg cac aac cac tac acg cag aag agc ctc      1392
Ser Val Met His Glu Ala Leu His Asn His Tyr Thr Gln Lys Ser Leu
    450                 455                 460 tcc ctg tct ccg ggt aaa tga                                          1413
Ser Leu Ser Pro Gly Lys
465                 470

<210> SEQ ID NO 53
<211> LENGTH: 470
<212> TYPE: PRT
<213> ORGANISM: Artificial
<220> FEATURE:
<223> OTHER INFORMATION: Synthetic Construct (Recombinant Protein)

<400> SEQUENCE: 53

Met Gly Trp Ser Cys Ile Ile Phe Phe Leu Val Ala Thr Ala Thr Gly
1               5                   10                  15

Val His Ser Gln Val Gln Leu Gln Gln Ser Gly Pro Glu Leu Val Arg
            20                  25                  30

Pro Gly Val Ser Val Lys Ile Ser Cys Lys Gly Ser Gly Tyr Thr Phe
        35                  40                  45

Thr Asp Tyr Ala Met His Trp Val Lys Gln Ser His Ala Lys Ser Leu
    50                  55                  60

Glu Trp Ile Gly Val Ile Ser Thr Tyr Tyr Gly Asn Thr Asn Tyr Asn
65                  70                  75                  80

Gln Lys Phe Lys Gly Lys Ala Thr Met Thr Val Asp Lys Ser Ser Ser
                85                  90                  95

Thr Ala Tyr Met Glu Leu Ala Arg Leu Thr Ser Glu Asp Ser Ala Ile
            100                 105                 110

Tyr Tyr Cys Ala Arg Gly Gly Leu Arg Glu Tyr Tyr Ala Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270
```

```
Thr Leu Met Ile Ser Arg Thr Pro Glu Val Thr Cys Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 54
<211> LENGTH: 723
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(723)

<400> SEQUENCE: 54 atg gaa tca cag acc cag gtc ctc atg ttt ctt ctg ctc tgg gta tct     48
Met Glu Ser Gln Thr Gln Val Leu Met Phe Leu Leu Leu Trp Val Ser
1               5                   10                  15 ggt gcc tgt gca gac att gtg atg aca cag tct cca tcc tcc ctg gct    96
Gly Ala Cys Ala Asp Ile Val Met Thr Gln Ser Pro Ser Ser Leu Ala
            20                  25                  30 atg tca gta gga cag aag gtc act atg agc tgc aag tcc agt cag agc   144
Met Ser Val Gly Gln Lys Val Thr Met Ser Cys Lys Ser Ser Gln Ser
        35                  40                  45 ctt tta aat agt agc aat caa aag aac tat ttg gcc tgg tac cag cag   192
Leu Leu Asn Ser Ser Asn Gln Lys Asn Tyr Leu Ala Trp Tyr Gln Gln
    50                  55                  60 aaa cca gga cag tct cct aaa ctt ctg gta tac ttt gca tcc act agg   240
Lys Pro Gly Gln Ser Pro Lys Leu Leu Val Tyr Phe Ala Ser Thr Arg
65                  70                  75                  80 gaa tct ggg gtc cct gat cgc ttc ata ggc agt gga tct ggg aca gat   288
Glu Ser Gly Val Pro Asp Arg Phe Ile Gly Ser Gly Ser Gly Thr Asp
                85                  90                  95 ttc act ctt acc atc agc agt gtg cag gct gaa gac ctg gca gat tac   336
Phe Thr Leu Thr Ile Ser Ser Val Gln Ala Glu Asp Leu Ala Asp Tyr
```

```
ttc tgt cag caa cat tat agc act cct ccc acg ttc ggt gct ggg acc        384
Phe Cys Gln Gln His Tyr Ser Thr Pro Pro Thr Phe Gly Ala Gly Thr
        115                 120                 125 aag ctg gag ctg aaa cga act gtg gct gca cca tct gtc ttc atc ttc        432
Lys Leu Glu Leu Lys Arg Thr Val Ala Ala Pro Ser Val Phe Ile Phe
130                 135                 140 ccg cca tct gat gag cag ttg aaa tct gga act gcc tct gtt gtg tgc        480
Pro Pro Ser Asp Glu Gln Leu Lys Ser Gly Thr Ala Ser Val Val Cys
145                 150                 155                 160 ctg ctg aat aac ttc tat ccc aga gag gcc aaa gta cag tgg aag gtg        528
Leu Leu Asn Asn Phe Tyr Pro Arg Glu Ala Lys Val Gln Trp Lys Val
                165                 170                 175 gat aac gcc ctc caa tcg ggt aac tcc cag gag agt gtc aca gag cag        576
Asp Asn Ala Leu Gln Ser Gly Asn Ser Gln Glu Ser Val Thr Glu Gln
            180                 185                 190 gac agc aag gac agc acc tac agc ctc agc agc acc ctg acg ctg agc        624
Asp Ser Lys Asp Ser Thr Tyr Ser Leu Ser Ser Thr Leu Thr Leu Ser
        195                 200                 205 aaa gca gac tac gag aaa cac aaa gtc tac gcc tgc gaa gtc acc cat        672
Lys Ala Asp Tyr Glu Lys His Lys Val Tyr Ala Cys Glu Val Thr His
210                 215                 220 cag ggc ctg agc tcg ccc gtc aca aag agc ttc aac agg gga gag tgt        720
Gln Gly Leu Ser Ser Pro Val Thr Lys Ser Phe Asn Arg Gly Glu Cys
225                 230                 235                 240 tag                                                                    723

<210> SEQ ID NO 55
<211> LENGTH: 240
<212> TYPE: PRT
<213> ORGANISM: Artificial
<220> FEATURE:
<223> OTHER INFORMATION: Synthetic Construct (Recombinant Protein)

<400> SEQUENCE: 55

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Met Ser Cys Lys Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Ser Pro Lys Leu Leu Val Tyr Phe Ala Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln His Tyr Ser Thr Pro Pro Thr Phe Gly Ala Gly Thr
        115                 120                 125

Lys Leu Glu Leu Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175
```

```
Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 56
<211> LENGTH: 1413
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(1413)

<400> SEQUENCE: 56 atg ggt tgg agc tgt atc atc ttc ttt ctg gta gca aca gct aca ggc      48
Met Gly Trp Ser Cys Ile Ile Phe Phe Leu Val Ala Thr Ala Thr Gly
1               5                   10                  15 gtg cac tcc caa gtc cag ctg gtg cag tct ggg gct gaa gtg aag aag      96
Val His Ser Gln Val Gln Leu Val Gln Ser Gly Ala Glu Val Lys Lys
            20                  25                  30 cct ggg gcc tca gtg aaa gtc tcc tgc aag gct tcc ggc tac aca ttc     144
Pro Gly Ala Ser Val Lys Val Ser Cys Lys Ala Ser Gly Tyr Thr Phe
        35                  40                  45 act gat tat gct atg cac tgg gtg cga cag gcc cct gga caa ggc ctg     192
Thr Asp Tyr Ala Met His Trp Val Arg Gln Ala Pro Gly Gln Gly Leu
    50                  55                  60 gag tgg att gga gtt att agt act tac tat ggt aat aca aac tac aac     240
Glu Trp Ile Gly Val Ile Ser Thr Tyr Tyr Gly Asn Thr Asn Tyr Asn
65                  70                  75                  80 cag aag ttt aag ggc aag gcc aca atg act gtc gac aca tcc acc agc     288
Gln Lys Phe Lys Gly Lys Ala Thr Met Thr Val Asp Thr Ser Thr Ser
                85                  90                  95 aca gcc tat atg gaa ctt agg agc ttg aga tct gac gat act gcc gtg     336
Thr Ala Tyr Met Glu Leu Arg Ser Leu Arg Ser Asp Asp Thr Ala Val
            100                 105                 110 tat tac tgt gca aga gga gga ttg cga gag tat tac tat gct atg gac     384
Tyr Tyr Cys Ala Arg Gly Gly Leu Arg Glu Tyr Tyr Tyr Ala Met Asp
        115                 120                 125 tac tgg ggt caa gga acc atg gtc acc gtc tcc tca gcc tcc acc aag     432
Tyr Trp Gly Gln Gly Thr Met Val Thr Val Ser Ser Ala Ser Thr Lys
    130                 135                 140 ggc cca tcg gtc ttc ccc ctg gca ccc tcc tcc aag agc acc tct ggg     480
Gly Pro Ser Val Phe Pro Leu Ala Pro Ser Ser Lys Ser Thr Ser Gly
145                 150                 155                 160 ggc aca gcg gcc ctg ggc tgc ctg gtc aag gac tac ttc ccc gaa ccg     528
Gly Thr Ala Ala Leu Gly Cys Leu Val Lys Asp Tyr Phe Pro Glu Pro
                165                 170                 175 gtg acg gtg tcg tgg aac tca ggc gcc ctg acc agc ggc gtg cac acc     576
Val Thr Val Ser Trp Asn Ser Gly Ala Leu Thr Ser Gly Val His Thr
            180                 185                 190 ttc ccg gct gtc cta cag tcc tca gga ctc tac tcc ctc agc agc gtg     624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac     672
Val Thr Val Pro Ser Ser Ser Leu Gly Thr Gln Thr Tyr Ile Cys Asn
```

```
              210                 215                 220
gtg aat cac aag ccc agc aac acc aag gtg gac aag aaa gtt gag ccc      720
Val Asn His Lys Pro Ser Asn Thr Lys Val Asp Lys Lys Val Glu Pro
225                 230                 235                 240 aaa tct tgt gac aaa act cac aca tgc cca ccg tgc cca gca cct gaa      768
Lys Ser Cys Asp Lys Thr His Thr Cys Pro Pro Cys Pro Ala Pro Glu
                245                 250                 255 ctc ctg ggg gga ccg tca gtc ttc ctc ttc ccc cca aaa ccc aag gac      816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
    290                 295                 300 gtg gag gtg cat aat gcc aag aca aag ccg cgg gag gag cag tac aac      960
Val Glu Val His Asn Ala Lys Thr Lys Pro Arg Glu Glu Gln Tyr Asn
305                 310                 315                 320 agc acg tac cgt gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggg cag ccc cga gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gat gag ctg acc aag aac     1152
Pro Gln Val Tyr Thr Leu Pro Pro Ser Arg Asp Glu Leu Thr Lys Asn
    370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggg cag ccg gag aac aac tac aag acc     1248
Ala Val Glu Trp Glu Ser Asn Gly Gln Pro Glu Asn Asn Tyr Lys Thr
                405                 410                 415 acg cct ccc gtg ctg gac tcc gac ggc tcc ttc ttc ctc tac agc aag     1296
Thr Pro Pro Val Leu Asp Ser Asp Gly Ser Phe Phe Leu Tyr Ser Lys
            420                 425                 430 ctc acc gtg gac aag agc agg tgg cag cag ggg aac gtc ttc tca tgc     1344
Leu Thr Val Asp Lys Ser Arg Trp Gln Gln Gly Asn Val Phe Ser Cys
        435                 440                 445 tcc gtg atg cat gag gct ctg cac aac cac tac acg cag aag agc ctc     1392
Ser Val Met His Glu Ala Leu His Asn His Tyr Thr Gln Lys Ser Leu
    450                 455                 460 tcc ctg tct ccg ggt aaa tga                                         1413
Ser Leu Ser Pro Gly Lys
465                 470

<210> SEQ ID NO 57
<211> LENGTH: 470
<212> TYPE: PRT
<213> ORGANISM: Artificial
<220> FEATURE:
<223> OTHER INFORMATION: Synthetic Construct (Recombinant Protein)

<400> SEQUENCE: 57

Met Gly Trp Ser Cys Ile Ile Phe Phe Leu Val Ala Thr Ala Thr Gly
1               5                   10                  15
```

-continued

```
Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Asp Tyr Ala Met His Trp Val Arg Gln Ala Pro Gly Gln Gly Leu
     50                  55                  60

Glu Trp Ile Gly Val Ile Ser Thr Tyr Tyr Gly Asn Thr Asn Tyr Asn
 65                  70                  75                  80

Gln Lys Phe Lys Gly Lys Ala Thr Met Thr Val Asp Thr Ser Thr Ser
                 85                  90                  95

Thr Ala Tyr Met Glu Leu Arg Ser Leu Arg Ser Asp Asp Thr Ala Val
            100                 105                 110

Tyr Tyr Cys Ala Arg Gly Gly Leu Arg Glu Tyr Tyr Ala Met Asp
        115                 120                 125

Tyr Trp Gly Gln Gly Thr Met Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
```

```
                        435                 440                 445
Ser Val Met His Glu Ala Leu His Asn His Tyr Thr Gln Lys Ser Leu
    450                 455                 460

Ser Leu Ser Pro Gly Lys
465             470

<210> SEQ ID NO 58
<211> LENGTH: 1413
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(1413)

<400> SEQUENCE: 58 atg ggt tgg agc tgt atc atc ttc ttt ctg gta gca aca gct aca ggc      48
Met Gly Trp Ser Cys Ile Ile Phe Phe Leu Val Ala Thr Ala Thr Gly
1               5                   10                  15 gtg cac tcc caa gtc cag ctg gtg cag tct ggg gct gaa gtg aag aag      96
Val His Ser Gln Val Gln Leu Val Gln Ser Gly Ala Glu Val Lys Lys
            20                  25                  30 cct ggg gcc tca gtg aaa gtc tcc tgc aag gct tcc ggc tac aca ttc     144
Pro Gly Ala Ser Val Lys Val Ser Cys Lys Ala Ser Gly Tyr Thr Phe
        35                  40                  45 act gat tat gct atg cac tgg gtg cga cag gcc cct gga caa ggc ctg     192
Thr Asp Tyr Ala Met His Trp Val Arg Gln Ala Pro Gly Gln Gly Leu
    50                  55                  60 gag tgg att gga gtt att agt act tac tat ggt aat aca aac tac aac     240
Glu Trp Ile Gly Val Ile Ser Thr Tyr Tyr Gly Asn Thr Asn Tyr Asn
65                  70                  75                  80 cag aag ttt aag ggc cga gcc aca atg act gtc gac aca tcc acc agc     288
Gln Lys Phe Lys Gly Arg Ala Thr Met Thr Val Asp Thr Ser Thr Ser
                85                  90                  95 aca gcc tat atg gaa ctt agg agc ttg aga tct gac gat act gcc gtg     336
Thr Ala Tyr Met Glu Leu Arg Ser Leu Arg Ser Asp Asp Thr Ala Val
            100                 105                 110 tat tac tgt gca aga gga gga ttg cga gag tat tac tat gct atg gac     384
Tyr Tyr Cys Ala Arg Gly Gly Leu Arg Glu Tyr Tyr Tyr Ala Met Asp
        115                 120                 125 tac tgg ggt caa gga acc atg gtc acc gtc tcc tca gcc tcc acc aag     432
Tyr Trp Gly Gln Gly Thr Met Val Thr Val Ser Ser Ala Ser Thr Lys
    130                 135                 140 ggc cca tcg gtc ttc ccc ctg gca ccc tcc tcc aag agc acc tct ggg     480
Gly Pro Ser Val Phe Pro Leu Ala Pro Ser Ser Lys Ser Thr Ser Gly
145                 150                 155                 160 ggc aca gcg gcc ctg ggc tgc ctg gtc aag gac tac ttc ccc gaa ccg     528
Gly Thr Ala Ala Leu Gly Cys Leu Val Lys Asp Tyr Phe Pro Glu Pro
                165                 170                 175 gtg acg gtg tcg tgg aac tca ggc gcc ctg acc agc ggc gtg cac acc     576
Val Thr Val Ser Trp Asn Ser Gly Ala Leu Thr Ser Gly Val His Thr
            180                 185                 190 ttc ccg gct gtc cta cag tcc tca gga ctc tac tcc ctc agc agc gtg     624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac     672
Val Thr Val Pro Ser Ser Ser Leu Gly Thr Gln Thr Tyr Ile Cys Asn
    210                 215                 220 gtg aat cac aag ccc agc aac acc aag gtg gac aag aaa gtt gag ccc     720
Val Asn His Lys Pro Ser Asn Thr Lys Val Asp Lys Lys Val Glu Pro
```

```
                    225                 230                 235                 240
aaa tct tgt gac aaa act cac aca tgc cca ccg tgc cca gca cct gaa         768
Lys Ser Cys Asp Lys Thr His Thr Cys Pro Pro Cys Pro Ala Pro Glu
                245                 250                 255 ctc ctg ggg gga ccg tca gtc ttc ctc ttc ccc cca aaa ccc aag gac         816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac         864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc         912
Val Ser His Glu Asp Pro Glu Val Lys Phe Asn Trp Tyr Val Asp Gly
    290                 295                 300 gtg gag gtg cat aat gcc aag aca aag ccg cgg gag gag cag tac aac         960
Val Glu Val His Asn Ala Lys Thr Lys Pro Arg Glu Glu Gln Tyr Asn
305                 310                 315                 320 agc acg tac cgt gtg gtc agc gtc ctc acc gtc ctg cac cag gac tgg        1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca        1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggg cag ccc cga gaa        1104
Ala Pro Ile Glu Lys Thr Ile Ser Lys Ala Lys Gly Gln Pro Arg Glu
        355                 360                 365 cca cag gtg tac acc ctg ccc cca tcc cgg gat gag ctg acc aag aac        1152
Pro Gln Val Tyr Thr Leu Pro Pro Ser Arg Asp Glu Leu Thr Lys Asn
    370                 375                 380 cag gtc agc ctg acc tgc ctg gtc aaa ggc ttc tat ccc agc gac atc        1200
Gln Val Ser Leu Thr Cys Leu Val Lys Gly Phe Tyr Pro Ser Asp Ile
385                 390                 395                 400 gcc gtg gag tgg gag agc aat ggg cag ccg gag aac aac tac aag acc        1248
Ala Val Glu Trp Glu Ser Asn Gly Gln Pro Glu Asn Asn Tyr Lys Thr
                405                 410                 415 acg cct ccc gtg ctg gac tcc gac ggc tcc ttc ttc ctc tac agc aag        1296
Thr Pro Pro Val Leu Asp Ser Asp Gly Ser Phe Phe Leu Tyr Ser Lys
            420                 425                 430 ctc acc gtg gac aag agc agg tgg cag cag ggg aac gtc ttc tca tgc        1344
Leu Thr Val Asp Lys Ser Arg Trp Gln Gln Gly Asn Val Phe Ser Cys
        435                 440                 445 tcc gtg atg cat gag gct ctg cac aac cac tac acg cag aag agc ctc        1392
Ser Val Met His Glu Ala Leu His Asn His Tyr Thr Gln Lys Ser Leu
    450                 455                 460 tcc ctg tct ccg ggt aaa tga                                            1413
Ser Leu Ser Pro Gly Lys
465                 470

<210> SEQ ID NO 59
<211> LENGTH: 470
<212> TYPE: PRT
<213> ORGANISM: Artificial
<220> FEATURE:
<223> OTHER INFORMATION: Synthetic Construct (Recombinant Protein)

<400> SEQUENCE: 59

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
```

```
                35                  40                  45
Thr Asp Tyr Ala Met His Trp Val Arg Gln Ala Pro Gly Gln Gly Leu
 50                  55                  60
Glu Trp Ile Gly Val Ile Ser Thr Tyr Tyr Gly Asn Thr Asn Tyr Asn
 65                  70                  75                  80
Gln Lys Phe Lys Gly Arg Ala Thr Met Thr Val Asp Thr Ser Thr Ser
                 85                  90                  95
Thr Ala Tyr Met Glu Leu Arg Ser Leu Arg Ser Asp Asp Thr Ala Val
                100                 105                 110
Tyr Tyr Cys Ala Arg Gly Gly Leu Arg Glu Tyr Tyr Ala Met Asp
            115                 120                 125
Tyr Trp Gly Gln Gly Thr Met Val Thr Val Ser Ser Ala Ser Thr Lys
130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
                180                 185                 190
Phe Pro Ala Val Leu Gln Ser Ser Gly Leu Tyr Ser Leu Ser Ser Val
                195                 200                 205
Val Thr Val Pro Ser Ser Leu Gly Thr Gln Thr Tyr Ile Cys Asn
210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
                260                 265                 270
Thr Leu Met Ile Ser Arg Thr Pro Glu Val Thr Cys Val Val Val Asp
                275                 280                 285
Val Ser His Glu Asp Pro Glu Val Lys Phe Asn Trp Tyr Val Asp Gly
                290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
                340                 345                 350
Ala Pro Ile Glu Lys Thr Ile Ser Lys Ala Lys Gly Gln Pro Arg Glu
                355                 360                 365
Pro Gln Val Tyr Thr Leu Pro Pro Ser Arg Asp Glu Leu Thr Lys Asn
                370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
                420                 425                 430
Leu Thr Val Asp Lys Ser Arg Trp Gln Gln Gly Asn Val Phe Ser Cys
                435                 440                 445
Ser Val Met His Glu Ala Leu His Asn His Tyr Thr Gln Lys Ser Leu
                450                 455                 460
```

Ser Leu Ser Pro Gly Lys
465               470

<210> SEQ ID NO 60
<211> LENGTH: 723
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(723)

<400> SEQUENCE: 60

| | | | | | | | | | | | | | | | | |
|---|---|---|---|---|---|---|---|---|---|---|---|---|---|---|---|---|
| atg | gaa | tca | cag | acc | cag | gtc | ctc | atg | ttt | ctt | ctg | ctc | tgg | gta | tct | 48 |
| Met | Glu | Ser | Gln | Thr | Gln | Val | Leu | Met | Phe | Leu | Leu | Leu | Trp | Val | Ser | |
| 1 | | | | 5 | | | | | 10 | | | | | 15 | | |
| ggt | gcc | tgt | gca | gac | att | gtc | atg | aca | cag | tct | cca | gac | tcc | ctg | gct | 96 |
| Gly | Ala | Cys | Ala | Asp | Ile | Val | Met | Thr | Gln | Ser | Pro | Asp | Ser | Leu | Ala | |
| | | | 20 | | | | | 25 | | | | | 30 | | | |
| gtg | tca | ctg | gga | gag | agg | gcc | act | atc | aac | tgc | aag | tcc | agt | cag | agc | 144 |
| Val | Ser | Leu | Gly | Glu | Arg | Ala | Thr | Ile | Asn | Cys | Lys | Ser | Ser | Gln | Ser | |
| | | 35 | | | | | 40 | | | | | 45 | | | | |
| ctt | ctg | aat | agt | agc | aat | caa | aag | aac | tat | ttg | gcc | tgg | tac | cag | cag | 192 |
| Leu | Leu | Asn | Ser | Ser | Asn | Gln | Lys | Asn | Tyr | Leu | Ala | Trp | Tyr | Gln | Gln | |
| | 50 | | | | | 55 | | | | | 60 | | | | | |
| aaa | cca | gga | cag | cct | cct | aaa | ctt | ctg | gtc | tac | ttt | gca | tcc | act | agg | 240 |
| Lys | Pro | Gly | Gln | Pro | Pro | Lys | Leu | Leu | Val | Tyr | Phe | Ala | Ser | Thr | Arg | |
| 65 | | | | | 70 | | | | | 75 | | | | | 80 | |
| gaa | tct | ggg | gtc | cct | gat | cgc | ttc | agt | ggc | agt | gga | tct | ggg | aca | gat | 288 |
| Glu | Ser | Gly | Val | Pro | Asp | Arg | Phe | Ser | Gly | Ser | Gly | Ser | Gly | Thr | Asp | |
| | | | | 85 | | | | | 90 | | | | | 95 | | |
| ttc | act | ctt | acc | atc | agc | agt | ctg | cag | gct | gaa | gat | gtg | gca | gtt | tac | 336 |
| Phe | Thr | Leu | Thr | Ile | Ser | Ser | Leu | Gln | Ala | Glu | Asp | Val | Ala | Val | Tyr | |
| | | | 100 | | | | | 105 | | | | | 110 | | | |
| tac | tgt | cag | caa | cat | tat | agc | act | cct | ccc | aca | ttc | ggt | cag | ggg | acc | 384 |
| Tyr | Cys | Gln | Gln | His | Tyr | Ser | Thr | Pro | Pro | Thr | Phe | Gly | Gln | Gly | Thr | |
| | | 115 | | | | | 120 | | | | | 125 | | | | |
| aag | ctg | gag | atc | aaa | cga | act | gtg | gct | gca | cca | tct | gtc | ttc | atc | ttc | 432 |
| Lys | Leu | Glu | Ile | Lys | Arg | Thr | Val | Ala | Ala | Pro | Ser | Val | Phe | Ile | Phe | |
| | 130 | | | | | 135 | | | | | 140 | | | | | |
| ccg | cca | tct | gat | gag | cag | ttg | aaa | tct | gga | act | gcc | tct | gtt | gtg | tgc | 480 |
| Pro | Pro | Ser | Asp | Glu | Gln | Leu | Lys | Ser | Gly | Thr | Ala | Ser | Val | Val | Cys | |
| 145 | | | | | 150 | | | | | 155 | | | | | 160 | |
| ctg | ctg | aat | aac | ttc | tat | ccc | aga | gag | gcc | aaa | gta | cag | tgg | aag | gtg | 528 |
| Leu | Leu | Asn | Asn | Phe | Tyr | Pro | Arg | Glu | Ala | Lys | Val | Gln | Trp | Lys | Val | |
| | | | | 165 | | | | | 170 | | | | | 175 | | |
| gat | aac | gcc | ctc | caa | tcg | ggt | aac | tcc | cag | gag | agt | gtc | aca | gag | cag | 576 |
| Asp | Asn | Ala | Leu | Gln | Ser | Gly | Asn | Ser | Gln | Glu | Ser | Val | Thr | Glu | Gln | |
| | | | 180 | | | | | 185 | | | | | 190 | | | |
| gac | agc | aag | gac | agc | acc | tac | agc | ctc | agc | agc | acc | ctg | acg | ctg | agc | 624 |
| Asp | Ser | Lys | Asp | Ser | Thr | Tyr | Ser | Leu | Ser | Ser | Thr | Leu | Thr | Leu | Ser | |
| | | 195 | | | | | 200 | | | | | 205 | | | | |
| aaa | gca | gac | tac | gag | aaa | cac | aaa | gtc | tac | gcc | tgc | gaa | gtc | acc | cat | 672 |
| Lys | Ala | Asp | Tyr | Glu | Lys | His | Lys | Val | Tyr | Ala | Cys | Glu | Val | Thr | His | |
| | 210 | | | | | 215 | | | | | 220 | | | | | |
| cag | ggc | ctg | agc | tcg | ccc | gtc | aca | aag | agc | ttc | aac | agg | gga | gag | tgt | 720 |
| Gln | Gly | Leu | Ser | Ser | Pro | Val | Thr | Lys | Ser | Phe | Asn | Arg | Gly | Glu | Cys | |
| 225 | | | | | 230 | | | | | 235 | | | | | 240 | |
| tag | | | | | | | | | | | | | | | | 723 |

```
<210> SEQ ID NO 61
<211> LENGTH: 240
<212> TYPE: PRT
<213> ORGANISM: Artificial
<220> FEATURE:
<223> OTHER INFORMATION: Synthetic Construct (Recombinant Protein)

<400> SEQUENCE: 61

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Asp Ser Leu Ala
            20                  25                  30

Val Ser Leu Gly Glu Arg Ala Thr Ile Asn Cys Lys Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Pro Pro Lys Leu Leu Val Tyr Phe Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln His Tyr Ser Thr Pro Pro Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 62
<211> LENGTH: 1413
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(1413)

<400> SEQUENCE: 62 atg ggt tgg agc tgt atc atc ttc ttt ctg gta gca aca gct aca ggc        48
Met Gly Trp Ser Cys Ile Ile Phe Phe Leu Val Ala Thr Ala Thr Gly
1               5                   10                  15 gtg cac tcc caa gtc cag ctg gtg cag tct ggg gct gaa gtg aag aag        96
Val His Ser Gln Val Gln Leu Val Gln Ser Gly Ala Glu Val Lys Lys
            20                  25                  30 cct ggg gcc tca gtg aaa gtc tcc tgc aag gct tcc ggc tac aca ttc       144
Pro Gly Ala Ser Val Lys Val Ser Cys Lys Ala Ser Gly Tyr Thr Phe
        35                  40                  45
```

```
act gat tat gct atg cac tgg gtg cga cag gcc cct gga caa ggc ctg      192
Thr Asp Tyr Ala Met His Trp Val Arg Gln Ala Pro Gly Gln Gly Leu
     50                  55                  60 gag tgg att gga gtt att agt act tac tat ggt aat aca aac tac aac      240
Glu Trp Ile Gly Val Ile Ser Thr Tyr Tyr Gly Asn Thr Asn Tyr Asn
 65                  70                  75                  80 cag aag ttt aag ggc aag gcc aca atg act gtc gac aaa tcc acc agc      288
Gln Lys Phe Lys Gly Lys Ala Thr Met Thr Val Asp Lys Ser Thr Ser
                 85                  90                  95 aca gcc tat atg gaa ctt agg agc ttg aga tct gac gat act gcc gtg      336
Thr Ala Tyr Met Glu Leu Arg Ser Leu Arg Ser Asp Asp Thr Ala Val
             100                 105                 110 tat tac tgt gca aga gga gga ttg cga gag tat tac tat gct atg gac      384
Tyr Tyr Cys Ala Arg Gly Gly Leu Arg Glu Tyr Tyr Tyr Ala Met Asp
         115                 120                 125 tac tgg ggt caa gga acc atg gtc acc gtc tcc tca gcc tcc acc aag      432
Tyr Trp Gly Gln Gly Thr Met Val Thr Val Ser Ser Ala Ser Thr Lys
130                 135                 140 ggc cca tcg gtc ttc ccc ctg gca ccc tcc tcc aag agc acc tct ggg      480
Gly Pro Ser Val Phe Pro Leu Ala Pro Ser Ser Lys Ser Thr Ser Gly
145                 150                 155                 160 ggc aca gcg gcc ctg ggc tgc ctg gtc aag gac tac ttc ccc gaa ccg      528
Gly Thr Ala Ala Leu Gly Cys Leu Val Lys Asp Tyr Phe Pro Glu Pro
                 165                 170                 175 gtg acg gtg tcg tgg aac tca ggc gcc ctg acc agc ggc gtg cac acc      576
Val Thr Val Ser Trp Asn Ser Gly Ala Leu Thr Ser Gly Val His Thr
             180                 185                 190 ttc ccg gct gtc cta cag tcc tca gga ctc tac tcc ctc agc agc gtg      624
Phe Pro Ala Val Leu Gln Ser Ser Gly Leu Tyr Ser Leu Ser Ser Val
         195                 200                 205 gtg acc gtg ccc tcc agc agc ttg ggc acc cag acc tac atc tgc aac      672
Val Thr Val Pro Ser Ser Ser Leu Gly Thr Gln Thr Tyr Ile Cys Asn
     210                 215                 220 gtg aat cac aag ccc agc aac acc aag gtg gac aag aaa gtt gag ccc      720
Val Asn His Lys Pro Ser Asn Thr Lys Val Asp Lys Lys Val Glu Pro
225                 230                 235                 240 aaa tct tgt gac aaa act cac aca tgc cca ccg tgc cca gca cct gaa      768
Lys Ser Cys Asp Lys Thr His Thr Cys Pro Pro Cys Pro Ala Pro Glu
                 245                 250                 255 ctc ctg ggg gga ccg tca gtc ttc ctc ttc ccc cca aaa ccc aag gac      816
Leu Leu Gly Gly Pro Ser Val Phe Leu Phe Pro Pro Lys Pro Lys Asp
             260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
         275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
     290                 295                 300 gtg gag gtg cat aat gcc aag aca aag ccg cgg gag gag cag tac aac      960
Val Glu Val His Asn Ala Lys Thr Lys Pro Arg Glu Glu Gln Tyr Asn
305                 310                 315                 320 agc acg tac cgt gtg gtc agc gtc ctc acc gtc ctg cac cag gac tgg     1008
Ser Thr Tyr Arg Val Val Ser Val Leu Thr Val Leu His Gln Asp Trp
                 325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
             340                 345                 350 gcc ccc atc gag aaa acc atc tcc aaa gcc aaa ggg cag ccc cga gaa     1104
Ala Pro Ile Glu Lys Thr Ile Ser Lys Ala Lys Gly Gln Pro Arg Glu
```

```
                 355                 360                 365
cca cag gtg tac acc ctg ccc cca tcc cgg gat gag ctg acc aag aac    1152
Pro Gln Val Tyr Thr Leu Pro Pro Ser Arg Asp Glu Leu Thr Lys Asn
    370                 375                 380 cag gtc agc ctg acc tgc ctg gtc aaa ggc ttc tat ccc agc gac atc    1200
Gln Val Ser Leu Thr Cys Leu Val Lys Gly Phe Tyr Pro Ser Asp Ile
385                 390                 395                 400 gcc gtg gag tgg gag agc aat ggg cag ccg gag aac aac tac aag acc    1248
Ala Val Glu Trp Glu Ser Asn Gly Gln Pro Glu Asn Asn Tyr Lys Thr
                405                 410                 415 acg cct ccc gtg ctg gac tcc gac ggc tcc ttc ttc ctc tac agc aag    1296
Thr Pro Pro Val Leu Asp Ser Asp Gly Ser Phe Phe Leu Tyr Ser Lys
            420                 425                 430 ctc acc gtg gac aag agc agg tgg cag cag ggg aac gtc ttc tca tgc    1344
Leu Thr Val Asp Lys Ser Arg Trp Gln Gln Gly Asn Val Phe Ser Cys
        435                 440                 445 tcc gtg atg cat gag gct ctg cac aac cac tac acg cag aag agc ctc    1392
Ser Val Met His Glu Ala Leu His Asn His Tyr Thr Gln Lys Ser Leu
    450                 455                 460 tcc ctg tct ccg ggt aaa tga                                        1413
Ser Leu Ser Pro Gly Lys
465                 470

<210> SEQ ID NO 63
<211> LENGTH: 470
<212> TYPE: PRT
<213> ORGANISM: Artificial
<220> FEATURE:
<223> OTHER INFORMATION: Synthetic Construct (Recombinant Protein)

<400> SEQUENCE: 63

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ala Met His Trp Val Arg Gln Ala Pro Gly Gln Gly Leu
    50                  55                  60

Glu Trp Ile Gly Val Ile Ser Thr Tyr Tyr Gly Asn Thr Asn Tyr Asn
65                  70                  75                  80

Gln Lys Phe Lys Gly Lys Ala Thr Met Thr Val Asp Lys Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Gly Gly Leu Arg Glu Tyr Tyr Ala Met Asp
        115                 120                 125

Tyr Trp Gly Gln Gly Thr Met Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205
```

```
Val Thr Val Pro Ser Ser Leu Gly Thr Gln Thr Tyr Ile Cys Asn
    210             215                 220

Val Asn His Lys Pro Ser Asn Thr Lys Val Asp Lys Lys Val Glu Pro
225             230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305             310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385             390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 64
<211> LENGTH: 1413
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(1413)

<400> SEQUENCE: 64 atg ggt tgg agc tgt atc atc ttc ttt ctg gta gca aca gct aca ggc    48
Met Gly Trp Ser Cys Ile Ile Phe Phe Leu Val Ala Thr Ala Thr Gly
1               5                   10                  15 gtg cac tcc caa gtc cag ctg gtg cag tct ggg gct gaa gtg aag aag    96
Val His Ser Gln Val Gln Leu Val Gln Ser Gly Ala Glu Val Lys Lys
            20                  25                  30 cct ggg gcc tca gtg aaa gtc tcc tgc aag ggt tcc ggc tac aca ttc   144
Pro Gly Ala Ser Val Lys Val Ser Cys Lys Gly Ser Gly Tyr Thr Phe
        35                  40                  45 act gat tat gct atg cac tgg gtg cga cag gcc cct gga caa ggc ctg   192
Thr Asp Tyr Ala Met His Trp Val Arg Gln Ala Pro Gly Gln Gly Leu
    50                  55                  60
```

```
gag tgg att gga gtt att agt act tac tat ggt aat aca aac tac aac      240
Glu Trp Ile Gly Val Ile Ser Thr Tyr Tyr Gly Asn Thr Asn Tyr Asn
 65              70                  75                  80 cag aag ttt aag ggc aag gcc aca atg act gtc gac aaa tcc acc agc      288
Gln Lys Phe Lys Gly Lys Ala Thr Met Thr Val Asp Lys Ser Thr Ser
                 85                  90                  95 aca gcc tat atg gaa ctt agg agc ttg aga tct gac gat act gcc gtg      336
Thr Ala Tyr Met Glu Leu Arg Ser Leu Arg Ser Asp Asp Thr Ala Val
            100                 105                 110 tat tac tgt gca aga gga gga ttg cga gag tat tac tat gct atg gac      384
Tyr Tyr Cys Ala Arg Gly Gly Leu Arg Glu Tyr Tyr Tyr Ala Met Asp
        115                 120                 125 tac tgg ggt caa gga acc atg gtc acc gtc tcc tca gcc tcc acc aag      432
Tyr Trp Gly Gln Gly Thr Met Val Thr Val Ser Ser Ala Ser Thr Lys
130                 135                 140 ggc cca tcg gtc ttc ccc ctg gca ccc tcc tcc aag agc acc tct ggg      480
Gly Pro Ser Val Phe Pro Leu Ala Pro Ser Ser Lys Ser Thr Ser Gly
145                 150                 155                 160 ggc aca gcg gcc ctg ggc tgc ctg gtc aag gac tac ttc ccc gaa ccg      528
Gly Thr Ala Ala Leu Gly Cys Leu Val Lys Asp Tyr Phe Pro Glu Pro
                165                 170                 175 gtg acg gtg tcg tgg aac tca ggc gcc ctg acc agc ggc gtg cac acc      576
Val Thr Val Ser Trp Asn Ser Gly Ala Leu Thr Ser Gly Val His Thr
            180                 185                 190 ttc ccg gct gtc cta cag tcc tca gga ctc tac tcc ctc agc agc gtg      624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac      672
Val Thr Val Pro Ser Ser Ser Leu Gly Thr Gln Thr Tyr Ile Cys Asn
210                 215                 220 gtg aat cac aag ccc agc aac acc aag gtg gac aag aaa gtt gag ccc      720
Val Asn His Lys Pro Ser Asn Thr Lys Val Asp Lys Lys Val Glu Pro
225                 230                 235                 240 aaa tct tgt gac aaa act cac aca tgc cca ccg tgc cca gca cct gaa      768
Lys Ser Cys Asp Lys Thr His Thr Cys Pro Pro Cys Pro Ala Pro Glu
                245                 250                 255 ctc ctg ggg gga ccg tca gtc ttc ctc ttc ccc cca aaa ccc aag gac      816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
290                 295                 300 gtg gag gtg cat aat gcc aag aca aag ccg cgg gag gag cag tac aac      960
Val Glu Val His Asn Ala Lys Thr Lys Pro Arg Glu Glu Gln Tyr Asn
305                 310                 315                 320 agc acg tac cgt gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggg cag ccc cga gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gat gag ctg acc aag aac     1152
Pro Gln Val Tyr Thr Leu Pro Pro Ser Arg Asp Glu Leu Thr Lys Asn
```

```
                        370                 375                 380
cag gtc agc ctg acc tgc ctg gtc aaa ggc ttc tat ccc agc gac atc    1200
Gln Val Ser Leu Thr Cys Leu Val Lys Gly Phe Tyr Pro Ser Asp Ile
385                 390                 395                 400 gcc gtg gag tgg gag agc aat ggg cag ccg gag aac aac tac aag acc    1248
Ala Val Glu Trp Glu Ser Asn Gly Gln Pro Glu Asn Asn Tyr Lys Thr
                405                 410                 415 acg cct ccc gtg ctg gac tcc gac ggc tcc ttc ttc ctc tac agc aag    1296
Thr Pro Pro Val Leu Asp Ser Asp Gly Ser Phe Phe Leu Tyr Ser Lys
            420                 425                 430 ctc acc gtg gac aag agc agg tgg cag cag ggg aac gtc ttc tca tgc    1344
Leu Thr Val Asp Lys Ser Arg Trp Gln Gln Gly Asn Val Phe Ser Cys
        435                 440                 445 tcc gtg atg cat gag gct ctg cac aac cac tac acg cag aag agc ctc    1392
Ser Val Met His Glu Ala Leu His Asn His Tyr Thr Gln Lys Ser Leu
    450                 455                 460 tcc ctg tct ccg ggt aaa tga                                        1413
Ser Leu Ser Pro Gly Lys
465                 470

<210> SEQ ID NO 65
<211> LENGTH: 470
<212> TYPE: PRT
<213> ORGANISM: Artificial
<220> FEATURE:
<223> OTHER INFORMATION: Synthetic Construct (Recombinant Protein)

<400> SEQUENCE: 65

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Gly Ser Gly Tyr Thr Phe
            35                  40                  45

Thr Asp Tyr Ala Met His Trp Val Arg Gln Ala Pro Gly Gln Gly Leu
    50                  55                  60

Glu Trp Ile Gly Val Ile Ser Thr Tyr Tyr Gly Asn Thr Asn Tyr Asn
65                  70                  75                  80

Gln Lys Phe Lys Gly Lys Ala Thr Met Thr Val Asp Lys Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Gly Gly Leu Arg Glu Tyr Tyr Ala Met Asp
            115                 120                 125

Tyr Trp Gly Gln Gly Thr Met Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
    195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
```

```
                225                 230                 235                 240
        Lys Ser Cys Asp Lys Thr His Thr Cys Pro Pro Cys Pro Ala Pro Glu
                        245                 250                 255

Leu Leu Gly Gly Pro Ser Val Phe Leu Phe Pro Pro Lys Pro Lys Asp
                        260                 265                 270

Thr Leu Met Ile Ser Arg Thr Pro Glu Val Thr Cys Val Val Val Asp
                        275                 280                 285

Val Ser His Glu Asp Pro Glu Val Lys Phe Asn Trp Tyr Val Asp Gly
                        290                 295                 300

Val Glu Val His Asn Ala Lys Thr Lys Pro Arg Glu Glu Gln Tyr Asn
        305                 310                 315                 320

Ser Thr Tyr Arg Val Val Ser Val Leu Thr Val Leu His Gln Asp Trp
                        325                 330                 335

Leu Asn Gly Lys Glu Tyr Lys Cys Lys Val Ser Asn Lys Ala Leu Pro
                        340                 345                 350

Ala Pro Ile Glu Lys Thr Ile Ser Lys Ala Lys Gly Gln Pro Arg Glu
                        355                 360                 365

Pro Gln Val Tyr Thr Leu Pro Pro Ser Arg Asp Glu Leu Thr Lys Asn
                        370                 375                 380

Gln Val Ser Leu Thr Cys Leu Val Lys Gly Phe Tyr Pro Ser Asp Ile
        385                 390                 395                 400

Ala Val Glu Trp Glu Ser Asn Gly Gln Pro Glu Asn Asn Tyr Lys Thr
                        405                 410                 415

Thr Pro Pro Val Leu Asp Ser Asp Gly Ser Phe Phe Leu Tyr Ser Lys
                        420                 425                 430

Leu Thr Val Asp Lys Ser Arg Trp Gln Gln Gly Asn Val Phe Ser Cys
                        435                 440                 445

Ser Val Met His Glu Ala Leu His Asn His Tyr Thr Gln Lys Ser Leu
                        450                 455                 460

Ser Leu Ser Pro Gly Lys
        465                 470

<210> SEQ ID NO 66
<211> LENGTH: 420
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(420)

<400> SEQUENCE: 66 atg ggt tgg agc tgt atc atc ttc ttt ctg gta gca aca gct aca ggc        48
Met Gly Trp Ser Cys Ile Ile Phe Phe Leu Val Ala Thr Ala Thr Gly
1               5                   10                  15 gtg cac tcc caa gtc cag ctg gtg cag tct ggg gct gaa gtg aag aag        96
Val His Ser Gln Val Gln Leu Val Gln Ser Gly Ala Glu Val Lys Lys
                20                  25                  30 cct ggg gcc tca gtg aaa gtc tcc tgc aag ggt tcc ggc tac aca ttc       144
Pro Gly Ala Ser Val Lys Val Ser Cys Lys Gly Ser Gly Tyr Thr Phe
            35                  40                  45 act gat tat gct atg cac tgg gtg cga cag gcc cct gga caa ggc ctg       192
Thr Asp Tyr Ala Met His Trp Val Arg Gln Ala Pro Gly Gln Gly Leu
        50                  55                  60 gag tgg att gga gtt att agt act tac tat ggt aat aca aac tac aac       240
Glu Trp Ile Gly Val Ile Ser Thr Tyr Tyr Gly Asn Thr Asn Tyr Asn
65                  70                  75                  80
```

```
cag aag ttt aag ggc aag gcc aca atg act gtc gac aca tcc acc agc      288
Gln Lys Phe Lys Gly Lys Ala Thr Met Thr Val Asp Thr Ser Thr Ser
                85                  90                  95 aca gcc tat atg gaa ctt agg agc ttg aga tct gac gat act gcc gtg      336
Thr Ala Tyr Met Glu Leu Arg Ser Leu Arg Ser Asp Asp Thr Ala Val
                100                 105                 110 tat tac tgt gca aga gga gga ttg cga gag tat tac tat gct atg gac      384
Tyr Tyr Cys Ala Arg Gly Gly Leu Arg Glu Tyr Tyr Tyr Ala Met Asp
                115                 120                 125 tac tgg ggt caa gga acc atg gtc acc gtc tcc tca                       420
Tyr Trp Gly Gln Gly Thr Met Val Thr Val Ser Ser
                130                 135                 140
```

<210> SEQ ID NO 67
<211> LENGTH: 140
<212> TYPE: PRT
<213> ORGANISM: Artificial
<220> FEATURE:
<223> OTHER INFORMATION: Synthetic Construct (Recombinant Protein)

<400> SEQUENCE: 67

```
Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Gly Ser Gly Tyr Thr Phe
            35                  40                  45

Thr Asp Tyr Ala Met His Trp Val Arg Gln Ala Pro Gly Gln Gly Leu
        50                  55                  60

Glu Trp Ile Gly Val Ile Ser Thr Tyr Tyr Gly Asn Thr Asn Tyr Asn
65                  70                  75                  80

Gln Lys Phe Lys Gly Lys Ala Thr Met Thr Val Asp Thr Ser Thr Ser
                85                  90                  95

Thr Ala Tyr Met Glu Leu Arg Ser Leu Arg Ser Asp Asp Thr Ala Val
                100                 105                 110

Tyr Tyr Cys Ala Arg Gly Gly Leu Arg Glu Tyr Tyr Tyr Ala Met Asp
                115                 120                 125

Tyr Trp Gly Gln Gly Thr Met Val Thr Val Ser Ser
                130                 135                 140
```

<210> SEQ ID NO 68
<211> LENGTH: 363
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(363)

<400> SEQUENCE: 68

```
caa gtc cag ctg gtg cag tct ggg gct gaa gtg aag aag cct ggg gcc       48
Gln Val Gln Leu Val Gln Ser Gly Ala Glu Val Lys Lys Pro Gly Ala
1               5                   10                  15 tca gtg aaa gtc tcc tgc aag ggt tcc ggc tac aca ttc act gat tat       96
Ser Val Lys Val Ser Cys Lys Gly Ser Gly Tyr Thr Phe Thr Asp Tyr
                20                  25                  30 gct atg cac tgg gtg cga cag gcc cct gga caa ggc ctg gag tgg att      144
Ala Met His Trp Val Arg Gln Ala Pro Gly Gln Gly Leu Glu Trp Ile
            35                  40                  45
```

```
gga gtt att agt act tac tat ggt aat aca aac tac aac cag aag ttt    192
Gly Val Ile Ser Thr Tyr Tyr Gly Asn Thr Asn Tyr Asn Gln Lys Phe
    50                  55                  60 aag ggc aag gcc aca atg act gtc gac aca tcc acc agc aca gcc tat    240
Lys Gly Lys Ala Thr Met Thr Val Asp Thr Ser Thr Ser Thr Ala Tyr
65                  70                  75                  80 atg gaa ctt agg agc ttg aga tct gac gat act gcc gtg tat tac tgt    288
Met Glu Leu Arg Ser Leu Arg Ser Asp Asp Thr Ala Val Tyr Tyr Cys
                85                  90                  95 gca aga gga gga ttg cga gag tat tac tat gct atg gac tac tgg ggt    336
Ala Arg Gly Gly Leu Arg Glu Tyr Tyr Tyr Ala Met Asp Tyr Trp Gly
            100                 105                 110 caa gga acc atg gtc acc gtc tcc tca                                363
Gln Gly Thr Met Val Thr Val Ser Ser
        115                 120

<210> SEQ ID NO 69
<211> LENGTH: 121
<212> TYPE: PRT
<213> ORGANISM: Artificial
<220> FEATURE:
<223> OTHER INFORMATION: Synthetic Construct (Recombinant Protein)

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Val Ile Ser Thr Tyr Tyr Gly Asn Thr Asn Tyr Asn Gln Lys Phe
    50                  55                  60

Lys Gly Lys Ala Thr Met Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Leu Arg Glu Tyr Tyr Tyr Ala Met Asp Tyr Trp Gly
            100                 105                 110

Gln Gly Thr Met Val Thr Val Ser Ser
        115                 120

<210> SEQ ID NO 70
<211> LENGTH: 420
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(420)

<400> SEQUENCE: 70 atg ggt tgg agc tgt atc atc ttc ttt ctg gta gca aca gct aca ggc     48
Met Gly Trp Ser Cys Ile Ile Phe Phe Leu Val Ala Thr Ala Thr Gly
1               5                   10                  15 gtg cac tcc caa gtc cag ctg gtg cag tct ggg gct gaa gtg aag aag     96
Val His Ser Gln Val Gln Leu Val Gln Ser Gly Ala Glu Val Lys Lys
            20                  25                  30 cct ggg gcc tca gtg aaa gtc tcc tgc aag gct tcc ggc tac aca ttc    144
Pro Gly Ala Ser Val Lys Val Ser Cys Lys Ala Ser Gly Tyr Thr Phe
        35                  40                  45
```

```
act gat tat gct atg cac tgg gtg cga cag gcc cct gga caa ggc ctg      192
Thr Asp Tyr Ala Met His Trp Val Arg Gln Ala Pro Gly Gln Gly Leu
     50                  55                  60 gag tgg att gga gtt att agt act tac tat ggt aat aca aac tac aac      240
Glu Trp Ile Gly Val Ile Ser Thr Tyr Tyr Gly Asn Thr Asn Tyr Asn
 65                  70                  75                  80 cag aag ttt aag ggc aag gcc aca atg act gtc gac aaa tcc acc agc      288
Gln Lys Phe Lys Gly Lys Ala Thr Met Thr Val Asp Lys Ser Thr Ser
                 85                  90                  95 aca gcc tat atg gaa ctt agg agc ttg aga tct gac gat act gcc gtg      336
Thr Ala Tyr Met Glu Leu Arg Ser Leu Arg Ser Asp Asp Thr Ala Val
            100                 105                 110 tat tac tgt gca aga gga gga ttg cga gag tat tac tat gct atg gac      384
Tyr Tyr Cys Ala Arg Gly Gly Leu Arg Glu Tyr Tyr Tyr Ala Met Asp
        115                 120                 125 tac tgg ggt caa gga acc atg gtc acc gtc tcc tca                      420
Tyr Trp Gly Gln Gly Thr Met Val Thr Val Ser Ser
    130                 135                 140
```

<210> SEQ ID NO 71
<211> LENGTH: 140
<212> TYPE: PRT
<213> ORGANISM: Artificial
<220> FEATURE:
<223> OTHER INFORMATION: Synthetic Construct (Recombinant Protein)

<400> SEQUENCE: 71

```
Met Gly Trp Ser Cys Ile Ile Phe Phe Leu Val Ala Thr Ala Thr Gly
 1               5                  10                  15

Val His Ser Gln Val Gln Leu Val Gln Ser Gly Ala Glu Val Lys Lys
                 20                  25                  30

Pro Gly Ala Ser Val Lys Val Ser Cys Lys Ala Ser Gly Tyr Thr Phe
             35                  40                  45

Thr Asp Tyr Ala Met His Trp Val Arg Gln Ala Pro Gly Gln Gly Leu
     50                  55                  60

Glu Trp Ile Gly Val Ile Ser Thr Tyr Tyr Gly Asn Thr Asn Tyr Asn
 65                  70                  75                  80

Gln Lys Phe Lys Gly Lys Ala Thr Met Thr Val Asp Lys Ser Thr Ser
                 85                  90                  95

Thr Ala Tyr Met Glu Leu Arg Ser Leu Arg Ser Asp Asp Thr Ala Val
            100                 105                 110

Tyr Tyr Cys Ala Arg Gly Gly Leu Arg Glu Tyr Tyr Tyr Ala Met Asp
        115                 120                 125

Tyr Trp Gly Gln Gly Thr Met Val Thr Val Ser Ser
    130                 135                 140
```

<210> SEQ ID NO 72
<211> LENGTH: 363
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(363)

<400> SEQUENCE: 72

```
caa gtc cag ctg gtg cag tct ggg gct gaa gtg aag aag cct ggg gcc       48
Gln Val Gln Leu Val Gln Ser Gly Ala Glu Val Lys Lys Pro Gly Ala
 1               5                  10                  15 tca gtg aaa gtc tcc tgc aag gct tcc ggc tac aca ttc act gat tat       96
Ser Val Lys Val Ser Cys Lys Ala Ser Gly Tyr Thr Phe Thr Asp Tyr
```

```
                Ser Val Lys Val Ser Cys Lys Ala Ser Gly Tyr Thr Phe Thr Asp Tyr
                            20                  25                  30 gct atg cac tgg gtg cga cag gcc cct gga caa ggc ctg gag tgg att              144
Ala Met His Trp Val Arg Gln Ala Pro Gly Gln Gly Leu Glu Trp Ile
        35                  40                  45 gga gtt att agt act tac tat ggt aat aca aac tac aac cag aag ttt              192
Gly Val Ile Ser Thr Tyr Tyr Gly Asn Thr Asn Tyr Asn Gln Lys Phe
 50                  55                  60 aag ggc aag gcc aca atg act gtc gac aaa tcc acc agc aca gcc tat              240
Lys Gly Lys Ala Thr Met Thr Val Asp Lys Ser Thr Ser Thr Ala Tyr
 65                  70                  75                  80 atg gaa ctt agg agc ttg aga tct gac gat act gcc gtg tat tac tgt              288
Met Glu Leu Arg Ser Leu Arg Ser Asp Asp Thr Ala Val Tyr Tyr Cys
                85                  90                  95 gca aga gga gga ttg cga gag tat tac tat gct atg gac tac tgg ggt              336
Ala Arg Gly Gly Leu Arg Glu Tyr Tyr Tyr Ala Met Asp Tyr Trp Gly
            100                 105                 110 caa gga acc atg gtc acc gtc tcc tca                                          363
Gln Gly Thr Met Val Thr Val Ser Ser
        115                 120
```

<210> SEQ ID NO 73
<211> LENGTH: 121
<212> TYPE: PRT
<213> ORGANISM: Artificial
<220> FEATURE:
<223> OTHER INFORMATION: Synthetic Construct (Recombinant Protein)

<400> SEQUENCE: 73

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Val Ile Ser Thr Tyr Tyr Gly Asn Thr Asn Tyr Asn Gln Lys Phe
 50                  55                  60

Lys Gly Lys Ala Thr Met Thr Val Asp Lys Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Gly Gly Leu Arg Glu Tyr Tyr Tyr Ala Met Asp Tyr Trp Gly
            100                 105                 110

Gln Gly Thr Met Val Thr Val Ser Ser
        115                 120
```

<210> SEQ ID NO 74
<211> LENGTH: 420
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(420)

<400> SEQUENCE: 74

```
atg ggt tgg agc tgt atc atc ttc ttt ctg gta gca aca gct aca ggc               48
Met Gly Trp Ser Cys Ile Ile Phe Phe Leu Val Ala Thr Ala Thr Gly
 1               5                  10                  15 gtg cac tcc caa gtc cag ctg gtg cag tct ggg gct gaa gtg aag aag               96
```

```
                Val His Ser Gln Val Gln Leu Val Gln Ser Gly Ala Glu Val Lys Lys
                            20                  25                  30 cct ggg gcc tca gtg aaa gtc tcc tgc aag ggt tcc ggc tac aca ttc        144
Pro Gly Ala Ser Val Lys Val Ser Cys Lys Gly Ser Gly Tyr Thr Phe
            35                  40                  45 act gat tat gct atg cac tgg gtg cga cag gcc cct gga caa ggc ctg        192
Thr Asp Tyr Ala Met His Trp Val Arg Gln Ala Pro Gly Gln Gly Leu
50                  55                  60 gag tgg att gga gtt att agt act tac tat ggt aat aca aac tac aac        240
Glu Trp Ile Gly Val Ile Ser Thr Tyr Tyr Gly Asn Thr Asn Tyr Asn
65                  70                  75                  80 cag aag ttt aag ggc aag gcc aca atg act gtc gac aaa tcc acc agc        288
Gln Lys Phe Lys Gly Lys Ala Thr Met Thr Val Asp Lys Ser Thr Ser
                85                  90                  95 aca gcc tat atg gaa ctt agg agc ttg aga tct gat gat act gcc gtg        336
Thr Ala Tyr Met Glu Leu Arg Ser Leu Arg Ser Asp Asp Thr Ala Val
            100                 105                 110 tat tac tgt gca aga gga gga ttg cga gag tat tac tat gct atg gac        384
Tyr Tyr Cys Ala Arg Gly Gly Leu Arg Glu Tyr Tyr Tyr Ala Met Asp
        115                 120                 125 tac tgg ggt caa gga acc atg gtc acc gtc tcc tca                        420
Tyr Trp Gly Gln Gly Thr Met Val Thr Val Ser Ser
130                 135                 140

<210> SEQ ID NO 75
<211> LENGTH: 140
<212> TYPE: PRT
<213> ORGANISM: Artificial
<220> FEATURE:
<223> OTHER INFORMATION: Synthetic Construct (Recombinant Protein)

<400> SEQUENCE: 75

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Gly Ser Gly Tyr Thr Phe
        35                  40                  45

Thr Asp Tyr Ala Met His Trp Val Arg Gln Ala Pro Gly Gln Gly Leu
    50                  55                  60

Glu Trp Ile Gly Val Ile Ser Thr Tyr Tyr Gly Asn Thr Asn Tyr Asn
65                  70                  75                  80

Gln Lys Phe Lys Gly Lys Ala Thr Met Thr Val Asp Lys Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Gly Gly Leu Arg Glu Tyr Tyr Tyr Ala Met Asp
        115                 120                 125

Tyr Trp Gly Gln Gly Thr Met Val Thr Val Ser Ser
    130                 135                 140

<210> SEQ ID NO 76
<211> LENGTH: 363
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(363)
```

<400> SEQUENCE: 76

```
caa gtc cag ctg gtg cag tct ggg gct gaa gtg aag aag cct ggg gcc    48
Gln Val Gln Leu Val Gln Ser Gly Ala Glu Val Lys Lys Pro Gly Ala
1               5                   10                  15 tca gtg aaa gtc tcc tgc aag ggt tcc ggc tac aca ttc act gat tat    96
Ser Val Lys Val Ser Cys Lys Gly Ser Gly Tyr Thr Phe Thr Asp Tyr
            20                  25                  30 gct atg cac tgg gtg cga cag gcc cct gga caa ggc ctg gag tgg att   144
Ala Met His Trp Val Arg Gln Ala Pro Gly Gln Gly Leu Glu Trp Ile
        35                  40                  45 gga gtt att agt act tac tat ggt aat aca aac tac aac cag aag ttt   192
Gly Val Ile Ser Thr Tyr Tyr Gly Asn Thr Asn Tyr Asn Gln Lys Phe
    50                  55                  60 aag ggc aag gcc aca atg act gtc gac aaa tcc acc agc aca gcc tat   240
Lys Gly Lys Ala Thr Met Thr Val Asp Lys Ser Thr Ser Thr Ala Tyr
65                  70                  75                  80 atg gaa ctt agg agc ttg aga tct gac gat act gcc gtg tat tac tgt   288
Met Glu Leu Arg Ser Leu Arg Ser Asp Asp Thr Ala Val Tyr Tyr Cys
                85                  90                  95 gca aga gga gga ttg cga gag tat tac tat gct atg gac tac tgg ggt   336
Ala Arg Gly Gly Leu Arg Glu Tyr Tyr Tyr Ala Met Asp Tyr Trp Gly
            100                 105                 110 caa gga acc atg gtc acc gtc tcc tca                               363
Gln Gly Thr Met Val Thr Val Ser Ser
        115                 120
```

<210> SEQ ID NO 77
<211> LENGTH: 121
<212> TYPE: PRT
<213> ORGANISM: Artificial
<220> FEATURE:
<223> OTHER INFORMATION: Synthetic Construct (Recombinant Protein)

<400> SEQUENCE: 77

```
Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Val Ile Ser Thr Tyr Tyr Gly Asn Thr Asn Tyr Asn Gln Lys Phe
    50                  55                  60

Lys Gly Lys Ala Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Leu Arg Glu Tyr Tyr Tyr Ala Met Asp Tyr Trp Gly
            100                 105                 110

Gln Gly Thr Met Val Thr Val Ser Ser
        115                 120
```

<210> SEQ ID NO 78
<211> LENGTH: 420
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(420)

<400> SEQUENCE: 78

```
atg ggt tgg agc tgt atc atc ttc ttt ctg gta gca aca gct aca ggc      48
Met Gly Trp Ser Cys Ile Ile Phe Phe Leu Val Ala Thr Ala Thr Gly
1               5                   10                  15 gtg cac tcc caa gtc cag ctg gtg cag tct ggg gct gaa gtg aag aag      96
Val His Ser Gln Val Gln Leu Val Gln Ser Gly Ala Glu Val Lys Lys
            20                  25                  30 cct ggg gcc tca gtg aaa gtc tcc tgc aag ggt tcc ggc tac aca ttc     144
Pro Gly Ala Ser Val Lys Val Ser Cys Lys Gly Ser Gly Tyr Thr Phe
        35                  40                  45 act gat tat gct atg cac tgg gtg cga cag gcc cct gga caa ggc ctg     192
Thr Asp Tyr Ala Met His Trp Val Arg Gln Ala Pro Gly Gln Gly Leu
    50                  55                  60 gag tgg att gga gtt att agt act tac tat ggt aat aca aac tac aac     240
Glu Trp Ile Gly Val Ile Ser Thr Tyr Tyr Gly Asn Thr Asn Tyr Asn
65                  70                  75                  80 cag aag ttt aag ggc cga gcc aca atg act gtc gac aca tcc acc agc     288
Gln Lys Phe Lys Gly Arg Ala Thr Met Thr Val Asp Thr Ser Thr Ser
                85                  90                  95 aca gcc tat atg gaa ctt agg agc ttg aga tct gac gat act gcc gtg     336
Thr Ala Tyr Met Glu Leu Arg Ser Leu Arg Ser Asp Asp Thr Ala Val
            100                 105                 110 tat tac tgt gca aga gga gga ttg cga gag tat tac tat gct atg gac     384
Tyr Tyr Cys Ala Arg Gly Gly Leu Arg Glu Tyr Tyr Tyr Ala Met Asp
        115                 120                 125 tac tgg ggt caa gga acc atg gtc acc gtc tcc tca                     420
Tyr Trp Gly Gln Gly Thr Met Val Thr Val Ser Ser
    130                 135                 140
```

<210> SEQ ID NO 79
<211> LENGTH: 140
<212> TYPE: PRT
<213> ORGANISM: Artificial
<220> FEATURE:
<223> OTHER INFORMATION: Synthetic Construct (Recombinant Protein)

<400> SEQUENCE: 79

```
Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Gly Ser Gly Tyr Thr Phe
        35                  40                  45

Thr Asp Tyr Ala Met His Trp Val Arg Gln Ala Pro Gly Gln Gly Leu
    50                  55                  60

Glu Trp Ile Gly Val Ile Ser Thr Tyr Tyr Gly Asn Thr Asn Tyr Asn
65                  70                  75                  80

Gln Lys Phe Lys Gly Arg Ala Thr Met Thr Val Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Gly Gly Leu Arg Glu Tyr Tyr Tyr Ala Met Asp
        115                 120                 125

Tyr Trp Gly Gln Gly Thr Met Val Thr Val Ser Ser
    130                 135                 140
```

<210> SEQ ID NO 80
<211> LENGTH: 363
<212> TYPE: DNA

```
<213> ORGANISM: Artificial
<220> FEATURE:
<223> OTHER INFORMATION: Recombinant DNA
<220> FEATURE:
<221> NAME/KEY: CDS
<222> LOCATION: (1)..(363)

<400> SEQUENCE: 80 caa gtc cag ctg gtg cag tct ggg gct gaa gtg aag aag cct ggg gcc      48
Gln Val Gln Leu Val Gln Ser Gly Ala Glu Val Lys Lys Pro Gly Ala
1               5                   10                  15 tca gtg aaa gtc tcc tgc aag ggt tcc ggc tac aca ttc act gat tat      96
Ser Val Lys Val Ser Cys Lys Gly Ser Gly Tyr Thr Phe Thr Asp Tyr
            20                  25                  30 gct atg cac tgg gtg cga cag gcc cct gga caa ggc ctg gag tgg att     144
Ala Met His Trp Val Arg Gln Ala Pro Gly Gln Gly Leu Glu Trp Ile
        35                  40                  45 gga gtt att agt act tac tat ggt aat aca aac tac aac cag aag ttt     192
Gly Val Ile Ser Thr Tyr Tyr Gly Asn Thr Asn Tyr Asn Gln Lys Phe
    50                  55                  60 aag ggc cga gcc aca atg act gtc gac aca tcc acc agc aca gcc tat     240
Lys Gly Arg Ala Thr Met Thr Val Asp Thr Ser Thr Ser Thr Ala Tyr
65                  70                  75                  80 atg gaa ctt agg agc ttg aga tct gac gat act gcc gtg tat tac tgt     288
Met Glu Leu Arg Ser Leu Arg Ser Asp Asp Thr Ala Val Tyr Tyr Cys
                85                  90                  95 gca aga gga gga ttg cga gag tat tac tat gct atg gac tac tgg ggt     336
Ala Arg Gly Gly Leu Arg Glu Tyr Tyr Tyr Ala Met Asp Tyr Trp Gly
            100                 105                 110 caa gga acc atg gtc acc gtc tcc tca                                  363
Gln Gly Thr Met Val Thr Val Ser Ser
        115                 120

<210> SEQ ID NO 81
<211> LENGTH: 121
<212> TYPE: PRT
<213> ORGANISM: Artificial
<220> FEATURE:
<223> OTHER INFORMATION: Synthetic Construct (Recombinant Protein)

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Val Ile Ser Thr Tyr Tyr Gly Asn Thr Asn Tyr Asn Gln Lys Phe
    50                  55                  60

Lys Gly Arg Ala Thr Met Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Leu Arg Glu Tyr Tyr Tyr Ala Met Asp Tyr Trp Gly
            100                 105                 110

Gln Gly Thr Met Val Thr Val Ser Ser
        115                 120

<210> SEQ ID NO 82
<211> LENGTH: 420
<212> TYPE: DNA
```

<213> ORGANISM: Artificial
<220> FEATURE:
<223> OTHER INFORMATION: Recombinant DNA
<220> FEATURE:
<221> NAME/KEY: CDS
<222> LOCATION: (1)..(420)

<400> SEQUENCE: 82

| | | | | | | | | | | | | | | | | |
|---|---|---|---|---|---|---|---|---|---|---|---|---|---|---|---|---|
| atg | ggt | tgg | agc | tgt | atc | atc | ttc | ttt | ctg | gta | gca | aca | gct | aca | ggc | 48 |
| Met | Gly | Trp | Ser | Cys | Ile | Ile | Phe | Phe | Leu | Val | Ala | Thr | Ala | Thr | Gly | |
| 1 | | | | 5 | | | | | 10 | | | | | 15 | | |
| gtg | cac | tcc | caa | gtc | cag | ctg | gtg | cag | tct | ggg | gct | gaa | gtg | aag | aag | 96 |
| Val | His | Ser | Gln | Val | Gln | Leu | Val | Gln | Ser | Gly | Ala | Glu | Val | Lys | Lys | |
| | | | 20 | | | | | 25 | | | | | 30 | | | |
| cct | ggg | gcc | tca | gtg | aaa | gtc | tcc | tgc | aag | gct | tcc | ggc | tac | aca | ttc | 144 |
| Pro | Gly | Ala | Ser | Val | Lys | Val | Ser | Cys | Lys | Ala | Ser | Gly | Tyr | Thr | Phe | |
| | | | 35 | | | | | 40 | | | | | 45 | | | |
| act | gat | tat | gct | atg | cac | tgg | gtg | cga | cag | gcc | cct | gga | caa | ggc | ctg | 192 |
| Thr | Asp | Tyr | Ala | Met | His | Trp | Val | Arg | Gln | Ala | Pro | Gly | Gln | Gly | Leu | |
| | 50 | | | | | 55 | | | | | 60 | | | | | |
| gag | tgg | att | gga | gtt | att | agt | act | tac | tat | ggt | aat | aca | aac | tac | aac | 240 |
| Glu | Trp | Ile | Gly | Val | Ile | Ser | Thr | Tyr | Tyr | Gly | Asn | Thr | Asn | Tyr | Asn | |
| 65 | | | | | 70 | | | | | 75 | | | | | 80 | |
| cag | aag | ttt | aag | ggc | cga | gcc | aca | atg | act | gtc | gac | aaa | tcc | acc | agc | 288 |
| Gln | Lys | Phe | Lys | Gly | Arg | Ala | Thr | Met | Thr | Val | Asp | Lys | Ser | Thr | Ser | |
| | | | | 85 | | | | | 90 | | | | | 95 | | |
| aca | gcc | tat | atg | gaa | ctt | agg | agc | ttg | aga | tct | gac | gat | act | gcc | gtg | 336 |
| Thr | Ala | Tyr | Met | Glu | Leu | Arg | Ser | Leu | Arg | Ser | Asp | Asp | Thr | Ala | Val | |
| | | | 100 | | | | | 105 | | | | | 110 | | | |
| tat | tac | tgt | gca | aga | gga | gga | ttg | cga | gag | tat | tac | tat | gct | atg | gac | 384 |
| Tyr | Tyr | Cys | Ala | Arg | Gly | Gly | Leu | Arg | Glu | Tyr | Tyr | Tyr | Ala | Met | Asp | |
| | | 115 | | | | | 120 | | | | | 125 | | | | |
| tac | tgg | ggt | caa | gga | acc | atg | gtc | acc | gtc | tcc | tca | | | | | 420 |
| Tyr | Trp | Gly | Gln | Gly | Thr | Met | Val | Thr | Val | Ser | Ser | | | | | |
| | 130 | | | | | 135 | | | | | 140 | | | | | |

<210> SEQ ID NO 83
<211> LENGTH: 140
<212> TYPE: PRT
<213> ORGANISM: Artificial
<220> FEATURE:
<223> OTHER INFORMATION: Synthetic Construct (Recombinant Protein)

<400> SEQUENCE: 83

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ala Met His Trp Val Arg Gln Ala Pro Gly Gln Gly Leu
    50                  55                  60

Glu Trp Ile Gly Val Ile Ser Thr Tyr Tyr Gly Asn Thr Asn Tyr Asn
65                  70                  75                  80

Gln Lys Phe Lys Gly Arg Ala Thr Met Thr Val Asp Lys Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Gly Gly Leu Arg Glu Tyr Tyr Tyr Ala Met Asp
        115                 120                 125

```
Tyr Trp Gly Gln Gly Thr Met Val Thr Val Ser Ser
        130                 135                 140

<210> SEQ ID NO 84
<211> LENGTH: 363
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(363)

<400> SEQUENCE: 84 caa gtc cag ctg gtg cag tct ggg gct gaa gtg aag aag cct ggg gcc      48
Gln Val Gln Leu Val Gln Ser Gly Ala Glu Val Lys Lys Pro Gly Ala
1               5                   10                  15 tca gtg aaa gtc tcc tgc aag gct tcc ggc tac aca ttc act gat tat      96
Ser Val Lys Val Ser Cys Lys Ala Ser Gly Tyr Thr Phe Thr Asp Tyr
            20                  25                  30 gct atg cac tgg gtg cga cag gcc cct gga caa ggc ctg gag tgg att     144
Ala Met His Trp Val Arg Gln Ala Pro Gly Gln Gly Leu Glu Trp Ile
        35                  40                  45 gga gtt att agt act tac tat ggt aat aca aac tac aac cag aag ttt     192
Gly Val Ile Ser Thr Tyr Tyr Gly Asn Thr Asn Tyr Asn Gln Lys Phe
    50                  55                  60 aag ggc cga gcc aca atg act gtc gac aaa tcc acc agc aca gcc tat     240
Lys Gly Arg Ala Thr Met Thr Val Asp Lys Ser Thr Ser Thr Ala Tyr
65                  70                  75                  80 atg gaa ctt agg agc ttg aga tct gac gat act gcc gtg tat tac tgt     288
Met Glu Leu Arg Ser Leu Arg Ser Asp Asp Thr Ala Val Tyr Tyr Cys
                85                  90                  95 gca aga gga gga ttg cga gag tat tac tat gct atg gac tac tgg ggt     336
Ala Arg Gly Gly Leu Arg Glu Tyr Tyr Tyr Ala Met Asp Tyr Trp Gly
            100                 105                 110 caa gga acc atg gtc acc gtc tcc tca                                 363
Gln Gly Thr Met Val Thr Val Ser Ser
        115                 120

<210> SEQ ID NO 85
<211> LENGTH: 121
<212> TYPE: PRT
<213> ORGANISM: Artificial
<220> FEATURE:
<223> OTHER INFORMATION: Synthetic Construct (Recombinant Protein)

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Val Ile Ser Thr Tyr Tyr Gly Asn Thr Asn Tyr Asn Gln Lys Phe
    50                  55                  60

Lys Gly Arg Ala Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Leu Arg Glu Tyr Tyr Tyr Ala Met Asp Tyr Trp Gly
            100                 105                 110
```

Gln Gly Thr Met Val Thr Val Ser Ser
        115                 120

<210> SEQ ID NO 86
<211> LENGTH: 420
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(420)

<400> SEQUENCE: 86

```
atg ggt tgg agc tgt atc atc ttc ttt ctg gta gca aca gct aca ggc      48
Met Gly Trp Ser Cys Ile Ile Phe Phe Leu Val Ala Thr Ala Thr Gly
1               5                   10                  15 gtg cac tcc caa gtc cag ctg gtg cag tct ggg gct gaa gtg aag aag      96
Val His Ser Gln Val Gln Leu Val Gln Ser Gly Ala Glu Val Lys Lys
                20                  25                  30 cct ggg gcc tca gtg aaa gtc tcc tgc aag ggt tcc ggc tac aca ttc     144
Pro Gly Ala Ser Val Lys Val Ser Cys Lys Gly Ser Gly Tyr Thr Phe
            35                  40                  45 act gat tat gct atg cac tgg gtg cga cag gcc cct gga caa ggc ctg     192
Thr Asp Tyr Ala Met His Trp Val Arg Gln Ala Pro Gly Gln Gly Leu
        50                  55                  60 gag tgg att gga gtt att agt act tac tat ggt aat aca aac tac aac     240
Glu Trp Ile Gly Val Ile Ser Thr Tyr Tyr Gly Asn Thr Asn Tyr Asn
65                  70                  75                  80 cag aag ttt aag ggc cga gcc aca atg act gtc gac aaa tcc acc agc     288
Gln Lys Phe Lys Gly Arg Ala Thr Met Thr Val Asp Lys Ser Thr Ser
                85                  90                  95 aca gcc tat atg gaa ctt agg agc ttg aga tct gac gat act gcc gtg     336
Thr Ala Tyr Met Glu Leu Arg Ser Leu Arg Ser Asp Asp Thr Ala Val
            100                 105                 110 tat tac tgt gca aga gga gga ttg cga gag tat tac tat gct atg gac     384
Tyr Tyr Cys Ala Arg Gly Gly Leu Arg Glu Tyr Tyr Tyr Ala Met Asp
        115                 120                 125 tac tgg ggt caa gga acc atg gtc acc gtc tcc tca                     420
Tyr Trp Gly Gln Gly Thr Met Val Thr Val Ser Ser
        130                 135                 140
```

<210> SEQ ID NO 87
<211> LENGTH: 140
<212> TYPE: PRT
<213> ORGANISM: Artificial
<220> FEATURE:
<223> OTHER INFORMATION: Synthetic Construct (Recombinant Protein)

<400> SEQUENCE: 87

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Gly Ser Gly Tyr Thr Phe
            35                  40                  45

Thr Asp Tyr Ala Met His Trp Val Arg Gln Ala Pro Gly Gln Gly Leu
        50                  55                  60

Glu Trp Ile Gly Val Ile Ser Thr Tyr Tyr Gly Asn Thr Asn Tyr Asn
65                  70                  75                  80

Gln Lys Phe Lys Gly Arg Ala Thr Met Thr Val Asp Lys Ser Thr Ser
                85                  90                  95

```
Thr Ala Tyr Met Glu Leu Arg Ser Leu Arg Ser Asp Asp Thr Ala Val
            100                 105                 110

Tyr Tyr Cys Ala Arg Gly Gly Leu Arg Glu Tyr Tyr Ala Met Asp
        115                 120                 125

Tyr Trp Gly Gln Gly Thr Met Val Thr Val Ser Ser
    130                 135                 140

<210> SEQ ID NO 88
<211> LENGTH: 363
<212> TYPE: DNA
<213> ORGANISM: Artificial
<220> FEATURE:
<223> OTHER INFORMATION: Recombinant DNA
<220> FEATURE:
<221> NAME/KEY: CDS
<222> LOCATION: (1)..(363)

<400> SEQUENCE: 88 caa gtc cag ctg gtg cag tct ggg gct gaa gtg aag aag cct ggg gcc        48
Gln Val Gln Leu Val Gln Ser Gly Ala Glu Val Lys Lys Pro Gly Ala
1               5                   10                  15 tca gtg aaa gtc tcc tgc aag ggt tcc ggc tac aca ttc act gat tat        96
Ser Val Lys Val Ser Cys Lys Gly Ser Gly Tyr Thr Phe Thr Asp Tyr
                20                  25                  30 gct atg cac tgg gtg cga cag gcc cct gga caa ggc ctg gag tgg att       144
Ala Met His Trp Val Arg Gln Ala Pro Gly Gln Gly Leu Glu Trp Ile
            35                  40                  45 gga gtt att agt act tac tat ggt aat aca aac tac aac cag aag ttt       192
Gly Val Ile Ser Thr Tyr Tyr Gly Asn Thr Asn Tyr Asn Gln Lys Phe
        50                  55                  60 aag ggc cga gcc aca atg act gtc gac aaa tcc acc agc aca gcc tat       240
Lys Gly Arg Ala Thr Met Thr Val Asp Lys Ser Thr Ser Thr Ala Tyr
65                  70                  75                  80 atg gaa ctt agg agc ttg aga tct gac gat act gcc gtg tat tac tgt       288
Met Glu Leu Arg Ser Leu Arg Ser Asp Asp Thr Ala Val Tyr Tyr Cys
                85                  90                  95 gca aga gga gga ttg cga gag tat tac tat gct atg gac tac tgg ggt       336
Ala Arg Gly Gly Leu Arg Glu Tyr Tyr Tyr Ala Met Asp Tyr Trp Gly
            100                 105                 110 caa gga acc atg gtc acc gtc tcc tca                                   363
Gln Gly Thr Met Val Thr Val Ser Ser
        115                 120

<210> SEQ ID NO 89
<211> LENGTH: 121
<212> TYPE: PRT
<213> ORGANISM: Artificial
<220> FEATURE:
<223> OTHER INFORMATION: Synthetic Construct (Recombinant Protein)

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
                20                  25                  30

Ala Met His Trp Val Arg Gln Ala Pro Gly Gln Gly Leu Glu Trp Ile
            35                  40                  45

Gly Val Ile Ser Thr Tyr Tyr Gly Asn Thr Asn Tyr Asn Gln Lys Phe
        50                  55                  60

Lys Gly Arg Ala Thr Met Thr Val Asp Lys Ser Thr Ser Thr Ala Tyr
65                  70                  75                  80
```

```
Met Glu Leu Arg Ser Leu Arg Ser Asp Asp Thr Ala Val Tyr Tyr Cys
                85              90                  95

Ala Arg Gly Gly Leu Arg Glu Tyr Tyr Tyr Ala Met Asp Tyr Trp Gly
            100             105                 110

Gln Gly Thr Met Val Thr Val Ser Ser
        115             120
```

ANTI-HDLK-1 ANTIBODY HAVING AN ANTITUMOR ACTIVITY IN VIVO

CROSS-REFERENCE TO RELATED APPLICATIONS

The present application claims benefit of priority to U.S. Provisional Patent Application No. 61/709,282 filed on Oct. 3, 2012, the entire contents of which are hereby incorporated by reference.

FIELD OF THE INVENTION

The present invention relates to anti-human Dlk-1 antibodies having anti-tumor activity and particularly to anti-human Dlk-1 antibodies having anti-tumor activity in vivo. In addition, the present invention also relates to hybridomas that produce the aforementioned antibodies and a use of the aforementioned antibodies.

BACKGROUND OF THE INVENTION

Human Dlk-1 (delta-like 1 homolog (*Drosophila*); which may be hereinafter referred to as "hDlk-1") is a type I transmembrane (one-transmembrane-type) protein with a full length of 383 amino acid residues which has 6 EGF-like motifs in its extracellular region. The extracellular region shows homology with a Notch/Delta/Serrate family. A hDlk-1 gene has been cloned as a molecule expressed in a GRP (gastrin releasing peptide)-responsive lung small cell carcinoma-derived cell line (Non-Patent Document 1), or as a factor for suppressing preadipocyte differentiation (Non-Patent Document 2). From the viewpoint of the homology of the amino acid sequence of hDlk-1 with that of Delta that is a ligand of a Notch receptor as a cell differentiation regulator, such Dlk-1 is generally referred to as a gene symbol, DLK1. It also has several other gene symbols such as Pref-1 (Non-Patent Document 2), pG2 (Non-Patent Document 3), SCP-1 (Non-Patent Document 4) and ZOG (Non-Patent Document 5). However, these gene symbols basically indicate the same molecule.

Moreover, hDlk-1 is cleaved with an unidentified protease which cuts the neighborhood of cell membrane in the extracellular region of hDlk-1 and it is then secreted into blood. Free hDlk-1 (hDlk-1 extracellular region) is a molecule identical to a glycoprotein called FA-1 (Fetal antigen-1) (Non-Patent Document 6) consisting of 225 to 262 amino acid residues.

The hDlk-1 gene and a gene product thereof are expressed at a high level in undifferentiated, highly proliferative, fetal cells. In particular, the hDlk-1 gene and the gene product thereof are highly expressed in fetal liver, fetal kidney, fetal skeletal muscle, fetal brain and the like. After birth, however, expression of such a hDlk-1 gene and a gene product thereof cannot be observed in most of the tissues. In normal adult tissues, the hDlk-1 gene and the gene product thereof are localized in adrenal gland, placenta and hypophysis (Patent Document 1, Non-Patent Document 2).

Furthermore, even in mature tissues, expression of hDlk-1 is observed in cells that are considered to be undifferentiated stem cells or precursor cells. For example, it has been reported that expression of hDlk-1 has been observed in hepatic oval cells that are undifferentiated and have pluripotency in adult liver (Non-Patent Documents 7 and 8), in mesenchymal stem cells that are the stem cells of bone/cartilage/adipose cells (Non-Patent Document 9), and in prostatic epithelial precursor cells in the basal cell layer of the prostate (Non-Patent Document 18). Further, it has also been reported that, in the case of mouse mesenchymal stem cells, free Dlk-1 (mouse Dlk-1 extracellular region) activates ERK/MAP kinase and induces expression of Sox-9, so that differentiation of the cells into adipose cells can be suppressed and at the same time, differentiation of the cells into chondrocytes can be induced, but that such free Dlk-1 suppresses differentiation of the cells into osteoblasts and maturation of chondrocytes (Non-Patent Documents 19 and 20). It has been suggested that hDlk-1 is associated with the properties of such tissue stem cells, such as the maintenance of undifferentiation ability.

Such an expression pattern of hDlk-1 restricted in fetal cells or stem cells and a family of genes/gene products having EGF-like motifs (Notch-receptor, Notch ligand (Delta, Jagged, serrate), etc.) generally controls the growth or differentiation of cells by intercellular interaction via EGF-like motifs. Thus, it has been suggested that hDlk-1 also has such functions. In fact, it has been well known that expression of hDlk-1 is decreased concomitant with differentiation of adipose precursor cells and that adipose differentiation is suppressed, if the hDlk-1 gene is forced to express in adipose precursor cells (Non-Patent Document 2). However, at the present time, details regarding a molecule (a ligand) interacting with hDlk-1 are unknown.

On the other hand, it has been reported that the hDlk-1 gene and the gene product thereof are expressed with a high frequency in various types of cancers or tumors. The types of cancers, in which expression of hDlk-1 has been confirmed so far, include: solid cancers such as neuroendocrine tumor, neuroblastoma, glioma, neurofibromatosis type 1, small cell lung cancer, liver cancer, kidney cancer, ovarian cancer, colon cancer, breast cancer, and pancreatic cancer (Patent Documents 1, 2, 4 and 5 and Non-Patent Documents 1, 3, 10, 11, 12, 13, 14 and 21); and blood cancers such as myelodysplastic syndrome (Patent Document 3 and Non-Patent Documents 15 and 16) and acute myelocytic leukemia (Non-Patent Document 16). It has been reported that cell growth is accelerated if a hDlk-1 gene is introduced into a K562 cell that is an erythroleukemia cell line (Non-Patent Document 16) and also that, if such a hDlk-1 gene is introduced into glioblastomas, it causes the disappearance of contact inhibition of cells as well as acceleration of cell growth, so that anchorage-independent cell growth ability can be achieved. The relationship between hDlk-1 and carcinogenesis has been suggested (Non-Patent Document 17).

Conventionally, as anti-hDlk-1 monoclonal antibodies showing cytotoxicity on human liver cancer cells in vitro in the presence of complement, rat anti-hDlk-1 monoclonal antibodies 1C1, 4C4 and 31C4 (clone names) have been known (Patent Document 1). On the other hand, these clone antibodies have also been known as antibodies that do not show anti-tumor activity (tumor growth-inhibiting activity) in vivo (in treatment models with human cancer cell-bearing mice) (Patent Documents 4 and 5).

Patent Document 1: WO 2005/052156
Patent Document 2: WO 02/081625
Patent Document 3: Japanese Patent Laid-Open No. 2001-269174
Patent Document 4: WO 2008/056833
Patent Document 5: WO 2009/116670
Non-Patent Document 1: Laborda, J. et al., J. Biol. Chem., vol. 268 (6), pp. 3817-3820 (1993)
Non-Patent Document 2: Smas, C. M. et al., Cell, vol. 73 (4), pp. 725-734 (1993)
Non-Patent Document 3: Helman, L. J. et al., Proc. Natl. Acad. Sci. USA, vol. 84, pp. 2336-2339 (1987)

Non-Patent Document 4: Maruyama, K. et al., Unpublished, Genebank accession number D16847 (1993)
Non-Patent Document 5: Halder, S. K. et al., Endocrinology, vol. 139, pp. 3316-3328 (1998)
Non-Patent Document 6: Fay, T. N. et al., Eur. J. Obstet. Gynecol. Reprod. Biol., vol. 29, pp. 73-85 (1988)
Non-Patent Document 7: Tanimizu, N. et al., Gene Expression Patterns, vol. 5, pp. 209-218 (2004)
Non-Patent Document 8: Jensen, C H. et al., Am. J. Pathol., vol. 164 (4), pp. 1347-1359 (2004)
Non-Patent Document 9: Abdallah, B. M. et al., J. Bone Miner. Res., vol. 19 (5), pp. 841-852 (2004)
Non-Patent Document 10: Jensen, C. H. et al., Br. J. Dermatol., vol. 140 (6), pp. 1054-1059 (1999)
Non-Patent Document 11: Jensen, C. H. et al., Tumour Biol., vol. 20 (5), pp. 256-262 (1999)
Non-Patent Document 12: Yin, D. et al., Int. J. Oncol., vol. 24 (4), pp. 1011-1015 (2004)
Non-Patent Document 13: Yin, D. et al., Oncogene, vol. 25 (13), pp. 1852-1861 (2006)
Non-Patent Document 14: Fukuzawa, R. et al., J. Clin. Pathol., vol. 58, pp. 145-150 (2006)
Non-Patent Document 15: Miyazato, A. et al., Blood, vol. 98, pp. 422-427 (2001)
Non-Patent Document 16: Sakajiri, S. et al., Leukemia, vol. 19 (8), pp. 1404-1410 (2005)
Non-Patent Document 17: Yin, D. et al., Oncogene, vol. 25 (13), pp. 1852-1861 (2006)
Non-Patent Document 18: Ceder, J. A. et al., Eur. Urol., Vol. 54(6), pp. 1344-1353 (2008)
Non-Patent Document 19: Sul, H S., Mol. Endocrinol., Vol. 23 (11), pp. 1717-1725 (2009)
Non-Patent Document 20: Wang, Y. et al., Mol. Cell Biol., Vol. 30(14), pp. 3480-3492 (2010)
Non-Patent Document 21: Yanai, H. et al., J. Biochem., Vol. 148(1), pp. 85-92 (2010)

SUMMARY OF THE INVENTION

As described above, in the case of normal tissues, expression of hDlk-1 is restricted in embryonic cells or stem cells. However, in the case of cancer tissues, hDlk-1 is expressed with a high frequency in various types of cells. Such hDlk-1 is a cell membrane protein/secretory protein. Based on these facts, hDlk-1 is considered to become a good target in the treatment of various types of tumors, etc. When such hDlk-1 is targeted, an anti-hDlk-1 antibody is considered to be useful. In order to be used as an antibody for cancer therapy for example, the antibody more desirably has an ability to retain a stable antigen-binding activity in a liquid formulation and in human or monkey blood, as well as showing a significant anti-tumor activity by administration of the antibody alone in human-cancer-bearing mouse treatment models.

Thus, an object of the present invention is to provide an anti-hDlk-1 antibody having anti-tumor activity, specifically an anti-hDlk-1 monoclonal antibody having anti-tumor activity in vivo and particularly the aforementioned antibody, which is a humanized antibody. Moreover, another object of the present invention is to provide a hybridoma that produces the aforementioned antibody, a complex of the aforementioned antibody and an agent, and the like. Furthermore, a further object of the present invention is to provide a pharmaceutical composition for diagnosing or treating tumor, a pharmaceutical composition for inducing apoptosis in tumor cells, a tumor therapeutic agent, a tumor diagnostic agent, an agent for inducing apoptosis in tumor cells, a method for treating tumor, a method for detecting tumor, a method for inducing apoptosis in tumor cells, a kit for detecting or diagnosing tumor and a kit for inducing apoptosis in tumor cells, each of which comprises the aforementioned antibody, the aforementioned complex or the like.

The present inventors have conducted intensive studies directed towards achieving the aforementioned objects. As a result, the inventors have found an antibody that specifically reacts with hDlk-1 (particularly, an anti-hDlk-1 monoclonal antibody) and has anti-tumor activity (particularly, a humanized anti-hDlk-1 antibody). The inventors have then confirmed that such an antibody and a complex have anti-tumor activity in vivo. Further, the present inventors have succeeded in producing the aforementioned antibody, which is a humanized antibody. Still further, the present inventors have also found that such an antibody and a complex are useful for the treatment, diagnosis and detection of a tumor, and induction of apoptosis in tumor cells, thereby completing the present invention.

That is to say, the present invention is as follows.

(1) An antibody against human Dlk-1, wherein the amino acid sequence of the H chain V region comprises the amino acid sequence as shown in any one of SEQ ID NOS: 35, 40, 69, 73, 77, 81, 85 and 89, and the amino acid sequence of the L chain V region comprises the amino acid sequence as shown in SEQ ID NO: 45.

The antibody according to (1) above is an antibody having an anti-tumor activity in vivo, for example. Herein, the tumor is at least one type selected from, for example, the group consisting of human colon cancer, human breast cancer, human liver cancer, human pancreatic cancer, human small cell lung cancer and human neuroblastoma.

The antibody according to (1) above is a humanized antibody, for example.

The antibody according to (1) above is a monoclonal antibody, for example.

The antibody according to (1) above is, for example, an antibody, which binds to at least a portion of a region comprising amino acids at positions 24 to 91 in the amino acid sequence of human Dlk-1 as shown in SEQ ID NO: 2.

(2) An antibody fragment derived from the antibody according to (1) above.

Examples of the antibody fragment according to (2) above include an antibody fragment comprising the amino acid sequence as shown in any one of SEQ ID NOS: 35, 40, 69, 73, 77, 81, 85 and 89, and an antibody fragment comprising the amino acid sequence as shown in SEQ ID NO: 45; and an antibody fragment comprising both the amino acid sequence as shown in any one of SEQ ID NOS: 35, 40, 69, 73, 77, 81, 85 and 89 and an antibody fragment comprising the amino acid sequence as shown in SEQ ID NO: 45.

(3) An antibody-agent complex, which comprises the antibody according to (1) above and a compound having an anti-tumor activity and/or a cell-killing activity.

(4) An antibody fragment-agent complex, which comprises the antibody fragment according to (2) above and a compound having an anti-tumor activity and/or a cell-killing activity.

(5) A pharmaceutical composition, which comprises at least one type selected from the group consisting of the antibody according to (1) above, the antibody fragment according to (2) above and the complex according to (3) or (4) above.

The pharmaceutical composition according to (5) above is used in the treatment of tumor, for example, and a particular example of the pharmaceutical composition is a pharmaceutical composition, which does not cause weight reduction as a side effect. In addition, the pharmaceutical composition according to (5) above is used in the diagnosis of tumor, for example. Moreover, the pharmaceutical composition according to (5) above is used in induction of apoptosis in tumor cells, for example.

(6) A tumor therapeutic agent, which comprises at least one type selected from the group consisting of the antibody according to (1) above, the antibody fragment according to (2) above and the complex according to (3) or (4) above.

An example of the tumor therapeutic agent according to (6) above is a tumor therapeutic agent, which does not cause weight reduction as a side effect.

(7) An agent for inducing apoptosis in tumor cells, which comprises at least one type selected from the group consisting of the antibody according to (1) above, the antibody fragment according to (2) above and the complex according to (3) or (4) above.

Herein, in the pharmaceutical composition according to (5) above, the tumor therapeutic agent according to (6) above and the apoptosis-inducing agent according to (7) above, the tumor is at least one type selected from, for example, the group consisting of human colon cancer, human breast cancer, human liver cancer, human pancreatic cancer, human small cell lung cancer and human neuroblastoma.

(8) A method for treating a tumor, which comprises administering to a patient at least one type selected from the group consisting of the antibody according to (1) above, the antibody fragment according to (2) above and the complex according to (3) or (4) above.

An example of the treatment method according to (8) above is a treatment method, which does not cause weight reduction as a side effect.

(9) A method for detecting a tumor, which comprises: allowing at least one type selected from the group consisting of the antibody according to (1) above, the antibody fragment according to (2) above and the complex according to (3) or (4) above, to react with a sample collected from a living body; and detecting a signal(s) of the reacted antibody and/or antibody fragment.

(10) A method for inducing apoptosis in tumor cells, which comprises: allowing at least one type selected from the group consisting of the antibody according to (1) above, the antibody fragment according to (2) above and the complex according to (3) or (4) above, to react with a sample collected from a living body; and detecting a signal(s) of the reacted antibody and/or antibody fragment.

Herein, in the treatment method according to (8) above, the detection method according to (9) above and the apoptosis induction method according to (10) above, the tumor is at least one type selected from, for example, the group consisting of human colon cancer, human breast cancer, human liver cancer, human pancreatic cancer, human small cell lung cancer and human neuroblastoma.

(11) A kit for treating, diagnosing, or detecting a tumor, which comprises at least one type selected from the group consisting of the antibody according to (1) above, the antibody fragment according to (2) above and the complex according to (3) or (4) above.

(12) A kit for inducing apoptosis in tumor cells, which comprises at least one type selected from the group consisting of the antibody according to (1) above, the antibody fragment according to (2) above and the complex according to (3) or (4) above.

Herein in the kits according to (11) and (12) above, the tumor is at least one type selected from, for example, the group consisting of human colon cancer, human breast cancer, human liver cancer, human pancreatic cancer, human small cell lung cancer and human neuroblastoma.

BRIEF DESCRIPTION OF THE DRAWINGS

FIG. 1 shows the cDNA nucleotide sequence (SEQ ID NO: 12) of the H chain (heavy chain) variable region (VH) of mouse anti-hDlk-1 monoclonal antibody clone BA-1-3D and a putative amino acid sequence thereof (SEQ ID NO: 13). The amino acid residue is indicated with a single letter, and signal peptides (peptides consisting of 19 amino acids from the N-terminus of the putative amino acid sequence) are described in italics. The double-lined glutamine (Q) represents the N-terminal amino acid residue of a mature peptide of BA-1-3D VH. The cDNA nucleotide sequence of the mature peptide of BA-1-3D VH is as shown in SEQ ID NO: 14, and a putative amino acid sequence thereof is as shown in SEQ ID NO: 15. The CDR sequences (underlined) were provided in accordance with the definition of Kabat et al. (Sequences of Proteins of Immunological Interests, Fifth edition, NIH Publication No. 91-3242, U.S. Department of Health and Human Services, 1991). The amino acid sequences of CDR1 (DYAMH), CDR2 (VISTYYGNTNYNQKFKG) and CDR3 (GGLREYYYAMDY) of BA-1-3D VH are as shown in SEQ ID NOS: 16 to 18, respectively.

FIG. 2 shows the cDNA nucleotide sequence (SEQ ID NO: 19) of the L chain (light chain) variable region (VL) of mouse anti-hDlk-1 monoclonal antibody clone BA-1-3D and a putative amino acid sequence thereof (SEQ ID NO: 20). The amino acid residue is indicated with a single letter, and signal peptides (peptides consisting of 20 amino acids from the N-terminus of the putative amino acid sequence) are described in italics. The double-lined aspartic acid (D) represents the N-terminal amino acid residue of a mature peptide of BA-1-3D VL. The cDNA nucleotide sequence of the mature peptide of BA-1-3D VL is as shown in SEQ ID NO: 21, and a putative amino acid sequence thereof is as shown in SEQ ID NO: 22. The CDR sequences (underlined) were provided in accordance with the definition of Kabat et al. (Sequences of Proteins of Immunological Interests, Fifth edition, NIH Publication No. 91-3242, U.S. Department of Health and Human Services, 1991). The amino acid sequences of CDR1 (KSSQSLLNSSNQKNYLA), CDR2 (FASTRES) and CDR3 (QQHYSTPPT) of BA-1-3D VL are as shown in SEQ ID NOS: 23 to 25, respectively.

FIG. 3 shows the nucleotide sequence (SEQ ID NO: 26) and amino acid sequence of a BA-1-3D VH gene that has been designed such that it is sandwiched between a SpeI site (ACTAGT; underlined) and a HindIII site (AAGCTT; underlined). The nucleotide sequence described in italics (22 nucleotides on the 3'-terminal side including the HindIII site) indicates an intron sequence. Other than these, FIG. 3 is the same as described in FIG. 1.

FIG. 4 shows the nucleotide sequence (SEQ ID NO: 27) and amino acid sequence of a BA-1-3D VL gene that has been designed such that it is sandwiched between a NheI site (GCTAGC; underlined) and an EcoRI site (GAATTC; underlined). The nucleotide sequence described in italics (22 nucleotides on the 3'-terminal side including the EcoRI site) indicates an intron sequence. Other than these, FIG. 4 is the same as described in FIG. 2.

FIG. 6 shows an alignment of the amino acid sequences of, BA-1-3D VH, two types of humanized BA-1-3D VH (HuBA-1-3D VH1 and HuBA-1-3D VH2) and U00503 VH as an acceptor. The amino acid residue is indicated with a single letter, and the number indicated above each sequence was positioned in accordance with the definition of Kabat et al. (1991). The underlines in the amino acid sequence of BA-1-3D VH indicate CDR sequences as determined in accordance with the definition of Kabat et al. (1991). The underlines in the amino acid sequences of HuBA-1-3D VH1 and HuBA-1-3D VH2 indicate amino acid residues that retain the amino acid residues at the same position in the amino acid sequence of the corresponding mouse BA-1-3D VH, and these amino acid residues are assumed to be important for formation of the structures of CDRs. The CDR sequences of U00503 VH are not shown in the figure.

Figure 5:
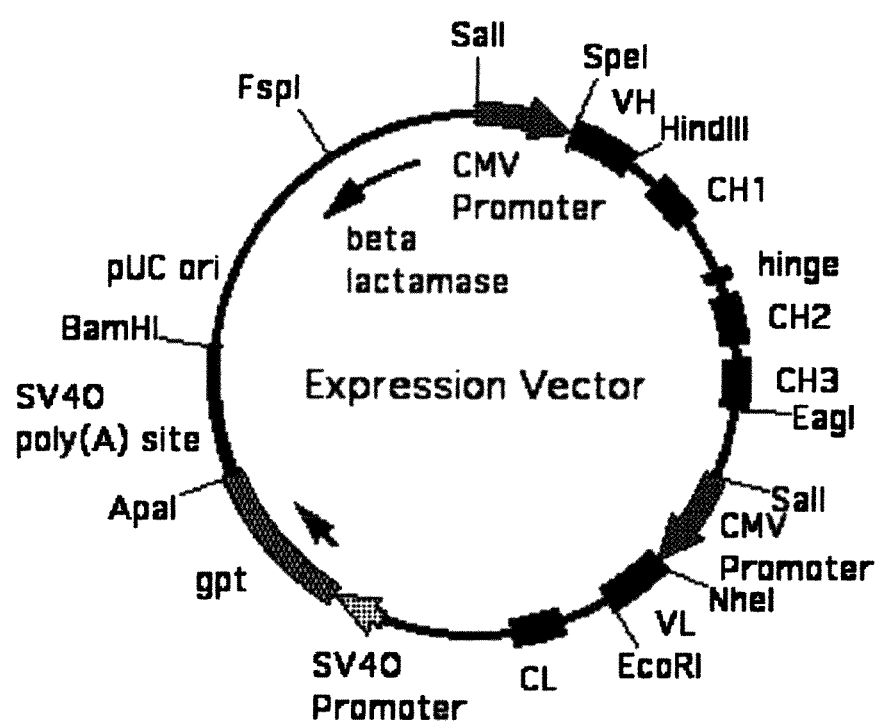
FIG. 5 is a schematic view showing the structures of an expression vector for chimeric and humanized BA-1-3D IgGa/κ antibodies. In a clockwise direction starting from the restriction enzyme site for SalI, such an expression vector comprises a H chain translation unit starting with a human cytomegalovirus (CMV) major immediate early promoter/an enhancer (CMV promoter) used for initiation of the transcription of an antibody H chain gene. The CMV promoter then proceeds to a VH exon, the exons of CH1, a hinge region, CH2 and CH3, and introns interspersed among the exons, and after the CH3 exon, a polyadenylation sequence is ligated. After the H chain gene sequence, the vector comprises a L chain translation unit starting with a CMV promoter, a VL exon, a part of intron, and then, the exon of a human κ chain constant region (CL) and a polyadenylation sequence. Thereafter, the L chain gene proceeds to a segment comprising an SV40 early promoter (SV40 promoter), an *E. coli* xanthine guanine phosphoribosyl transferase (gpt) gene and the polyadenylation site of SV40 (SV40 poly(A) site). Finally, the plasmid has a part of a pUC19 plasmid comprising the replication origin (pUC ori) and a β-lactamase gene of *E. coli*.

It is to be noted that the amino acid sequence of BA-1-3D VH in the figure is as shown in SEQ ID NO: 15 (a nucleotide sequence encoding this sequence is as shown in SEQ ID NO: 14), the amino acid sequence of HuBA-1-3D VH1 in the figure is as shown in SEQ ID NO: 35 (a nucleotide sequence encoding this sequence is as shown in SEQ ID NO: 34), the amino acid sequence of HuBA-1-3D VH2 in the figure is as shown in SEQ ID NO: 40 (a nucleotide sequence encoding this sequence is as shown in SEQ ID NO: 39), and the amino acid sequence of U00503 VH in the figure is as shown in SEQ ID NO: 29 (a nucleotide sequence encoding this sequence is as shown in SEQ ID NO: 28).

FIG. 7 shows an alignment of the amino acid sequences of, BA-1-3D VL, humanized BA-1-3D VL (HuBA-1-3D VL) and Z46622 VL as an acceptor. The amino acid residue is indicated with a single letter, and the number indicated above each sequence was positioned in accordance with the definition of Kabat et al. (1991). The underlines in the amino acid sequence of BA-1-3D VL indicate CDR sequences as determined in accordance with the definition of Kabat et al. (1991). The underline in the amino acid sequence of HuBA-1-3D VL indicates the amino acid residue that retains the amino acid residue at the same position in the amino acid sequence of the corresponding mouse BA-1-3D VL, and this amino acid residue is assumed to be important for formation of the structures of CDRs. The CDR sequences of Z46622 VL are not shown in the figure.

It is to be noted that the amino acid sequence of BA-1-3D VL in the figure is as shown in SEQ ID NO: 22 (a nucleotide sequence encoding this sequence is as shown in SEQ ID NO: 21), the amino acid sequence of HuBA-1-3D VL in the figure is as shown in SEQ ID NO: 45 (a nucleotide sequence encoding this sequence is as shown in SEQ ID NO: 44), and the amino acid sequence of Z46622 VL in the figure is as shown in SEQ ID NO: 31 (a nucleotide sequence encoding this sequence is as shown in SEQ ID NO: 30).

FIG. 8 shows the nucleotide sequence (SEQ ID NO: 36) and amino acid sequence of a HuBA-1-3D VH1 gene that has been designed such that it is sandwiched between a SpeI site and a HindIII site. The nucleotide sequence described in italics (23 nucleotides on the 3'-terminal side including the HindIII site) indicates an intron sequence.

The cDNA nucleotide sequence of HuBA-1-3D VH1 is as shown in SEQ ID NO: 32, and a putative amino acid sequence thereof is as shown in SEQ ID NO: 33. The amino acid residue is indicated with a single letter, and signal peptides (peptides consisting of 19 amino acids from the N-terminus of the putative amino acid sequence) are described in italics. The double-lined glutamine (Q) represents the N-terminal amino acid residue of a mature peptide of HuBA-1-3D VH1. The cDNA nucleotide sequence of the mature peptide of HuBA-1-3D VH1 is as shown in SEQ ID NO: 34, and a putative amino acid sequence thereof is as shown in SEQ ID NO: 35. The CDR sequences (underlined) were provided in accordance with the definition of Kabat et al. (Sequences of Proteins of Immunological Interests, Fifth edition, NIH Publication No. 91-3242, U.S. Department of Health and Human Services, 1991). The amino acid sequences of CDR1 (DYAMH), CDR2 (VISTYYGNTNYNQKFKG) and CDR3 (GGLREYYYAMDY) of HuBA-1-3D VH1 are as shown in SEQ ID NOS: 16 to 18, respectively.

FIG. 9 shows the nucleotide sequence (SEQ ID NO: 41) and amino acid sequence of a HuBA-1-3D VH2 gene that has been designed such that it is sandwiched between a SpeI site (ACTAGT; underlined) and a HindIII site (AAGCTT; underlined). The nucleotide sequence described in italics (23 nucleotides on the 3'-terminal side including the HindIII site) indicates an intron sequence.

The cDNA nucleotide sequence of HuBA-1-3D VH2 is as shown in SEQ ID NO: 37, and a putative amino acid sequence thereof is as shown in SEQ ID NO: 38. The amino acid residue is indicated with a single letter, and signal peptides (peptides consisting of 19 amino acids from the N-terminus of the putative amino acid sequence) are described in italics. The double-lined glutamine (Q) represents the N-terminal amino acid residue of a mature peptide of HuBA-1-3D VH2. The cDNA nucleotide sequence of the mature peptide of HuBA-1-3D VH2 is as shown in SEQ ID NO: 39, and a putative amino acid sequence thereof is as shown in SEQ ID NO: 40. The CDR sequences (underlined) were provided in accordance with the definition of Kabat et al. (Sequences of Proteins of Immunological Interests, Fifth edition, NIH Publication No. 91-3242, U.S. Department of Health and Human Services, 1991). The amino acid sequences of CDR1 (DYAMH), CDR2 (VISTYYGNTNYNQKFKG) and CDR3 (GGLREYYYAMDY) of HuBA-1-3D VH2 are as shown in SEQ ID NOS: 16 to 18, respectively.

FIG. 10 shows the nucleotide sequence (SEQ ID NO: 46) and amino acid sequence of a HuBA-1-3D VL gene that has been designed such that it is sandwiched between a NheI site (GCTAGC; underlined) and an EcoRI site (GAATTC; underlined). The nucleotide sequence described in italics (23 nucleotides on the 3'-terminal side including the EcoRI site) indicates an intron sequence.

The cDNA nucleotide sequence of HuBA-1-3D VL is as shown in SEQ ID NO: 42, and a putative amino acid sequence thereof is as shown in SEQ ID NO: 43. The amino acid residue is indicated with a single letter, and signal peptides (peptides consisting of 20 amino acids from the N-terminus of the putative amino acid sequence) are described in italics. The double-lined aspartic acid (D) represents the N-terminal amino acid residue of a mature peptide of HuBA-1-3D VL. The cDNA nucleotide sequence of the mature peptide of HuBA-1-3D VL is as shown in SEQ ID NO: 44, and a putative amino acid sequence thereof is as shown in SEQ ID NO: 45. The CDR sequences (underlined) were provided in accordance with the definition of Kabat et al. (Sequences of Proteins of Immunological Interests, Fifth edition, NIH Publication No. 91-3242, U.S. Department of Health and Human Services, 1991). The amino acid sequences of CDR1 (KSSQSLLNSSNQKNYLA), CDR2 (FASTRES) and CDR3 (QQHYSTPPT) of HuBA-1-3D VL are as shown in SEQ ID NOS: 23 to 25, respectively.

FIG. 11 shows the nucleotide sequences of oligonucleotide primers (CMV2, JNT026, JNT082, JNT097 and JNT098), which were used in the PCR amplification of the cDNAs of the H chain and L chain and sequence reactions in Examples 4 of the present application. The nucleotide sequences of CMV2, JNT026, JNT082, JNT097 and JNT098 are as shown in SEQ ID NOS: 47 to 51, respectively.

FIG. 12 shows the nucleotide sequence (SEQ ID NO: 52) and amino acid sequence (SEQ ID NO: 53) of the coding region of the H chain (γ1 chain) of a pChBA-1-3D vector. The amino acid residue is indicated with a single letter, and the position of a termination codon is indicated with the symbol "•".

FIG. 13 shows the nucleotide sequence (SEQ ID NO: 54) and amino acid sequence (SEQ ID NO: 55) of the coding region of the L chain (κ chain) of a pChBA-1-3D vector. The amino acid residue is indicated with a single letter, and the position of a termination codon is indicated with the symbol "•".

FIG. 14 shows the nucleotide sequence (SEQ ID NO: 56) and amino acid sequence (SEQ ID NO: 57) of the coding region of the H chain (γ1 chain) of a pHuBA-1-3D-1 vector. The amino acid residue is indicated with a single letter, and the position of a termination codon is indicated with the symbol "•".

FIG. 15 shows the nucleotide sequence (SEQ ID NO: 58) and amino acid sequence (SEQ ID NO: 59) of the coding region of the H chain (γ1 chain) of a pHuBA-1-3D-2 vector. The amino acid residue is indicated with a single letter, and the position of a termination codon is indicated with the symbol "•".

FIG. 16 shows the nucleotide sequence (SEQ ID NO: 60) and amino acid sequence (SEQ ID NO: 61) of the coding region of the L chain (κ chain) in each of a pHuBA-1-3D-1 vector, a pHuBA-1-3D-2 vector, a pHuBA-1-3D-1-T73K vector and a pHuBA-1-3D-1-A24G/T73K vector. In short, the L chains (κ chains) of the antibodies HuBA-1-3D-1, HuBA-1-3D-2, HuBA-1-3D-1-T73K and HuBA-1-3D-1-A24G/T73K have the same nucleotide sequence and the same amino acid sequence. In the figure, each amino acid is indicated with a single letter, and the position of a termination codon is indicated with the symbol "•".

Figure 17:
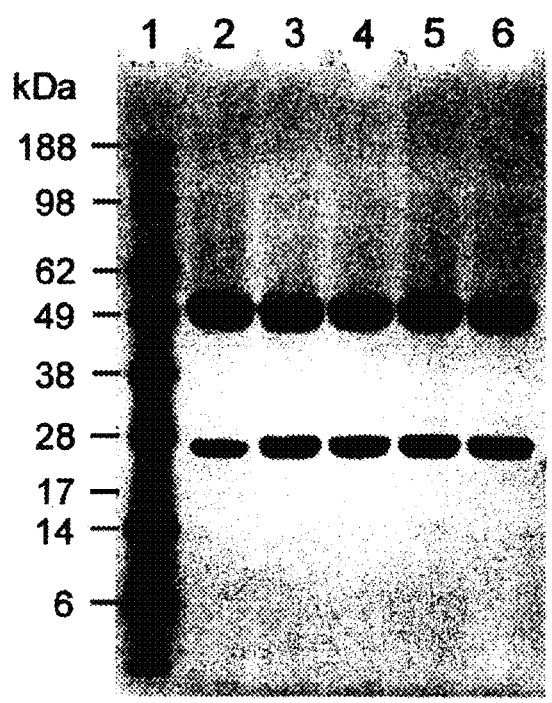

FIG. 17 shows SDS-PAGE performed on the purified antibodies (lane 1: molecular weight marker SEEBLUE Plus2 Prestained Standard (Invitrogen)), lane 2: ChBA-1-3D, lane 3: HuBA-1-3D-1, lane 4: HuBA-1-3D-2, lane 5: HuBA-1-3D-1-T73K, and lane 6: HuBA-1-3D-1-A24G/T73K). The figure shows the results obtained by applying 7.5 µg of each antibody onto 4%-20% NuPAGE Bis-Tris gel under reduced conditions using a MES-SDS Running buffer (Invitrogen). The numerical values on the left side of the figure indicate molecular weights.

Figure 18:
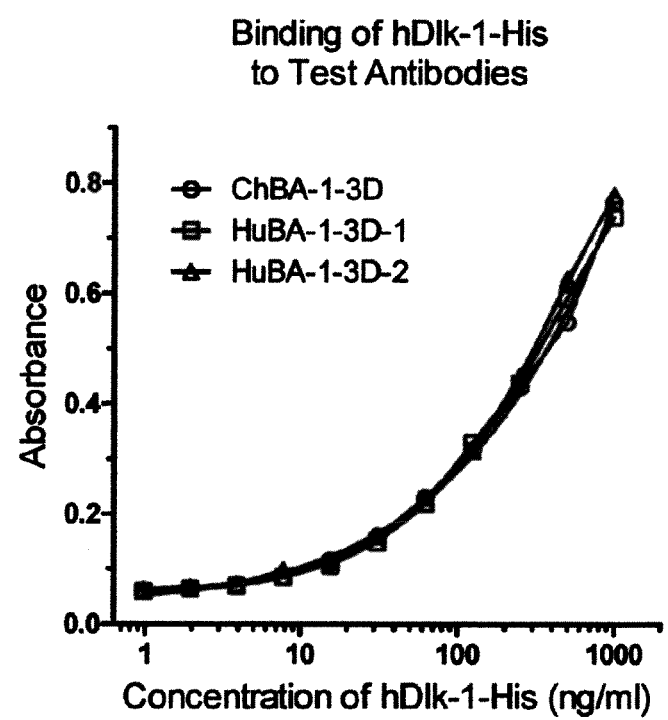

FIG. 18 shows the results of ELISA regarding the binding activity of a recombinant protein (hDlk-1-His) in the extracellular region of hDlk-1 to ChBA-1-3D, HuBA-1-3D-1 and HuBA-1-3D-2. An ELISA plate was coated with each of 1 µg/mL ChBA-1-3D, HuBA-1-3D-1 and HuBA-1-3D-2. Then, a dilution series of hDlk-1-His were produced (diluted by 2-fold from 1 µg/mL), and were then added to the aforementioned plate for reaction. The binding of hDlk-1-His was detected with a HRP-labeled anti-His-tag antibody.

Figure 19:
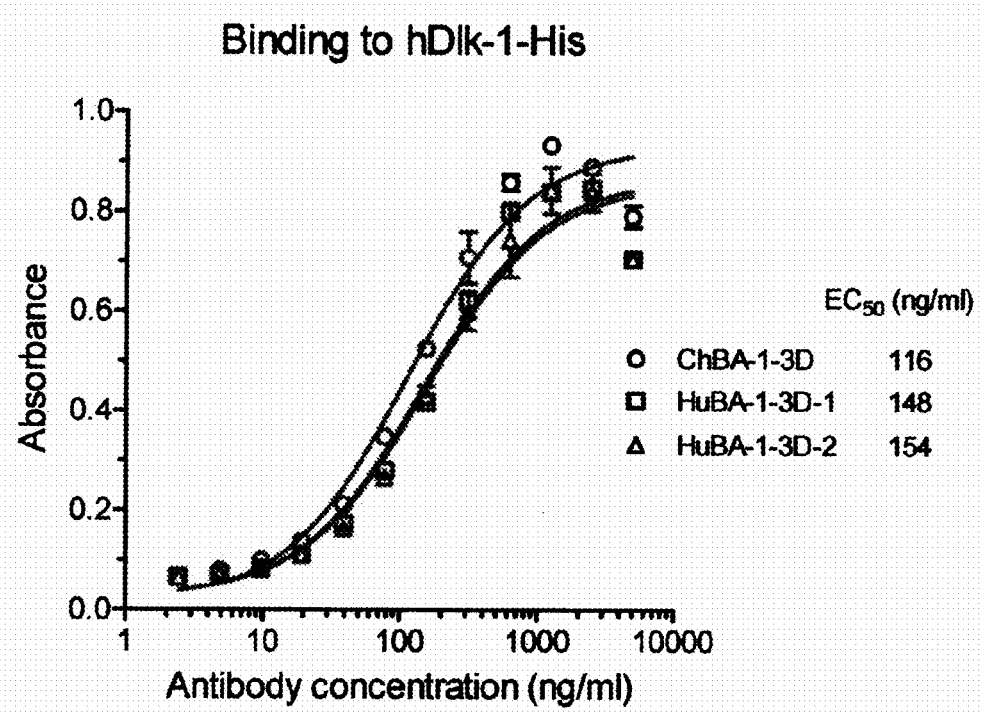

FIG. 19 shows the results of ELISA regarding the binding activity of ChBA-1-3D, HuBA-1-3D-1 and HuBA-1-3D-2 to hDlk-1-His. An ELISA plate was coated with 0.5 µg/mL hDlk-1-His. Then, a dilution series of the test antibodies (ChBA-1-3D, HuBA-1-3D-1 and HuBA-1-3D-2) were produced (diluted by 2-fold from 5 µg/mL), and were then added to the aforementioned plate for reaction. The $EC_{50}$ values of ChBA-1-3D, HuBA-1-3D-1 and HuBA-1-3D-2 are shown in the figure.

Figure 20:
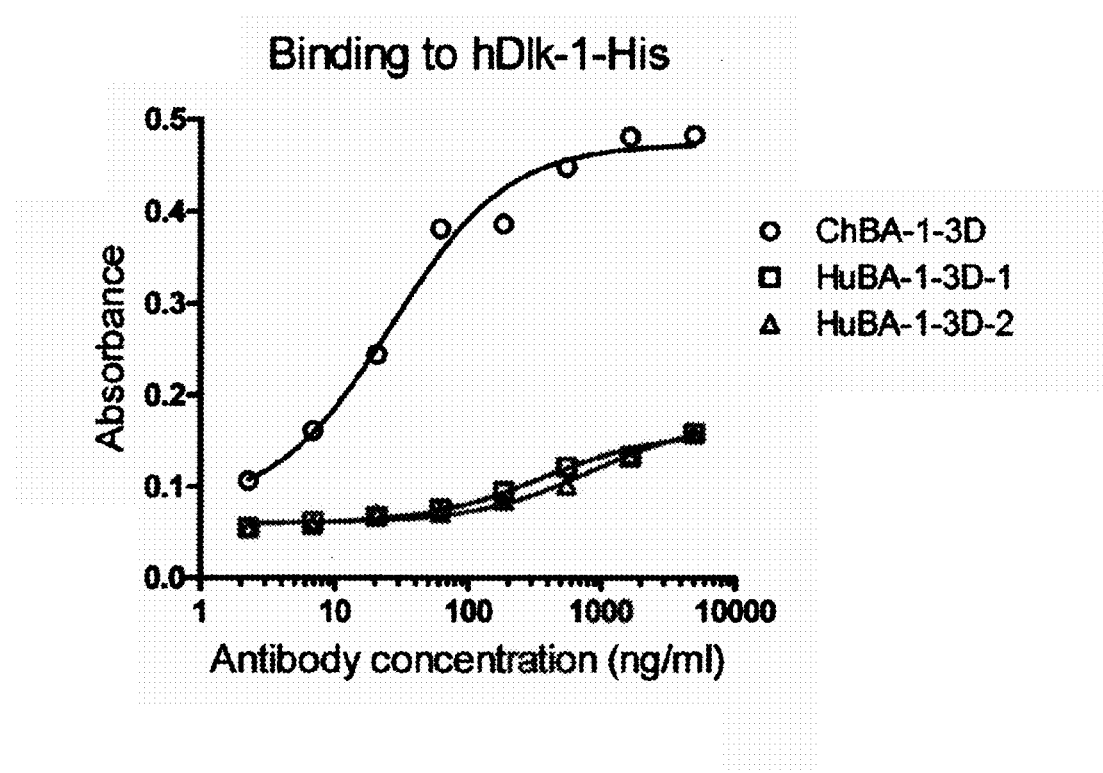

FIG. 20 shows the results of ELISA regarding the binding activity of ChBA-1-3D, HuBA-1-3D-1 and HuBA-1-3D-2 to hDlk-1-His. An ELISA plate was coated with 0.05 µg/mL hDlk-1-His. Then, a dilution series of the test antibodies (ChBA-1-3D, HuBA-1-3D-1 and HuBA-1-3D-2) were produced (diluted by 2-fold from 5 µg/mL), and were then added to the aforementioned plate for reaction.

Figure 21:
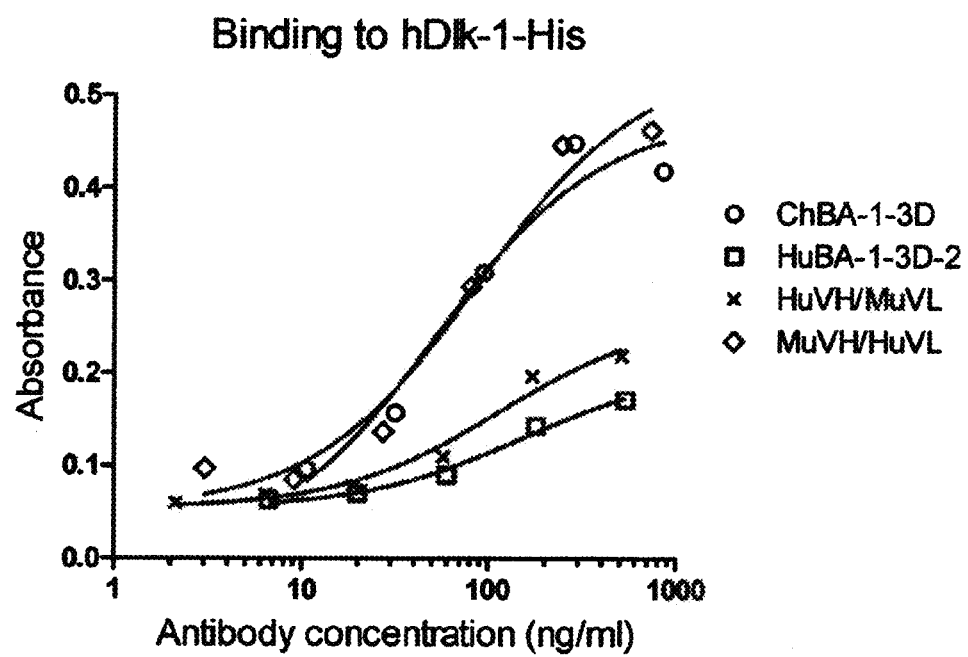

FIG. 21 shows the results of ELISA regarding the binding activity of ChBA-1-3D, HuBA-1-3D-2, HuVH/MuVL (wherein the VL of HuBA-1-3D-2 (HuBA-1-3D VL) was substituted with the VL of mouse BA-1-3D) and MuVH/HuVL (wherein the VH of HuBA-1-3D-2 (HuBA-1-3D VH2) was substituted with the VH of mouse BA-1-3D) to hDlk-1-His. An ELISA plate was coated with 0.05 µg/mL hDlk-1-His. Then, a 2-fold dilution series of a culture supernatant of cells, in which each of the test antibodies (ChBA-1-3D, HuBA-1-3D-2, HuVH/MuVL and MuVH/HuVL) had been transiently expressed, were produced, and were then added to the aforementioned plate for reaction.

FIG. 22 shows the amino acid sequences of HuBA-1-3D VH1 and amino acid substitution mutants thereof (V5Q to T73K/T75S). The amino acid is indicated with a single letter. In each amino acid substitution mutant, the same amino acids as those in HuBA-1-3D VH1 are indicated with the symbol "-", and only the substituted amino acids are indicated with single letters. The number above each sequence indicates an amino acid number (Kabat et al., 1991).

Figure 23:
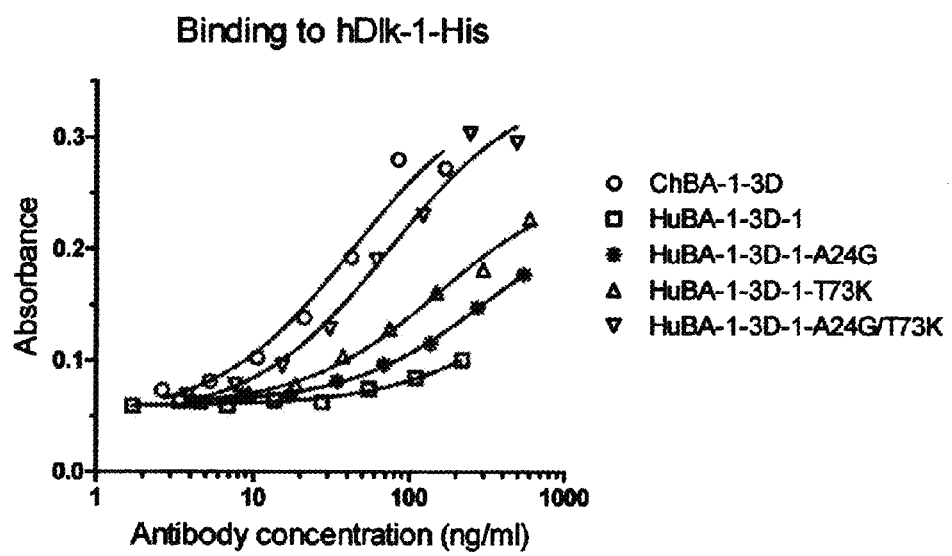

FIG. 23 shows the results of ELISA regarding the binding activity of ChBA-1-3D, HuBA-1-3D-1, HuBA-1-3D-1-A24G, HuBA-1-3D-1-T73K and HuBA-1-3D-1-A24G/T73K to hDlk-1-His. An ELISA plate was coated with 0.05 µg/mL hDlk-1-His. Then, a 2-fold dilution series of a culture supernatant of cells, in which each of the test antibodies (ChBA-1-3D, HuBA-1-3D-1, HuBA-1-3D-1-A24G, HuBA-1-3D-1-T73K and HuBA-1-3D-1-A24G/T73K) had been transiently expressed, were produced, and were then added to the aforementioned plate for reaction.

FIG. 24 shows the nucleotide sequence (SEQ ID NO: 62) and amino acid sequence (SEQ ID NO: 63) of the coding region of the H chain (γ1 chain) of pHuBA-1-3D-1-T73K. The amino acid residue is indicated with a single letter, and the position of a termination codon is indicated with the symbol "•".

Herein, the cDNA nucleotide sequence (SEQ ID NO: 70) of the H chain variable region (VH) of HuBA-1-3D-1-T73K is a sequence comprising nucleotides at positions 1 to 420 in the nucleotide sequence as shown in SEQ ID NO: 62, and the putative amino acid sequence (SEQ ID NO: 71) of the VH of HuBA-1-3D-1-T73K is a sequence comprising amino acids at positions 1 to 140 in the amino acid sequence as shown in SEQ ID NO: 63. In the aforementioned putative amino acid sequence (SEQ ID NO: 71) of the VH of HuBA-1-3D-1-T73K, peptides consisting of 19 amino acids from the N-terminus are signal peptides. The cDNA nucleotide sequence of a mature peptide of HuBA-1-3D-1-T73K VH is as shown in SEQ ID NO: 72, and a putative amino acid sequence thereof is as shown in SEQ ID NO: 73.

FIG. 25 shows the nucleotide sequence (SEQ ID NO: 64) and amino acid sequence (SEQ ID NO: 65) of the coding region of the H chain (γ1 chain) of pHuBA-1-3D-1-A24G/T73K. The amino acid residue is indicated with a single letter, and the position of a termination codon is indicated with the symbol "•".

Herein, the cDNA nucleotide sequence (SEQ ID NO: 74) of the H chain variable region (VH) of HuBA-1-3D-1-A24G/T73K is a sequence comprising nucleotides at positions 1 to 420 in the nucleotide sequence as shown in SEQ ID NO: 64, and the putative amino acid sequence (SEQ ID NO: 75) of the VH of HuBA-1-3D-1-A24G/T73K is a sequence comprising amino acids at positions 1 to 140 in the amino acid sequence as shown in SEQ ID NO: 65. In the aforementioned putative amino acid sequence (SEQ ID NO: 75) of the VH of HuBA-1-3D-1-A24G/T73K, peptides consisting of 19 amino acids from the N-terminus are signal peptides. The cDNA nucleotide sequence of a mature peptide of HuBA-1-3D-1-A24G/T73K is as shown in SEQ ID NO: 76, and a putative amino acid sequence thereof is as shown in SEQ ID NO: 77.

Figure 26:
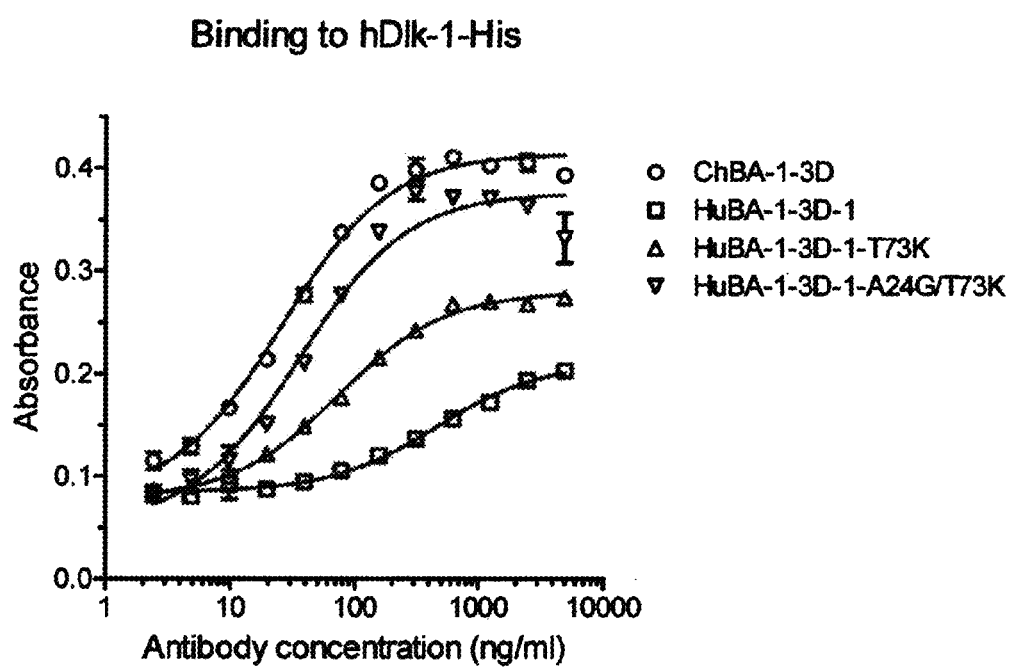

FIG. 26 shows the results of ELISA regarding the binding activity of ChBA-1-3D, HuBA-1-3D-1, HuBA-1-3D-1-T73K and HuBA-1-3D-1-A24G/T73K to hDlk-1-His. An ELISA plate was coated with 0.05 g/mL hDlk-1-His. Then, a 2-fold dilution series of the test antibodies were produced from 5 μg/mL, and were then added to the aforementioned plate for reaction.

FIG. 27 shows the stability of the antigen binding activity of HuBA-1-3D-1-A24G/T73K in a liquid formulation. HuBA-1-3D-1-A24G/T73K was preserved in liquid formulation with various pH values at 40° C. for 1 month, and the binding activity thereof was then examined by flow cytometry and antigen-immobilized ELISA. An antibody that had been preserved in liquid formulation with various pH values at −80° C. was used as an activity standard product.

FIG. 27(A): Using 293 cells that constantly express hDlk-1, the antigen-binding activity of the antibody was measured by flow cytometry. The vertical axis indicates a mean value of fluorescent intensity (MFI: mean fluoro-intensity), and the horizontal axis indicates antibody concentration.

FIG. 27(B): Using hDlk-1-His-coated antigen-immobilized ELISA, antigen-binding activity was examined. The vertical axis indicates absorbance, and the horizontal axis indicates antibody concentration.

Figure 28:
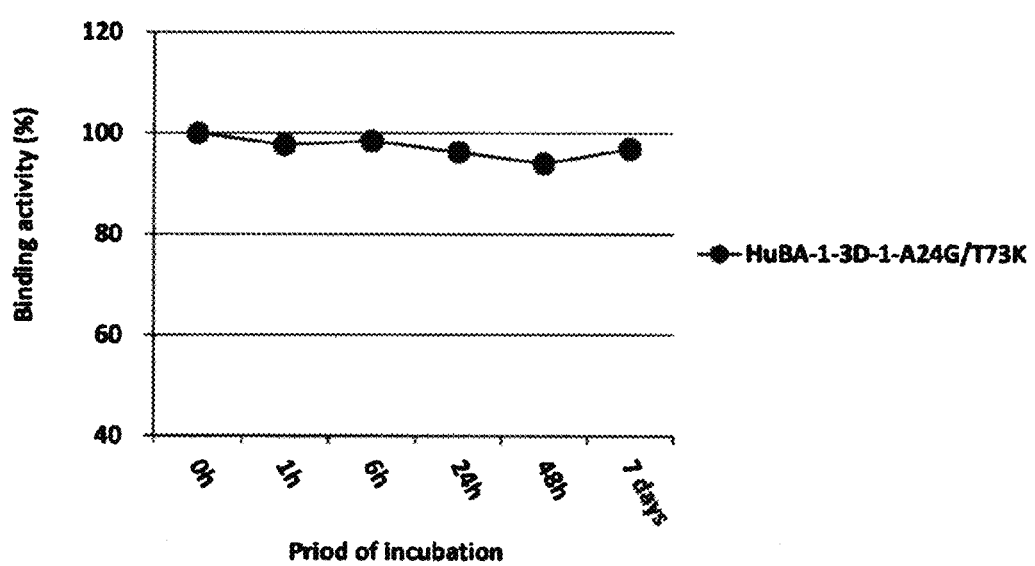

FIG. 28 shows the results obtained by analyzing the stability of the antigen-binding activity of an antibody in cynomolgus monkey plasma. HuBA-1-3-D1-A24G/T73K was preserved at 37° C. in cynomolgus monkey plasma for a period of incubation indicated in the figure. Thereafter, the antigen-binding activity of the antibody was examined using hDlk-1-His-coated antigen-immobilized ELISA. The vertical axis indicates the percentage of the antigen-binding activity (absorbance value) after each period of incubation, when the percentage of the antigen-binding activity at 0 h is defined as 100%. The horizontal axis indicates period of incubation.

FIG. 29 shows the anti-tumor activity of HuBA-1-3D-1-A24G/T73K on xenograft treatment models using human hepatocellular carcinoma HepG2 cells.

FIG. 29A shows tumor formation over time in a control group (●: PBS) and in HuBA-1-3D-1-A24G/T73K administration groups (○: 1 mg/kg, Δ: 5 mg/kg, □: 10 mg/kg) (a mean value±standard deviation). The arrow heads on the horizontal axis indicate the time points at which the antibody was administered. In all of the antibody administration groups, significant anti-tumor effects (P<0.01 (by Student's t-test)) were observed after the 13$^{th}$ day (Day 13) in comparison with the control group.

FIG. 29B shows the plotted tumor weight of each mouse at the time of the 23$^{rd}$ day (Day 23) (the final day of experiment) in the test of FIG. 29A. ** P<0.01 (by Student's t-test).

FIG. 30 shows the anti-tumor activity of HuBA-1-3D-1-A24G/T73K on xenograft treatment models using human neuroblastoma SK-N-F1 cells.

FIG. 30A shows tumor formation over time in a control group (●: PBS) and in HuBA-1-3D-1-A24G/T73K administration groups (○: 1 mg/kg, Δ: 5 mg/kg, □: 10 mg/kg) (a mean value±standard deviation). The arrow heads on the horizontal axis indicate the time points at which the antibody was administered. * P<0.05, ** P<0.01 (by Student's t-test).

FIG. 30B shows the plotted tumor weight of each mouse at the time of the 34$^{th}$ day (Day 34) (the final day of experiment) in the test of FIG. 30A. ** P<0.01 (by Student's t-test).

Figure 31:
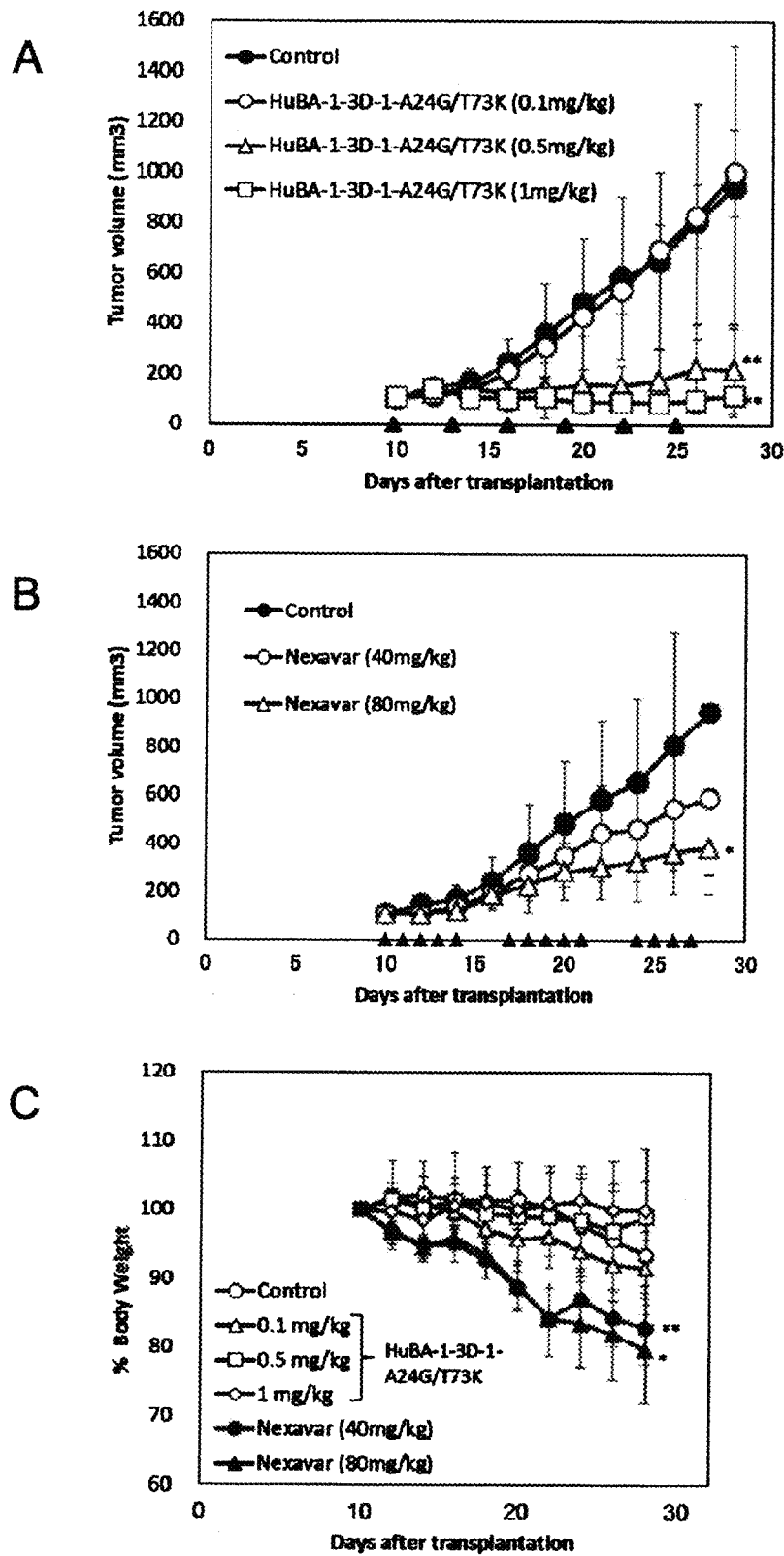

FIG. 31 shows the anti-tumor activities of HuBA-1-3D-1-A24G/T73K and NEXAVAR on xenograft treatment models using human hepatocellular carcinoma HepG2 cells.

FIG. 31A shows a change over time in the tumor volumes of a control group (●: PBS) and HuBA-1-3D-1-A24G/T73K administration groups (○: 0.1 mg/kg, Δ: 0.5 mg/kg, □: 1 mg/kg) (a mean value±standard deviation). The arrow heads on the horizontal axis indicate administration of the antibody. **P<0.01 (by Student's t-test).

FIG. 31B shows a change over time in the tumor volumes of a control group (●: PBS) and NEXAVAR administration groups (○: 40 mg/kg, Δ: 80 mg/kg) (a mean value±standard deviation). The arrow heads on the horizontal axis indicate the time points at which the NEXAVAR was administered. *P<0.05 (by Student's t-test).

FIG. 31C shows a change over time in the body weights of mice in the experiments A and B. Such a change in body weights is shown as the percentage of the body weight on each day of measurement, when the body weight of each mouse at the time of being divided into groups is defined at 100% (a mean value±standard deviation). *P<0.05, **P<0.01 (by Student's t-test).

FIG. 32 shows the anti-tumor activity of HuBA-1-3D-1-A24G/T73K on xenograft treatment models using human hepatocellular carcinoma HepG2/C3A cells.

FIG. 32A shows a change over time in the tumor volumes of a control group (●: PBS) and HuBA-1-3D-1-A24G/T73K administration groups (○: 0.1 mg/kg, Δ: 0.5 mg/kg, □: 1 mg/kg, ◊: 5 mg/kg) (a mean value±standard deviation). The arrow heads on the horizontal axis indicate administration of the antibody. **P<0.01 (by Student's t-test).

FIG. 32B shows the plotted tumor weight of each mouse at the time of the 26$^{th}$ day (Day 26) (the final day of experiment) in the test of FIG. 32A. ** P<0.01 (by Student's t-test).

FIG. 33 shows the anti-tumor activity of HuBA-1-3D-1-A24G/T73K on xenograft treatment models using human small cell lung cancer Lu-135 cells.

FIG. 33A shows a change over time in the tumor volumes of a control group (●: PBS) and HuBA-1-3D-1-A24G/T73K administration groups (○: 1 mg/kg, Δ: 10 mg/kg) (a mean value±standard deviation). The arrow heads on the horizontal axis indicate administration of the antibody. **P<0.05 (by Student's t-test).

FIG. 33B shows the plotted tumor weight of each mouse at the time of the 34$^{th}$ day (Day 34) (the final day of experiment) in the test of FIG. 33A. ** P<0.05 (by Student's t-test).

Figure 34:
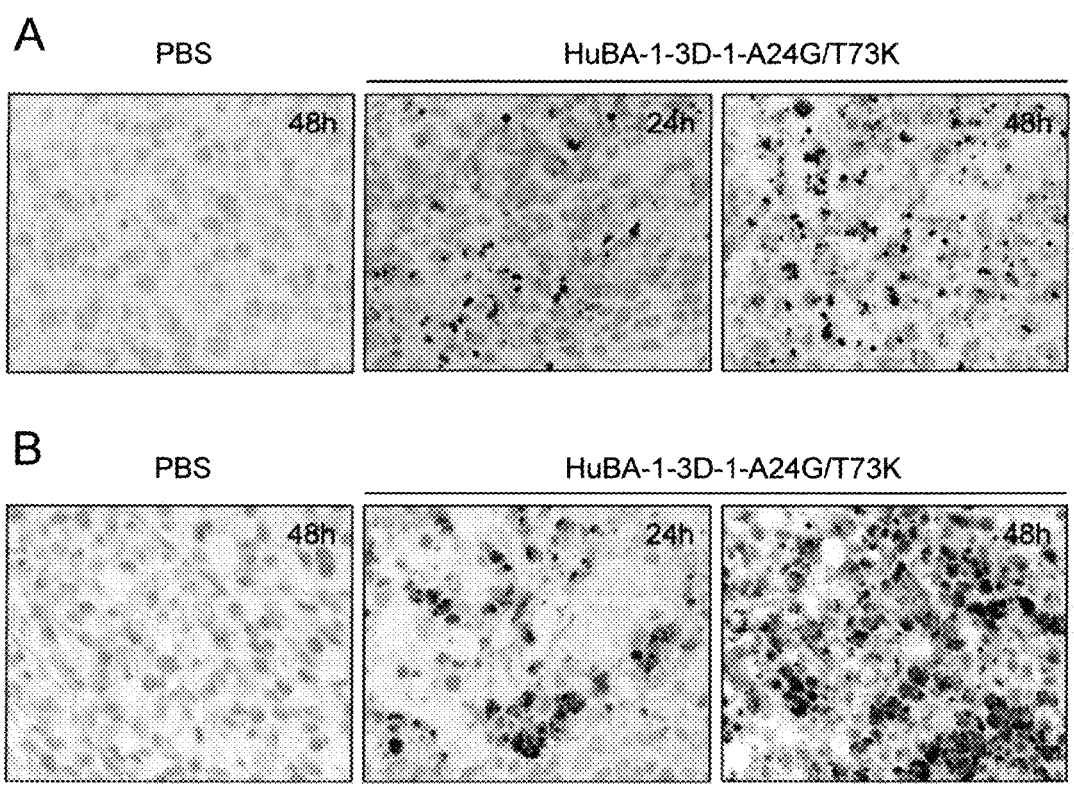

FIG. 34 shows photographs in which cell death caused by apoptosis was detected in the frozen sections of xenograft tumors after administration of HuBA-1-3D-1-A24G/T73K to xenograft treatment models using human hepatocellular carcinoma HepG2 cells.

FIG. 34A shows photographs in which cell death caused by apoptosis was detected by TUNEL staining. From the left, the photographs show stained images 48 hours after administration of PBS, 24 hours after administration of HuBA-1-3D-1-A24G/T73K (5 mg/kg), and 48 hours after administration of HuBA-1-3D-1-A24G/T73K (5 mg/kg), respectively. Cancer cells in which dark brown nuclear staining was observed indicate TUNEL-positive apoptotic cells (the objective lens of a microscope: 400-fold).

FIG. 34B shows photographs in which cell death caused by apoptosis was detected by immunohistochemistry using an anti-cleaved caspase-3 antibody. From the left, the photographs show stained images 48 hours after administration of PBS, 24 hours after administration of HuBA-1-3D-1-A24G/T73K (5 mg/kg), and 48 hours after administration of HuBA-1-3D-1-A24G/T73K (5 mg/kg), respectively. Cancer cells whose cytoplasm was stained into dark brown indicate active caspase-3-positive apoptotic cells (the objective lens of a microscope: 400-fold).

DETAILED DESCRIPTION OF THE INVENTION

Hereinafter, the present invention will be described in detail. The following descriptions are not intended to limit the scope of the present invention. Other than the following examples, the present invention may be modified and may be carried out, as appropriate, within a range that does not impair the intention of the present invention.

The present specification includes all of the contents as disclosed in the specification of U.S. Provisional Patent Application No. 61/709,282 (filed on Oct. 3, 2012), which is a priority document of the present application. Moreover, all publications cited in the present specification, which include prior art documents and patent documents such as laid-open application publications and patent publications, are incorporated herein by reference in their entirety.

1. SUMMARY OF THE PRESENT INVENTION

As described above, human Dlk-1 (delta-like 1 homolog (*Drosophila*); hDlk-1) is a type I transmembrane (one-transmembrane-type) protein with a full length of 383 amino acid residues and this protein has 6 EGF-like motifs in its extracellular region. It has been known that a hDlk-1 gene and a gene product thereof are expressed with a high frequency in various types of cancer or tumor cells. In general, it is difficult to prepare and obtain an antibody exhibiting anti-tumor activity in vivo. Thus, even if an anti-hDlk-1 monoclonal antibody is produced, it has anti-tumor activity in vitro but it does not exhibit the activity in vivo in many cases. Moreover, the functional domain of hDlk-1 that acts on the growth of cancer cells, a ligand (or a receptor) of hDlk-1, its intracellular signal-transducing pathway and the like have not been clarified. Thus, it is substantially impossible to efficiently produce an antibody by narrowing down its target. Under such circumstances, in the present invention, a clone having anti-tumor activity in vivo has been successfully obtained by screening it from a large number of clones.

First, based on immunohistochemistry using known anti-hDlk-1 antibodies, the present inventors have discovered that hDlk-1 is expressed in colon cancer, breast cancer and pancreatic cancer, in addition to the aforementioned cancers and tumor cells, in which expression of hDlk-1 had previously been confirmed.

Next, the present inventors have newly produced approximately 100 clones of anti-hDlk-1 monoclonal antibodies for the purpose of producing anti-hDlk-1 antibodies capable of killing hDlk-1-expressing cancer cells at an individual level or inhibiting tumor growth, namely, anti-hDlk-1-antibodies having anti-tumor activity in vivo. Thereafter, the inventors have evaluated the in vivo pharmaceutical effects (anti-tumor action) of these clones, using tumor-bearing mice established by transplanting various types of cancer cell lines subcutaneously in nude mice. As a result, the present inventors have succeeded in obtaining several clones exhibiting significant tumor growth-inhibiting activity (clone name: BA-1-3D, DI-2-14, 2-13, DI-6 and M3-1).

Moreover, among the aforementioned anti-hDlk-1 antibodies, the present inventors have discovered an antibody exhibiting a significant anti-tumor activity on cancer-bearing mouse treatment models using human cancer cells, when it is administered alone, which would be important for the development of a cancer therapeutic antibody, and the inventors have also developed a humanized antibody thereof. Furthermore, the present inventors have added a specific modification (amino acid substitution mutation) to this humanized anti-hDlk-1 antibody, so as to discover a modified humanized anti-hDlk-1 antibody having avidity equivalent to that of a parent antibody (mouse BA-1-3D). Further, the inventors have demonstrated that this modified humanized anti-hDlk-1 antibody retains a stable antigen-binding activity for a long period of time in a liquid formulation and in monkey or human blood (plasma), etc.

2. PREPARATION OF ANTI-HDLK-1 ANTIBODY (1) Preparation of Antigen

Information regarding the amino acid sequence (SEQ ID NO: 2) of hDlk-1 is disclosed as "Accession number: NP_003827" at the website of NCBI (GENBANK) (www.ncbi.nlm.nih.gov), for example. Moreover, information regarding a nucleotide sequence (SEQ ID NO: 1) encoding the amino acid sequence of hDlk-1 is disclosed as "Accession number: NM_003836" at the same above website.

As an antigen, a polypeptide or peptide (which may be simply referred to as a "peptide" at times) comprising at least a portion of (entire or a part of) the amino acid sequence of hDlk-1 can be used and preferably, a peptide comprising at least a portion of (entire or a part of) the amino acid sequence of the extracellular region (FA-1) of hDlk-1 can be used. As stated above, the extracellular region of hDlk-1 comprises 6 EGF-like motifs (EGF-1 to EGF-6). This region indicates a region comprising amino acids at positions 24 to 244 in the amino acid sequence as shown in SEQ ID NO: 2 and preferably a region consisting of amino acids from "position 24" to "positions 248 to 285" (approximately 225 to 262 amino acid residues) in the amino acid sequence as shown in SEQ ID NO: 2.

Herein, in the case of a peptide used as an antigen, the length of the aforementioned "at least a portion of the amino acid sequence" is not particularly limited. For example, a region comprising one or two or more out of the 6 EGF-like motifs is preferable. More preferable examples include a region comprising EGF-1 and EGF-2 (namely, a region consisting of amino acids at positions 24 to 91 in the amino acid sequence as shown in SEQ ID NO: 2), a region comprising EGF-3 and EGF-4 (namely, a region consisting of amino acids at positions 92 to 167 in the amino acid sequence as shown in SEQ ID NO: 2) and a region comprising EGF-4, EGF-5 and EGF-6 (namely, a region consisting of amino acids at positions 131 to 244 in the amino acid sequence as shown in SEQ ID NO: 2).

As a method for preparing a peptide used as an antigen, either a chemical synthesis, or a synthesis by a genetic engineering means using *Escherichia coli* or the like, may be applied. Methods well known to persons skilled in the art may be applied.

In the case of performing a chemical synthesis of peptide, such a peptide may be synthesized by well-known methods for synthesizing peptides. As such a synthesis, either a solid-phase synthesis method or a liquid-phase synthesis method may be applied. Commercially available peptide synthesizing apparatuses (e.g. PSSM-8, etc.; manufactured by Shimadzu Corp.) may be used.

In the case of synthesizing a peptide by genetic engineering, DNA encoding the peptide is first designed and synthesized. The designing and synthesis of the DNA can be carried out, for example, by a PCR method, using a vector comprising a full-length hDlk-1 gene or the like as a template and also using primers designed such that a desired DNA region can be synthesized therewith. Thereafter, the thus synthesized DNA is ligated to a suitable vector to obtain a recombinant vector used in expression of a protein. This recombinant vector is then introduced into a host such that a gene of interest can be expressed therein, so as to obtain a transformant (Sambrook J. et al., Molecular Cloning, A Laboratory Manual, 3$^{rd}$ edition, Cold Spring Harbor Laboratory Press, 2001).

As a vector, a phage or plasmid capable of autonomously replicating in host microorganisms can be used. Further, an animal virus or insect virus vector can also be used. For preparation of a recombinant vector, the purified DNA may be cleaved with suitable restriction enzymes, the obtained DNA portion may be then inserted into the restriction site of suitable vector DNA, etc. and it may be then ligated to a vector. The type of a host used in transformation is not particularly limited, as long as it is able to express a gene of interest. Examples of such a host include bacteria (*Escherichia coli, Bacillus subtilis*, etc.), yeasts, animal cells (COS cells, CHO cells, etc.), insect cells and insects. It is also possible to use a mammal such as a goat as a host. A method for introducing a recombinant vector into a host is known.

The aforementioned transformant is cultured and a peptide used as an antigen is then collected from the culture. The term "culture" is used to mean any one of (a) a culture supernatant and (b) cultured cells, a cultured cell mass, or a disintegrated product thereof.

After completion of the culture, when a peptide of interest is produced in a bacterial cells (bacterial bodies) or in cells, such bacterial cells or cells are disintegrated and a peptide is then extracted. On the other hand, a peptide of interest is produced outside the bacterial cell or cells, a culture solution is directly used, or the bacterial cells or cells are eliminated by centrifugation or the like. Thereafter, common biochemical methods used in isolation and purification of peptides, such as ammonium sulfate precipitation, gel filtration, ion exchange chromatography and affinity chromatography, are applied singly or in combination, so as to isolate and purify a peptide of interest.

In the present invention, a peptide used as an antigen can also be obtained by in vitro translation using a cell-free synthesis system. In this case, two types of methods, namely, a method using RNA as a template and a method using DNA as a template (transcription/translation) can be applied. As such a cell-free synthesis system, commercially available systems such as EXPRESSWAY™ system (Invitrogen), PURESYS-TEM (registered trade mark; Post Genome Institute Co., Ltd.) and TNT system (registered trade mark; Promega) can be used.

The thus obtained peptide may also be bound to a suitable carrier protein such as bovine serum albumin (BSA), keyhole limpet hemocyanin (KLH), human thyroglobulin, or chicken gamma globulin.

Furthermore, such an antigen may be a peptide, which consists of an amino acid sequence comprising a deletion, substitution or addition of one or multiple amino acids with respect to the amino acid sequence of hDlk-1 (SEQ ID NO: 2) or the aforementioned partial sequence thereof. For example, there can also be used a peptide, which consists of an amino acid sequence comprising a deletion of one or multiple (preferably one or several (for example 1 to 10 and more preferably 1 to 5)) amino acids, a substitution of one or multiple (preferably one or several (for example 1 to 10 and more preferably 1 to 5)) amino acids with other amino acids, or an addition of one or multiple (preferably one or several (for example 1 to 10 and more preferably 1 to 5)) amino acids, with respect to the amino acid sequence of hDlk-1 or a partial sequence thereof.

In the present invention, an example of a gene to be introduced into cells or the like is a gene encoding a hDlk-1 protein, a partial fragment thereof, a mutant protein thereof, or a fragment thereof. As such a gene, a gene having the nucleotide sequence as shown in SEQ ID NO: 1 or a partial sequence thereof can be used, for example.

Further, as such a gene to be introduced into cells or the like, a nucleotide sequence, which hybridizes with a sequence complementary to the nucleotide sequence as shown in SEQ ID NO: 1 under stringent conditions and encodes a protein having hDlk-1 activity, or a partial sequence thereof can also be used.

The term "stringent conditions" is used to mean conditions applied to washing after hybridization, which consist of a salt (sodium) concentration of buffer between 10 and 500 mM and a temperature between 42° C. and 72° C. and preferably consist of the aforementioned salt concentration of buffer between 50 and 300 mM and a temperature between 55° C. and 68° C.

Mutation can be introduced into a gene by known methods such as a Kunkel method or a Gapped duplex method, using mutation introduction kits that utilize site-directed mutagenesis, such as GENETAILOR™ Site-Directed Mutagenesis System (manufactured by Invitrogen) or TaKaRa Site-Directed Mutagenesis System (PRIME STAR (registered trademark) Mutagenesis Basal Kit, MUTAN (registered trademark)-Super Express Km, etc.; manufactured by Takara Bio Inc.).

(2) Preparation of Polyclonal Antibody

The prepared antigen is administered to a mammal for immunization. The type of such a mammal is not particularly limited. Examples of such a mammal include a rat, a mouse and a rabbit. Among others, a mouse is preferable.

The dose of the antigen per animal can be determined, as appropriate, depending on the presence or absence of an adjuvant. Examples of such an adjuvant include a Freund's complete adjuvant (FCA), a Freund's incomplete adjuvant (FIA) and an aluminum hydroxide adjuvant. Immunization can be carried out by injecting the antigen into the vein, footpad, subcutis, abdominal cavity, etc. In addition, immunization interval is not particularly limited. Immunization is carried out 1 to 10 times and preferably 2 or 3 times, at intervals of several days to several weeks and preferably at intervals of 1 week. Three to seven days after the final immunization, an antibody titer is measured by enzyme immunoassay (ELISA or EIA), radioimmunoassay (RIA), etc. On the day at which a desired antibody titer is obtained, blood is collected and antiserum is then obtained. In a case where an antibody should be purified in the aforementioned method for collecting the antibody, a suitable method is appropriately selected from known methods such as an ammonium sulfate salting-out method, ion exchange chromatography, gel filtration chromatography and affinity chromatography, or these methods may be used in combination, so as to purify the antibody. Thereafter, the reactivity of a polyclonal antibody contained in the antiserum is measured by ELISA, etc.

(3) Preparation of Monoclonal Antibody (3-1) Collection of Antibody-Producing Cells The type of the anti-hDlk-1 antibody of the present invention is not limited. A monoclonal antibody is preferable.

The prepared antigen is administered to a mammal such as a rat, a mouse or a rabbit for immunization. The dose of the antigen per animal can be determined, as appropriate, depending on the presence or absence of an adjuvant. The same adjuvants as those described above are used herein. Also, the same immunization methods as described above are applied herein. One to sixty days and preferably one to fourteen days after the final immunization, antibody-producing cells are collected. Examples of such antibody-producing cells include splenic cells, lymph node cells and peripheral blood cells. Among others, lymph node cells and splenic cells are preferable.

(3-2) Cell Fusion

In order to obtain a hybridoma (an antibody-producing cell line), cell fusion is carried out between antibody-producing cells and myeloma cells. As myeloma cells to be fused with antibody-producing cells, easily available, established cell lines, such as the cell lines of animals such as mice, can be used. As available cell lines, those, which have drug selectivity, cannot survive in a HAT selective medium (containing hypoxanthine, aminopterin and thymidine) when they are in an unfused state and can survive therein only when they are fused with antibody-producing cells, are preferable.

Examples of myeloma cells used herein include mouse myeloma cell lines such as P3-X63-Ag8.653, P3-X63-Ag8 (X63), P3-X63-Ag8.U1(P3U1), P3/NS I/1-Ag4-1(NS1) and Sp2/0-Ag14(Sp2/0). Such myeloma cells can be selected, while taking into consideration the compatibility with antibody-producing cells, as appropriate.

Subsequently, myeloma cells are fused with antibody-producing cells for cell fusion. For such cell fusion, antibody-producing cells at a cell density of $1 \times 10^6$ to $1 \times 10^7$ cells/mL are mixed with myeloma cells at a cell density of $2 \times 10^5$ to $2 \times 10^6$ cells/mL, in a medium used for animal cells that does not contain serum, such as DMEM or a RPMI-1640 medium. The cell ratio between such antibody-producing cells and such myeloma cells (antibody-producing cells:myeloma cells) is not limited. In general, such a cell ratio is preferably between 1:1 and 10:1 and more preferably 3:1. Subsequently, a fusion reaction is carried out in the presence of a cell fusion promoter. As such a cell fusion promoter, polyethylene glycol having a mean molecular weight between 1,000 and 6,000 daltons (D) or the like can be used, for example. Also, antibody-producing cells can be fused with myeloma cells using a commercially available cell fusion device that utilizes electrical stimulation (e.g. electroporation).

(3-3) Selection of Hybridoma and Cloning

A hybridoma of interest is selected from cells obtained after the cell fusion treatment. As a selection method, a cell suspension is diluted with a fetal bovine serum-containing RPMI-1640 medium or the like, as appropriate and the diluted solution is then dispersed on a microtiter plate. A selective medium is added to each well and culture is then carried out while the selective medium is appropriately exchanged with a fresh one. As a result, cells that grow approximately 14 days after initiation of the culture in the selective medium can be obtained as hybridomas.

Subsequently, the presence or absence of an antibody against hDlk-1 in a culture supernatant of the growing hybridomas is screened. Such screening of hybridomas may be carried out in accordance with ordinary methods and thus the type of the screening method is not particularly limited. For example, a portion of the culture supernatant of the growing hybridomas contained in the well may be collected and such hybridomas may be then screened by ELISA, EIA, RIA, etc.

The fused cells may be cloned by limiting dilution or the like. An antibody exhibiting strong reactivity with hDlk-1 is determined by flow cytometry or the like and a hybridoma that produces the antibody is selected and is established as a clone.

(3-4) Collection of Monoclonal Antibody

As a method of culturing the established hybridomas and then collecting a monoclonal antibody from the obtained culture, a common cell culture method, an ascites formation method, etc. can be adopted. The term "culture" is used to mean that a hybridoma is allowed to grow in a culture dish or culture bottle, or that a hybridoma is allowed to proliferate in the abdominal cavity of an animal, as described below.

In the cell culture method, hybridomas may be cultured in an animal cell culture medium such as a 10% fetal bovine serum-containing RPMI-1640 medium, an MEM medium or a serum-free medium under common culture conditions (e.g. 37° C., 5% $CO_2$ concentration) for 7 to 14 days and an antibody may be then obtained from the culture supernatant.

In the ascites formation method, hybridomas are administered at a cell density of approximately $1 \times 10^7$ cells into the abdominal cavity of an animal of the same species as a mammal from which myeloma cells are derived, so as to cause proliferation of a large amount of hybridomas. Thereafter, ascites is preferably collected 2 to 3 weeks later.

In a case where an antibody should be purified in the aforementioned method for collecting the antibody, a suitable method is appropriately selected from known methods such as an ammonium sulfate salting-out method, ion exchange chromatography, gel filtration and affinity chromatography, or these methods are used in combination, so as to purify the aforementioned antibody.

(3-5) Selection of Clone Having Anti-Tumor Activity

The anti-hDlk-1 antibody of the present invention is an antibody having anti-tumor activity in vivo.

Herein, the term "anti-tumor activity" is used to mean activity of killing tumor cells (cancer cells) or inhibiting tumor growth. In the present invention, as such anti-tumor activity, tumor angiogenesis-inhibiting activity is preferable, for example. Moreover, the types of human tumors (tumor cells), on which the antibody of the present invention is able to exhibit anti-tumor activity, include: the aforementioned known human tumors in which expression of hDlk-1 had been confirmed (specifically, solid cancers such as neuroendocrine tumor, neuroblastoma, glioma, neurofibromatosis type 1, small cell lung cancer, liver cancer, kidney cancer and ovarian cancer and blood cancers such as myelodysplastic syndrome and acute myelocytic leukemia); and human colon cancer, human breast cancer and human pancreatic cancer, in which expression of hDlk-1 has been newly confirmed by the present inventors. Of these, one or two or more types selected from human colon cancer, human breast cancer, human pancreatic cancer, human liver cancer, human small cell lung cancer and human neuroblastoma are particularly preferable.

The presence of anti-tumor activity in vivo can be confirmed by using a cancer-bearing mouse, in which desired tumor cells have been transplanted subcutaneously, and then administering the obtained antibody to the mouse. In this case, the antibody may be administered to the mouse immediately after transplantation of the tumor cells (a prevention model), or the antibody may also be administered to the mouse after the tumor has grown up to a desired volume after transplantation (a treatment model). The administration method is not limited at all. For example, the antibody may be administered into the abdominal cavity of the mouse once every 3 days at a dose of 20 mg/kg body weight via intraperitoneal administration. In the case of the prevention model, the presence or absence of anti-tumor activity and the level thereof can be evaluated depending on tumor formation frequency and tumor volume. In the case of the treatment model, the presence or absence of anti-tumor activity and the level thereof can be evaluated depending on tumor volume and tumor weight.

In the present invention, preferred examples of an anti-hDlk-1 antibody having anti-tumor activity in vivo include an anti-hDlk-1 monoclonal antibody (clone name: BA-1-3D) produced by a hybridoma having accession No. FERM BP-11337, an anti-hDlk-1 monoclonal antibody (clone name: M3-1) produced by a hybridoma having accession No. FERM BP-10707, an anti-hDlk-1 monoclonal antibody (clone name: DI-2-14) produced by a hybridoma having accession No. FERM BP-10899 and an anti-hDlk-1 monoclonal antibody (clone name: DI-6) produced by a hybridoma having accession No. FERM BP-10900. Furthermore, an anti-hDlk-1 monoclonal antibody with a clone name of DI-2-14 can be preferably used as an antibody having high anti-tumor activity in vivo.

Herein, the hybridoma having accession No. FERM BP-11337 has been referred to as "Mouse-Mouse hybridoma BA-1-3D," and has been deposited with International Patent Organism Depositary (IPOD), National Institute of Advanced Industrial Science and Technology (AIST Tsukuba Central 6, Higashi 1-1-1, Tsukuba, Ibaraki, Japan, postal code: 305-8566), on Feb. 1, 2011. The hybridoma having accession No. FERM BP-10707 has been referred to as "Mouse-Mouse hybridoma: M3-1," and has been deposited with the same national institute as described above on Oct. 18, 2006. The hybridoma having accession No. FERM BP-10899 has been referred to as "Mouse-Mouse hybridoma DI-2-14," and has been deposited with the same national institute as described above on Aug. 21, 2007. The hybridoma having accession No. FERM BP-10900 has been referred to as "Mouse-Mouse hybridoma DI-6," and has been deposited with the same national institute as described above on Aug. 21, 2007.

Further, preferred examples of the anti-hDlk-1 antibody of the present invention include an anti-hDlk-1 antibody wherein the amino acid sequences of CDRs 1 to 3 of the H chain V region are the amino acid sequences as shown in SEQ ID NOS: 16 to 18, respectively, and/or an anti-hDlk-1 antibody wherein the amino acid sequences of CDRs 1 to 3 of the L chain V region are the amino acid sequences as shown in SEQ ID NOS: 23 to 25, respectively. The aforementioned H chain V region preferably consists of, for example, the amino acid sequence as shown in SEQ ID NO: 13, and particularly preferably consists of the amino acid sequence as shown in SEQ ID NO: 15 (mature peptide). The aforementioned L chain V region preferably consists of, for example, the amino acid sequence as shown in SEQ ID NO: 20, and particularly preferably consists of the amino acid sequence as shown in SEQ ID NO: 22 (mature peptide).

Still further, another preferred example of the anti-hDlk-1 antibody of the present invention is an anti-hDlk-1 antibody that binds to a site (e.g. an epitope), to which a monoclonal antibody produced by the hybridoma having accession No. FERM BP-11337, FERM BP-10707, FERM BP-10899 or FERM BP-10900 binds (recognizes).

(3-6) Epitope of Anti-hDlk-1 Antibody

An epitope (an antigenic determinant) of the anti-hDlk-1 antibody of the present invention is not limited, as long as it is at least a portion of hDlk-1 as an antigen. For example, such an epitope is preferably at least a portion of a region consisting of amino acids at positions 24 to 91 (a region comprising EGF-1 to EGF-2 of hDlk-1), a region consisting of amino acids at positions 92 to 167 (a region comprising EGF-3 to EGF-4 of hDlk-1), or a region consisting of amino acids at positions 131 to 244 (a region comprising EGF-4 to EGF-6 of hDlk-1), in the amino acid sequence of hDlk-1 as shown in SEQ ID NO: 2. Among others, a region comprising EGF-1 to EGF-2 of hDlk-1 is more preferable. An anti-hDlk-1 antibody that recognizes (binds to) such regions has high internalization activity into tumor cells, for example and thus it is extremely useful as an immunoconjugate as described later.

(4) Genetically Recombinant Antibody and Antibody Fragment (4-1) Genetically Recombinant Antibody In a preferred embodiment of the anti-hDlk-1 antibody of the present invention, there is provided a genetically recombinant antibody. The type of such a genetically recombinant antibody is not limited. Examples include a chimeric antibody, a humanized antibody and a human antibody.

A chimeric antibody (that is, a humanized chimeric antibody) is an antibody formed by ligating (conjugating) the variable region of a mouse-derived antibody to the constant region of a human-derived antibody (please refer to Proc. Natl. Acad. Sci. U.S.A. 81, 6851-6855, (1984), etc.). When such a chimeric antibody is produced, the thus ligated antibody can be easily constructed by a genetic recombination technique. As such variable regions of the mouse-derived antibody used herein, the H chain V region preferably consists of, for example, the amino acid sequence as shown in SEQ ID NO: 13, and particularly preferably consists of the amino acid sequence as shown in SEQ ID NO: 15 (mature peptide), and the L chain V region preferably consists of, for example, the amino acid sequence as shown in SEQ ID NO: 20, and particularly preferably consists of the amino acid sequence as shown in SEQ ID NO: 22 (mature peptide).

When a humanized antibody is produced, a complementarity determining region (CDR) is transplanted from the variable region of a mouse antibody into the variable region of a human antibody, so as to produce a reconstructed variable region, in which a framework region (FR) is derived from the human and CDR is derived from the mouse (what is called CDR grafting (CDR transplantation)). Subsequently, the thus humanized, reconstructed human variable region is ligated to a human constant region. Herein, as such humanized, reconstructed human variable regions, the H chain V region preferably consists of, for example, the amino acid sequence as shown in SEQ ID NO: 33, and particularly preferably consists of the amino acid sequence as shown in SEQ ID NO: 35 (mature peptide), or it preferably consists of, for example, the amino acid sequence as shown in SEQ ID NO: 38, and particularly preferably consists of the amino acid sequence as shown in SEQ ID NO: 40 (mature peptide). On the other hand, the L chain V region preferably consists of, for example, the amino acid sequence as shown in SEQ ID NO: 43, and particularly preferably consists of the amino acid sequence as shown in SEQ ID NO: 45 (mature peptide). For a method for producing such humanized antibodies, Nature, 321, 522-525 (1986); J. Mol. Biol., 196, 901-917 (1987); Queen C et al., Proc. Natl. Acad. Sci. USA, 86: 10029-10033 (1989); JP Patent Publication (Kohyo) No. 4-502408 A (1992) (Japanese Patent No. 2828340; Queen et al.), etc. can be referred, for example. The type of a mouse-derived CDR sequence that can be used herein for the humanized anti-hDlk-1 antibody of the present invention is not limited. As preferred examples of such mouse-derived CDR sequences, the amino acid sequences as shown in SEQ ID NOS: 16 to 18 are preferable as the CDRs 1 to 3 of the H chain V region (in this order), and the amino acid sequences as shown in SEQ ID NOS: 23 to 25 are preferable as the CDRs 1 to 3 of the L chain V region (in this order).

Moreover, the present invention includes modified amino acids, in which an amino acid(s) (preferably one to several, and more preferably one or two amino acids) in a part of the V region (excluding a CDR sequence) of the H chain or L chain of the aforementioned humanized antibody are substituted with other amino acids.

Preferred examples of such modified amino acids include modified amino acids, in which one or two amino acids in the H chain V region (excluding a CDR sequence) of the aforementioned humanized antibody are substituted with other amino acids. Preferred examples of the thus substituted amino acids include those in which the H chain V region is the following:
(1-1) the H chain V region consisting of the amino acid sequence as shown in SEQ ID NO: 67 (the nucleotide sequence: SEQ ID NO: 66), and particularly consisting of the amino acid sequence as shown in SEQ ID NO: 69 (mature peptide) (the nucleotide sequence: SEQ ID NO: 68);
(1-2) the H chain V region consisting of the amino acid sequence as shown in SEQ ID NO: 71 (the nucleotide sequence: SEQ ID NO: 70), and particularly consisting of the amino acid sequence as shown in SEQ ID NO: 73 (mature peptide) (the nucleotide sequence: SEQ ID NO: 72);
(1-3) the H chain V region consisting of the amino acid sequence as shown in SEQ ID NO: 75 (the nucleotide sequence: SEQ ID NO: 74), and particularly consisting of the amino acid sequence as shown in SEQ ID NO: 77 (mature peptide) (the nucleotide sequence: SEQ ID NO: 76);
(2-1) the H chain V region consisting of the amino acid sequence as shown in SEQ ID NO: 79 (the nucleotide sequence: SEQ ID NO: 78), and particularly consisting of the amino acid sequence as shown in SEQ ID NO: 81 (mature peptide) (the nucleotide sequence: SEQ ID NO: 80);
(2-2) the H chain V region consisting of the amino acid sequence as shown in SEQ ID NO: 83 (the nucleotide sequence: SEQ ID NO: 82), and particularly consisting of the amino acid sequence as shown in SEQ ID NO: 85 (mature peptide) (the nucleotide sequence: SEQ ID NO: 84); or
(2-3) the H chain V region consisting of the amino acid sequence as shown in SEQ ID NO: 87 (the nucleotide sequence: SEQ ID NO: 86), and particularly consisting of the amino acid sequence as shown in SEQ ID NO: 89 (mature peptide) (the nucleotide sequence: SEQ ID NO: 88). Of these, the amino acid sequences according to (1-3) and (2-3) above are more preferable. Hence, a modified humanized anti-hDlk-1 antibody, in which the H chain V region is modified to the amino acid sequence according to any one of (1-1) to (2-3) above and the L chain V region consists of the aforementioned amino acid sequence as shown in SEQ ID NO: 43, and particularly consists of the amino acid sequence as shown in SEQ ID NO: 45 (mature peptide), is a humanized antibody having a much higher avidity (antigen-binding activity), and for example, this antibody is able to retain a binding activity to cancer cells, on the surface of which the expression level of antigen is low. In addition, the modified humanized anti-hDlk-1 antibody is able to retain a stable antigen-binding activity for a long period of time in a liquid formulation, in monkey or human blood (plasma), etc.

Herein, with regard to the amino acid sequence as shown in SEQ ID NO: 67 according to (1-1) above, the alanine (A) at position 43 is substituted with glycine (G) in the amino acid sequence as shown in SEQ ID NO: 33; and with regard to the amino acid sequence as shown in SEQ ID NO: 69 according to (1-1) above, the alanine (A) at position 24 is substituted with glycine (G) in the amino acid sequence as shown in SEQ ID NO: 35 (mature peptide).

In addition, with regard to the amino acid sequence as shown in SEQ ID NO: 71 according to (1-2) above, the threonine (T) at position 93 is substituted with lysine (K) in the amino acid sequence as shown in SEQ ID NO: 33; and with regard to the amino acid sequence as shown in SEQ ID NO: 73 according to (1-2) above, the threonine (T) at position 74 is substituted with lysine (K) in the amino acid sequence as shown in SEQ ID NO: 35 (mature peptide).

Moreover, with regard to the amino acid sequence as shown in SEQ ID NO: 75 according to (1-3) above, the alanine (A) at position 43 is substituted with glycine (G) and the threonine (T) at position 93 is substituted with lysine (K) in the amino acid sequence as shown in SEQ ID NO: 33; and with regard to the amino acid sequence as shown in SEQ ID NO: 77 according to (1-3) above, the alanine (A) at position 24 is substituted with glycine (G) and the threonine (T) at position 74 is substituted with lysine (K) in the amino acid sequence as shown in SEQ ID NO: 35 (mature peptide).

Furthermore, with regard to the amino acid sequence as shown in SEQ ID NO: 79 according to (2-1) above, the alanine (A) at position 43 is substituted with glycine (G) in the amino acid sequence as shown in SEQ ID NO: 38; and with regard to the amino acid sequence as shown in SEQ ID NO: 81 according to (2-1) above, the alanine (A) at position 24 is substituted with glycine (G) in the amino acid sequence as shown in SEQ ID NO: 40 (mature peptide).

Further, with regard to the amino acid sequence as shown in SEQ ID NO: 83 according to (2-2) above, the threonine (T) at position 93 is substituted with lysine (K) in the amino acid sequence as shown in SEQ ID NO: 38; and with regard to the amino acid sequence as shown in SEQ ID NO: 85 according to (2-2) above, the threonine (T) at position 74 is substituted with lysine (K) in the amino acid sequence as shown in SEQ ID NO: 40 (mature peptide).

Still further, with regard to the amino acid sequence as shown in SEQ ID NO: 87 according to (2-3) above, the alanine (A) at position 43 is substituted with glycine (G) and the threonine (T) at position 93 is substituted with lysine (K) in the amino acid sequence as shown in SEQ ID NO: 38; and with regard to the amino acid sequence as shown in SEQ ID NO: 89 according to (2-3) above, the alanine (A) at position 24 is substituted with glycine (G) and the threonine (T) at position 74 is substituted with lysine (K) in the amino acid sequence as shown in SEQ ID NO: 40 (mature peptide).

In general, in the case of a human antibody (a complete human antibody), its structure comprising a Hyper Variable region that is the antigen-binding site of a V region, other parts of the V region and a constant region is the same as the structure of the antibody of a human. However, such a Hyper Variable site may also be derived from other animals. A technique of producing a human antibody is publicly known and a method for producing gene sequences that are common in humans by genetic engineering has been established. A human antibody can be obtained, for example, by a method using a human antibody-producing mouse that has human chromosomal fragments comprising the genes of the H chain and L chain of the human antibody (please refer to Tomizuka, K. et al., Nature Genetics, (1977) 16, 133-143; Kuroiwa, Y. et. al., Nuc. Acids Res., (1998) 26, 3447-3448; Yoshida, H. et. al., Animal Cell Technology: Basic and Applied Aspects, (1999) 10, 69-73 (Kitagawa, Y., Matsuda, T. and Iijima, S. eds.), Kluwer Academic Publishers; Tomizuka, K. et. al., Proc. Natl. Acad. Sci. USA, (2000) 97, 722-727, etc.), or by a method of obtaining a phage display-derived human antibody selected from a human antibody library (please refer to Wormstone, I. M. et. al, Investigative Ophthalmology & Visual Science., (2002) 43 (7), 2301-8; Carmen, S. et. al., Briefings in Functional Genomics and Proteomics, (2002) 1 (2), 189-203; Siriwardena, D. et. al., Opthalmology, (2002) 109 (3), 427-431, etc.).

In the case of the aforementioned chimeric antibody, humanized antibody and human antibody, the N-glycoside-linked sugar chain in the antibody Fc region is preferably, for example, a sugar chain, in which fucose does not bind to N-acetylglucosamine at the reducing terminal thereof. A specific example is an antibody consisting of genetically recombinant antibody molecules, which has, in the Fc region of the antibody molecules, a sugar chain in which the position 1 of the fucose does not bind to the position 6 of the N-acetylglucosamine at the reducing terminal of the N-glycoside-linked sugar chain via an a bond. Such an antibody is able to significantly improve ADCC activity. This point (the characteristics of the N-glycoside-linked sugar chain in the antibody Fc region) is preferable also for the aforementioned polyclonal antibody and monoclonal antibody.

(4-2) Antibody Fragment

The anti-hDlk-1 antibody fragment of the present invention is included in the antibody of the present invention. Herein, the antibody fragment of the present invention has binding activity to hDlk-1 and anti-tumor activity in vivo, as in the case of the anti-hDlk-1 antibody of the present invention (including humanized antibodies and the like, other than mouse antibodies).

The fragment of the antibody means a region of a portion of an anti-hDlk-1 polyclonal antibody or anti-Dlk-1 monoclonal antibody (namely, an antibody fragment derived from the anti-hDlk-1 antibody of the present invention). Examples of such an antibody fragment include peptides comprising, as at least a portion thereof, Fab, Fab', F(ab')$_2$, Fv (variable fragment of antibody), a single-stranded antibody (an H chain, an L chain, an H chain V region and an L chain V region, etc.), scFv, diabody (scFv dimer), dsFv (a disulfide-stabilized V region) and a complementarity determining region (CDR).

Fab is an antibody fragment with a molecular weight of approximately 50,000 having antigen-binding activity, which is formed by binding about a half of the N-terminal side of the H chain and the entire L chain via a disulfide bond, among fragments obtained by treating antibody molecules with a protease, papain. In addition, it is also possible to produce such Fab by inserting DNA encoding the Fab of an antibody into a prokaryote expression vector or a eukaryote expression vector and then introducing the vector into a prokaryote or a eukaryote so as to allow the DNA to express therein.

F(ab')$_2$ is an antibody fragment with a molecular weight of approximately 100,000 having antigen-binding activity, whose size is slightly greater than Fab that binds to Fab via disulfide bond in the hinge region, among fragments obtained by treating antibody molecules with a protease, pepsin. In addition, it is also possible to produce such F(ab')$_2$ by the thioether bond or disulfide bond of Fab, as described later.

Fab' is an antibody fragment with a molecular weight of approximately 50,000 having antigen-binding activity, which is formed by cleaving the disulfide bond in the hinge region of the aforementioned F(ab')$_2$. In addition, it is also possible to produce such Fab' by inserting DNA encoding the Fab' fragment of an antibody into a prokaryote expression vector or a eukaryote expression vector and then introducing the vector into a prokaryote or a eukaryote so as to allow the DNA to express therein.

scFv is an antibody fragment having antigen-binding activity, which is a VH-P-VL or VL-P-VH polypeptide formed by ligating a single H chain V region (VH) to a single L chain V region (VL) using a suitable peptide linker (P). Such scFv can be produced by obtaining cDNA encoding the VH and VL of an antibody, constructing DNA encoding scFv, inserting the DNA into an expression vector for prokaryote or an expression vector for eukaryote and then introducing the vector into a prokaryote or a eukaryote so as to allow the DNA to express therein.

Diabody is an antibody fragment formed by dimerization of scFv, which has divalent antigen-binding activities. Such divalent antigen-binding activities may be identical to each other, or they may also be different from each other. Such diabody can be produced by obtaining cDNA encoding the VH and VL of an antibody, constructing DNA encoding scFv such that the length of the amino acid sequence of P is 8 residues or less, inserting the DNA into an expression vector for prokaryote or an expression vector for eukaryote and then introducing the vector into a prokaryote or a eukaryote so as to allow the DNA to express therein.

dsFv is an antibody fragment formed by binding polypeptides, in which one amino acid residue in each of VH and VL has been substituted with a cysteine residue, to each other via a disulfide bond between the cysteine residues. The amino acid residue to be substituted with cysteine residues can be selected based on estimation of the three-dimensional structure of the antibody according to the method of Reiter et al. (Protein Engineering, 7, 697-704, 1994). Such dsFv can be produced by obtaining cDNA encoding the VH and VL of an antibody, constructing DNA encoding dsFv, inserting the DNA into an expression vector for prokaryote or an expression vector for eukaryote and then introducing the vector into a prokaryote or a eukaryote so as to allow the DNA to express therein.

A peptide comprising CDRs comprises at least one region of CDRs (CDRs 1 to 3) of VH or VL. A peptide multiple peptides comprising CDRs can be bound to one another, directly or via a suitable peptide linker. Such a peptide comprising CDRs can be produced by constructing DNA encoding the VH and VL of an antibody, inserting the DNA into an expression vector for prokaryote or an expression vector for eukaryote and then introducing the expression vector into a prokaryote or a eukaryote so as to allow the DNA to express therein. Moreover, such a peptide comprising CDRs can also be produced by chemical synthesis methods such as a Fmoc method (a fluorenylmethyloxycarbonyl method) and a tBoc method (a t-butyloxycarbonyl method).

The antibody fragment of the present invention, as is, may be an antibody fragment, which comprises a part of or the entire antibody Fc region in which fucose does not bind to N-acetylglucosamine at the reducing terminal of an N-glycoside-linked sugar chain. Otherwise, the antibody fragment of the present invention may also be a fusion protein, in which the aforementioned antibody fragment is fused with a part of or the entire antibody Fc region in which fucose does not bind to N-acetylglucosamine at the reducing terminal of an N-glycoside-linked sugar chain. Such an antibody fragment is able to significantly improve ADCC activity and thus it is preferable.

The type of the antibody fragment of the present invention is not limited. Specific examples of the present antibody fragment include antibody fragments comprising, as at least a portion thereof, the amino acid sequences as shown in SEQ ID NOS: 16 to 18 (CDRs 1 to 3 of the H chain V region). Specifically, examples of such antibody fragments include antibody fragments each comprising the amino acid sequence (the H chain V region) as shown in any one of SEQ ID NO: 13 (in particular, SEQ ID NO: 15), SEQ ID NO: 33 (in particular, SEQ ID NO: 35), SEQ ID NO: 38 (in particular, SEQ ID NO: 40), SEQ ID NO: 67 (in particular, SEQ ID NO: 69), SEQ ID NO: 71 (in particular, SEQ ID NO: 73), SEQ ID NO: 75 (in particular, SEQ ID NO: 77), SEQ ID NO: 79 (in particular, SEQ ID NO: 81), SEQ ID NO: 83 (in particular, SEQ ID NO: 85) and SEQ ID NO: 87 (in particular, SEQ ID NO: 89). Moreover, other specific examples of the present antibody fragments include antibody fragments comprising, as at least a portion thereof, the amino acid sequence as shown in any one of SEQ ID NOS: 23 to 25 (CDRs 1 to 3 of the L chain V region). A specific example is an antibody fragment comprising the amino acid sequence (the L chain V region) as shown in SEQ ID NO: 20 (in particular, SEQ ID NO: 22) or SEQ ID NO: 43 (in particular, SEQ ID NO: 45).

Hereinafter, in the descriptions of the present specification, the aforementioned antibody fragments are also included in the anti-hDlk-1 antibody of the present invention.

3. PREPARATION OF ANTIBODY-AGENT COMPLEX

As an immunoconjugate prepared using the aforementioned anti-hDlk-1 antibody of the present invention, there can be provided an antibody-agent complex, which comprises the aforementioned antibody and a compound having anti-tumor activity and/or cell-killing activity. It is to be noted that a complex formed by previously preparing each of the aforementioned antibody molecule and the aforementioned compound having anti-tumor activity and/or cell-killing activity, separately and then combining them is generally referred to as an immunoconjugate. On the other hand, a complex obtained by ligating a protein toxin used as such a compound having anti-tumor activity and/or cell-killing activity to an antibody gene on a gene according to a genetic recombination technique, so as to allow it to express as a single protein (a fusion protein), is generally referred to as an immunotoxin.

Examples of a compound having anti-tumor activity include doxorubicin, calicheamicin, mitomycin C and Auristatin E.

Examples of a compound having cell-killing activity include saporin, lysine, *pseudomonas* exotoxin and diphtheria toxin. Of these, saporin and *pseudomonas* exotoxin are preferably used.

A method for producing an antibody-agent complex is not limited. For example, a method of coupling an antibody with an agent via a disulfide bond or a hydrazone bond is applied.

The aforementioned anti-hDlk-1 antibody of the present invention is excellent in terms of internalization activity into target tumor cells that express hDlk-1. Thus, by previously combining a compound having anti-tumor activity and cell-killing activity with the anti-hDlk-1 antibody, it becomes possible to allow such a compound to directly and highly selectively act on the tumor cells. The antibody-agent complex of the present invention is extremely excellent in terms of ability to deliver the agent to the target tumor cells.

The internalization activity into cells can be evaluated by fluorescently labeling an antibody with rhodamine or the like and then observing the migratory behavior and localization of the antibody using a fluorescence microscope or the like.

Moreover, in the present invention, in addition to the aforementioned antibody-agent complex, there can also be provided an antibody fragment-agent complex, in which the aforementioned antibody fragment is used instead of an antibody. With regard to the details of such an antibody fragment-agent complex, the descriptions of the aforementioned antibody-agent complex can be applied, as appropriate.

Hereinafter, in the descriptions of the present specification, such an antibody fragment-agent complex is also included in the antibody-agent complex of the present invention.

4. PHARMACEUTICAL COMPOSITION

The anti-hDlk-1 antibody and antibody-agent complex of the present invention are useful as active ingredients contained in a pharmaceutical composition.

The pharmaceutical composition is useful as a pharmaceutical composition for treating and/or diagnosing a tumor. That is to say, the anti-hDlk-1 antibody and antibody-agent complex of the present invention are useful as active ingredients contained in a tumor therapeutic agent or a tumor diagnostic agent. Herein, the treatment of a tumor includes inhibition of tumor angiogenesis (hereinafter, the same applies throughout the present specification).

The anti-hDlk-1 antibody and antibody-agent complex of the present invention are preferable in that they do not cause side effects such as weight reduction when they are used in the treatment of a tumor.

Moreover, the present pharmaceutical composition is useful as a pharmaceutical composition used in induction of apoptosis in tumor cells. That is to say, the anti-hDlk-1 antibody and antibody-agent complex of the present invention are useful as active ingredients contained in an agent for inducing apoptosis in tumor cells.

It is preferable to provide the pharmaceutical composition of the present invention in the form of a pharmaceutical composition comprising the anti-hDlk-1 antibody and/or antibody-agent complex of the present invention as active ingredient(s) and further comprising a pharmacologically acceptable carrier.

Target diseases (tumors), to which the pharmaceutical composition of the present invention is applied, include: the aforementioned known human tumors, in which expression of hDlk-1 had previously been confirmed (specifically, solid cancers such as neuroendocrine tumor, neuroblastoma, glioma, neurofibromatosis type 1, small cell lung cancer, liver cancer, kidney cancer and ovarian cancer, and blood cancers such as myelodysplastic syndrome and acute myelocytic leukemia); and human colon cancer, human breast cancer and human pancreatic cancer, in which expression of hDlk-1 has been confirmed by the present inventors for the first time. Among others, one or two or more types selected from human colon cancer, human breast cancer, human liver cancer, human pancreatic cancer, human small cell lung cancer and human neurocytoma are particularly preferable. Such target disease may be a single disease, or two or more diseases may be developed in combination.

Examples of the "pharmacologically acceptable carrier" include an excipient, a diluent, an extender, a disintegrator, a stabilizer, a preservative, a buffer, an emulsifier, an aromatic, a coloring agent, a sweetener, a thickener, a corrigent, a solubilizer and other additives. Using one or more types of such carriers, a pharmaceutical composition can be prepared in the form of an injection, a liquid agent, a capsule, a suspension, an emulsion, a syrup, etc. These pharmaceutical compositions can be administered orally or parenterally. Another form for parenteral administration is an injection comprising one or more active ingredients, which is prepared by an ordinary method. Such an injection can be produced by dissolving or suspending the present antibody in a pharmacologically acceptable carrier such as a normal saline solution or a commercially available distilled water used for injection.

In particular, when an antibody fragment derived from the anti-hDlk-1 antibody of the present invention (particularly, an antibody fragment with a low molecular weight) is administered into a living body, a colloidal dispersion system can be used in addition to the aforementioned components. Such a colloidal dispersion system is anticipated to have an effect of enhancing the stability of a compound (an antibody fragment) in a living body or an effect of efficiently transporting such a compound to a specific organ, tissue, or cell. The type of such a colloidal dispersion system is not limited, as long as it is commonly used. An example of such a colloidal dispersion system is a dispersion system comprising, as a base, polyethylene glycol, a macromolecular complex, a macromolecular aggregate, a nanocapsule, microsphere, beads and lipids including an oil in water emulsifier, micelle, mixed micelle and liposome. Preferred examples of such a colloidal dispersion system include multiple liposomes and the vesicles of artificial membrane, which have an effect of efficiently transporting such a compound to a specific organ, tissue, or cell (Mannino et al., Biotechniques, 1988, 6, 682; Blume and Cevc, Biochem. et Biophys. Acta, 1990, 1029, 91; Lappalainen et al., Antiviral Res., 1994, 23, 119; Chonn and Cullis, Current Op. Biotech., 1995, 6, 698).

The dose of the pharmaceutical composition of the present invention differs depending on the age, sex, body weight and symptoms of a patient, therapeutic effects, an administration method, a treatment time, the types of the anti-hDlk-1 antibody and antibody-agent complex of the present invention contained in the pharmaceutical composition, etc. In general, the present pharmaceutical composition may be administered within the range between 600 µg and 6,000 mg per adult per administration. However, the dose is not limited to the aforementioned range.

In a case where the pharmaceutical composition is administered in the form of an injection, for example, it may be administered at a dose of 10 µg to 100 mg, or 30 µg to 100 mg, or 50 µg to 100 mg, or 100 µg to 100 mg, per administration and per body weight of a human patient, or it may be administered at a dose in a range in which the lower limits of the aforementioned doses are combined as appropriate (e.g. 30 µg to 200 µg or 100 µg to 500 µg), once or divided over several administrations, as an average daily dose. Examples of the dosage form include intravenous injection, subcutaneous injection, intradermal injection, intramuscular injection and intraperitoneal injection. Of these, intravenous injection is preferable. In addition, such an injection may be prepared in the form of a nonaqueous diluent (e.g. polyethylene glycol, vegetable oil such as olive oil, alcohols such as ethanol, etc.), a suspension, or an emulsion. Such an injection can be sterilized by mechanical sterilization using a filter, the mixing of a microbicide, etc. The injection can be produced in the form of an injection to be prepared before using. That is, a sterilized solid composition is prepared by a freeze-drying method or the like and the composition is then dissolved in sterilized distilled water used for injection or other solvents before it is used, so that it can be then used.

The present invention provides the use of the aforementioned anti-hDlk-1 antibody and/or antibody-agent complex of the present invention in production of a pharmaceutical (an agent) for treating a tumor, diagnosing a tumor and/or inducing apoptosis in tumor cells. In addition, the present invention provides the aforementioned anti-hDlk-1 antibody and/or antibody-agent complex of the present invention, which are used for treating a tumor, diagnosing a tumor and/or inducing apoptosis in tumor cells.

Moreover, the present invention provides a method for treating a tumor, a method for diagnosing a tumor and/or a method for inducing apoptosis in tumor cells, which comprises using (namely, administering to patients) the aforementioned anti-hDlk-1 antibody and/or antibody-agent complex of the present invention. Furthermore, the present invention also provides the use of the aforementioned anti-hDlk-1 antibody and/or antibody-agent complex of the present invention for treating a tumor, diagnosing a tumor and/or inducing apoptosis in tumor cells.

5. METHOD FOR DETECTING TUMOR

The method for detecting a tumor of the present invention (which may be a method for diagnosing a tumor) is characterized in that it comprises allowing the aforementioned anti-hDlk-1 antibody of the present invention to react with a sample collected from a living body (hereinafter referred to as a biological sample) and detecting a signal of the reacted antibody.

As described above, since hDlk-1 has been confirmed to be specifically expressed in various types of tumor cells, hDlk-1 and particularly, free hDlk-1 (an extracellular region portion of hDlk-1) can be used as a marker for various types of tumors. In particular, such hDlk-1 can be preferably used as a marker for human colon cancer, human breast cancer, human liver cancer and human pancreatic cancer.

Thus, the anti-hDlk-1 antibody of the present invention is allowed to react with a biological sample and a signal of the reacted antibody is then detected, so as to detect a tumor. The obtained antibody signal can be used as an indicator of the amount of an antigen in the biological sample (that is, an hDlk-1 amount or a free hDlk-1 amount). In detection of the tumor using the antibody of the present invention, first, a biological sample collected as an analyte from a subject, such as a tissue section or blood used as a test target, is allowed to bind to the antibody of the present invention by an antigen-antibody reaction. Subsequently, based on the measurement results of the amount of the bound antibody, the amount of an antigen of interest contained in the biological sample is measured. This measurement may be carried out in accordance with known immunoassay methods. For example, an immunoprecipitation method, an immunoagglutination method, radioimmunoassay, immunonephelometry, a Western blot method, flowcytometry and the like can be used. In radioimmunoassay, a labeled antibody is used and thus an antibody signal is expressed as the amount of the labeled antibody that is directly detected. Otherwise, an antibody whose concentration or antibody titer has been known may be used as a standard solution and thus a signal of the target antibody may be expressed as a relative value. That is, both the standard solution and the analyte may be measured using a measurement device and an antibody signal in a biological sample may be expressed as a value relative to the value of the standard solution used as a criterion. Examples of such radioimmunoassay include the ELISA method, the EI method, the RIA method, fluorescence immunoassay (FIA) and luminescence immunoassay. Of these, the ELISA method is particularly preferable in that it is simple and highly sensitive.

In the present invention, the state of tumor can be evaluated or diagnosed, using the detection result obtained by the aforementioned detection method as an indicator. For example, when the detection result exceeds a predetermined standard value, the state of tumor is defined as tumor positive and when the detection result is less than the predetermined standard value, it is defined as tumor negative. In the case of tumor positive, it is determined that a certain type of tumor could have been developed and thus the tumor state can be evaluated. The term "the state of tumor" is used herein to mean the presence or absence of the development of tumor, or the progression degree thereof. Thus, specific examples of the state of tumor include the presence or absence of the development of tumor, the progression degree thereof, the degree of malignancy, the presence or absence of metastasis and the presence or absence of recurrence.

In the aforementioned evaluation, as a state of tumor to be evaluated, only one state may be selected from the aforementioned examples, or multiple examples may be combined and selected. The presence or absence of tumor can be evaluated by determining whether or not the tumor has been developed, with reference to the predetermined standard value used as a boundary, based on the obtained detection result. The degree of malignancy is used as an indicator that indicates the progression degree of cancer. Based on the detection result, the target tumor can be classified into a certain disease stage and it can be evaluated. Otherwise, early cancer and advanced cancer can be distinguished from each other and then they can be evaluated. For example, it is also possible to determine the target tumor as early cancer or advanced cancer, using the detection result as an indicator. The metastasis of tumor can be evaluated by determining whether or not neoplasm has appeared at a site apart from the position of the initial lesion, using the detection result as an indicator. The recurrence can be evaluated by determining whether or not the detection result has exceeded the predetermined standard value again after interval stage or remission.

6. KIT FOR DETECTING OR DIAGNOSING TUMOR, AND KIT FOR TREATING TUMOR OR INDUCING APOPTOSIS IN TUMOR CELLS

The anti-hDlk-1 antibody of the present invention can be provided in the form of a kit for detecting a tumor or a kit for diagnosing a tumor. In addition, the anti-hDlk-1 antibody and antibody-drug complex of the present invention can be provided in the form of a kit for treating a tumor or a kit for inducing apoptosis in tumor cells.

The kit of the present invention comprises a labeling substance, a solid-phase reagent on which the antibody or the labeled antibody has been immobilized, etc., as well as the aforementioned antibody. A labeling substance that labels the antibody means a substance labeled with an enzyme, a radioisotope, a fluorescent compound, a chemiluminescent compound, etc. The kit of the present invention may also comprise other reagents used for carrying out the detection of the present invention, in addition to the aforementioned constitutional elements. For example, when such a labeling substance is an enzyme labeling substance, the kit of the present invention may comprise an enzyme substrate (a chromogenic substrate, etc.), an enzyme substrate-solving solution, an enzyme reaction stop solution, a diluent used for analytes, etc. Moreover, the present kit may further comprise various types of buffers, sterilized water, various types of cell culture vessels, various types of reactors (an EPPENDORF tube, etc.), a blocking agent (a serum component such as bovine serum albumin (BSA), skim milk, or goat serum), a washing agent, a surfactant, various types of plates, an antiseptic such as sodium azide, an experimental operation manual (instruction), etc.

The kit of the present invention can be effectively used to carry out the above-described method for detecting a tumor, method for treating a tumor, and method for inducing apoptosis in tumor cells of the present invention, etc. Thus, the present kit is extremely useful.

Hereinafter, the present invention will be more specifically described in the following examples. However, these examples are not intended to limit the scope of the present invention.

Example 1

Cloning of Mouse Anti-Human Dlk-1 Monoclonal Antibody (Clone BA-1-3D) Gene and Determination of Variable Region Sequences A mouse anti-human Dlk-1 monoclonal antibody, clone BA-1-3D (mouse IgG2a) that exhibited significant tumor growth-inhibiting activity in WO 2008/056833 (as described above; Patent Document 4) and WO 2009/116670 (as described above; Patent Document 5) (hereinafter referred to as "mouse BA-1-3D") was used. A hybridoma generating the mouse BA-1-3D has been referred to as "Mouse-Mouse hybridoma BA-1-3D" and has been deposited with International Patent Organism Depositary (IPOD), National Institute of Advanced Industrial Science and Technology (AIST Tsukuba Central 6, Higashi 1-1-1, Tsukuba, Ibaraki, Japan, postal code: 305-8566) on Feb. 1, 2011 (Accession No.: FERM BP-11337).

The aforementioned mouse BA-1-3D-generating hybridoma was cultured at 37° C. in a RPMI-1640 medium containing 20% fetal bovine serum (FBS; HyClone), 1 mM sodium pyruvate, 100 units/ml penicillin, 100 µg/ml streptomycin and 1× Hybridoma Fusion and Cloning Supplement (Roche Diagnostics, Indianapolis, Ind.) in a 7.5% $CO_2$ incubator. Total RNA was extracted from $10^7$ hybridomas using a TRIZOL reagent (Invitrogen), and thereafter, using oligo dT primers, cDNA was synthesized from the total RNA employing SMARTER RACE cDNA Amplification Kit (Clontech, Mountain View, Calif.) in accordance with the method included in the kit. Using the thus synthesized cDNA as a template, genes encoding the H chain variable region (VH) and L chain variable region (VL) of the mouse BA-1-3D were cloned by a PCR method employing PHUSION DNA polymerase (New England Biolabs, Beverly, Mass.). In the PCR method, Universal Primer A Mix (UPM) or Nested Universal Primer A (NUP) included with the kit was used as a 5'-primer. On the other hand, as a 3'-primer for VH amplification, a primer having a sequence complementary to a mouse γ2a constant region was used, and as a 3'-primer for VL amplification, a primer having a sequence complementary to a mouse κ constant region was used.

5'-Primer (F primer; Universal Primer A Mix (UPM)):
Long:
(SEQ ID NO: 3)
5'-CTAATACGACTCACTATAGGGCAAGCAGTGGTATCAACGCAGAGT-3'

Short:
(SEQ ID NO: 4)
5'-CTAATACGACTCACTATAGGGC-3'

```
5'-Primer (F primer; Nested Universal Primer A
(NUP)):
                                        (SEQ ID NO: 5)
5'-AAGCAGTGGTATCAACGCAGAGT-3'

3'-Primer (R primer):
                                        (SEQ ID NO: 6)
VH: 5'-GCCAGTGGATAGACCGATGG-3'

(SEQ ID NO: 7)
VL: 5'-GATGGATACAGTTGGTGCAGC-3'
```

The PCR reaction was carried out with the following composition of a reaction solution under the following reaction conditions using each of the aforementioned primers.

<Composition of Reaction Solution>

| Template cDNA: | 2.5 µL |
| 5x PrimeSTAR buffer (Mg²⁺ plus): | 10 µL |
| 2.5 mM dNTP: | 4 µL |
| Phusoin DNA polymerase (2.0 U/µl): | 0.5 µL |
| 10x UPM or NUP: | 5 µL |
| R primer (10 µM): | 1 µL |
| Sterilized water: | 27 µL |
| Total: | 50 µL |

<Reaction Conditions>

After completion of the reaction at 94° C. (10 sec), one cycle consisting of "Heat denaturation/dissociation: 98° C. (10 sec)→Annealing: 60° C. (5 sec)→Synthesis/elongation: 72° C. (60 sec)" was repeated 30 times (total 30 cycles). Finally, reaction was carried out at 72° C. (3 min)

The synthesized cDNAs of the VH and VL (BA-1-3D VH and BA-1-3D VL) of the mouse BA-1-3D were each subcloned into a pCR-BluntII-TOPO vector (Invitrogen), and the nucleotide sequences thereof were then determined. The nucleotide sequences of a plurality of VH clones and VL clones were decoded, and the typical nucleotide sequences of the variable regions of mouse H chain and L chain were identified. FIG. 1 and FIG. 2 show the consensus cDNA nucleotide sequences of BA-1-3D VH and BA-1-3D VL and their putative amino acid sequences.

Example 2

Construction of Mouse/Human Chimeric BA-1-3D IgG1/κ Expression Vector

A gene encoding BA-1-3D VH (BA-1-3D VH gene) was generated as an exon, to which a mouse germ cell line JH4 sequence-derived splice donor signal was added and to both ends of which restriction enzyme sites were added. Specifically, the gene was synthesized according to a PCR method using the cDNA of the BA-1-3D VH gene as a template. During the PCR reaction, a 5'-primer, to which a SpeI site had been added as a restriction enzyme site to be inserted into an animal cell expression vector, and a 3'-primer, to which a HindIII site had been added as such a restriction enzyme site, were used.

```
5'-Primer (F primer):
                                        (SEQ ID NO: 8)
5'-GCAACTAGTACCACCATGGGTTGGAGCTGTATC-3'
(Underline: SpeI site)

3'-Primer (R primer):
                                        (SEQ ID NO: 9)
5'-GGGAAGCTTGAGAGGCCATTCTTACCTGAGGAGACGGTGACTGAGGT-
3'
(Underline: HindIII site)
```

The PCR reaction was carried out with the following composition of a reaction solution under the following reaction conditions, using each of the aforementioned primers (SEQ ID NOS: 8 and 9).

<Composition of Reaction Solution>

| Template cDNA: | 1.0 µL |
| 5x PrimeSTAR buffer (Mg²⁺ plus): | 10 µL |
| 2.5 mM dNTP: | 4 µL |
| Phusoin DNA polymerase (2.0 U/µl): | 0.5 µL |
| F primer (10 µM): | 3 µL |
| R primer (10 µM): | 1.0 µL |
| Sterilized water: | 30.5 µL |
| Total: | 50 µL |

<Reaction Conditions>

One cycle consisting of "Heat denaturation/dissociation: 98° C. (10 sec)→Annealing: 57° C. (10 sec)→Synthesis/elongation: 72° C. (60 sec)" was repeated 35 times (total 35 cycles).

Likewise, a gene encoding BA-1-3D VL (BA-1-3D VL gene) was generated as an exon, to which a mouse germ cell line Jκ5 sequence-derived splice donor signal was added and to both ends of which restriction enzyme sites were added. Specifically, the gene was synthesized according to a PCR method using the cDNA of the BA-1-3D VL gene as a template. During the PCR reaction, a 5'-primer, to which a NheI site had been added as a restriction enzyme site to be inserted into an animal cell expression vector, and a 3'-primer, to which an EcoRI site had been added as such a restriction enzyme site, were used.

```
5'-Primer (F primer):
                                        (SEQ ID NO: 10)
5'-GCTGCTAGCACCACCATGGAATCACAGACCCAG-3'
(Underline: NheI site)

3'-Primer (R primer):
                                        (SEQ ID NO: 11)
5'-GCAGAATTCAGAAAAGTGTACTTACGTTTCAGCTCCAGCTTGGTCC-
3'
(Underline: EcoRI site)
```

The PCR reaction was carried out with the following composition of a reaction solution under the following reaction conditions, using each of the aforementioned primers (SEQ ID NOS: 10 and 11).

| Template cDNA: | 1.0 µL |
| 5x PrimeSTAR buffer (Mg²⁺ plus): | 10 µL |
| 2.5 mM dNTP: | 4 µL |
| Phusoin DNA polymerase (2.0 U/µl): | 0.5 µL |
| F primer (10 µM): | 3 µL |
| R primer (10 µM): | 1.0 µL |
| Sterilized water: | 30.5 µL |
| Total: | 50 µL |

<Reaction Conditions>

One cycle consisting of "Heat denaturation/dissociation: 98° C. (10 sec)→Annealing: 57° C. (10 sec)→Synthesis/elongation: 72° C. (60 sec)" was repeated 35 times (total 35 cycles).

The thus generated BA-1-3D VH and BA-1-3D VL genes having functions as exons are shown in FIG. 3 and FIG. 4, respectively.

The generated BA-1-3D VH and BA-1-3D VL genes were each subcloned into a pCR-BluntII-TOPO vector (Invitrogen), and the nucleotide sequences thereof were then determined. Thereafter, using a SpeI/HindIII site for insertion of the BA-1-3D VH gene and also using a NheI/EcoRI site for insertion of the BA-1-3D VL gene, these genes were each inserted into an animal cell expression vector (FIG. 5) having the constant regions of human γ1 chain and κ chain, so as to generate a mouse-human chimeric BA-1-3D IgG1/κ antibody (ChBA-1-3D) expression vector (pChBA-1-3D).

Example 3

Generation of Humanized BA-1-3D VH and VL Genes

Humanization designing of BA-1-3D VH and BA-1-3D VL was carried out as follows according to the method of Queen et al. (Proc. Natl. Acad. Sci. USA 86: 10029-10033, 1989). First, the molecular modeling of the three-dimensional structures of the variable regions of the antibody BA-1-3D was carried out using computers, and amino acids in a framework region important for formation of CDR structures were then identified. At the same time, a homology search was performed between the BA-1-3D variable regions and the variable region sequences of human antibody genes, so as to select cDNA (U00503 VH) with GENBANK accession number: U00503 (Huang and Stollar, J. Immunol. 151: 5290, 1993) as an acceptor for providing a framework (FR) region necessary for humanization of BA-1-3D VH. Likewise, cDNA (Z46222 VL) with GENBANK accession number: Z46222 (Giachino et al., J. Exp. Med. 181:1245, 1995) was selected as an acceptor for providing a framework (FR) region necessary for humanization of BA-1-3D VL.

For humanization of BA-1-3D VH, the CDR sequence of BA-1-3D VH was first transplanted into the corresponding position in U00503 VH as an acceptor. Subsequently, as a result of the analysis of three-dimensional structures by computer modeling performed on mouse BA-1-3D variable regions, with regard to amino acid residues in FR region (isoleucine (I) at position 48, lysine (K) at position 66, alanine (A) at position 67, and valine (V) at position 71), which are adjacent to the CDRs of BA-1-3D VH and are assumed to play important roles in the maintenance of the structures, those of the BA-1-3D VH were retained, and other FR regions were substituted with those of the human acceptor sequences. The positional numbers of the amino acid residues in VH were used in accordance with the definitions of Kabat et al. (Sequences of Proteins of Immunological Interests, Fifth edition, NIH Publication No. 91-3242, U.S. Department of Health and Human Services, 1991). The thus generated, humanized BA-1-3D VH was referred to as HuBA-1-3D VH1.

The lysine (K) at position 66 in BA-1-3D VH is adjacent to the CDR sequences. As a result of the more detailed analysis of BA-1-3D variable regions by computer modeling, it was suggested that the lysine (K) at position 66 in HuBA-1-3D VH1 could be substituted with arginine (R) at a position corresponding to U00503 VH without impairing affinity for antigen. Thus, for the purpose of reducing potential immunogenicity, humanized BA-1-3D VH, in which the lysine (K) at position 66 of HuBA-1-3D VH1 was substituted with arginine (R), was also produced. The thus substituted, humanized BA-1-3D VH was referred to as HuBA-1-3D VH2.

The alignment of the amino acid sequences of BA-1-3D VH, HuBA-1-3D VH1, HuBA-1-3D VH2 and U00503 VH is shown in FIG. 6.

For humanization of BA-1-3D VL as well, the CDR sequence of BA-1-3D VL was transplanted into the corresponding position in Z46222 VL as an acceptor. Subsequently, as a result of the analysis of three-dimensional structures by computer modeling performed on mouse BA-1-3D variable regions, with regard to an amino acid residue in FR region (valine (V) at position 48), which is adjacent to the CDRs of BA-1-3D VL and is assumed to play an important role in the maintenance of the structures, that of the BA-1-3D VL was retained, and other FR regions were substituted with those of the human acceptor sequences. The positional numbers of the amino acid residues in VL were used in accordance with the definitions of Kabat et al. (Sequences of Proteins of Immunological Interests, Fifth edition, NIH Publication No. 91-3242, U.S. Department of Health and Human Services, 1991). The thus produced, humanized BA-1-3D VL was referred to as HuBA-1-3D VL.

The alignment of the amino acid sequences of BA-1-3D VL, HuBA-1-3D VL and Z46622 VL is shown in FIG. 7.

Genes encoding HuBA-1-3D VH1 and HuBA-1-3D VH2 were generated by gene synthesis (GenScript USA, Piscataway, N.J.) as exons, each of which comprised a mouse BA-1-3D VH signal peptide and a human germ line JH3 sequence-derived splice donor signal, and to both ends of each of which suitable restriction enzyme sites for insertion of an animal cell expression vector were added (SpeI added to the 5'-terminal side and HindIII added to the 3'-terminal side). The gene sequences of the thus generated HuBA-1-3D VH1 gene and HuBA-1-3D VH2 gene, and the amino acid sequences of HuBA-1-3D VH1 and HuBA-1-3D VH2, are shown in FIG. 8 and FIG. 9, respectively.

Likewise, a gene encoding HuBA-1-3D VL was generated by gene synthesis (GenScript USA, Piscataway, N.J.) as an exon, which comprised a mouse BA-1-3D VL signal peptide and a human germ line Jκ2 sequence-derived splice donor signal, and to both ends of which suitable restriction enzyme sites for insertion of an animal cell expression vector were added (NheI added to the 5'-terminal side and EcoRI added to the 3'-terminal side). The gene sequence of the thus generated HuBA-1-3D VL gene and the amino acid sequence of HuBA-1-3D VL are shown in FIG. 10.

Subsequently, using a SpeI/HindIII site for insertion of the HuBA-1-3D VH1 and VH2 genes, and also using a NheI/EcoRI site for insertion of the HuBA-1-3D VL gene, these sites were each inserted into an animal cell expression vector (FIG. 5) having the constant regions of human γ1 chain and κ chain. Specifically, a combination of the HuBA-1-3D VH1 gene with the HuBA-1-3D VL gene, and a combination of the HuBA-1-3D VH2 gene with the HuBA-1-3D VL gene, were each inserted into the aforementioned expression vector. Thus, an expression vector (pHuBA-1-3D-1) for expressing a humanized BA-1-3D IgG1/κ antibody (HuBA-1-3D-1) constituted with HuBA-1-3D VH1 and HuBA-1-3D VL, and an expression vector (pHuBA-1-3D-2) for expressing a humanized BA-1-3D IgG1/κ antibody (HuBA-1-3D-2) constituted with HuBA-1-3D VH2 and HuBA-1-3D VL, were generated.

Example 4

Generation of NS0 Cell Lines Stably Producing Mouse-Human Chimeric BA-1-3D Antibody (ChBA-1-3D) and Humanized BA-1-3D Antibodies (HuBA-1-3D-1 and HuBA-1-3D-2)

A mouse myeloma cell line NS0 (European Collection of Animal Cell Cultures, Salisbury, Wiltshire, UK) was cultured at 37° C. in a DME medium containing 10% fetal bovine serum in a 7.5% $CO_2$ incubator. In order to generate cell lines capable of stably producing ChBA-1-3D, HuBA-1-3D-1 and HuBA-1-3D-2, 20 μg each of antibody gene expression vectors (pChBA-1-3D, pHuBA-1-3D-1 and pHuBA-1-3D-2) (previously linearized with a restriction enzyme FspI) was transfected into NS0 cells (approximately $10^7$ cells) by electroporation according to the method of Bebbington et al. (Bio/Technology 10: 169-175, 1992). Forty-eight hours later, the medium was exchanged with a selective medium (a 10% FBS-containing DME medium, HT media supplement (Sigma, St. Louis, Mo.), 0.25 mg/ml xanthine, and 1 μg/ml mycophenolic acid), and then, approximately ten days later, the presence or absence of an antibody produced in a culture supernatant was analyzed.

ChBA-1-3D, HuBA-1-3D-1 and HuBA-1-3D-2 in the culture supernatant were detected and measured by a sandwich ELISA method. Specifically, a goat anti-human IgG Fcγ chain-specific polyclonal antibody (Sigma) diluted with PBS to a concentration of 1/2,000 was added in an amount of 100 μl per well to a 96-well plate, so that the 96-well plate was coated with the aforementioned antibody at 4° C. overnight. Thereafter, the plate was washed with a washing buffer (PBS+0.05% TWEEN 20). Subsequently, 300 μl of a blocking buffer (PBS+2% skim milk+0.05% TWEEN 20) was added to each well, so that the plate was blocked with the blocking buffer at room temperature for 30 minutes. Thereafter, the plate was washed with a washing buffer, and 100 μl of a culture supernatant that had been diluted at a suitable dilution magnification with an ELISA buffer (PBS+1% skim milk+0.025% TWEEN 20) was then added to each well. The obtained mixture was reacted at room temperature for 1 hour. A human or humanized IgG1/κ antibody was used as a standard. The reaction mixture washed with a washing buffer. Thereafter, 100 μl of an HRP-conjugated goat anti-human kappa chain polyclonal antibody (Southern Biotech) that had been diluted with an ELISA buffer to a concentration of 1/2,000 was added as a detection antibody to each well, followed by reaction at room temperature for 30 minutes. Thereafter, the resultant was washed with a washing buffer, and 100 μl of an ABTS substrate was then added to each well to perform a color reaction. Then, 100 μl of 2% oxalic acid was added to each well to terminate the reaction. Thereafter, the absorbance at 405 nm was measured.

NS0-ChBA-1-3D 2A4, NS0-HuBA-1-3D-1 2D2 and NS0-HuBA-1-3D-2 3F7 were established as NS0 cell lines stably producing ChBA-1-3D, HuBA-1-3D-1 and HuBA-1-3D-2 antibodies, respectively, and these cell lines were then acclimated to a serum-free medium (Hybridoma SFM (Invitrogen)).

The sequences of the H chain and L chain of antibodies produced by the individual NS0 cell lines, NS0-ChBA-1-3D 2A4, NS0-HuBA-1-3D-1 2D2 and NS0-HuBA-1-3D-2 3F7, were confirmed by cDNA sequencing. Specifically, total RNA was first extracted from each cell line using a TRIZOL reagent (Invitrogen), and thereafter, using oligo dT primers, cDNA was synthesized from the total RNA employing SUPERSCRIPT III First-Strand Synthesis System for RT-PCR (Invitrogen) in accordance with the method included in the kit. Subsequently, the coding region of a human γ1 chain was amplified by PCR using CMV2 and JNT098 as primers, and sequencing was then carried out using CMV2, JNT082, JNT097 and JNT098 as primers. Likewise, the coding region of a human κ1 chain was amplified by PCR using CMV2 and JNT026 as primers, and sequencing was then carried out using CMV2 and JNT026 as primers. It is to be noted that the aforementioned primers (CMV2, JNT026, JNT082, JNT097 and JNT098) each consist of the nucleotide sequences shown in FIG. 11.

As a result, the cDNA sequences of the H chain and L chain of ChBA-1-3D, HuBA-1-3D-1 and HuBA-1-3D-2 produced by the aforementioned NS0 cell lines were completely matched with the corresponding cDNA sequences of the vectors pChBA-1-3D, pHuBA-1-3D-1 and pHuBA-1-3D-2 (FIGS. 12 to 16).

Example 5

Purification of ChBA-1-3D, HuBA-1-3D-1 and HuBA-1-3D-2

The each of NS0 cell lines NS0-ChBA-1-3D 2A4, NS0-HuBA-1-3D-1 2D2 and NS0-HuBA-1-3D-2 3F7 were cultured using a roller bottle. As a medium, Hybridoma-SFM (Invitrogen) was used. At a stage where the cell density had reached approximately $1 \times 10^6$ cells/mL, 60 mg/ml Ultrafiltered Soy Hydrolysate (Irvine Scientific, Santa Ana, Calif.) (which had been dissolved in SFM4MAb media (HyClone)) was added in an amount of 1/10 to the cells. Then, the cell culture was carried out until the percentage of living cells became 50% or less. A culture supernatant was recovered by centrifugation and filtration, and the recovered cell supernatant was loaded onto a Protein-A SEPHAROSE column (HI-TRAP MABSELECT SURE, GE Healthcare, Piscataway, N.J.). The column was washed with PBS, and elution was then carried out with 0.1 M Glycine-HCl (pH3.0). The antibody was neutralized with 1M Tris-HCl (pH 8.0), and the buffer was then replaced with PBS by dialysis. The concentration of the antibody was determined by measuring the absorbance at 280 nm (1 mg/ml=1.4 OD). With regard to the yield of the antibody by the culture of 500 mL of each NS0 cell line, 6.1 mg of ChBA-1-3D, 5.0 mg of HuBA-1-3D-1 and 3.8 mg of HuBA-1-3D-2 were each obtained.

The purified antibodies ChBA-1-3D, HuBA-1-3D-1 and HuBA-1-3D-2 were subjected to SDS-PAGE under reduced conditions according to an ordinary method. As a result, an approximately 50-kDa H chain band and an approximately 25-kDa L chain band were confirmed in all of the antibodies (FIG. 17). In addition, all of the antibodies had a purity of 95% or more after purification.

Example 6

Characterization of ChBA-1-3D, HuBA-1-3D-1 and HuBA-1-3D-2

The binding activity of ChBA-1-3D, HuBA-1-3D-1 and HuBA-1-3D-2 to an antigen (human Dlk-1) was analyzed using three different types of formats of ELISA.

As a first format of ELISA, ELISA was carried out to analyze a monovalent antigen-antibody reaction. The antibodies ChBA-1-3D, HuBA-1-3D-1 and HuBA-1-3D-2 antibodies, which had been each diluted with PBS to a concentration of 1 μg/ml, were each added in an amount of 100 μl/well to a 96-well plate, followed by coating at 4° C. overnight. The plate was washed with a washing buffer, and it was then blocked with a blocking buffer. Thereafter, the plate was washed with a washing buffer again. A dilution series was produced by mixing a recombinant protein of the hDlk-1 extracellular region (hDlk-1-His) (Nakamura and Tajima, US2009/0326205 A1) with an ELISA buffer by 2-fold dilution from a concentration of 1 μg/ml, and the thus diluted recombinant protein was then added in an amount of 100

µl/well to the plate, followed by reaction at room temperature for 1 hour. Subsequently, the plate was washed with a washing buffer, and an HRP-conjugated mouse anti-His tag antibody (Hypromatrix, Worcester, Mass.) that had been diluted with an ELISA buffer to a concentration of 1/2,000 was added in an amount of 100 µl/well to the plate, followed by reaction at room temperature for 30 minutes. Thereafter, the resultant was washed with a washing buffer, and 100 µl of an ABTS substrate was then added to each well to perform a color reaction. Then, 100 µl of 2% oxalic acid was added to each well to terminate the reaction. Thereafter, the absorbance at 405 nm was measured. As a result, the binding curves of hDlk-1-His to ChBA-1-3D, HuBA-1-3D-1 and HuBA-1-3D-2 were completely overlapped (FIG. 18). Thus, it was demonstrated that the antigen affinity of HuBA-1-3D-1 and HuBA-1-3D-2 retained the antigen affinity of ChBA-1-3D, and that humanization of BA-1-3D was successful.

As a second format of ELISA, hDlk-1-His, which had been diluted with PBS to a concentration of 0.5 µg/ml, was added in an amount of 100 µl/well to a 96-well plate, followed by coating at 4° C. overnight. The plate was washed with a washing buffer, and it was then blocked with a blocking buffer. Thereafter, the plate was washed with a washing buffer again. ChBA-1-3D, HuBA-1-3D-1 and HuBA-1-3D-2, in each of which a 2-fold dilution series was produced with an ELISA buffer from a concentration of 5 µg/ml, were each added in an amount of 100 µl/well to the plate, followed by reaction at room temperature for 1 hour. Subsequently, the plate was washed with a washing buffer, and an HRP-conjugated goat anti-human kappa chain polyclonal antibody that had been diluted with an ELISA buffer to a concentration of 1/2,000 was added in an amount of 100 µl/well to the plate, followed by reaction at room temperature for 30 minutes. Thereafter, a color reaction was carried out by the same method as described above. As a result, the $EC_{50}$ values of ChBA-1-3D, HuBA-1-3D-1 and HuBA-1-3D-2 were found to be 116 ng/ml, 148 ng/ml and 154 ng/ml, respectively (FIG. 19), and the humanized antibodies HuBA-1-3D-1 and HuBA-1-3D-2 both showed antigen affinity equivalent to that of ChBA-1-3D.

As a third format of ELISA, hDlk-1-His to be coated on a 96-well plate was diluted to a concentration of 1/10, and 0.05 µg/ml hDlk-1-His was then added in an amount of 100 µl/well to the 96-well plate, followed by coating at 4° C. overnight, so as to produce an ELISA plate coated with a low concentration of hDlk-1-His. Other than the aforementioned operations, the binding of ChBA-1-3D, HuBA-1-3D-1 and HuBA-1-3D-2 to hDlk-1-His was measured in the same manner as that in the second format of ELISA. As a result, the binding activities of HuBA-1-3D-1 and HuBA-1-3D-2 were unexpectedly reduced in comparison with ChBA-1-3D (FIG. 20).

As demonstrated in the first format of ELISA, the monovalent binding activities of ChBA-1-3D, HuBA-1-3D-1 and HuBA-1-3D-2 to hDlk-1-His were not substantially different from one another (FIG. 18). In addition, as demonstrated in the second format of ELISA, even in ELISA involving the coating with a high concentration of hDlk-1-His, the binding activities of ChBA-1-3D, HuBA-1-3D-1 and HuBA-1-3D-2 to the hDlk-1-His protein were not substantially different from one another (FIG. 18). Accordingly, it was considered that the results of the third format of ELISA regarding a reduction in the binding activities of HuBA-1-3D-1 and HuBA-1-3D-2 to a low concentration of hDlk-1-His in comparison with ChBA-1-3D (FIG. 20) were obtained from a reduction in avidity (antigen-binding activity) caused by a reduction of flexibility in the movement of the two binding arms of a humanized antibody to an antigen. As in the case of the second format of ELISA, when the density of an antigen is high, all of the ChBA-1-3D, HuBA-1-3D-1 and HuBA-1-3D-2 can divalently bind to an antigen. Accordingly, their binding activities are detected at equivalent levels (FIG. 19). As in the case of the third format ELISA, when the density of an antigen is low, ChBA-1-3D can divalently bind to an antigen. However, HuBA-1-3D-1 and HuBA-1-3D-2 can only monovalently bind to an antigen due to their reduced avidity. Thus, it was considered that HuBA-1-3D-1 and HuBA-1-3D-2 showed lower antigen-binding activities than that of ChBA-1-3D.

Example 7

Generation of Mutants of Humanized BA-1-3D Antibody and Characterization

In order to determine VH or VL, which causes a reduction in the avidity of HuBA-1-3D-1 and HuBA-1-3D-2, the following experiment was carried out. First, a HuBA-1-3D VL gene fragment (FIG. 10) sandwiched between the restriction enzyme sites NheI and EcoRI in a pHuBA-1-3D-2 vector was substituted with the NheI-EcoRI fragment (FIG. 4) of mouse BA-1-3D VL, so as to generate an expression vector (pHuVH2/MuVL) constituted with HuBA-1-3D VH2 and mouse BA-1-3D VL, namely, with humanized VH and mouse VL (HuVH/MuVL). Then, a HuBA-1-3D VH2 gene fragment (FIG. 9) sandwiched between the restriction enzyme sites SpeI and HindIII in a pHuBA-1-3D-2 vector was substituted with the SpeI-HindIII fragment (FIG. 3) of mouse BA-1-3D VH, so as to generate an expression vector (pMuVH/HuVL) constituted with mouse BA-1-3D VH and HuBA-1-3D VL, namely, with mouse VH and humanized VL (MuVH/HuVL).

Subsequently, the expression vectors pChBA-1-3D, pHuBA-1-3D-2, pHuVH2/MuVL and pMuVH/HuVL were each transfected into HEK293 cells using LIPOFECTAMINE 2000 reagent (Invitrogen) according to the method included with the reagent. The resulting cells were then cultured at 37° C. in a 10% fetal bovine serum-containing DME medium in a 7.5% $CO_2$ incubator for several days, and a culture supernatant was then recovered. The concentration of an antibody in the culture supernatant was measured by the above-mentioned sandwich ELISA. The binding activity of each of ChBA-1-3D, HuBA-1-3D-2, HuVH2/MuVL and MuVH/HuVL to hDlk-1 was measured by the above-mentioned third format of ELISA (that is, ELISA in which hDlk-1-His was coated in a concentration of 0.05 µg/ml on the plate). As a result, the binding activities of HuVH2/MuVL and HuBA-1-3D-2 to hDlk-1-His were weak, whereas the binding activity of MuVH/HuVL to hDlk-1-His was equivalent to that of ChBA-1-3D (FIG. 21). Thus, it was demonstrated that HuBA-1-3D VL does not contribute to a reduction in avidity and that HuBA-1-3D VH causes such a reduction in avidity.

In order to recover the reduced avidity, amino acid substitution was performed on HuBA-1-3D VH1. As shown in FIG. 6, a total of 23 amino acids (amino acid numbers 5, 9, 11, 12, 13, 16, 20, 24, 38, 40, 41, 42, 43, 44, 73, 75, 82a, 82b, 83, 85, 87, 89 and 108 (which were assigned in accordance with the definitions of Kabat et al. (1991)) were different between the alignments of the amino acid sequences of HuBA-1-3D VH1 and mouse BA-1-3D VH. Hence, there was generated an expression vector for a mutant (pHuBA1-3D-1 mutant), in which the amino acids with these amino acid numbers in HuBA-1-3D VH1 were substituted with the corresponding amino acids in mouse BA-1-3D VH.

It is to be noted that, with regard to amino acid numbers in the alignments shown in FIG. 6, there are also assigned numbers that are similar to but are distinguished from 52 or 82 (e.g. 52a, 82a, etc.), such as 52 and 52a, 82 and 82a, 82b, and 82c (this also applies to FIG. 22). Accordingly, the amino acid numbers used in FIG. 6 (and FIG. 22) are different from the amino acid numbers in the amino acid sequences (SEQ ID NOS: 15, 35, 40, 67 and 73) of mature peptides of VH in each figure. Since the numbers of the substituted amino acids are indicated based on the descriptions of amino acid numbers in FIG. 6 (and FIG. 22) (e.g. T73K, etc.) in the present specification and drawings, for example, the amino acid at position 73 in FIG. 6 (and FIG. 22) corresponds to the amino acid at position 74 in the amino acid sequences (SEQ ID NOS: 15, 35 and 40) of mature peptides of VH in FIGS. 1, 8 and 9 (the same applies to amino acids with other amino acid numbers or the amino acid numbers of VL).

Herein, each amino acid substitution mutant can be prepared from DNA encoding it based on the common technical knowledge of a person skilled in the art regarding gene recombination technology. In order to prepare each substitution mutant, a mutation can be introduced into DNA by known methods such as a Kunkel method or a Gapped duplex method, using mutation introduction kits that utilize site-directed mutagenesis, such as GENETAILOR™ Site-Directed Mutagenesis System (manufactured by Invitrogen) or TaKaRa Site-Directed Mutagenesis System (PRIME STAR (registered trademark) Mutagenesis Basal kit, MUTAN(registered trademark)-Super Express Km, etc.; manufactured by Takara Bio Inc.). An expression vector for each substitution mutant can be prepared, for example, by introducing a mutation into DNA encoding HuBA-1-3D VH1 in a pHuBA1-3D-1 vector.

FIG. 22 shows the names of the generated 23 types of HuBA-1-3D VH1 mutants (V5Q to T73K/T75S) and the amino acid sequences thereof (wherein only amino acids different from those in the amino acid sequence of HuBA-1-3D VH1 are shown).

Expression vectors for individual pHuBA-1-3D-1 mutants were each transfected into HEK293 cells, and then, using a culture supernatant, the binding activity of each amino acid substitution antibody to hDlk-1 was measured by the third format of ELISA (that is, ELISA in which a low concentration of hDlk-1-His (0.05 g/ml) was coated on the plate). Among the 23 types of HuBA-1-3D VH1 mutants, a T73K mutant (HuBA-1-3D-1-T73K) in which the threonine (T) with amino acid number 73 was substituted with lysine (K) was found to recover its antigen-binding activity, partially but apparently. In addition, an A24G mutant (HuBA-1-3D-1-A24G) in which the alanine (A) with amino acid number 24 was substituted with glycine (G) was also found to recover its antigen-binding activity (FIG. 23). Other 21 types of mutants were not found to recover their antigen-binding activity, in comparison with HuBA-1-3D-1, or the recovered antigen-binding activity was only slightly observed.

Moreover, to recover the reduced avidity of HuBA-1-3D-1, a two-amino acid substitution (A24G/T73K), in which the amino acid substitution A24G was combined with the amino acid substitution T73K, was performed to generate a mutant (FIG. 22). Furthermore, it had previously been reported that the $5^{th}$ amino acid (V) and the $75^{th}$ amino acid (T) are positioned close to the $73^{rd}$ amino acid in the three-dimensional structure of a variable region, and that the $11^{th}$ amino acid (V) is contained in a ball-and-socket joint between the VH and CH of a γ chain (Landolfi et al., J. Immunol. 166: 1748, 2001). Hence, mutants (V5Q/T73K, V11L/T73K and T73K/T75S), in which the $5^{th}$, $11^{th}$ and $75^{th}$ amino acids were substituted with other amino acids, as well as the T73K substitution, were also generated (FIG. 22). These amino acid substitution mutants and the expression vectors therefor were prepared by the same method as that for preparation of the aforementioned 23 types of amino acid substitution mutants.

Expression vectors (pHuBA-1-3D-1-A24G/T73K, pHuBA-1-3D-1-V5Q/T73K, pHuBA-1-3D-1-V11L/T73K and pHuBA-1-3D-1-T73K/T75S) for the aforementioned 4 types of two-amino acid substitution mutants (HuBA-1-3D-1-A24G/T73K, HuBA-1-3D-1-V5Q/T73K, HuBA-1-3D-1-V11L/T73K and HuBA-1-3D-1-T73K/T75S) and the expression vectors pChBA-1-3D and pHuBA-1-3D-1 were each transfected into HEK293 cells, and then, using a culture supernatant, the binding activity of each amino acid substitution antibody to hDlk-1 was measured by the third format of ELISA (that is, ELISA in which a low concentration of hDlk-1-His (0.05 µg/ml) was coated on the plate). As a result, among the aforementioned 4 types of mutants, the A24G/T73K mutant (HuBA-1-3D-1-A24G/T73K) exhibited a strong binding activity to hDlk-1-His, which was equivalent to ChBA-1-3D (FIG. 23), and other 3 types of mutants hardly improved from the T73K mutant (HuBA-1-3D-1-T73K) as a one-amino acid substitution mutant.

Example 8

Expression, Purification and Characterization of HuBA-1-3D-1-T73K and HuBA-1-3D-1-A24G/T73K Expression vectors (pHuBA-1-3D-1-T73K and pHuBA-1-3D-1-A24G/T73K) for HuBA-1-3D-1-T73K and HuBA-1-3D-1-A24G/T73K as mutant antibodies were transfected into NS0 cells by the same method as that described in Example 4, so that a NS0 cell line (NS0-HuBA-1-3D-1-T73K 3E12) stably producing HuBA-1-3D-1-T73K and NS0 cell lines (NS0-HuBA-1-3D-1-A24G/T73K 2G3, NS0-HuBA-1-3D-1-A24G/T73K 5C7 and NS0-HuBA-1-3D-1-A24G/T73K 5F9) stably producing HuBA-1-3D-1-A24G/T73K could be established. The established cell lines were adapted to a serum-free medium (Hybridoma SFM (Invitrogen)).

The sequences of the H chain and L chain of an antibody produced by each of these NS0 cell lines NS0-HuBA-1-3D-1-T73K 3E12, NS0-HuBA-1-3D-1-A24G/T73K 2G3, NS0-HuBA-1-3D-1-A24G/T73K 5C7 and NS0-HuBA-1-3D-1-A24G/T73K 5F9 were confirmed by cDNA sequencing that was the same method as that described in Example 4. The cDNA sequences of the H chain and L chain of HuBA-1-3D-1-T73K and HuBA-1-3D-1-A24G/T73K produced by the aforementioned NS0 cell lines were complexly matched with the corresponding cDNA sequences of the vectors pHuBA-1-3D-1-T73K and pHuBA-1-3D-1-A24G/T73K, respectively (FIGS. 16, 24 and 25).

NS0-HuBA-1-3D-1-T73K 3E12 cells and NS0-HuBA-1-3D-1-A24G/T73K 2G3 cells were cultured in a Hybridoma SFM medium by the same method as that described in Example 5, and thereafter, HuBA-1-3D-1-T73K and HuBA-1-3D-1-A24G/T73K were purified from each culture supernatant using a Protein A column. The purified HuBA-1-3D-1-T73K and HuBA-1-3D-1-A24G/T73K were subjected to SDS-PAGE under reduced conditions. As a result, an approximately 50-kDa H chain and an approximately 25-kDa L chain were confirmed (FIG. 17), and the purity of each antibody was 95% or more.

Subsequently, the avidity (antigen-binding activity) of the purified ChBA-1-3D, HuBA-1-3D-1, HuBA-1-3D-1-T73K and HuBA-1-3D-1-A24G/T73K to an antigen was analyzed by the aforementioned third format of ELISA, in which hDlk-1-His was coated in a low concentration (0.05 µg/ml) on a 96-well plate. As a result, the antigen-binding activity of HuBA-1-3D-1-T73K was stronger than that of HuBA-1-3D-1, but was weaker than that of the antibody ChBA-1-3D. On the other hand, the $EC_{50}$ value of HuBA-1-3D-A24G/T73K was 35.5 ng/ml, which was close to the $EC_{50}$ value of ChBA-1-3D (25.4 ng/ml). Thus, it was demonstrated that HuBA-1-3D-1-A24G/T73K had an improved avidity, which was reduced in HuBA-1-3D-1, and thus that HuBA-1-3D-1-A24G/T73K acquired an antigen-binding activity equivalent to that of ChBA-1-3D (FIG. 26).

Example 9

Generation of NS0 Cell Line Highly Producing HuBA-1-3D-1-A24G/T73K

Transfection of the vector pHuBA-1-3D-1-A24G/T73K into NS0 cells, construction of a stable cell line, and adaptation of the cell line to a serum-free medium (Hybridoma SFM) were carried out in the same manners as those described in Example 4 and Example 8. NS0-HuBA-1-3D-1-A24G/T73K 8A3, one of the established NS0 cell lines highly producing the antibody HuBA-1-3D-1-A24G/T73K, was cultured at 37° C. in 40 ml of a Hybridoma SFM medium containing 2 mM L-glutamine and 0.1% PLURONIC F-68 solution (Sigma) in a 250-ml plastic Erlenmeyer flask in a 5% $CO_2$ incubator, using a rotary shaker at a rotation number of 100 rpm.

At the time at which the cell density reached approximately $2\times10^6$ cells/ml, 35 mg/ml CELL BOOST 4 (HyClone) in an amount of 1/10 and a 0.1% PLURONIC F-68 solution were added to the medium. Two days later, 60 mg/ml Ultrafiltered Soy Hydrolysate (Irvine Scientific) diluted with a SFM4MAb medium (HyClone) in an amount of 1/10 and a 0.1% PLURONIC F-68 solution were further added to the medium, and the culture was continued until the percentage of living cells became 50% or less. The concentration of HuBA-1-3D-1-A24G/T73K in the culture supernatant was 73 g/ml.

The sequences of the H chain and L chain of an antibody produced by NS0-HuBA-1-3D-1-A24G/T73K 8A3 cells were confirmed by cDNA sequencing that was the same method as that described in Example 4. The thus confirmed sequences were completely matched with the corresponding cDNA sequences of the vector pHuBA-1-3D-1-A24G/T73K (FIGS. 16 and 25).

Example 10

Examination of Antigen-Binding Stability of HuBA-1-3-D-1-A24G/T73K

The antigen-binding stability of HuBA-1-3D-1-A24G/T73K as a mutant antibody was examined by an accelerated test in a liquid formulation and a preservation test in cynomolgus monkey plasma.

First, an accelerated test in a liquid formlation was carried out as follows. HuBA-1-3D-1-A24G/T73K was preserved in 3 types of buffers having different pH values at 40° C. for 1 month. The used buffer was a solution containing 10 mM sodium glutamate (Wako), 262 mM D-sorbitol (Wako) and 0.05 mg/ml polysolvate 80 (Wako), and this solution was adjusted to have 3 types of pH values, namely, pH 4.0, 5.5 and 7.0. The concentrations of the antibody in the buffers having different pH values were 0.977 mg/ml (pH 4.0), 0.996 mg/ml (pH 5.5) and 0.959 mg/ml (pH 7.0), and preservation was initiated at 40° C. After completion of the preservation, each sample was preserved at –80° C. until the measurement of antigen-binding activity. In addition, as an activity standard product, a sample prepared by preserving at –80° C. an antibody solution before preservation at 40° C. for 1 month was used. For the measurement of antigen-binding activity, FACS analysis and antigen-immobilized ELISA were carried out. The FACS analysis was carried out using HEK293-hDlk-1 cells prepared by allowing a full-length human Dlk-1 gene to stably express in HEK293 cells (Nakamura and Tajima, US2009/0326205 A1). The cells were removed from the culture dish by a treatment with trypsin. To a cell suspension of the $5\times10^5$ cells, 100 µl of an antibody solution prepared by diluting the accelerated test sample or the activity standard product to a concentration of 10, 3, 1, 0.3 or 0.1 µg/ml with a 10% FCS-containing medium was added as a primary antibody. The obtained mixture was incubated at 4° C. for 20 minutes. Thereafter, the reaction product was washed with 1 ml of a 10% FCS-containing medium, and 100 µl of a secondary antibody solution that contained a 2000-fold diluted biotin-labeled anti-human IgG Fc antibody (Rockland) and 500-fold diluted streptavidin-labeled PE (BD Pharmingen) was then added to the resultant. The obtained mixture was incubated at 4° C. for 20 minutes, and the reaction product was then washed with 1 ml of a 10% FCS-containing medium again. Thereafter, the sample that contained the labeled cells was suspended in 1 ml of PBS containing 1% FCS and 2 mM EDTA, and the obtained suspension was then analyzed using FACSCalibur (Becton Dickinson). As a result of the accelerated test at 40° C. for 1 month, the samples exhibited an antigen-binding activity equivalent to that of the activity standard product preserved at –80° C. in all of the examined buffers with 3 types of pH values (FIG. 27A).

Moreover, the measurement of antigen-binding activity was carried out by antigen-immobilized ELISA. The antigen-immobilized ELISA was carried out as follows. A 96-well plate (BD FALCON) was coated with a recombinant protein of the hDlk-1 extracellular region (hDlk-1 His) that had been diluted with PBS to a concentration of 3 µg/ml in an amount of 50 µl/well (4° C., overnight). Thereafter, the plate was washed with a washing buffer (PBS containing 0.01% TWEEN 20), and a blocking buffer (PBS containing 2% skim milk and 0.05% TWEEN 20) was added in an amount of 200 µl/well to the plate, so as to block it (room temperature, 1 hour). After the plate had been washed with a washing buffer, a test antibody was diluted with an ELISA buffer (PBS containing 1% skim milk and 0.025% TWEEN 20) to concentrations of 1, 0.1, 0.03, 0.01 and 0.001 µg/ml, and each antibody solution was then added in an amount of 50 µl/well to the plate (room temperature, 2 hours). Thereafter, the plate was washed with a washing buffer, and as a detection antibody, a HRP-labeled goat anti-human κ chain antibody (Southern Biotech) that had been 2,000-fold diluted with an ELISA buffer was then added in an amount of 50 µl/well to the plate (room temperature, 1 hour). The plate was washed with a washing buffer, and TMB (3,3',5,5'-tetramethylbenzidine; SIGMA) was then added as a substrate solution in an amount of 50 µl/well to the plate to perform a color reaction. 1 M sulfuric acid was added in an amount of 25 µl/well to the plate to terminate the reaction. Thereafter, employing iMark Microplate reader (Bio Rad), the absorbance at 450 nm was measured using the absorbance at 655 nm as a reference. As a result, as with the results of the FACS analysis, a decrease in the activity due to preservation at 40° C. for 1 month in the buffers with the 3 different types of pH values was not observed (FIG. 27B).

From these results, it became clear that HuBA-1-3D-1-A24G/T73K retains a stable antigen-binding activity in a liquid formulation.

Next, the antigen-binding activity of HuBA-1-3D-1-A24G/T73K in cynomolgus monkey plasma was examined by antigen-immobilized ELISA. The used cynomolgus monkey plasma was heparin-treated, pooled plasma, which was purchased from Japan SLC, Inc. Then, the cynomolgus monkey plasma was preserved at −80° C. before use. When used, the thawed cynomolgus monkey plasma was centrifuged with a small centrifuge (Beckman) at 12,000 rpm for 5 minutes, and the obtained supernatant was then used. A sample to be used in antigen-immobilized ELISA was prepared as follows. HuBA-1-3D-1-A24G/T73K was mixed with cynomolgus monkey plasma to prepare a solution of 10 µg/ml HuBA-1-3D-1-A24G/T73K, and the solution was then incubated at 37° C. for 1, 6, 24, 48 hours and 7 days. The samples that had been incubated for different time periods were preserved at −80° C. before measurement. As an activity standard product, a sample immediately after being prepared as a 10 µg/ml HuBA-1-3D-1-A24G/T73K solution was used. Upon the measurement of antigen-binding activity, the thawed measurement samples were each centrifuged with a small centrifuge (Beckman) at 12,000 rpm for 5 minutes, and the obtained supernatants were then used. Antigen-immobilized ELISA was carried out as follows. A 96-well plate (BD FALCON) was coated with a recombinant protein (hDlk-1 His) of the hDlk-1 extracellular region that had been diluted with PBS to a concentration of 3 µg/ml in an amount of 50 µl/well (4° C., overnight). Thereafter, the plate was washed with a washing buffer (PBS containing 0.05% TWEEN 20), and a blocking buffer (PBS containing 1% casein) was added in an amount of 200 µl/well to the plate, so as to block it (room temperature, 1 hour). After the plate had been washed with a washing buffer, the measurement sample was diluted with a blocking buffer to a concentration of 0.1 µg/ml, and the diluted solution was then added in an amount of 50 µl/well to the plate (room temperature, 1 hour). Thereafter, the plate was washed with a washing buffer, and for detection of HuBA-1-3D-1-A24G/T73K, a HRP-labeled goat anti-human κ chain antibody (Southern Biotech) that had been 2,000-fold diluted with a blocking buffer was added in an amount of 50 µl/well to the plate (room temperature, 1 hour). The plate was washed with a washing buffer, and TMB (3,3',5,5'-tetramethylbenzidine; SIGMA) was then added as a substrate solution in an amount of 50 µl/well to the plate to perform a color reaction. 1 M sulfuric acid was added in an amount of 25 µl/well to the plate to terminate the reaction. Thereafter, employing iMark Microplate reader or Microplate reader Model 550 (Bio Rad), the absorbance at 450 nm was measured using the absorbance at 655 nm as a reference. As a result, a significant decrease in the antigen-binding activity was not observed in HuBA-1-3D-1-A24G/T73K even after incubation for 7 days (FIG. 28). Accordingly, it was demonstrated that HuBA-1-3D-1-A24G/T73K can retain a stable antigen-binding activity in cynomolgus monkey plasma. These results suggested that HuBA-1-3D-1-A24G/T73K could retain a stable antigen-binding activity also in human plasma (in human blood).

Example 11

Anti-Tumor Activity of Humanized Anti-Human Dlk-1 Antibody (HuBA-1-3D-1-A24G/T73K) In Vivo (this Title is Also Applied to Examples 11 to 16)

<Anti-Tumor Activity of HuBA-1-3D-1-A24G/T73K on Xenograft Treatment Models of Human Hepatocellular Carcinoma HepG2 Cells>

The anti-tumor activity of HuBA-1-3D-1-A24G/T73K in vivo was examined with xenograft treatment models using human hepatocellular carcinoma HepG2 cells, in which hDlk-1 was endogenously expressed on the cell surface thereof.

HepG2 cells ($5\times10^6$ cells) were transplanted into the subcutis of the right flank of each of 7-week-old female NOD-scid mice (Day 0). Nine days after the transplantation (Day 9), when the mean tumor volume reached about 100 mm$^3$, the mice were divided into a control group (PBS administration group, N=8, 96.6±11.0 mm$^3$), a HuBA-1-3D-1-A24G/T73K (1 mg/kg body weight) administration group (N=8, 96.2±8.5 mm$^3$), a HuBA-1-3D-1-A24G/T73K (5 mg/kg body weight) administration group (N=8, 96.3±8.6 mm$^3$), and a HuBA-1-3D-1-A24G/T73K (10 mg/kg body weight) administration group (N=8, 96.2±8.5 mm$^3$). From the same day, the antibody was intraperitoneally administered to the mice at intervals of once every 3 days.

As a result, on the 23$^{rd}$ day after transplantation of cancer cells (Day 23), the tumor volume was 900.1±248.6 mm$^3$ in the control group, whereas an extremely high anti-tumor activity (tumor formation-inhibiting activity) was observed in all of the HuBA-1-3D-1-A24G/T73K administration groups with different doses. That is, the tumor volume was 93.4±47.3 mm$^3$ in the 1 mg/kg body weight administration group (inhibitory rate: 89.6%, P<0.01 by Student's t-test), it was 102.6±39.7 mm$^3$ in the 5 mg/kg body weight administration group (inhibitory rate: 88.6%, P<0.01 by Student's t-test), and it was 140.6±55.0 mm$^3$ in the 10 mg/kg body weight administration group (inhibitory rate: 84.4%, P<0.01 by Student's t-test) (FIG. 29A).

Likewise, with regard to the tumor weight on the 23$^{rd}$ day (Day 23) after transplantation of cancer cells as well, the tumor weight was 0.440±0.105 g in the control group, whereas an extremely high anti-tumor activity (tumor formation-inhibiting activity) was observed in all of the HuBA-1-3D-1-A24G/T73K administration groups with different doses. That is, the tumor weight was 0.030±0.026 g in the HuBA-1-3D-1-A24G/T73K (1 mg/kg body weight) administration group (inhibitory rate: 93.2%, P<0.01 by Student's t-test), it was 0.042±0.026 g in the 5 mg/kg body weight administration group (inhibitory rate: 90.5%, P<0.01 by Student's t-test), and it was 0.065±0.039 g in the 10 mg/kg body weight administration group (inhibitory rate: 85.1%, P<0.01 by Student's t-test) (FIG. 29B).

Example 12

Anti-Tumor Activity of HuBA-1-3D-1-A24G/T73K on Xenograft Treatment Models of Human Neuroblastoma SK-N-F1 Cells The anti-tumor activity of HuBA-1-3D-1-A24G/T73K in vivo was examined with Xenograft treatment models using human neuroblastoma SK-N-F1 cells, in which hDlk-1 was endogenously expressed on the cell surface thereof.

SK-N-F1 cells (approximately $5\times10^6$ cells) were transplanted into the subcutis of the right flank of each of 7-week-old female NOD-scid mice (Day 0). Thirteen days after the transplantation (Day 13), when the mean tumor volume reached about 100 mm$^3$, the mice were divided into a control group (PBS administration group, N=8, 91.7±18.3 mm$^3$), a HuBA-1-3D-1-A24G/T73K (1 mg/kg body weight) administration group (N=8, 91.9±16.9 mm$^3$), a HuBA-1-3D-1-A24G/T73K (5 mg/kg body weight) administration group (N=8, 91.5±16.5 mm$^3$), and a HuBA-1-3D-1-A24G/T73K (10 mg/kg body weight) administration group (N=8, 90.2±11.7 mm$^3$). From the same day, the antibody was intraperitoneally administered to the mice at intervals of once every 3 days.

As a result, on the 34$^{th}$ day after transplantation of cancer cells (Day 34), the tumor volume was 1231.6±411.1 mm$^3$ in the control group, whereas a dose-dependent anti-tumor activity (tumor formation-inhibiting activity) was observed in the HuBA-1-3D-1-A24G/T73K administration groups. That is, the tumor volume was 713.6±343.8 mm$^3$ in the 1 mg/kg body weight administration group (inhibitory rate: 42.1%, P<0.05 by Student's t-test), it was 317.0±160.6 mm$^3$ in the 5 mg/kg body weight administration group (inhibitory rate: 74.3%, P<0.01 by Student's t-test), and it was 189.0±104.0 mm$^3$ in the 10 mg/kg body weight administration group (inhibitory rate: 84.7%, P<0.01 by Student's t-test) (FIG. 30A).

Likewise, with regard to the tumor weight on the 34$^{th}$ day (Day 34) after transplantation of cancer cells as well, the tumor weight was 0.584±0.213 g in the control group, whereas a dose-dependent anti-tumor activity (tumor formation-inhibiting activity) was observed in the HuBA-1-3D-1-A24G/T73K administration groups. That is, the tumor weight was 0.379±0.183 g in the HuBA-1-3D-1-A24G/T73K (1 mg/kg body weight) administration group (inhibitory rate: 64.8%), it was 0.165±0.115 g in the 5 mg/kg body weight administration group (inhibitory rate: 71.8%, P<0.01 by Student's t-test), and it was 0.093±0.059 g in the 10 mg/kg body weight administration group (inhibitory rate: 84.1%, P<0.01 by Student's t-test) (FIG. 30B).

Example 13

Evaluation of Drug Efficacys of Low-Dose HuBA-1-3D-1-A24G/T73K on Xenograft Treatment Models of Human Hepatocellular Carcinoma HepG2 Cells, and Comparison with Drug Efficacys of Existing Anticancer Agent The anti-tumor activity of HuBA-1-3D-1-A24G/T73K in vivo was examined with xenograft treatment models using human hepatocellular carcinoma HepG2 cells, in which hDlk-1 was endogenously expressed on the cell surface thereof. At the same time, HuBA-1-3D-1-A24G/T73K was compared with the existing "NEXAVAR" (sorafenib tosylate tablets, Bayer) approved as a therapeutic agent for liver cancer, in terms of anti-tumor activity.

HepG2 cells (5×10$^6$ cells) were transplanted into the subcutis of the right flank of each of 7-week-old female NOD-scid mice (Day 0). Ten days after the transplantation (Day 10), when the mean tumor volume reached about 100 mm$^3$, the mice were divided into a control group (PBS administration group, N=8, 107.0±16.8 mm$^3$), a HuBA-1-3D-1-A24G/T73K (0.1 mg/kg body weight) administration group (N=8, 108.0±13.9 mm$^3$), a HuBA-1-3D-1-A24G/T73K (0.5 mg/kg body weight) administration group (N=8, 107.9±10.5 mm$^3$), and a HuBA-1-3D-1-A24G/T73K (1 mg/kg body weight) administration group (N=8, 107.9±10.0 mm$^3$). From the same day, the antibody was intraperitoneally administered to the mice at intervals of once every 3 days. In addition, with regard to a NEXAVAR (40 mg/kg body weight) administration group (N=8, 107.7±9.7 mm$^3$) and a NEXAVAR (80 mg/kg body weight) administration group (N=8, 107.9±9.6 mm$^3$) as well, from the same day, the agent was orally administered to the mice at a cycle consisting of 5 days a week of administration and 2 days a week of drug withdrawal.

As a result, on the 28$^{th}$ day after transplantation of cancer cells (Day 28), the tumor volume was 945.2±562.1 mm$^3$ in the control group, whereas it was 219.4±182.8 mm$^3$ in the 0.5 mg/kg HuBA-1-3D-1-A24G/T73K administration group (inhibitory rate: 76.8%, P<0.01 by Student's t-test) and it was 116.5±69.2 mm$^3$ in the 1 mg/kg HuBA-1-3D-1-A24G/T73K administration group (inhibitory rate: 87.7%, P<0.01 by Student's t-test) (FIG. 31A). Thus, an extremely high anti-tumor activity was observed even at a low dose (0.5 mg/kg) in the cases of the HuBA-1-3D-1-A24G/T73K administration groups. The anti-tumor activity in the NEXAVAR administration groups was weaker than that in the HuBA-1-3D-1-A24G/T73K administration groups. A significant anti-tumor activity was not observed in the 40 mg/kg NEXAVAR administration group (588.0±314.0 mm$^3$) in comparison with the control group, and it was 384.1±190.4 mm$^3$ even in the 80 mg/kg NEXAVAR administration group (inhibitory rate: 59.4%, P<0.05 by Student's t-test) (FIG. 31B).

As an indicator of side effects, with regard to a change in the body weights of the mice after transplantation of cancer cells, the mean value of the body weights of the mice in each group at the time of the grouping (Day 10) was set at 100%, and an increase rate in the body weights of the mice in each group was examined over time until the 28$^{th}$ day (Day 28). In the control group, a decrease in the body weight of the mice was observed with the growth of tumor (93.0±8.5%, N=8, Day 28). In the HuBA-1-3D-1-A24G/T73K administration groups, which exhibited anti-tumor effects, such a decrease in the body weights of the mice was not observed (0.5 mg/kg administration group: 99.0±10.0%, 1 mg/kg administration group: 100.0±4.2%). In the NEXAVAR administration groups, a decrease in the body weights was observed over time, and the body weight-decreasing rate on Day 28 was 83.0±5.2% in the 40 mg/kg NEXAVAR administration group (N=8, P<0.01 by Student's t-test), and it was 80.0±7.7% in the 80 mg/kg NEXAVAR administration group (N=7, P<0.05 by Student's t-test) (FIG. 31C). From the above results, it became clear that the antibody HuBA-1-3D-1-A24G/T73K has an activity of almost completely inhibiting the growth of tumor even it is administered at a low dose such as 0.5 mg/kg body weight. Moreover, it also became clear that the antibody HuBA-1-3D-1-A24G/T73K exhibits a strong anti-tumor activity when compared with NEXAVAR, an existing therapeutic agent for liver cancer, and does not cause side effects.

Example 14

Evaluation of Drug Efficacys of HuBA-1-3D-1-A24G/T73K on Xenograft Treatment Models of Human Hepatocellular Carcinoma HepG2/C3A Cells The anti-tumor activity of HuBA-1-3D-1-A24G/T73K on liver cancer was examined with xenograft treatment models using human hepatocellular carcinoma HepG2/C3A cells (ATCC, Cat#CRL-10741).

HepG2/C3A cells (5×10$^6$ cells) were transplanted into the subcutis of the right flank of each of 7-week-old female NOD-scid mice (Day 0). Ten days after the transplantation (Day 10), when the mean tumor volume reached 100 mm$^3$, the mice were divided into a control group (PBS administration group, N=8, 120.8±22.6 mm$^3$), a HuBA-1-3D-1-A24G/T73K (0.1 mg/kg body weight) administration group (N=8, 120.4±18.4 mm$^3$), a HuBA-1-3D-1-A24G/T73K (0.5 mg/kg body weight) administration group (N=8, 120.1±18.8 mm$^3$), a HuBA-1-3D-1-A24G/T73K (1 mg/kg body weight) administration group (N=8, 120.3±18.8 mm$^3$), and a HuBA-1-3D-1-A24G/T73K (5 mg/kg body weight) administration group (N=8, 120.6±21.0 mm³). From the same day, the antibody was intraperitoneally administered to the mice at intervals of once every 3 days.

As a result, on the 26$^{th}$ day after transplantation of cancer cells (Day 26), the tumor volume was 637.6±353.9 mm³ in the control group (N=8), whereas a statistically significant anti-tumor activity was observed in the 1 mg/kg body weight HuBA-1-3D-1-A24G/T73K administration group and the 5 mg/kg body weight HuBA-1-3D-1-A24G/T73K administration group. The tumor volume was 132.9±266.1 mm³ in the 1 mg/kg body weight administration group (inhibitory rate: 79.2%, N=8, P<0.01 by Student's t-test), and it was 128.0±75.6 mm³ in the 5 mg/kg body weight administration group (inhibitory rate: 79.9%, N=8, P<0.01 by Student's t-test) (FIG. 32A).

Likewise, with regard to the tumor weight on the 26$^h$ day (Day 26) after transplantation of cancer cells as well, the tumor weight was 0.624±0.381 g in the control group, whereas it was 0.107±0.117 g in the 1 mg/kg body weight HuBA-1-3D-1-A24G/T73K administration group (inhibitory rate: 82.9%, P<0.01 by Student's t-test), and it was 0.079±0.056 g in the 5 mg/kg body weight HuBA-1-3D-1-A24G/T73K administration group (inhibitory rate: 87.3%, P<0.01 by Student's t-test), and thus, an extremely strong anti-tumor activity was confirmed (FIG. 32B).

Example 15

Evaluation of Drug Efficacys of HuBA-1-3D-1-A24G/T73K on Xenograft Treatment Models of Human Small Cell Lung Cancer Lu-135 Cells The anti-tumor activity of HuBA-1-3D-1-A24G/T73K on small cell lung cancer was examined with xenograft treatment models using human small cell lung cancer Lu-135 cells (purchased from the Health Science Research Resources Bank, the Japan Health Sciences Foundation, Cat#JCRB0170), in which hDlk-1 was endogenously expressed on the cell surface thereof.

Lu-135 cells (5×10⁶ cells) were transplanted into the subcutis of the right flank of each of 7-week-old female NOD-scid mice (Day 0). Ten days after the transplantation (Day 10), when the mean tumor volume reached about 100 mm³, the mice were divided into a control group (PBS administration group, N=8, 100.9±12.7 mm³), a HuBA-1-3D-1-A24G/T73K (1 mg/kg body weight) administration group (N=8, 100.6±8.1 mm³), and a HuBA-1-3D-1-A24G/T73K (10 mg/kg body weight) administration group (N=8, 102.9±12.0 mm³). From the same day, the antibody was intraperitoneally administered to the mice at intervals of once every 3 days. As a result, on the 34$^{th}$ day after transplantation of cancer cells (Day 34), the tumor volume was 972.7±266.8 mm³ in the control group, whereas it was 631.9±218.9 mm³ in the 1 mg/kg body weight HuBA-1-3D-1-A24G/T73K administration group (inhibitory rate: 35.0%, P<0.05 by Student's t-test), and it was 582.3±220.4 mm³ in the 10 mg/kg body weight HuBA-1-3D-1-A24G/T73K administration group (inhibitory rate: 40.1%, P<0.05 by Student's t-test). Thus, a statistically significant anti-tumor activity was confirmed in the HuBA-1-3D-1-A24G/T73K administration groups (FIG. 33A).

Likewise, with regard to the tumor weight on the 34$^{th}$ day (Day 34) after transplantation of cancer cells as well, the tumor weight was 0.632±0.177 g in the control group, whereas it was 0.429±0.161 g in the 1 mg/kg body weight HuBA-1-3D-1-A24G/T73K administration group (inhibitory rate: 32.1%, P<0.05 by Student's t-test), and it was 0.420±0.178 g in the 10 mg/kg body weight HuBA-1-3D-1-A24G/T73K administration group (inhibitory rate: 33.5%, P<0.05 by Student's t-test). Thus, a statistically significant anti-tumor activity was confirmed in the HuBA-1-3D-1-A24G/T73K administration groups (FIG. 33B).

Example 16

Induction of Apoptosis in Cancer Cells by Administration of HuBA-1-3D-1-A24G/T73K in Xenograft Treatment Models of Human Hepatocellular Carcinoma HepG2 Cells Next, with regard to the action mechanism of anti-tumor activity exhibited by HuBA-1-3D-1-A24G/T73K, the apoptosis of cancer cells in xenograft tumors after administration of the antibody was examined by a TUNEL method and an immunohistostaining method using an anti-Cleaved Caspase-3 antibody.

HepG2 cells (5×10⁶ cells) were transplanted into the subcutis of the right flank of each of 7-week-old female NOD-scid mice. When the mean tumor volume reached 200 mm³, the mice were divided into a control group (PBS administration group) and a HuBA-1-3D-1-A24G/T73K administration group (5 mg/kg body weight). Forty-eight hours after administration of PBS, xenograft tumors were recovered from the control group (N=3). Twenty-four and forty-eight hours after administration of the antibody, xenograft tumors were recovered from the HuBA-1-3D-1-A24G/T73K administration group (N=3 in each time). The thus recovered xenograft tumors were embedded in O.C.T Compound (TISSUE-TEK® O.C.T. Compound, Funakoshi), and frozen blocks were then prepared under liquid nitrogen. Frozen sections of the xenograft tumors were produced in a cryostat, and the apoptosis of the cancer cells were detected by the TUNEL method in accordance with a method described in TUMOR-TACS™ In Situ Apoptosis Detection Kit (Trevigen, 4815-30-K).

The prepared frozen sections were fully air-dried at room temperature, and were then rehydrated with an ethanol series, followed by immobilization with PBS containing 3.7% formaldehyde (Wako, 064-00406). The resultant was washed with PBS at room temperature for 5 minutes twice, and was then permeabilized with Cytonin (Trevigen, 4876-05-01). Thereafter, the resultant was washed with distilled water at room temperature for 2 minutes twice, and was then treated with a solution prepared by adding a hydrogen peroxide solution (Wako, 081-04215) to methanol to a final concentration of 3% at room temperature for 5 minutes, so as to remove endogenous peroxidase. Thereafter, the residue was washed with PBS at room temperature for 1 minute, and was then pretreated with a solution prepared by 10-fold diluting 10× TdT Labeling Buffer (Trevigen, 4810-30-02) with distilled water (hereinafter referred to as a "1× TdT Labeling Buffer"). The resultant was allowed to react with Labeling Reaction Mix produced by mixing TdT dNTP Mix (Trevigen, 4810-30-04), 50× Mn²⁺ (Trevigen, 4810-30-14), TdT Enzyme (Trevigen, 4810-30-05) and 1× TdT Labeling Buffer, in accordance with an instruction manual included with TUMORTACS™ In Situ Apoptosis Detection Kit at 37° C. for 1 hour, and biotin-labeled dNTP was added to fragmented DNA. Subsequently, the reaction mixture was allowed to react with a solution prepared by 10-fold diluting 10× Stop Buffer (Trevigen, 4810-30-03) with distilled water at room temperature for 5 minutes, so as to terminate the labeling reaction. Thereafter, the reaction mixture was washed with PBS at room temperature for 2 minutes twice, and was then allowed to react with a solution prepared by 50-fold diluting Strep-HRP (Trevigen, 4800-30-06) with PBS at room temperature for 10 minutes, thereby forming an ABC complex. The thus obtained ABC complex was washed with PBS at room temperature for 2 minutes twice, and color development was then carried out using a DAB solution prepared by mixing PBS, DAB (Trevigen, 4800-30-09) and a 30% hydrogen peroxide solution in accordance with an instruction manual included with TUMORTACS™ In Situ Apoptosis Detection Kit. After confirmation of the color development, the reaction mixture was washed with deionized water for 2 minutes 4 times, and the nucleus was then stained with 1% Methyl Green (Trevigen, 4800-30-18). Thereafter, the resultant was dehydrated with ethanol, was then penetrated with xylene, and was then mounted in ENTELLAN® NEW (MERCK, 1079610100), followed by observation under a microscope. A tissue section, in which 10% or more of all cancer cells were stained in the tissue section, was defined as a positive section.

As a result, in xenograft tumors in the control group (PBS administration group, N=3), cancer cells, in which TUNEL-positive apoptosis was induced, were not observed. In contrast, in the 5 mg/kg body weight HuBA-1-3D-1-A24G/T73K administration group, 24 hours after administration of the antibody, cancer cells in which TUNEL-positive apoptosis was induced were observed. Forty-eight hours after administration of the antibody, such apoptosis was observed in 30% or more of all cancer cells in all of the three cases (FIG. 34A).

Likewise, the apoptosis of cancer cells in xenograft tumors was examined by immunostaining with activated caspase-3. Frozen sections were fixed by treatment with PBS containing 4% Paraformaldehyde (Wako, 160-16061) at 4° C. for 15 minutes. The resultant was washed with PBS at room temperature for 5 minutes twice, and was then treated at room temperature for 10 minutes with a solution prepared by adding a hydrogen peroxide solution (Wako, 081-04215) to methanol to a final concentration of 3%, so as to remove endogenous peroxidase. Thereafter, the resultant was washed with PBS at room temperature for 5 minutes twice, and was then blocked with PBS containing 1.5% normal goat serum (Vector, S-1000) (for 1 hour at room temperature).

Subsequently, the resultant was allowed to react with an anti-Cleaved Caspase-3 antibody (Cell Signaling Technology, cat#9661) that had been 600-fold diluted with a blocking buffer at 4° C. overnight, and was then allowed to react with ChemMate ENVISION polymer reagent (DAKO, K5027) at room temperature for 30 minutes. Thereafter, the resultant was washed with PBS at room temperature for 5 minutes three times, and color development was then carried out using HISTOFINE® Peroxidase Substrate Simple Stain DAB solution (Nichirei Bioscience, 415171). The resultant was washed with deionized water for 5 minutes, and the nucleus was then stained with Mayer's Hematoxylin Solution (Wako, 131-09665). Thereafter, the resultant was dehydrated with ethanol, was then penetrated with xylene, and was then mounted in ENTELLAN® NEW (MERCK, 1079610100), followed by observation under a microscope. A tissue section, in which 10% or more of all cancer cells were stained in the tissue section, was defined as a positive section.

As a result, in xenograft tumors in the control group (PBS administration group, N=3), activated caspase-3 was not detected. In contrast, in the HuBA-1-3D-1-A24G/T73K (5 mg/kg body weight) administration group, 24 hours after administration of the antibody, activated caspase-3-positive apoptosis was induced in cancer cells in 2 out of 3 cases, and 48 hours after administration of the antibody, such induction of activated caspase-3-positive apoptosis in cancer cells was observed in all of the 3 cases. In particular, in the xenograft tumors 48 hours after administration of the antibody, cell death caused by activated caspase-3-positive apoptosis was observed in 80% or more of all cancer cells (FIG. 34B).

From the above results, it became clear that HuBA-1-3D-1-A24G/T73K induces cell death caused by apoptosis in hepatocellular carcinoma HepG2 cells, and it was demonstrated that this is at least one of the action mechanisms of the anti-tumor activity of HuBA-1-3D-1-A24G/T73K.

INDUSTRIAL APPLICABILITY

According to the present invention, there can be provided anti-hDlk-1 antibodies having an anti-tumor activity, specifically, anti-hDlk-1 monoclonal antibodies having a significant anti-tumor activity in vivo even by administration of antibodies alone, and particularly, the aforementioned antibodies, which are humanized antibodies. In addition, among the humanized antibodies, the present invention can provide amino acid substitution type humanized anti-hDlk-1 monoclonal antibodies, which have been modified to have a higher avidity (antigen-binding activity).

Moreover, the present invention can provide hybridomas that produce the aforementioned antibodies, and a complex of the aforementioned antibodies and various types of agents.

Furthermore, the present invention can also provide a pharmaceutical composition for diagnosing or treating a tumor, a pharmaceutical composition for inducing apoptosis in tumor cells, a tumor therapeutic agent, a tumor diagnostic agent, an agent for inducing apoptosis in tumor cells, a method for treating a tumor, a method for detecting a tumor, a kit for detecting or diagnosing a tumor and a kit for inducing apoptosis in tumor cells, each of which comprises the aforementioned antibody, the aforementioned complex or the like.

SEQUENCE LISTING FREE TEXT

| | |
|---|---|
| SEQ ID NOS: 3 to 11 | Synthetic DNAs |
| SEQ ID NO: 26 | Recombinant DNA |
| SEQ ID NO: 27 | Recombinant DNA |
| SEQ ID NO: 32 | Recombinant DNA |
| SEQ ID NO: 33 | Recombinant protein |
| SEQ ID NO: 34 | Recombinant DNA |
| SEQ ID NO: 35 | Recombinant protein |
| SEQ ID NO: 36 | Recombinant DNA |
| SEQ ID NO: 37 | Recombinant DNA |
| SEQ ID NO: 38 | Recombinant protein |
| SEQ ID NO: 39 | Recombinant DNA |
| SEQ ID NO: 40 | Recombinant protein |
| SEQ ID NO: 41 | Recombinant DNA |
| SEQ ID NO: 42 | Recombinant DNA |
| SEQ ID NO: 43 | Recombinant protein |
| SEQ ID NO: 44 | Recombinant DNA |
| SEQ ID NO: 45 | Recombinant protein |
| SEQ ID NO: 46 | Recombinant DNA |
| SEQ ID NOS: 47 to 51 | Synthetic DNAs |
| SEQ ID NO: 52 | Recombinant DNA |
| SEQ ID NO: 53 | Recombinant protein |
| SEQ ID NO: 54 | Recombinant DNA |
| SEQ ID NO: 55 | Recombinant protein |
| SEQ ID NO: 56 | Recombinant DNA |
| SEQ ID NO: 57 | Recombinant protein |
| SEQ ID NO: 58 | Recombinant DNA |
| SEQ ID NO: 59 | Recombinant protein |
| SEQ ID NO: 60 | Recombinant DNA |
| SEQ ID NO: 61 | Recombinant protein |
| SEQ ID NO: 62 | Recombinant DNA |
| SEQ ID NO: 63 | Recombinant protein |
| SEQ ID NO: 64 | Recombinant DNA |
| SEQ ID NO: 65 | Recombinant protein |
| SEQ ID NO: 66 | Recombinant DNA |

| | |
|---|---|
| SEQ ID NO: 67 | Recombinant protein |
| SEQ ID NO: 68 | Recombinant DNA |
| SEQ ID NO: 69 | Recombinant protein |
| SEQ ID NO: 70 | Recombinant DNA |
| SEQ ID NO: 71 | Recombinant protein |
| SEQ ID NO: 72 | Recombinant DNA |
| SEQ ID NO: 73 | Recombinant protein |
| SEQ ID NO: 74 | Recombinant DNA |
| SEQ ID NO: 75 | Recombinant protein |
| SEQ ID NO: 76 | Recombinant DNA |
| SEQ ID NO: 77 | Recombinant protein |
| SEQ ID NO: 78 | Recombinant DNA |
| SEQ ID NO: 79 | Recombinant protein |
| SEQ ID NO: 80 | Recombinant DNA |
| SEQ ID NO: 81 | Recombinant protein |
| SEQ ID NO: 82 | Recombinant DNA |
| SEQ ID NO: 83 | Recombinant protein |
| SEQ ID NO: 84 | Recombinant DNA |
| SEQ ID NO: 85 | Recombinant protein |
| SEQ ID NO: 86 | Recombinant DNA |
| SEQ ID NO: 87 | Recombinant protein |
| SEQ ID NO: 88 | Recombinant DNA |
| SEQ ID NO: 89 | Recombinant protein |

What is claimed is:

1. An antibody against human delta-like 1 homolog (*Drosophila*) (Dlk-1), wherein the amino acid sequence of the H chain V region comprises the amino acid sequence as shown in any one of SEQ ID NO: 35, 40, 69, 73, 77, 81, 85 and 89, and the amino acid sequence of the L chain V region comprises the amino acid sequence as shown in SEQ ID NO: 45.

2. The antibody according to claim 1, which has an anti-tumor activity in vivo; wherein the tumor is human Dlk-1-expressing human tumor.

3. The antibody according to claim 2, wherein the tumor is at least one type selected from the group consisting of human colon cancer, human breast cancer, human liver cancer, human pancreatic cancer, human small cell lung cancer and human neuroblastoma.

4. The antibody according to claim 1, which is a humanized antibody.

5. The antibody according to claim 1, which is a monoclonal antibody.

6. The antibody according to claim 1, which binds to at least a portion of a region comprising amino acids at positions 24 to 91 in the amino acid sequence of human Dlk-1 as shown in SEQ ID NO: 2.

7. An antigen-binding antibody fragment derived from the antibody according to claim 1.

8. The antibody fragment according to claim 7, which comprises the amino acid sequence as shown in any one of SEQ ID NO: 35, 40, 69, 73, 77, 81, 85 and 89.

9. The antibody fragment according to claim 7, which comprises the amino acid sequence as shown in SEQ ID NO: 45.

10. The antibody fragment according to claim 7, which comprises both the amino acid sequence as shown in any one of SEQ ID NO: 35, 40, 69, 73, 77, 81, 85 and 89 and the amino acid sequence as shown in SEQ ID NO: 45.

11. An antibody-agent complex, which comprises the antibody according to claim 1 and a compound having an anti-tumor activity and/or a cell-killing activity.

12. A pharmaceutical composition, which comprises an antibody according to claim 1.

13. The composition according to claim 12, which is used in the treatment of a tumor.

14. The composition according to claim 13, which does not cause weight reduction as a side effect.

15. The composition according to claim 13, wherein the tumor is at least one type selected from the group consisting of human colon cancer, human breast cancer, human liver cancer, human pancreatic cancer, human small cell lung cancer and human neuroblastoma.

16. The composition according to claim 12, which comprises the antibody according to claim 1 and a compound having an anti-tumor activity and/or a cell-killing activity wherein the tumor is human Dlk-1-expressing human tumor.

17. A tumor therapeutic agent, which comprises an antibody according to claim 1.

18. The therapeutic agent according to claim 17, which does not cause weight reduction as a side effect.

19. The therapeutic agent according to claim 17, wherein the tumor is at least one type selected from the group consisting of human colon cancer, human breast cancer, human liver cancer, human pancreatic cancer, human small cell lung cancer and human neuroblastoma.

20. The tumor therapeutic agent according to claim 17, which comprises the antibody according to claim 1 and a compound having an anti-tumor activity and/or a cell-killing activity wherein the tumor is human Dlk-1-expressing human tumor.

21. A kit for treating, diagnosing, or detecting a tumor, which comprises an antibody according to claim 1.

22. The kit according to claim 21, wherein the tumor is at least one type selected from the group consisting of human colon cancer, human breast cancer, human liver cancer, human pancreatic cancer, human small cell lung cancer and human neuroblastoma.

23. The kit according to claim 21, which comprises the antibody according to claim 1 and a compound having an anti-tumor activity and/or a cell-killing activity wherein the tumor is human Dlk-1-expressing human tumor.

24. A kit for inducing apoptosis in tumor cells, which comprises an antibody according to claim 1.

25. The kit according to claim 24, which comprises the antibody according to claim 1 and a compound having an anti-tumor activity and/or a cell-killing activity wherein the tumor is human Dlk-1-expressing human tumor.

* * * * *